(12) United States Patent
Hecht et al.

(10) Patent No.: US 9,919,055 B2
(45) Date of Patent: Mar. 20, 2018

(54) SUGAR-LINKER-DRUG CONJUGATES

(71) Applicants: Sidney Hecht, Phoenix, AZ (US);
Rakesh Paul, Baltimore, MD (US);
Chenhong Tang, Tempe, AZ (US);
Manikandadas Mathilakathu Madathil, Tempe, AZ (US);
Chandrabali Bhattacharya, Tempe, AZ (US)

(72) Inventors: Sidney Hecht, Phoenix, AZ (US);
Rakesh Paul, Baltimore, MD (US);
Chenhong Tang, Tempe, AZ (US);
Manikandadas Mathilakathu Madathil, Tempe, AZ (US);
Chandrabali Bhattacharya, Tempe, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 1 day.

(21) Appl. No.: 14/776,396

(22) PCT Filed: Mar. 14, 2014

(86) PCT No.: PCT/US2014/029793
§ 371 (c)(1),
(2) Date: Sep. 14, 2015

(87) PCT Pub. No.: WO2014/145109
PCT Pub. Date: Sep. 18, 2014

(65) Prior Publication Data
US 2016/0045611 A1     Feb. 18, 2016

Related U.S. Application Data

(60) Provisional application No. 61/801,202, filed on Mar. 15, 2013.

(51) Int. Cl.
| | | |
|---|---|---|
| A61K 31/4745 | (2006.01) | |
| A61K 31/519 | (2006.01) | |
| A61K 47/48 | (2006.01) | |
| A61K 31/7042 | (2006.01) | |

(52) U.S. Cl.
CPC .... *A61K 47/48092* (2013.01); *A61K 31/4745* (2013.01); *A61K 31/519* (2013.01); *A61K 31/7042* (2013.01)

(58) Field of Classification Search
None
See application file for complete search history.

(56) References Cited

U.S. PATENT DOCUMENTS

| 6,506,734 | B1 * | 1/2003 | Lerchen | C07H 15/26 514/25 |
|---|---|---|---|---|
| 9,624,255 | B2 | 4/2017 | Hecht et al. | |
| 2007/0269380 | A1 | 11/2007 | Zhang et al. | |
| 2011/0293530 | A1 | 12/2011 | Hecht et al. | |
| 2012/0094946 | A1 | 4/2012 | Thorson et al. | |
| 2012/0148502 | A1 * | 6/2012 | Hecht | A61K 47/48869 424/9.52 |
| 2013/0266518 | A1 | 10/2013 | Hecht et al. | |

FOREIGN PATENT DOCUMENTS

| CN | 102260875 A | * | 11/2011 |
|---|---|---|---|
| DE | 199 09 979 A1 | | 9/2000 |
| EP | 1 219 634 A1 | | 7/2002 |
| EP | 2 594 575 A1 | | 5/2013 |
| WO | WO 1996/039197 | | 12/1996 |
| WO | WO 1998/051703 | | 11/1998 |
| WO | WO 2011/019419 | | 2/2011 |
| WO | WO 2012/142141 | | 10/2012 |
| WO | WO 2014/145109 | | 9/2014 |

OTHER PUBLICATIONS

Machine translation of CN 102260875 A, Nov. 2011.*
Abraham, A.T. et al., "RNA Cleavage and Inhibition of Protein Synthesis by Bleomycin", In Chemistry & Biology, vol. 10, No. 1, Jan. 2003, pp. 45-52.
Bekerman, C. et al., "Scintigraphic Evaluation of Lymphoma: A Comparative Study of 67 Ga-Citrate and 111 In-Bleomycin", In Radiology, vol. 123, No. 3, Jun. 1977, pp. 687-694.
Boger, D.L, and Honda, T.J., "Total Synthesis of Bleomycin A2 and Related Agents. 4. Synthesis of the Disaccharide Subunit 2-O-(3-O-Carbamoyl-.apha.-D-mannopyranosyl)-L-gulopyranose and Completion of the Total Synthesis of Bleomycin A2", In J. of the Am. Chem. Soc., vol. 116, No. 13, Jun. 1994, pp. 5647-5656.
Burton, I.E. et al., "Static and Dynamic Imaging with Indium-111 Labelled Bleomycin in the Localization of Squamous Cell Neoplasia", In the British Journal of Radiology, vol. 50, No. 595, Jul. 1977, pp. 508-512.
Chen, E.X. et al., "Phase I and Pharmacokinetic Study of Bay 38-3441, a Camptothecin Glycoconjugate, Administered as a 30-minute Infusion Daily for Five Days every 3 Weeks in Patients with Advanced Solid Malignancies", In the Journal of New Anticancer Agents, vol. 23, No. 5, Oct. 2005, pp. 455-465.
Chen, J. and Stubbe, J., "Bleomycins: Towards Better Therapeutics", In Nature Reviews Cancer, vol. 5, No. 2, Feb. 2005, pp. 102-112.
Choudhury, A.K. et al. "Synthesis and DNA Cleavage Activity of a Novel Bleomycin A5 Glycoconjugate", In Organic Letters, vol. 3, No. 9, Apr. 2001, pp. 1291-1294.

(Continued)

*Primary Examiner* — Layla D Berry
(74) *Attorney, Agent, or Firm* — Byrne Poh LLP; Nina R. Horan

(57) ABSTRACT

The present disclosure relates to sugar-linker-drug conjugates, of the formula [A-B-]n-L-D, wherein A is a saccharide; B is a spacer, n is an integer selected from 1 to 3; L is a linker group and D is a drug having a chemically reactive functional group selected from the group consisting of a primary or secondary amine, hydroxyl, sulfhydryl, carboxyl, aldehyde and ketone. Pharmaceutical compositions comprising the conjugates and methods of using them are also provided.

17 Claims, No Drawings

(56) References Cited

OTHER PUBLICATIONS

Christiansen, J.P. et al., "Noninvasive Imaging of Myocardial Reperfusion Injury using Leukocyte-Targeted Contrast Echocardiography", In Circulation, vol. 105, No. 15, Apr. 2002, pp. 1764-1767.
Claussen, C.A. and Long, E.C., "Nucleic Acid Recognition by Metal Complexes of Bleomycin", In Chemical Reviews, vol. 99, No. 9, Sep. 1999, pp. 2797-2816.
Dehuyser, L. et al., "Synthesis of Novel Mannoside Glycolipid Conjugates for Inhibition of HIV-1 Trans-Infection", In Bioconjugate Chemistry, vol. 23, No. 9, Sep. 19, 2012, pp. 1731-1739.
Dondoni, A. et al., "Carbohydrate Homologation by the Use of 2-(Trimethylsilyl)thiazole. Preparative Scale Synthesis of Rare Sugars: L-Gulose, L-Idose, and the Disaccharide Subunit of Bleomycin A2", In the Journal of Organic Chemistry, vol. 62, No. 18, Sep. 1997, pp. 6261-6267.
Dongbang, S. et al., "Camptothecin Delivery into Hepatoma Cell Line by Galactose-Appended Fluorescent Drug Deliver System", in RSC Advances, vol. 4, No. 36, Jan. 2014, pp. 1-5.
Extended European Search Report dated Oct. 31, 2016 in European Patent Application No. 14764855.4.
Goodwin, D.A. et al., "Clinical Studies with In-111 BLEDTA, a Tumor-Imaging Conjugate of Bleomycin with a Bifunctional Chelating Agent", In the Journal of Nuclear Medicine, vol. 22, No. 9, Sep. 1981, pp. 787-792.
Grote, J. et al., "Methodology for the Regiospecific Synthesis and Characterization of Methotrexate Conjugates", In Tetrahedron Letters, vol. 53, No. 39, Sep. 2012, pp. 5331-5334.
Hamilton, A.J. et al., "Intravascular Ultrasound Molecular Imaging of Atheroma Components in Vivo", In the Journal of the American College of Cardiology, vol. 43, No. 3, Feb. 4, 2004, pp. 453-460.
Hecht, S.M., "Bleomycin: New Perspectives on the Mechanism of Action", In the Journal of Natural Products, vol. 63, No. 1, Dec. 1999, pp. 158-168.
Holmes, C.E. et al., "Characterization of Iron(II)·bleomycin-mediated RNA Strand Scission", In Biochemistry, vol. 32, No. 16, Apr. 1993, pp. 4293-4307.
Iglesias-Guerra, F. et al., "Alkylating Agents from Sugars: Synthesis of Chlorambucil Derivatives Carried by Chiral Glycosyl Glycerols Derived from D-Glucosamine", In Chirality, vol. 14, No. 2-3, Jan. 2002, pp. 199-203.
International Preliminary Report on Patentability dated Jul. 21, 2014 in International Patent Application No. PCT/US2014/027656.
International Preliminary Report on Patentability dated Aug. 1, 2014 in International Patent Application No. PCT/US2014/029793.
International Search Report and Written Opinion dated Jul. 21, 2014 in International Patent Application No. PCT/US2014/027656.
International Search Report and Written Opinion dated Aug. 1, 2014 in International Patent Application No. PCT/US2014/029793.
Jones, S.E. et al., "Indium-111 Bleomycin Tumor Scanning in Lymphoma", In Medical and Pediatric Oncology, vol. 1, No. 1, Feb. 1975, pp. 11-21.
Kane, S.A. and Hecht, S.M., "Polynucleotide Recognition and Degradation by Bleomycin", In Progress in Nucleic Acid Research and Molecular Biology, vol. 49, 1994, pp. 313-352.
Klibanov, A.L., "Ligand-Carrying Gas-Filled Microbubbles: Ultrasound Contrast Agents for Targeted Molecular Imaging", In Bioconjugate Chemistry, vol. 16, No. 1, Jan.-Feb. 2005, pp. 9-17.

Kralovec, J. et al., "Synthesis of Methotrexate-Antibody Conjugates by Regiospecific Coupling and Assessment of Drug and Antitumor Activities", In the Journal of Medicinal Chemistry, vol. 32, No. 11, Nov. 1989, pp. 2426-2431.
Levi, J.A. et al., "The Importance of Bleomycin in Combination Chemotherapy for Good-Prognosis Germ Cell Carcinoma", In the Journal of Clinical Oncology, vol. 11, No. 7, Jul. 1993, pp. 1300-1305.
Lindner, J.R., "Microbubbles in Medical Imaging: Current Applications and Future Directions", In Nature Reviews Drug Discovery, vol. 3, Jun. 2004, pp. 527-533.
Nagy et al., "Selective Coupling of Methotrexate to Peptide Hormone Carriers through a Gamma-Carboxamide Linkage of its Glutamic Acid Moiety: Benzotriazol-1-yloxytris(dimenthylamino)phosphonium Hexafluorophosphate Activation in Salt Coupling", In Proc. Nat. Acad. Of Sci., vol. 90, Jul. 1993, pp. 6373-6376.
Pignatello, R. et al., "Lipophilic Conjugates of Methotrexate with Glucosyl-Lipoamino Acids: Calorimetric Study of the Interaction with a Biomembrane Model", In Thermochimica Acta, Elsevier Science Publishers, Amsterdam, NL, vol. 426, No. 102, Feb. 2005, pp. 163-171.
Pignatello, R. et al., "Lipophilic Methotrexate Conjugates with Glucose-Lipoamino Acid Moieties: Synthesis and in Vitro Antitumor Activity", In Drug Development Research, vol. 52, No. 3, Mar. 2001, pp. 454-461.
Rychak, J.J. et al., "Deformable Gas-Filled Microbubbles Targeted to P-Selectin", In Journal of Controlled Release, vol. 114, Jun. 2006, pp. 288-299.
Silverstein, M.J. et al., "Indium-Bleomycin Breast and Axilla Imaging", In Cancer, vol. 37, No. 1, Jan. 1976, pp. 36-42.
Stern, P.H. et al., "Cytotoxic Activity, Tumor Accumulation, and Tissue Distribution of Ruthenium-103-labeled Bleomycin", In the Journal of the National Cancer Institute, vol. 66, No. 5, May 1981, pp. 807-811.
Tao, Z.F. et al., "An Efficient Mammalian Transfer RNA Target for Bleomycin", In the Journal of the American Chemical Society, vol. 128, No. 46, Nov. 2006, pp. 14806-14807.
Totani, K. et al., "Tight Binding Ligand Approach to Oligosaccharide-Grafted Protein", In Bioorganic & Medicinal Chemistry Letters, vol. 14, No. 9, May 2004, pp. 2285-2289.
U.S. Food and Drug Administration, "List of Approved Oncology Drugs with Approved Indications", Jan. 17, 2009, pp. 1-48, available at: http://web.archive.org/web/20090117201233/http://www.fda.gov/cder/cancer/druglistframe.htm.
Yu, Z. et al. "Selective Tumor Cell Targeting by the Disaccharide Moiety of Bleomycin", In the Journal of American Chemistry Society, vol. 135, No. 8, Feb. 27, 2013, pp. 2833-2886.
Zhang, Z. et al., "Bioreduction Activated Prodrugs of Camptothecin: Molecular Design, Syntehsis, Activation Mechanism and Hypoxia Selective Cytotoxicity", In Organic & Biomolecular Chemistry, Royal Society of Chemistry, GB, vol. 3, No. 10, May 21, 2005, pp. 1905-1910.
Office Action dated Mar. 12, 2013 in U.S. Appl. No. 13/128,142.
Office Action dated Mar. 22, 2016 in U.S. Appl. No. 13/382,581.
Office Action dated Mar. 23, 2016 in U.S. Appl. No. 13/910,565.
Office Action dated May 16, 2017 in U.S. Appl. No. 14/776,578.
Office Action dated Sep. 8, 2016 in U.S. Appl. No. 13/382,581.
Office Action dated Sep. 21, 2016 in U.S. Appl. No. 13/910,565.

* cited by examiner

SUGAR-LINKER-DRUG CONJUGATES

This application is a national stage application under 35 U.S.C. § 371 of the International Application No. PCT/US2014/29793, filed Mar. 14, 2014, claims the benefit U.S. Provisional Application No. 61/801,202, filed Mar. 15, 2013, which is incorporated by reference herein in its entirety.

FEDERALLY SPONSORED RESEARCH OR DEVELOPMENT

This invention was made with government support under R01 CA140471 awarded by the National Institutes of Health. The government has certain rights in the invention.

FIELD OF THE INVENTION

The present disclosure relates to sugar-linker-drug conjugates, compositions comprising them and methods of using them.

BACKGROUND OF THE INVENTION

The bleomycins (BLMs) are a family of glycopeptide-derived antitumor antibiotics used clinically for the treatment of squamous cell carcinomas and malignant lymphomas. [Levi, J. A. et al., J. Clin. Oncol. 1993, 11, 1300; Bleomycin Chemotherapy; Sikic, B. I., Rozencweig, M., Carter, S. K., Eds.; Academic Press: Orlando, Fla., 1985.] Their antitumor activity is thought to result from selective oxidative cleavage of 5'-GC-3' and 5'-GT-3' sequences in DNA and possibly also from oxidative degradation of RNA. [Holmes, C. E. et al., Biochemistry 1993, 32, 4293; Kane. S. A.; Hecht. S. M. Prog. Nucleic Acid Res. Mol. Biol. 1994, 49, 313; Claussen, C. A.; Long, E. C. Chem. Rev. 1999, 99, 2797; Hecht, S. M. J. Nat. Prod. 2000, 63, 158; Abraham, A. T. et al., Chem. Biol. 2003, 10, 45; Chen, J.; Stubbe, J. Nat. Rev. Cancer 2005, 5, 102; Tao, Z. F.; Konishi, K. et al., J. Am. Chem. Soc. 2006, 128, 14806]. In addition to its antitumor activity, BLM has been recognized for its ability to target tumors and shown to act as a tumor-imaging agent. [Jones, S. E.; Lilien, D. L.; O'Mara, R. E.; Durie, B. G.; Salmon, S. E. Med. Pediatr. Oncol. 1975, 1, 11; Silverstein, M. J.; Verma, R. C.; Greenfield, L.; Morton, D. L. Cancer 1976, 37, 36; Bekerman, C.; Moran, E. M.; Hoffer, P. B.; Hendrix, R. W.; Gottschalk. A. Radiology 1977, 123, 687; Burton, I. E.; Todd, J. H.; Turner, R. L. Br. J. Radiol. 1977, 50, 508; Goodwin, D. A.; Meares. C. F.; DeRiemer, L. H.; Diamanti, C. I.; Goode, R. L.; Baumert, J. E., Jr.; Sartoris, D. J.; Lantieri, R. L.; Fawcett. H. D. J. Nucl. Med. 1981, 22, 787; Stem, P. H.; Helpern, S. E.; Hagan, P. L.; Howell, S. B.; Dabbs, J. E.; Gordon, R. M. J, Natl. Cancer Inst. 1981, 66, 807].

SUMMARY OF THE INVENTION

The present disclosure provides a sugar-linker-drug conjugate of formula (I):

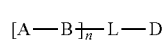
(I)

or a pharmaceutically acceptable salt thereof.

wherein A is:

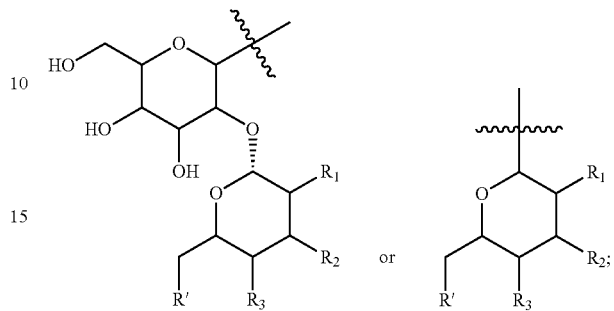

$R_1$ is selected from the group consisting of H, OH, SH, $NH_2$, $OR_4$, $OC(O)R_4$, $OC(O)NHR_4$, $OC(O)NR_4R_5$, $OC(S)NHR_4$, $OC(S)NR_4R_5$, $SC(O)NHR_4$, $SC(O)NR_4R_5$, $NHC(O)NHR_4$, $NHC(O)NR_4R_5$, $NHC(S)NHR_4$, $NHC(S)NR_4R_5$, $NHC(N)NHR_4$, $NHC(N)NR_4R_5$, $OCH_2C(O)NHR_4$, $OCH_2C(O)NR_4R_5$, $OCH_2C(S)NHR_4$, $OCH_2C(S)NR_4R_5$, $SCH_2C(O)NHR_4$, $SCH_2C(O)NR_4R_5$, $NHCH_2C(O)NHR_4$, $NHCH_2C(O)NR_4R_5$, $NHCH_2C(S)NHR_4$ and $NHCH_2C(S)NR_4R_5$;

each $R_4$ is selected from the group consisting of H, $C_1$-$C_6$ alkyl, $C_2$-$C_6$ alkenyl and $C_2$-$C_6$ alkynyl;

each $R_5$ is selected from the group consisting of $C_1$-$C_6$ alkyl, $C_2$-$C_6$ alkenyl and $C_2$-$C_6$ alkynyl;

$R_2$ is selected from the group consisting of H, OH, SH, $NH_2$, $OR_4$, $OC(O)R_4$, $OC(O)NHR_4$, $OC(O)NR_4R_5$, $OC(S)NHR_4$, $OC(S)NR_4R_5$, $SC(O)NHR_4$, $SC(O)NR_4R_5$, $NHC(O)NHR_4$, $NHC(O)NR_4R_5$, $NHC(S)NHR_4$, $NHC(S)NR_4R_5$, $NHC(N)NHR_4$, $NHC(N)NR_4R_5$, $OCH_2C(O)NHR_4$, $OCH_2C(O)NR_4R_5$, $OCH_2C(S)NHR_4$, $OCH_2C(S)NR_4R_5$, $SCH_2C(O)NHR_4$, $SCH_2C(O)NR_4R_5$, $NHCH_2C(O)NHR_4$, $NHCH_2C(O)NR_4R_5$, $NHCH_2C(S)NHR_4$ and $NHCH_2C(S)NR_4R_5$;

$R_3$ is selected from the group consisting of H, OH, SH, $NH_2$, $OR_4$, $OC(O)R_4$, $OC(O)NHR_4$, $OC(O)NR_4R_5$, $OC(S)NHR_4$, $OC(S)NR_4R_5$, $SC(O)NHR_4$, $SC(O)NR_4R_5$, $NHC(O)NHR_4$, $NHC(O)NR_4R_5$, $NHC(S)NHR_4$, $NHC(S)NR_4R_5$, $NHC(N)NHR_4$, $NHC(N)NR_4R_5$, $OCH_2C(O)NHR_4$, $OCH_2C(O)NR_4R_5$, $OCH_2C(S)NHR_4$, $OCH_2C(S)NR_4R_5$, $SCH_2C(O)NHR_4$, $SCH_2C(O)NR_4R_5$, $NHCH_2C(O)NHR_4$, $NHCH_2C(O)NR_4R_5$, $NHCH_2C(S)NHR_4$ and $NHCH_2C(S)NR_4R_5$;

R' is selected from the group consisting of H, OH and $NHR_4$;

B is a Spacer Unit;

n is an integer selected from 1 to 3;

L is absent or a Linker; and

D is a Drug Unit having one or more chemically reactive functional groups selected from the group consisting of a primary or secondary amine, hydroxyl, sulfhydryl, carboxyl, aldehyde and ketone.

In some embodiments, A is:
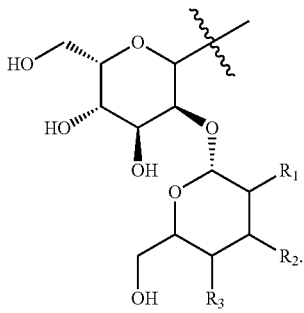
In alternative embodiments, A is
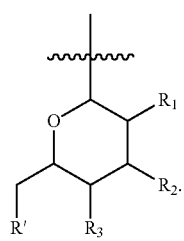
In some embodiments, A is selected from the group consisting of:
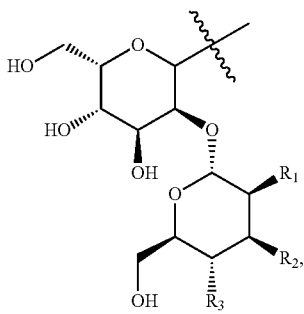
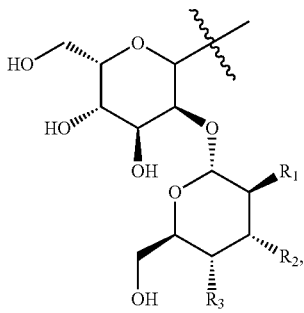
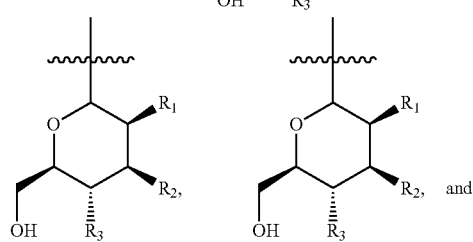 and
-continued
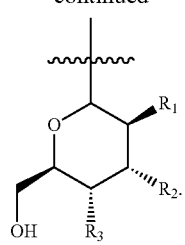
In some embodiments, A is:
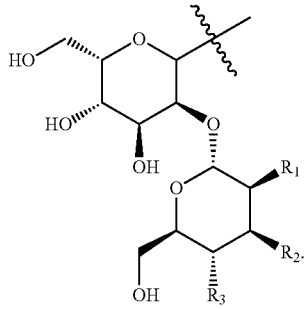
In alternative embodiments, A is:
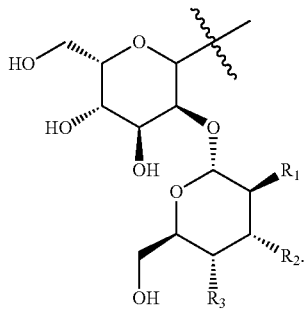
In alternative embodiments, A is:
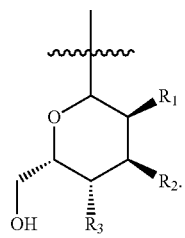

In alternative embodiments, A is:

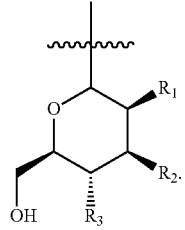

In alternative embodiments, A is:

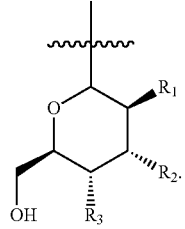

In some embodiments, $R_1$ is selected from the group consisting of H, OH, OC(O)$R_4$, OCONH$R_4$, and OCON$R_4R_5$.

In some embodiments, $R_2$ is selected from the group consisting of H, OH, OC(O)$R_4$, OCONH$R_4$, OCON$R_4R_5$, OCSNH$R_4$, NHCONH$R_4$, NHCON$R_4R_5$, OCH$_2$CONH$R_4$, and OCH$_2$CON$R_4R_5$.

In some embodiments, $R_3$ is selected from the group consisting of H, OH, OC(O)$R_4$, and OCONH$R_4$.

In some embodiments, R' is H or OH.

In some embodiments, each $R_4$ is selected from the group consisting of H, methyl and ethyl.

In some embodiments, each $R_5$ is selected from the group consisting of methyl, ethyl, and isobutyl.

In some embodiments, A is selected from the group consisting of:

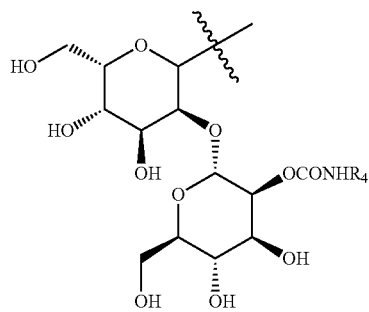

45 $R_4$ = H
46 $R_4$ = CH$_3$

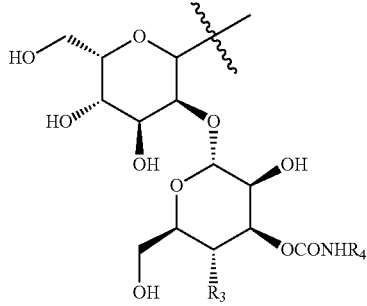

98 $R_4$ = H
53 $R_4$ = CH$_3$

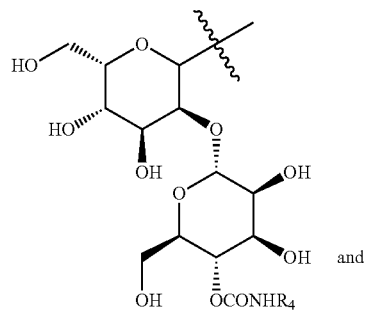

and

64 $R_4$ = H
65 $R_4$ = CH$_3$

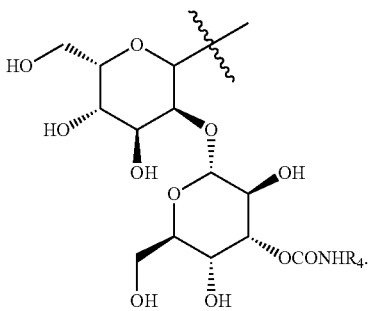

76 $R_4$ = H
77 $R_4$ = CH$_3$

In some embodiments, A is selected from the group consisting of:

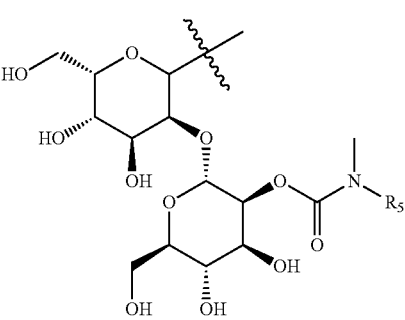

99 $R_5$ = CH$_3$
100 $R_5$ or C$_2$H$_5$

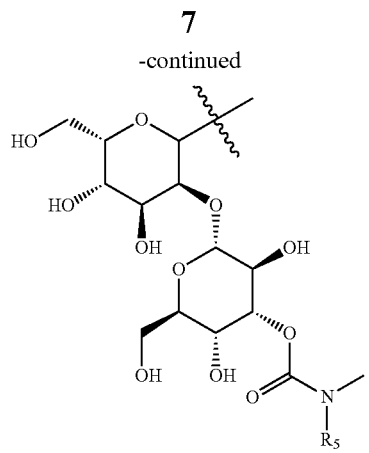
101 R$_5$ = CH$_3$
102 R$_5$ = C$_2$H$_5$
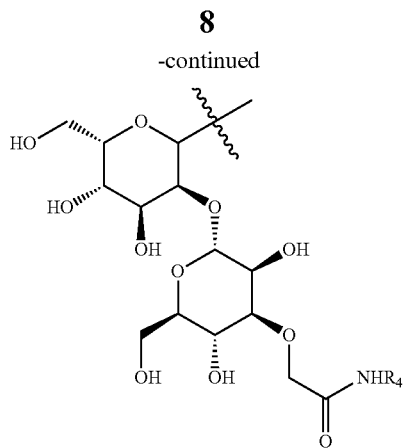
109 R$_4$ = H
110 R$_4$ = CH$_3$
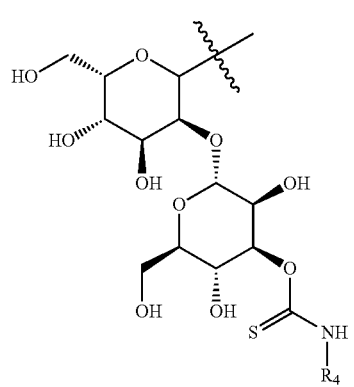
103 R$_4$ = H
104 R$_4$ = CH$_3$
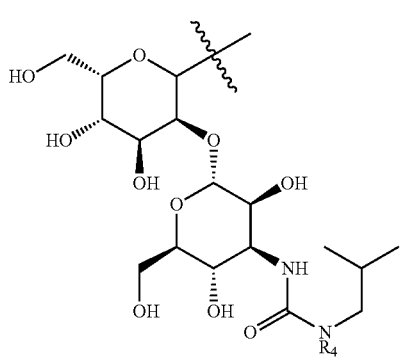
111 R$_4$ = H
112 R$_4$ = CH$_3$
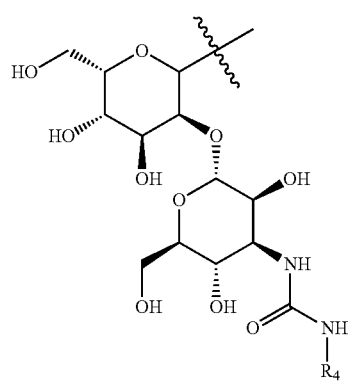
107 R$_4$ = H
108 R$_4$ = CH$_3$
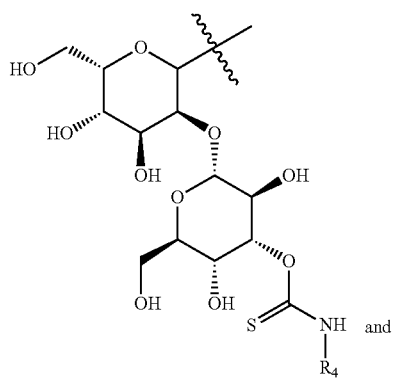
and
105 R$_4$ = H
106 R$_4$ = CH$_3$

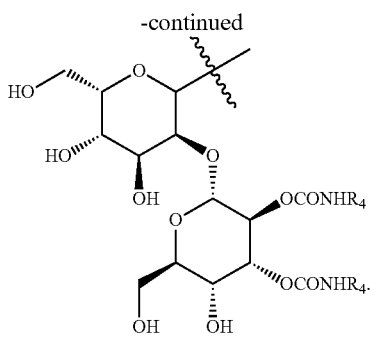

113 R$_4$ = H
114 R$_4$ = CH$_3$

In some embodiments A is selected from the group consisting of

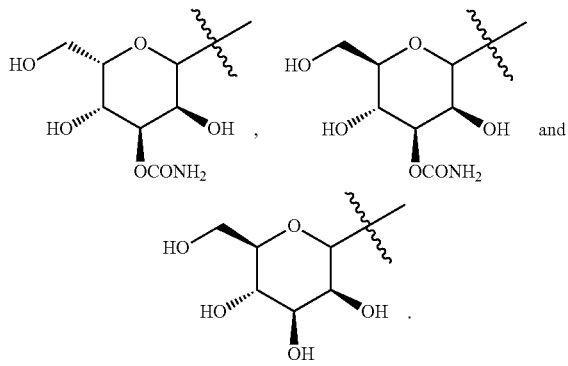

In some embodiments, B is a Spacer Unit selected from the group consisting of a bond, $C_1$-$C_{20}$ alkyl, $C_1$-$C_{20}$ alkenyl, $C_1$-$C_{20}$ alkynyl, aryl, heteroaryl, heterocyclyl, $C_3$-$C_5$ cycloalkyl, an oligoalkylene glycol, an oligopeptide and a dendrimer.

In some embodiments, the Spacer Unit is X-(L$^1$-Y)$_m$-L$^2$-Z,
wherein X is CH$_2$ or O;
L$^1$ is $C_2$-$C_6$ alkyl;
Y is O, S, or NR$^y$, wherein R$^y$ is hydrogen or $C_1$-$C_6$ alkyl;
m is an integer selected from 1 to 10;
L$^2$ is $C_1$-$C_{20}$ alkyl, $C_2$-$C_{20}$ alkenyl. $C_2$-$C_{20}$ alkynyl, aryl, heteroaryl, heterocyclyl, $C_3$-$C_5$ cycloalkyl; and
Z is absent, O, NR$^x$, S, C(O), S(O), S(O)$_2$, OC(O), N(R$^x$)C(O), N(R$^x$)S(O), N(R$^x$)S(O)$_2$, C(O)O, C(O)N(R$^x$), S(O)N(R$^x$), S(O)$_2$N(R$^x$), OC(O)O, OC(O)N(R$^x$), N(R$^x$)C(O)O, N(R$^x$)C(O)N(R$^x$), or N(R$^x$)S(O)$_2$N(R$^x$), wherein
each R$^x$ is independently hydrogen or $C_1$-$C_6$ alkyl.

In some aspects of this embodiment, X is O, L$^1$ is $C_2$-$C_4$ alkyl; L is $C_1$-$C_6$ alkyl; and Z is a bond, O, NR$^x$, S, C(O), S(O), S(O)$_2$, or N(R$^x$)C(O).

In some aspects of this embodiment, the Spacer Unit is O—(CH$_2$CH$_2$—O)$_m$—CH$_2$CH$_2$—Z, wherein Z is O, N(H), S or N(R$^x$)C(O), R$^x$ is H and m is an integer selected from 1 to 20.

In other embodiments, the Spacer Unit is O—(CH$_2$CH$_2$CH$_2$—O)$_m$—CH$_2$CH$_2$—Z, wherein Z is O, N(H), or S and m is an integer selected from 1 to 20.

In some aspects of this embodiments, the Spacer Unit is O—(CH$_2$CH$_2$—O)$_m$—CH$_2$CH$_2$—Z, wherein Z is C(O) or S(O)$_2$ and m is an integer selected from 1 to 20.

In some embodiments, the linker L is absent.

In some aspects of the embodiments in which the linker L is absent, the Spacer Unit is X-(L$^1$-Y)$_m$-L$^2$-Z, wherein X is O, L$^1$ is $C_2$-$C_4$ alkyl; L$^2$ is $C_1$-$C_6$ alkyl; and Z is a bond, O, NR$^x$, S, C(O), S(O), S(O)$_2$, or N(R$^x$)C(O). In some of these embodiments, X is O, L$^1$ is $C_2$-$C_4$ alkyl; L$^1$ is $C_1$-$C_6$ alkyl; and Z is N(R$^x$)C(O).

In other embodiments, the linker L is a non-cleavable linker.

In some aspects of this embodiment, L is (E-L$^3$-F-L$^4$)$_p$-C$_q$-G,
wherein each E is bond, O, NR$^x$, S, C(O), S(O), S(O)$_2$, OC(O), N(R$^x$)C(O), N(R$^x$)S(O), N(R$^x$)S(O)$_2$, C(O)O, C(O)N(R$^x$), S(O)N(R$^x$), S(O)$_2$N(R$^x$), OC(O)O, OC(O)N(R$^x$), N(R$^x$)C(O)O, N(R$^x$)C(O)N(R$^x$), or N(R$^x$)S(O)$_2$N(R$^x$);
each L$^3$ is $C_0$-$C_6$ alkyl;
each F is bond, O, NR$^x$, S, C(O), S(O), S(O)$_2$, OC(O), N(R$^x$)C(O), N(R$^x$)S(O), N(R$^x$)S(O)$_2$, C(O)O, C(O)N(R$^x$), S(O)N(R$^x$), S(O)$_2$N(R$^x$), OC(O)O, OC(O)N(R$^x$), N(R$^x$)C(O)O, N(R$^x$)C(O)N(R$^x$), or N(R$^x$)S(O)$_2$N(R$^x$);
each L$^4$ is $C_0$-$C_6$ alkyl;
p is 1, 2 or 3, when p is 2 or 3, then each (E-L$^3$-F-L$^4$) group may be the same or different;
q is 0 or 1; and
G is a bond, O, NR$^x$, S, C(O), S(O), S(O)$_2$, OC(O), N(R$^x$)C(O), N(R$^x$)S(O), N(R$^x$)S(O)$_2$, C(O)O, C(O)N(R$^x$), S(O)N(R$^x$), S(O)$_2$N(R$^x$), OC(O)O, OC(O)N(R$^x$), N(R$^x$)C(O)O, N(R$^x$)C(O)N(R$^x$), N(R$^x$)S(O)$_2$N(R$^x$), NR$^x$C(O)L$^5$NR$^x$, NR$^x$C(O)L$^5$NR$^x$C(O), NR$^x$C(O)L$^5$O or NR$^x$C(O)L$^5$C(O);
wherein L$^5$ is $C_1$-$C_6$ alkyl and
each R$^x$ is as defined above.

In some aspects of this embodiment, E is NR$^x$ or C(O);
L$^3$ is $C_4$-$C_6$ alkyl;
L$^4$ is $C_0$-$C_2$ alkyl;
p is 1;
F is a bond, NR$^x$, N(R$^x$)C(O), OC(O), C(O)O or C(O)N(R$^x$); and
G is O, S, C(O) or NR$^x$.

In some aspects of this embodiment, E is NR$^x$ or C(O);
each L$^3$ is $C_4$-$C_6$ alkyl;
each L$^4$ is $C_0$-$C_2$ alkyl;
p is 2;
each F is a bond. NR$^x$, N(R$^x$)C(O), OC(O), C(O)O or C(O)N(R$^x$);
and
G is O, S, C(O) or NR$^x$.

In some aspects of this embodiment, E is NR$^x$ or C(O);
each L$^3$ is $C_0$-$C_2$ alkyl;
each L$^4$ is $C_0$-$C_2$ alkyl;
p is 2;
each F is a bond, NR$^x$, N(R$^x$)C(O), OC(O), C(O)O or C(O)N(R$^x$); and
G is O, S, C(O), NR$^x$, NR$^x$C(O)L$^5$NR$^x$, NR$^x$C(O)L$^5$NR$^x$C(O), NR$^x$C(O)L$^5$O or NR$^x$C(O)L$^5$C(O).

In some aspects of this embodiment, E is NR$^x$ or C(O);
each L is $C_1$-$C_6$ alkyl;
each L$^4$ is $C_0$-$C_2$ alkyl;
p is 3;
each F is a bond, NR$^x$, N(R$^x$)C(O), OC(O), C(O)O or C(O)N(R$^x$);
q is 1; and
G is NR$^x$C(O)L$^5$NR$^x$ or NR$^x$C(O)L$^5$NR$^x$C(O).

In some embodiments, the linker L is a cleavable linker.

In embodiments wherein L is a cleavable linker, it is cleavable by a method selected from the group consisting of acid-induced cleavage, light-induced cleavage, peptidase-induced cleavage, esterase-induced cleavage, and disulfide bond cleavage.

In some embodiments, the cleavable linker comprises a hydrazone, a cathepsin-B-cleavable peptide, a disulfide or an ester bond.

In some embodiments, n is 1.
In some embodiments, n is 2.
In some embodiments, n is 3.

In some embodiments, D is a drug selected from the group consisting of a cytotoxic drug, a cytostatic drug and antiproliferative drug.

In some embodiments, D is an antitumor agent, cytotoxic or otherwise. In some aspects of this embodiment, D is an inhibitor of a cellular metabolic event. D can be an enzyme or protein inhibitor, such as an Hsp90 inhibitor or a protein kinase inhibitor.

In some embodiments, D is an amino containing drug selected from the group consisting of mitomycin-C, mitomycin-A, daunorubicin, doxorubicin, N-(5,5-diacetoxypentyl)doxorubicin, aminopterin, actinomycin, bleomycin, 9-amino camptothecin, $N^8$-acetyl spermidine, 1-(2 chloroethyl)-1,2-dimethanesulfonyl hydrazide, tallysomycin, methotrexate, amsacrin, cis-platin, mercaptopurine and derivatives thereof.

In some embodiments. D is a hydroxyl containing drug selected from the group consisting of etoposide, camptothecin, taxol, esperamicin, 1,8-dihydroxy-bicyclo[7.3.1]trideca-4,9-diene-2,6-diyne-13-one, anguidine, doxorubicin, morpholino-doxorubicin, N-(5,5-diacetoxypentyl)doxorubicin, vincristine, vinblastine, bleomycin, teniposide, podophyllotoxin and derivatives thereof.

In some embodiments, D is a sulfhydryl containing drug selected from the group consisting of esperamicin, 6-mercaptopurine, and derivatives thereof.

In some embodiments, D is a carboxyl containing drug selected from the group consisting of methotrexate, camptothecin (ring-opened form of the lactone), butyric acid, retinoic acid, nitrogen mustard drugs, chlorambucil, melphalan and derivatives thereof.

In some embodiments, D is methotrexate or a derivative thereof. In other embodiments, D is camptothecin or a derivate thereof. In yet other embodiments, D is a nitrogen mustard drug or a derivative thereof. In some aspects of this embodiment, D is chlorambucil or a derivative thereof. In other aspects, D is melphalan or a derivative thereof.

In some embodiments, D is an aldehyde containing drug, such as, cinnamaldehyde, inosine dialdehyde, and diglycoaldehyde.

In some embodiments, D is a ketone containing drug, such as an anthracycline or an epothilone.

In some embodiments, the conjugate is represented by formula:

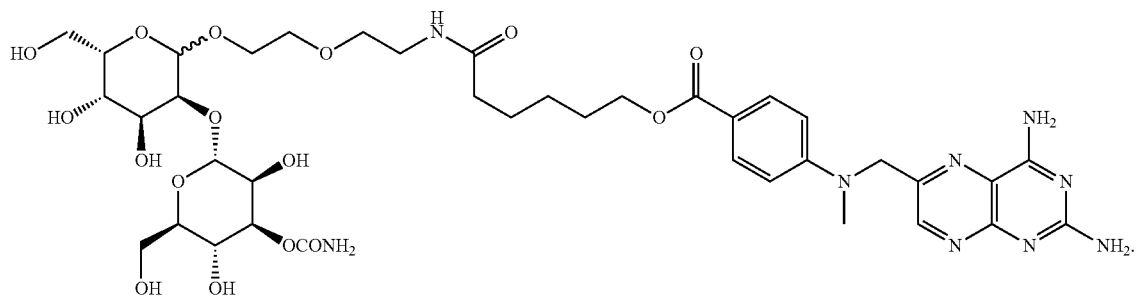

In some embodiments, the conjugate is represented by formula:

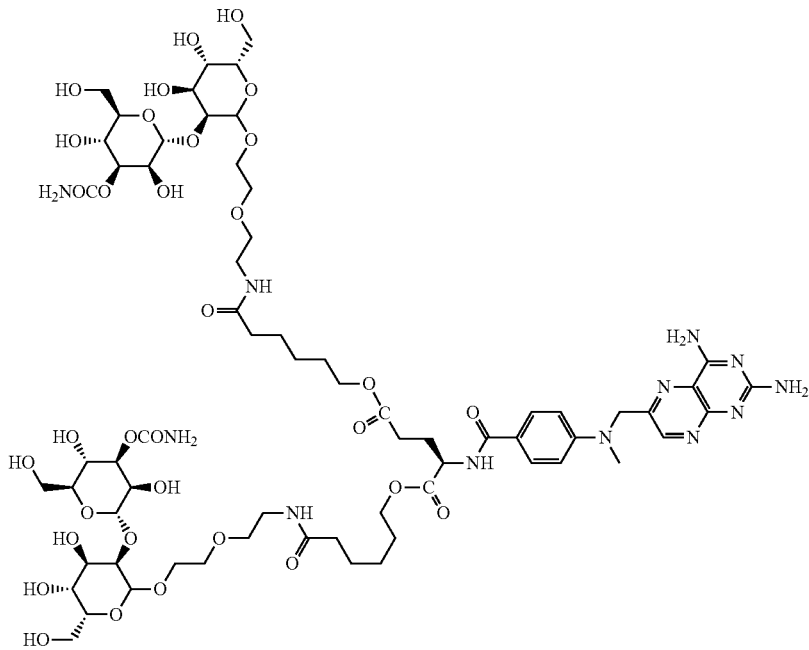

In some embodiments, the conjugate is represented by formula:
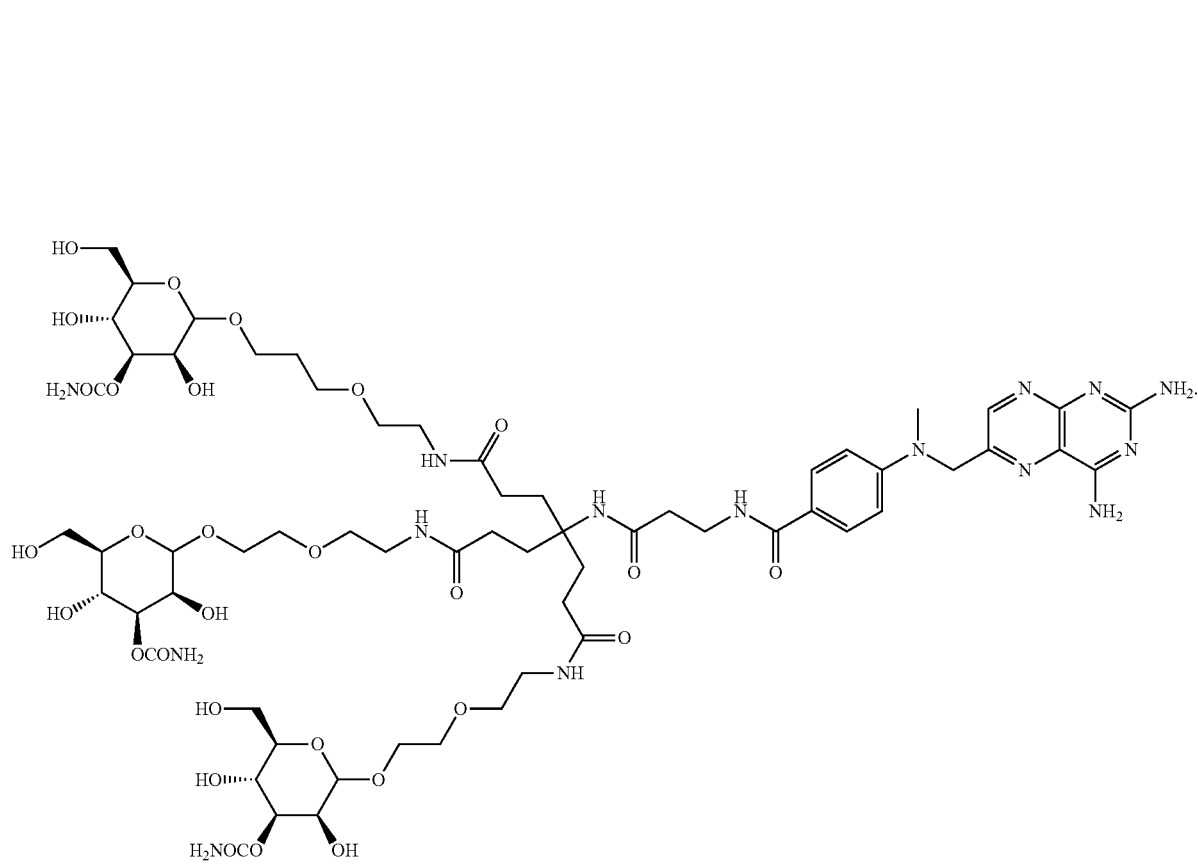
In some embodiments, the conjugate is represented by formula:
In some embodiments, the conjugate is represented by formula:
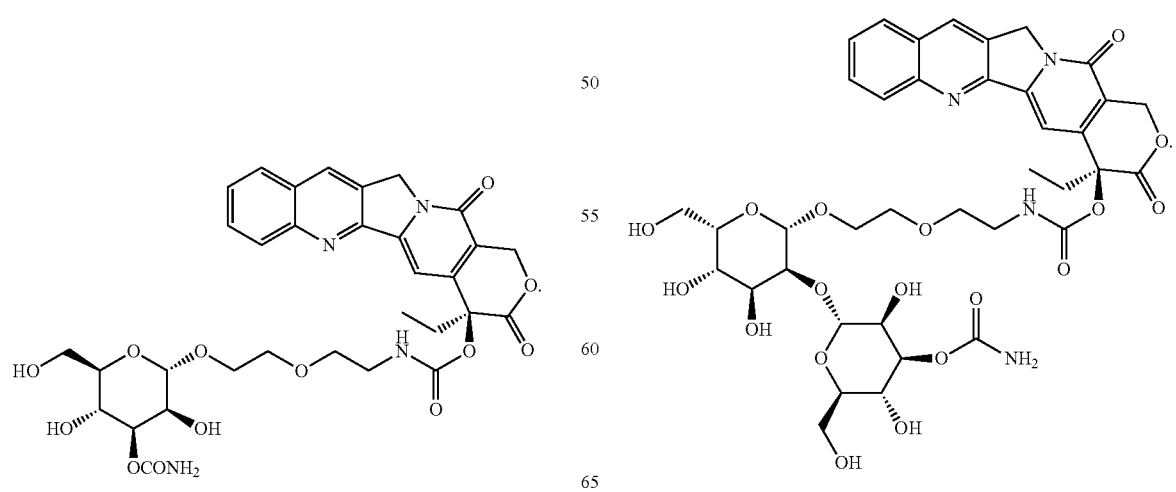

In some embodiments, the conjugate is represented by formula:
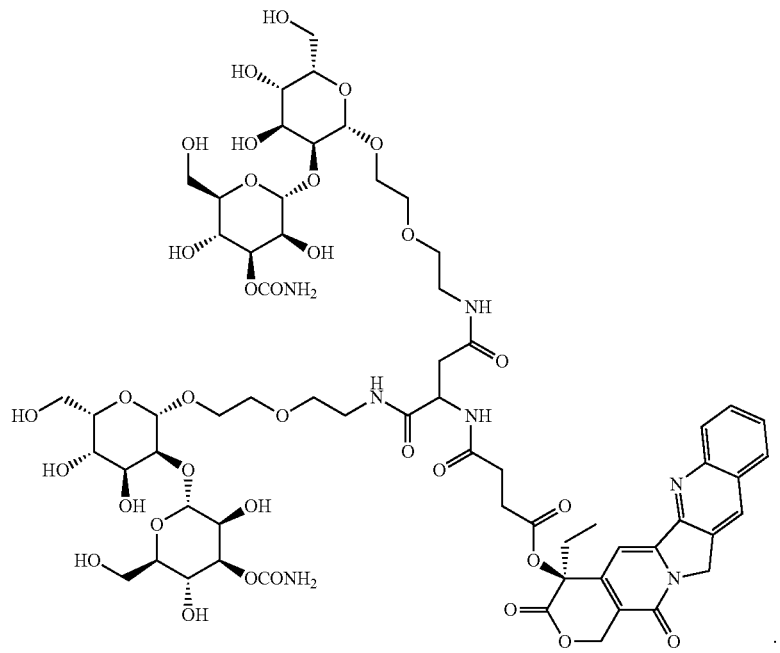
In some embodiments, the conjugate is represented by formula:
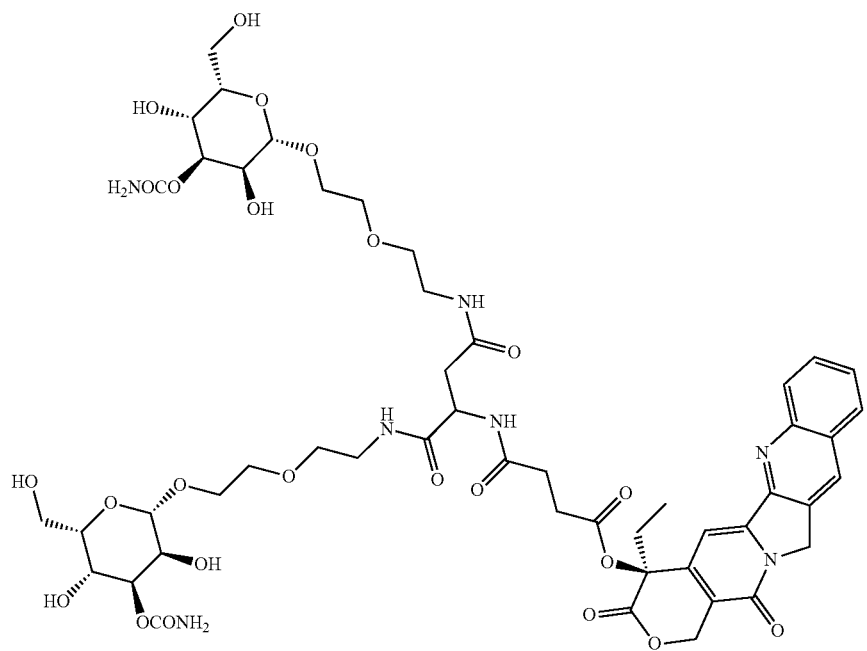

In some embodiments, the conjugate is represented by formula:
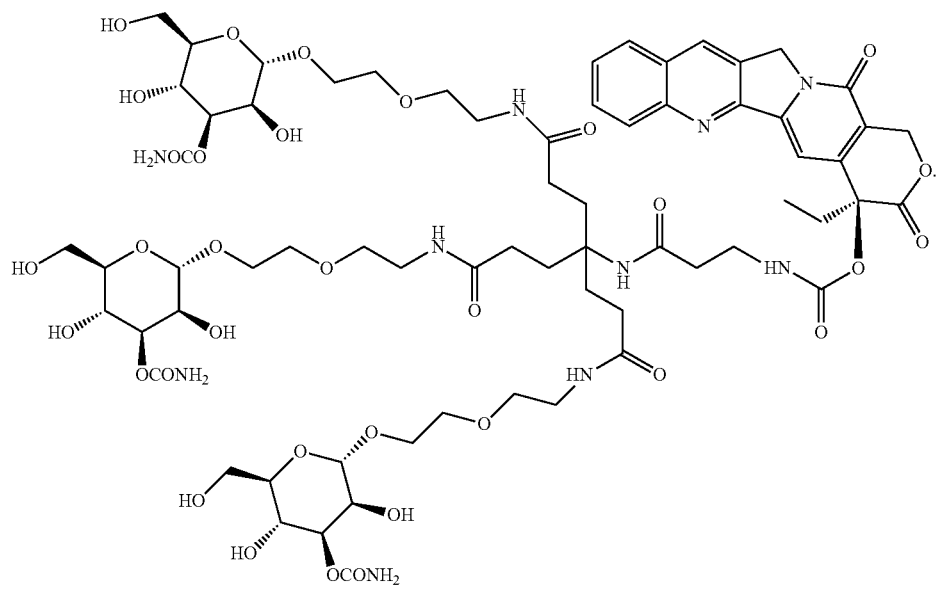
In some embodiments, the conjugate is represented by formula:
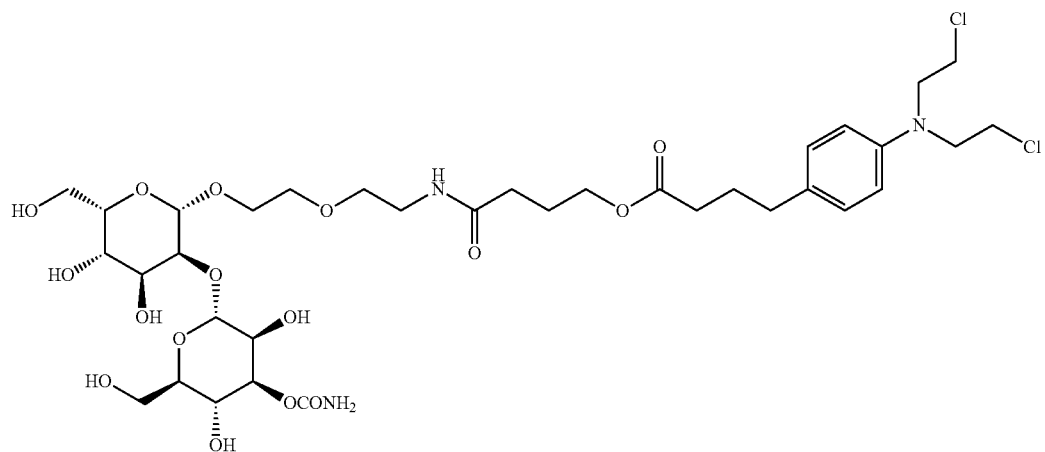
In some embodiments, the conjugate is represented by formula:
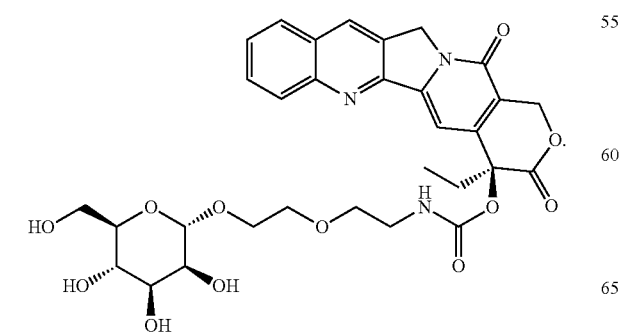

In some embodiments, the conjugate is represented by formula:
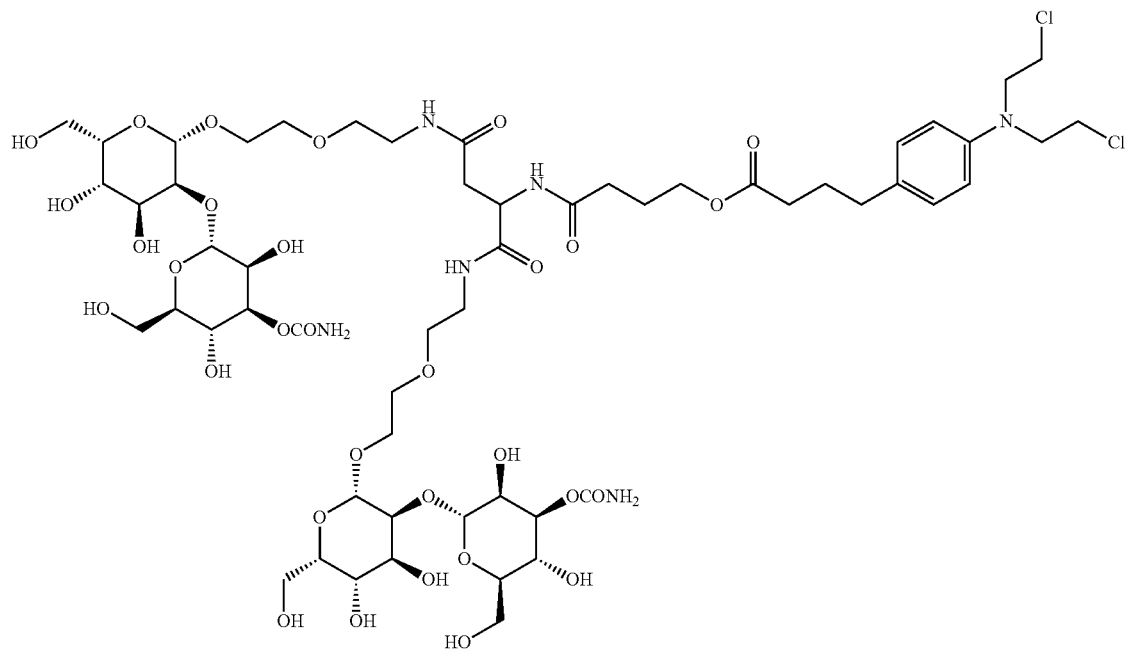
In some embodiments, the conjugate is represented by formula:
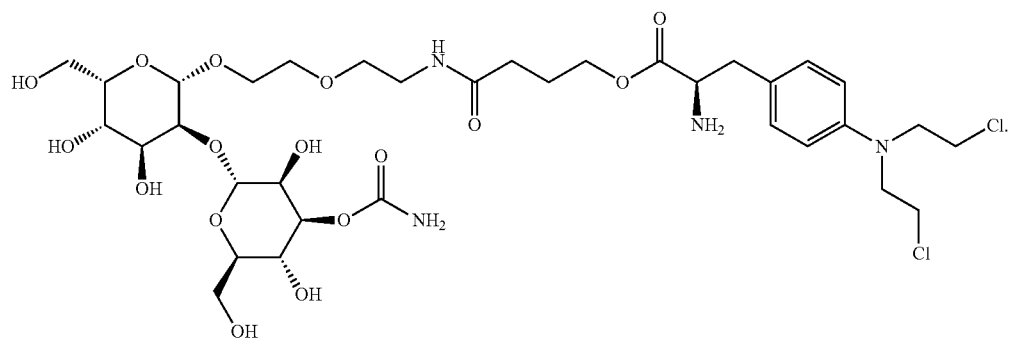 [SMILES: NC(=O)O[C@@H]1[C@H](O)[C@@H](O[C@@H]2[C@@H](OCCOCCNC(=O)CCCOC(=O)[C@H](N)Cc3ccc(N(CCCl)CCCl)cc3)O[C@@H](CO)[C@@H](O)[C@@H]2O)O[C@H](CO)[C@H]1O]

In some embodiments, the conjugate is represented by formula:

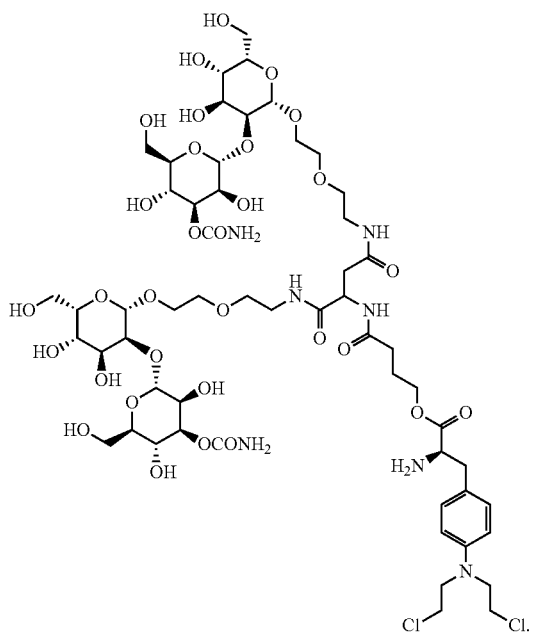

The present disclosure also provides a pharmaceutical composition comprising a conjugate of formula (I) and a pharmaceutically acceptable carrier.

The present disclosure also provides a method of treating cancer in a patient comprising administering to a patient in need thereof a conjugate of formula (I) or a pharmaceutical composition thereof. In some aspects of this embodiment, the sugar moiety binds to a cancer cell, the drug is releasable from the sugar moiety at or near the cancer cell by cleavage of the linker, and the drug, when released, is cytotoxic or cytostatic to the cancer cell.

The present disclosure also provides a method of reducing the toxic side effects of administering a drug to treat cancer, comprising administering to a patient an effective amount of a conjugate of formula (I) or a pharmaceutical composition thereof. In some aspects of this embodiment, the sugar moiety binds to a cancer cell, the drug is releasable from the sugar moiety at or near the cancer cell by cleavage of the linker, and the drug, when released, is cytotoxic or cytostatic to the cancer cell.

DETAILED DESCRIPTION OF THE INVENTION

In order that the invention herein described may be fully understood, the following detailed description is set forth.

Unless defined otherwise, all technical and scientific terms used herein have the same meaning as those commonly understood by one of ordinary skill in the art to which this invention belongs. Although methods and materials similar or equivalent to those described herein can be used in the practice or testing of the present invention, suitable methods and materials are described below. The materials, methods and examples are illustrative only, and are not intended to be limiting. All publications, patents and other documents mentioned herein are incorporated by reference in their entirety.

Throughout this specification, the word "comprise" or variations such as "comprises" or "comprising" will be understood to imply the inclusion of a stated integer or groups of integers but not the exclusion of any other integer or group of integers.

The term "a" or "an" may mean more than one of an item.

The terms "and" and "or" may refer to either the conjunctive or disjunctive and mean "and/or".

The term "about" means within plus or minus 10% of a stated value. For example, "about 100" would refer to any number between 90 and 110.

The term "alkenyl" as used herein, refers to a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkoxy" refers to an alkyl group, as defined herein, appended to a parent moiety via an oxygen atom. Representative examples of alkoxy include, but are not limited to, methoxy, ethoxy, n-propoxy, iso-propoxy, n-butoxy, sec-butoxy, iso-butoxy, tert-butoxy, n-pentoxy, isopentoxy, neopentyloxy, n-hexyloxy, 3-methylhexyloxy, 2,2-dimethylpentoxy, 2,3-dimethylpentoxy, n-heptyloxy, n-octyloxy, n-nonyloxy, and n-decoxy.

The term "alkoxyalkyl" as used herein, means an alkoxy group, as defined herein, appended to a parent moiety via an alkyl group, as defined herein. Representative examples of alkoxyalkyl include, but are not limited to, methoxymethyl, methoxyethyl, ethoxymethyl, ethoxyethyl, n-propoxymethyl, iso-propoxymethyl, n-butoxymethyl, sec-butoxymethyl, iso-butoxymethyl, and tert-butoxymethyl.

The term "alkyl" as used herein, means a straight or branched chain hydrocarbon containing from 1 to 10 carbon atoms, unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —CH$_2$—, —CH$_2$CH$_2$—, —CH$_2$CH$_2$CHC(CH$_3$)—, —CH$_2$CH—(CH$_2$CH$_3$)CH$_2$—.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, means a phenyl (i.e., monocyclic aryl), a bicyclic ring system containing at least one phenyl ring or an aromatic bicyclic ring containing only carbon atoms in the aromatic bicyclic ring system. The bicyclic aryl can be azulenyl, naphthyl, or a phenyl (base ring) fused to a monocyclic cycloalkyl, a monocyclic cycloalkenyl, or a monocyclic heterocyclyl. The bicyclic aryl is attached to the parent molecular moiety through any carbon atom contained within the base ring, or any carbon atom with the napthyl or azulenyl ring. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4- yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2,3-dihydrobenzo[b][1,4]dioxan-5-yl, and 2,3-dihydrobenzo[b][1,4]dioxan-6-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl.

The term "cycloalkyl" as used herein, means a monocyclic or bicyclic ring system. Monocyclic ring systems are cyclic hydrocarbon groups containing from 3 to 8 carbon atoms, where such groups can be saturated (i.e., cycloalkanyl) or unsaturated (i.e., cycloalkenyl), but not aromatic. Examples of monocyclic cycloalkyls include cyclopropyl, cyclobutyl, cyclopentyl, cyclopentenyl, cyclohexyl, cyclohexenyl, cycloheptyl, and cyclooctyl. In certain embodiments, monocyclic cycloalkyl groups are fully saturated. Bicyclic cycloalkyl groups are a monocyclic cycloalkyl ring (base ring) fused to one ring selected from the group consisting of a phenyl ring, a monocyclic cycloalkyl, a monocyclic cycloalkenyl, a monocyclic heterocyclyl, and a monocyclic heteroaryl. The bicyclic cycloalkyl is attached to the parent molecular moiety through any carbon atom contained within the base ring. In certain embodiments, bicyclic cycloalkyl groups are a monocyclic cycloalkyl ring (base ring) fused to one ring selected from the group consisting of a phenyl ring, a 5 or 6 membered monocyclic cycloalkyl, a 5 or 6 membered monocyclic cycloalkenyl, a 5 or 6 membered monocyclic heterocyclyl, and a 5 or 6 membered monocyclic heteroaryl.

The term "heteroaryl," as used herein, means a monocyclic or bicyclic heteroaryl ring system. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl ring (base ring) fused to a phenyl, a monocyclic cycloalkyl, a monocyclic cycloalkenyl, a monocyclic heterocyclyl, or a monocyclic heteroaryl. When the bicyclic heteroaryl contains a fused cycloalkyl, cycloalkenyl, or heterocyclyl ring, then the bicyclic heteroaryl group is connected to the parent molecular moiety through any carbon atom or nitrogen atom contained within the base ring. When the bicyclic heteroaryl is a monocyclic heteroaryl fused to a phenyl ring or a monocyclic heteroaryl, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, and thienopyridinyl. In certain embodiments, the bicyclic heteroaryl is a 5 or 6 membered monocyclic heteroaryl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl.

The term "heterocyclyl" as used herein, means a monocyclic or bicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, thiopyranyl, and trithianyl. The bicyclic heterocycle is a monocyclic heterocycle ring (base ring) fused to a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the base ring. In certain embodiments, bicyclic heterocycles are a monocyclic heterocycle ring (base ring) fused to a phenyl, a 5 or 6 membered monocyclic cycloalkyl, a 5 or 6 membered monocyclic cycloalkenyl, a 5 or 6 membered monocyclic heterocycle, or a 5 or 6 membered monocyclic heteroaryl. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl.

The term "nitro" as used herein, means a —$NO_2$ group.

The term "saturated" as used herein means the referenced chemical structure does not contain any multiple carbon-carbon bonds. For example, a saturated cycloalkyl group as defined herein includes cyclohexyl, cyclopropyl, and the like. The term "unsaturated" as used herein means the referenced chemical structure contains at least one multiple carbon-carbon bond, but is not aromatic. For example, an unsaturated cycloalkyl group as defined herein includes cyclohexenyl, cyclopentenyl, cyclohexadienyl, and the like.

The term "oligoalkylene glycol" refers to a linear oligoalkylene glycol, a branched oligoalkylene glycol, and a comb-oligoalkylene glycol, each comprising from about 1 to 1000 repeat units. In certain embodiments, an oligoalkylene glycol is a linear oligoalkylene glycol.

The term "oligopeptide" refers to a peptide with fewer than about 20 amino acid residues.

The term "dendrimer" refers to a highly branched polymer or oligomer having a well-defined chemical structure comprising a core and a given number of generations of branches, or spindles, and end groups. The generations of spindles consist of structural units that are identical for the same generation of spindles and that may be identical or different for different generations of spindles. The generations of spindles extend radially in a geometrical progression from the core. The end groups of a dendrimer from the Nth generation are the end functional groups of the spindles of the Nth generation or end generation.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Sugar-Linker-Drug Conjugates

The present disclosure provides a sugar-linker-drug conjugate of formula (I):

or a pharmaceutically acceptable salt thereof.
wherein A is:

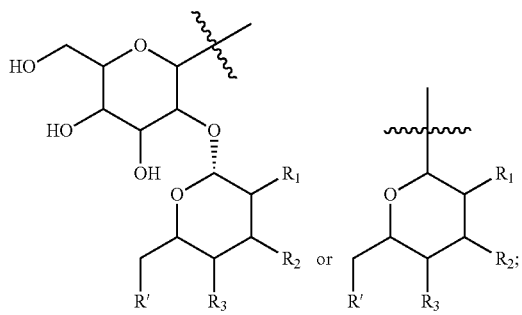

$R_1$ is selected from the group consisting of H, OH, SH, $NH_2$, $OR_4$, $OC(O)R_4$, $OC(O)NHR_4$, $OC(O)NR_4R_5$, $OC(S)NHR_4$, $OC(S)NR_4R_5$, $SC(O)NHR_4$, $SC(O)NR_4R_5$, $NHC(O)NHR_4$, $NHC(O)NR_4R_5$, $NHC(S)NHR_4$, $NHC(S)NR_4R_5$, $NHC(N)NHR_4$, $NHC(N)NR_4R_5$, $OCH_2C(O)NHR_4$, $OCH_2C(O)NR_4R_5$, $OCH_2C(S)NHR_4$, $OCH_2C(S)NR_4R_5$, $SCH_2C(O)NHR_4$, $SCH_2C(O)NR_4R_5$, $NHCH_2C(O)NHR_4$, $NHCH_2C(O)NR_4R_5$, $NHCH_2C(S)NHR_4$ and $NHCH_2C(S)NR_4R_5$;

each $R_4$ is selected from the group consisting of H, $C_1$-$C_6$ alkyl, $C_2$-$C_6$ alkenyl and $C_2$-$C_6$ alkynyl;

each $R_5$ is selected from the group consisting of $C_1$-$C_6$ alkyl, $C_2$-$C_6$ alkenyl and $C_2$-$C_6$ alkynyl;

$R_2$ is selected from the group consisting of H, OH, SH, $NH_2$, $OR_4$, $OC(O)R_4$, $OC(O)NHR_4$, $OC(O)NR_4R_5$, $OC(S)NHR_4$, $OC(S)NR_4R_5$, $SC(O)NHR_4$, $SC(O)NR_4R_5$, $NHC(O)NHR_4$, $NHC(O)NR_4R_5$, $NHC(S)NHR_4$, $NHC(S)NR_4R_5$, $NHC(N)NHR_4$, $NHC(N)NR_4R_5$, $OCH_2C(O)NHR_4$, $OCH_2C(O)NR_4R_5$, $OCH_2C(S)NHR_4$, $OCH_2C(S)NR_4R_5$, $SCH_2C(O)NHR_4$, $SCH_2C(O)NR_4R_5$, $NHCH_2C(O)NHR_4$, $NHCH_2C(O)NR_4R_5$, $NHCH_2C(S)NHR_4$ and $NHCH_2C(S)NR_4R_5$;

$R_3$ is selected from the group consisting of H, OH, SH, $NH_2$, $OR_4$, $OC(O)R_4$, $OC(O)NHR_4$, $OC(O)NR_4R_5$, $OC(S)NHR_4$, $OC(S)NR_4R_5$, $SC(O)NHR_4$, $SC(O)NR_4R_5$, $NHC(O)NHR_4$, $NHC(O)NR_4R_5$, $NHC(S)NHR_4$, $NHC(S)NR_4R_5$, $NHC(N)NHR_4$, $NHC(N)NR_4R_5$, $OCH_2C(O)NHR_4$, $OCH_2C(O)NR_4R_5$, $OCH_2C(S)NHR_4$, $OCH_2C(S)NR_4R_5$, $SCH_2C(O)NHR_4$, $SCH_2C(O)NR_4R_5$, $NHCH_2C(O)NHR_4$, $NHCH_2C(O)NR_4R_5$, $NHCH_2C(S)NHR_4$ and $NHCH_2C(S)NR_4R_5$;

R' is selected from the group consisting of H, OH and $NHR_4$;

B is a Spacer Unit;

n is an integer selected from 1 to 3;

L is absent or a Linker; and

D is a Drug Unit having one or more chemically reactive functional groups selected from the group consisting of a primary or secondary amine, hydroxyl, sulfhydryl, carboxyl, aldehyde and ketone.

In some embodiments, A is:

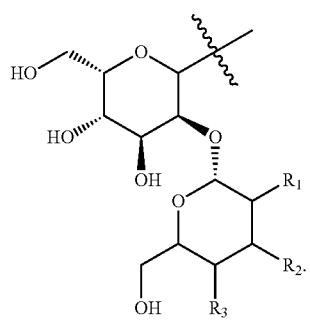

In alternative embodiments, A is

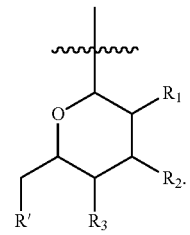

In some embodiments, A is selected from the group consisting of:

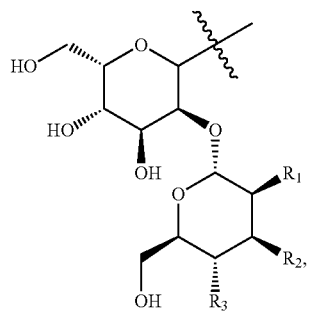

-continued

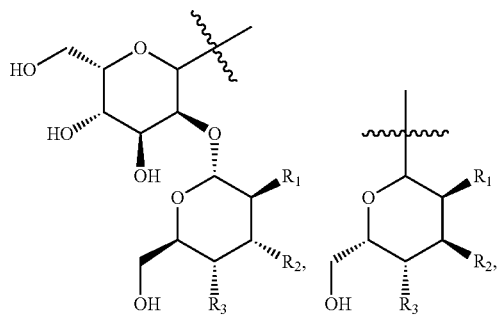

In some embodiments, A is:

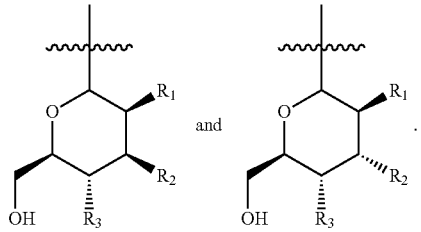

In alternative embodiments, A is:

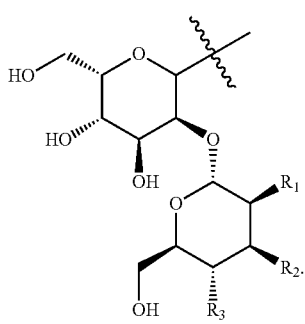

In alternative embodiments, A is:

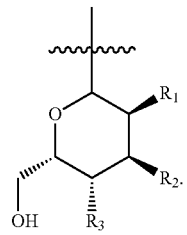

In alternative embodiments, A is:

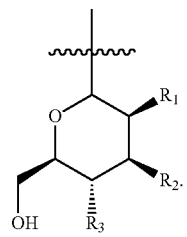

In alternative embodiments, A is:

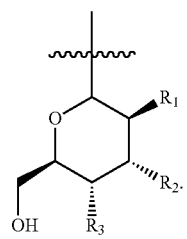

In alternative embodiments, A is:

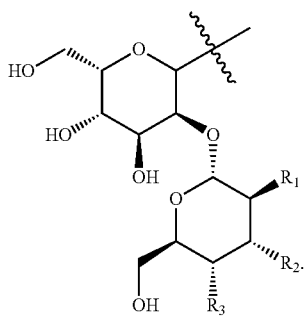

In some embodiments, $R_1$ is selected from the group consisting of H, OH, OC(O)$R_4$, OCONH$R_4$, and OCON$R_4R_5$.

In some embodiments, $R_2$ is selected from the group consisting of H, OH, OC(O)$R_4$, OCONH$R_4$, OCON$R_4R_5$, OCSNH$R_4$, NHCONH$R_4$, NHCON$R_4R_5$, OCH$_2$CONH$R_4$, and OCH$_2$CON$R_4R_5$.

In some embodiments, $R_3$ is selected from the group consisting of H, OH, OC(O)$R_4$, and OCONH$R_4$.

In some embodiments, R' is H or OH.

In some embodiments, each $R_4$ is selected from the group consisting of H, methyl and ethyl.

In some embodiments, each $R_5$ is selected from the group consisting of methyl, ethyl, and isobutyl.

In some embodiments, A is selected from the group consisting of:
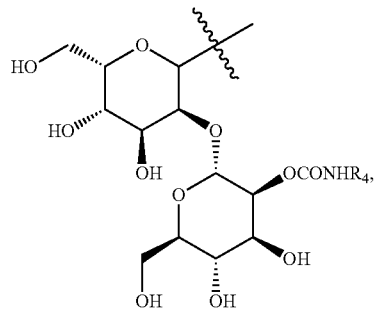
45 R$_4$ = H
46 R$_4$ = CH$_3$
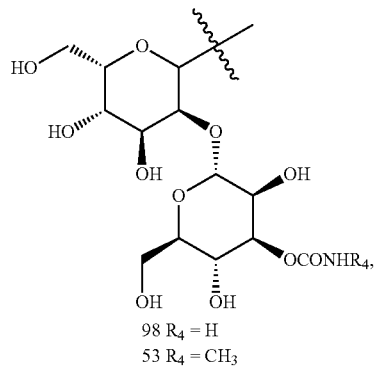
98 R$_4$ = H
53 R$_4$ = CH$_3$
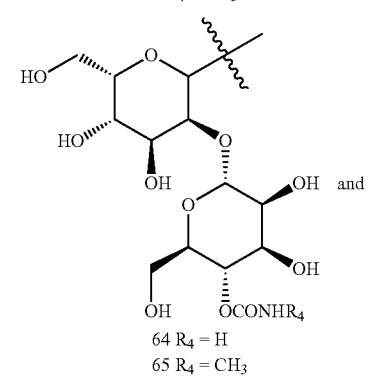
64 R$_4$ = H
65 R$_4$ = CH$_3$
and
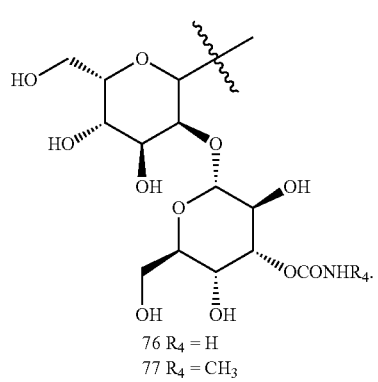
76 R$_4$ = H
77 R$_4$ = CH$_3$
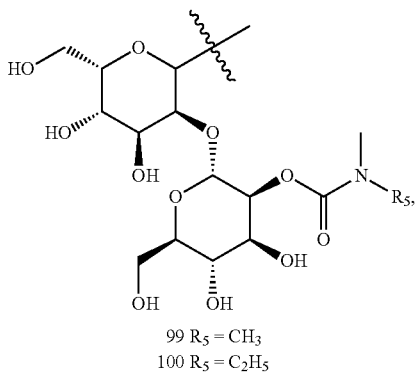
99 R$_5$ = CH$_3$
100 R$_5$ = C$_2$H$_5$
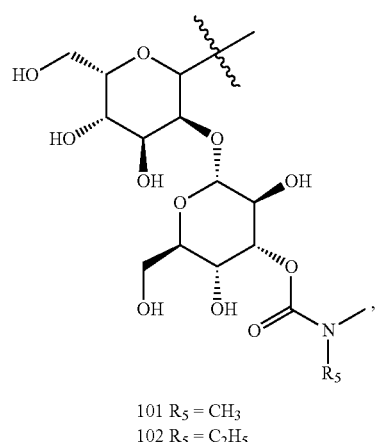
101 R$_5$ = CH$_3$
102 R$_5$ = C$_2$H$_5$
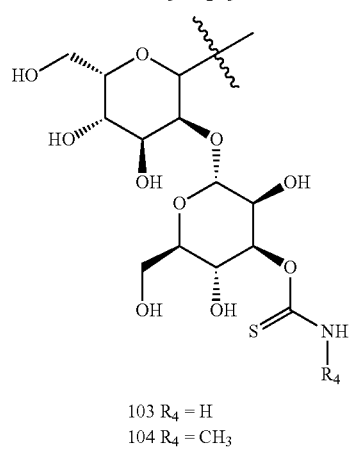
103 R$_4$ = H
104 R$_4$ = CH$_3$
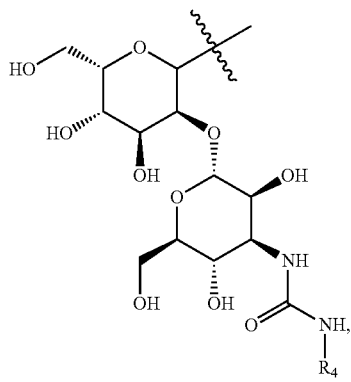
107 R$_4$ = H
108 R$_4$ = CH$_3$
In some embodiments, A is selected from the group consisting of:

-continued

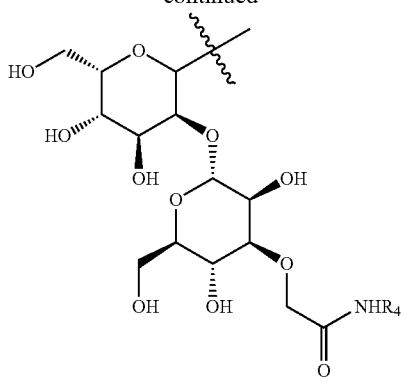

109 R$_4$ = H
110 R$_4$ = CH$_3$

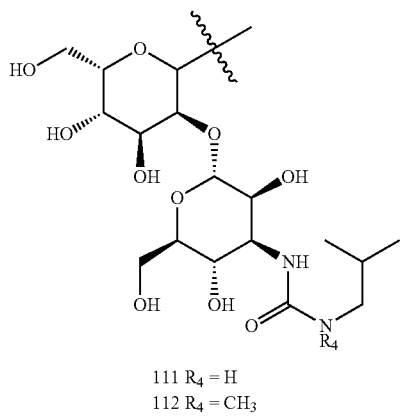

111 R$_4$ = H
112 R$_4$ = CH$_3$

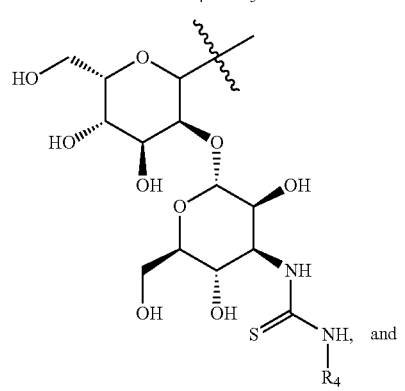

105 R$_4$ = H
106 R$_4$ = CH$_3$

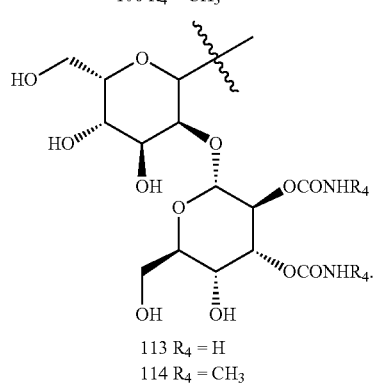

113 R$_4$ = H
114 R$_4$ = CH$_3$

In some embodiments, A is

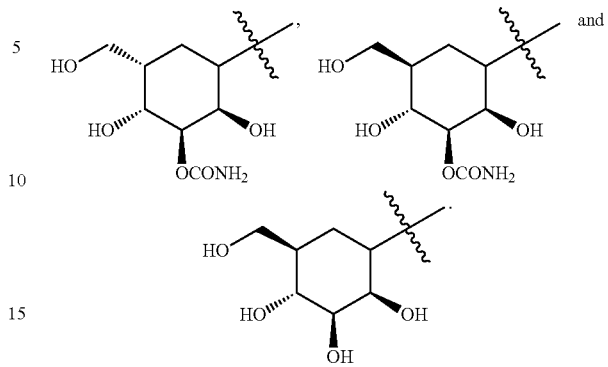

In some embodiments, B is a Spacer Unit selected from the group consisting of a bond, $C_1$-$C_{20}$ alkyl, $C_1$-$C_{20}$ alkenyl, $C_1$-$C_{20}$ alkynyl, aryl, heteroaryl, heterocyclyl, $C_3$-$C_5$ cycloalkyl, an oligoalkylene glycol, an oligopeptide and a dendrimer.

In some embodiments, the Spacer Unit is X-($L^1$-Y)$_m$-$L^2$-Z, wherein X is CH$_2$ or O;

$L^1$ is $C_2$-$C_6$ alkyl;

Y is O, S, or NR$^y$, wherein R$^y$ is hydrogen or $C_1$-$C_6$ alkyl;

m is an integer selected from 1 to 10;

$L^2$ is $C_1$-$C_{20}$ alkyl, $C_2$-$C_{20}$ alkenyl. $C_2$-$C_{20}$ alkynyl, aryl, heteroaryl, heterocyclyl, $C_3$-$C_5$ cycloalkyl; and Z is absent, O, NR$^x$, S, C(O), S(O), S(O)$_2$, OC(O), N(R$^x$)C(O), N(R$^x$)S(O), N(R$^x$)S(O), C(O)O, C(O)N (R$^x$), S(O)N(R$^x$), S(O)$_2$N(R$^x$), OC(O)O, OC(O)N(R$^x$), N(R$^x$)C(O)O, N(R$^x$)C(O)N(R$^x$), or N(R$^x$)S(O)$_2$N(R$^x$), wherein each R$^x$ is independently hydrogen or $C_1$-$C_6$ alkyl.

In some aspects of this embodiment, X is O, $L^1$ is $C_2$-$C_4$ alkyl; L is $C_1$-$C_6$ alkyl; and Z is a bond, O, NR$^x$, S, C(O), S(O), S(O)$_2$, or N(R$^x$)C(O).

In some aspects of this embodiment, the Spacer Unit is O—(CH$_2$CH$_2$—O)$_m$—CH$_2$CH$_2$—Z, wherein Z is O, N(H), S or N(R$^k$)C(O), R$^x$ is H and m is an integer selected from 1 to 20.

In other aspects of this embodiment, the Spacer Unit is O—(CH$_2$CH$_2$CH$_2$—O)$_m$—CH$_2$CH$_2$—Z, wherein Z is O, N(H), or S and m is an integer selected from 1 to 20.

In some aspects of this embodiments, the Spacer Unit is O—(CH$_2$CH$_2$—O)$_m$—CH$_2$CH$_2$—Z, wherein Z is C(O) or S(O)$_2$ and m is an integer selected from 1 to 20.

In some embodiments, the linker L is absent.

In some aspects of the embodiments in which the linker L is absent, the Spacer Unit is X-($L^1$-Y)$_m$-$L^2$-Z, wherein X is O, $L^1$ is $C_2$-$C_4$ alkyl; $L^2$ is $C_1$-$C_6$ alkyl; and Z is a bond, O, NR$^x$, S, C(O). S(O), S(O)$_2$, or N(R$^x$)C(O). In some of these embodiments, X is O, $L^1$ is $C_2$-$C_4$ alkyl; $L^1$ is $C_1$-$C_6$ alkyl; and Z is N(R$^x$)C(O).

In other embodiments, the linker L is a non-cleavable linker.

In some aspects of this embodiment, L is (E-$L^3$-F-$L^4$)$_p$-$C_q$-G, wherein each E is bond, O, NR$^x$, S, C(O), S(O), S(O)$_2$, OC(O), N(R$^x$)C(O), N(R$^x$)S(O), N(R$^x$)S(O)$_2$, C(O)O, C(O)N(R$^x$), S(O)N(R$^x$), S(O)$_2$N(R$^x$), OC(O)O, OC(O) N(R$^x$), N(R$^x$)C(O)O, N(R$^x$)C(O)N(R$^x$), or N(R$^x$)S(O)$_2$ N(R$^x$);

each $L^3$ is $C_0$-$C_6$ alkyl;
each F is bond, O, $NR^x$, S, C(O), S(O), $S(O)_2$, OC(O), $N(R^x)C(O)$, $N(R^x)S(O)$, $N(R^x)S(O)_2$, C(O)O, C(O)N$(R^x)$, $S(O)N(R^x)$, $S(O)_2N(R^x)$, OC(O)O, $OC(O)N(R^x)$, $N(R^x)C(O)O$, $N(R^x)C(O)N(R^x)$, or $N(R^x)S(O)_2N(R^x)$;
each $L^4$ is $C_0$-$C_6$ alkyl;
p is 1, 2 or 3 when p is 2 or 3, then each (E-$L^3$-F-$L^4$) group may be the same or different;
q is 0 or 1; and
G is a bond, O, $NR^x$, S, C(O), S(O), $S(O)_2$, OC(O), $N(R^x)C(O)$, $N(R^x)S(O)$, $N(R^x)S(O)_2$, C(O)O, C(O)N$(R^x)$, $S(O)N(R^x)$, $S(O)_2N(R^x)$, OC(O)O, $OC(O)N(R^x)$, $N(R^X)C(O)O$, $N(R^x)C(O)N(R^x)$, $N(R^x)S(O)N(R^x)$, $NR^xC(O)L^5NR^x$, $NR^xC(O)L^5NR^xC(O)$, $NR^xC(O)L^5O$ or $NR^xC(O)L^5C(O)$;
wherein $L^5$ is $C_1$-$C_6$ alkyl and
each $R^x$ is as defined above.

In some aspects of this embodiment, E is $NR^x$ or C(O); $L^3$ is $C_4$-$C_6$ alkyl;
$L^4$ is $C_0$-$C_2$ alkyl;
p is 1;
F is a bond, $NR^x$, $N(R^xC(O)$, OC(O), C(O)O or C(O)N$(R^x)$; and
G is O, S, C(O) or $NR^x$.

In some aspects of this embodiment, E is $NR^x$ or C(O);
each L is $C_4$-$C_6$ alkyl;
each $L^4$ is $C_0$-$C_2$ alkyl;
p is 2;
each F is a bond, $NR^x$, $N(R^x)C(O)$, OC(O), C(O)O or C(O)N$(R^x)$; and
G is O, S, C(O) or $NR^x$.

In some aspects of this embodiment, E is $NR^x$ or C(O);
each $L^3$ is $C_0$-$C_2$ alkyl;
each $L^4$ is $C_0$-$C_2$ alkyl;
p is 2;
each F is a bond, $NR^x$, $N(R^x)C(O)$, OC(O), C(O)O or C(O)N$(R^x)$; and
G is O, S, C(O), $NR^x$, $NR^xC(O)L^5NR^x$, $NR^xC(O)L^5NR^xC$(O), $NR^xC(O)L^5O$ or $NR^xC(O)L^5C(O)$.

In some aspects of this embodiment, E is $NR^x$ or C(O);
each L is $C_1$-$C_6$ alkyl;
each $L^4$ is $C_0$-$C_2$ alkyl;
p is 3;
each F is a bond, $NR^x$, $N(R^x)C(O)$, OC(O), C(O)O or C(O)N$(R^x)$;
q is 1; and
G is $NR^xC(O)L^5NR^x$ or $NR^xC(O)L^5NR^xC(O)$.

In some embodiments, the linker L is a cleavable linker.

In embodiments wherein L is a cleavable linker, it is cleavable by a method selected from the group consisting of acid-induced cleavage, light-induced cleavage, peptidase-induced cleavage, esterase-induced cleavage, and disulfide bond cleavage.

In some embodiments, the cleavable linker comprises a hydrazone, a cathepsin-B-cleavable peptide, a disulfide or an ester bond.

In some embodiments, n is 1.
In some embodiments, n is 2.
In some embodiments, n is 3.

The sugar-linker drug conjugates of the present disclosure are effective for the usual purposes for which the corresponding drugs are effective, and have superior efficacy because of the ability, inherent in the sugar, to transport the drug to the desired cell where it is of particular benefit. Further, because the conjugates of the disclosure can be used for modifying a given biological response, the drug moiety is not to be construed as limited to classical chemical therapeutic agents. For example, the drug moiety may be a protein or polypeptide possessing a desired biological activity. Such proteins may include, for example, a protein such as tumor necrosis factor. In some embodiments, the term "Drug" refers to any pharmacologically active agent capable of arresting cell growth, or killing the cell in which it is present. The drug can be selected from the group consisting of a cytotoxic drug, a cytostatic drug, antiproliferative drug and antitumor agent. In some embodiments, the drug is a cytotoxic drug.

In alternative embodiments, D is an antitumor agent. In some aspects of this embodiment, D is an inhibitor of a cellular metabolic event. D can be an enzyme or protein inhibitor, such as an Hsp90) inhibitor or a protein kinase inhibitor.

In some embodiments, D is an amino containing drug selected from the group consisting of mitomycin-C, mitomycin-A, daunorubicin, doxorubicin, N-(5,5-diacetoxypentyl)doxorubicin, aminopterin, actinomycin, bleomycin, 9-amino camptothecin, $N^8$-acetyl spermidine, 1-(2 chloroethyl)-1,2-dimethanesulfonyl hydrazide, tallysomycin, methotrexate, amsacrin, cis-platin, mercaptopurine and derivatives thereof.

In some embodiments, D is a hydroxyl containing drug selected from the group consisting of etoposide, camptothecin, taxol, esperamicin, 1,8-dihydroxy-bicyclo[7.3.1]trideca-4,9-diene-2,6-diyne-13-one, anguidine, doxorubicin, morpholino-doxorubicin. N-(5,5-diacetoxypentyl)doxorubicin, vincristine, vinblastine, bleomycin, teniposide, podophyllotoxin and derivatives thereof.

In some embodiments, D is a sulfhydryl containing drug selected from the group consisting of esperamicin, 6-mercaptopurine, and derivatives thereof.

In some embodiments, D is a carboxyl containing drug selected from the group consisting of methotrexate, camptothecin (ring-opened form of the lactone), butyric acid, retinoic acid, nitrogen mustard drugs, chlorambucil, melphalan and derivatives thereof.

In some embodiments, D is methotrexate or a derivative thereof. In alternate embodiments, D is camptothecin or a derivative thereof. In yet other embodiments, D is a nitrogen mustard drug or a derivative thereof. In some aspects of this embodiment, D is chlorambucil or a derivative thereof. In other aspects, D is melphalan or a derivative thereof.

In some embodiments, D is an aldehyde containing drug, such as, cinnamaldehyde, inosine dialdehyde, and diglycoaldehyde.

In some embodiments, D is a ketone containing drug, such as anthracycline or an epothilone.

In some embodiments, the conjugate represented by formula:
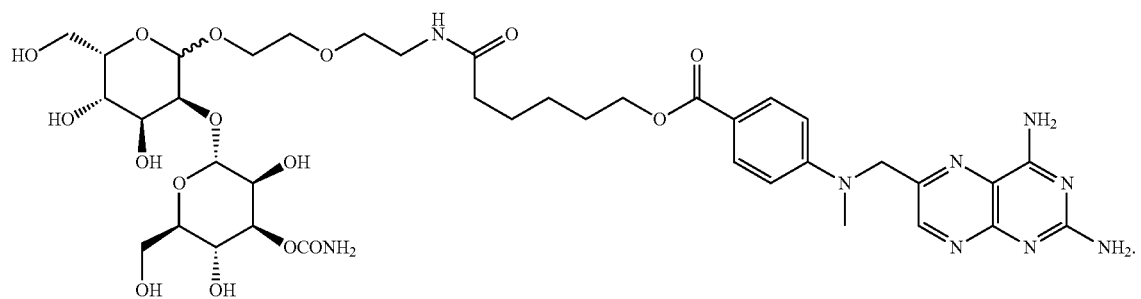
In some embodiments, the conjugate represented by formula:
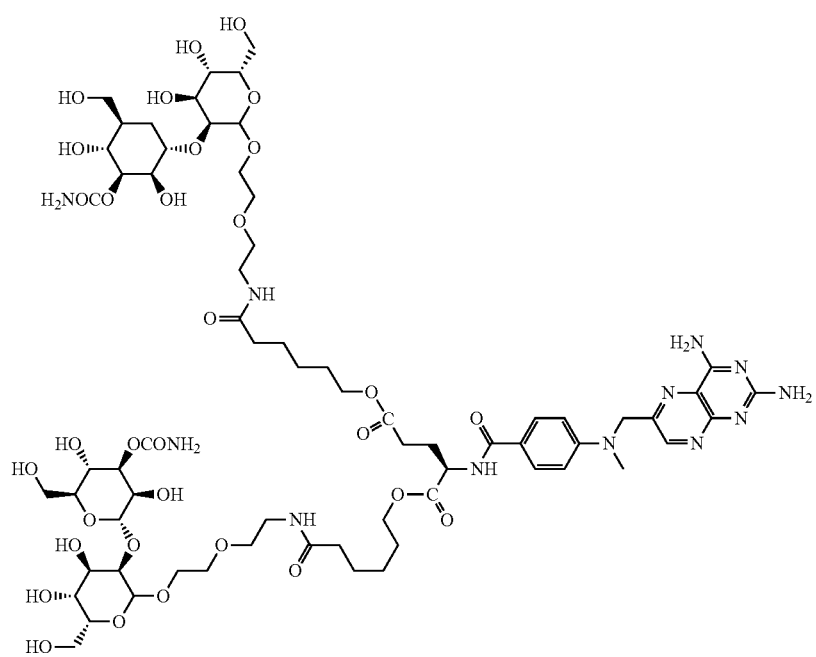

In some embodiments, the conjugate is represented by formula:
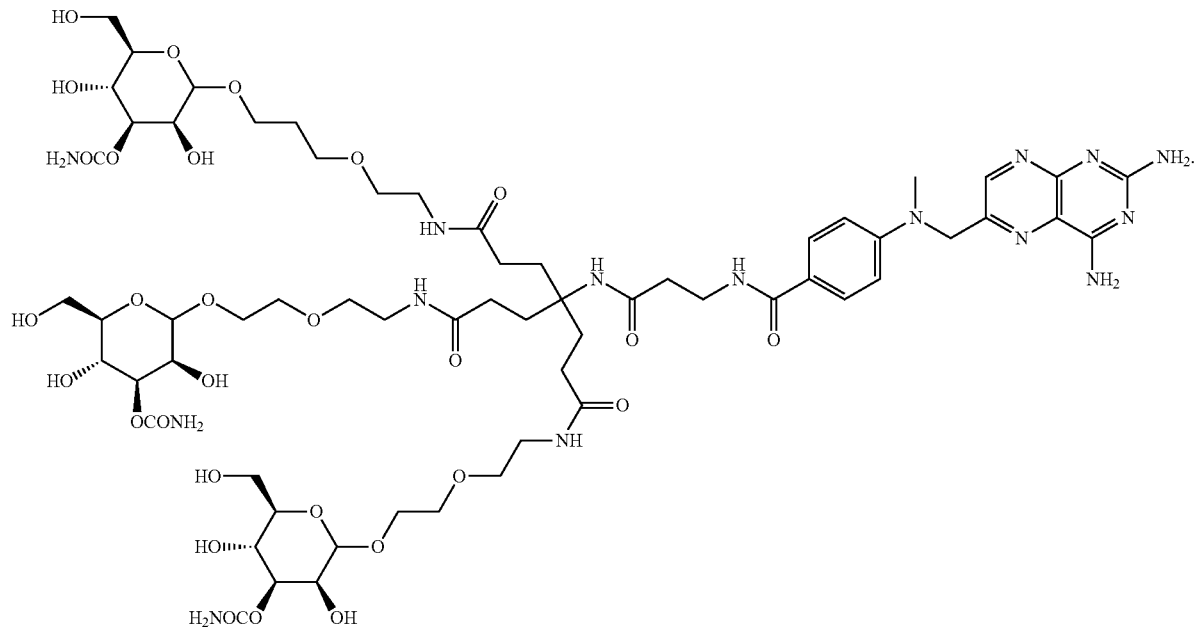
In some embodiments, the conjugate is represented by formula:
In some embodiments, the conjugate is represented by formula:
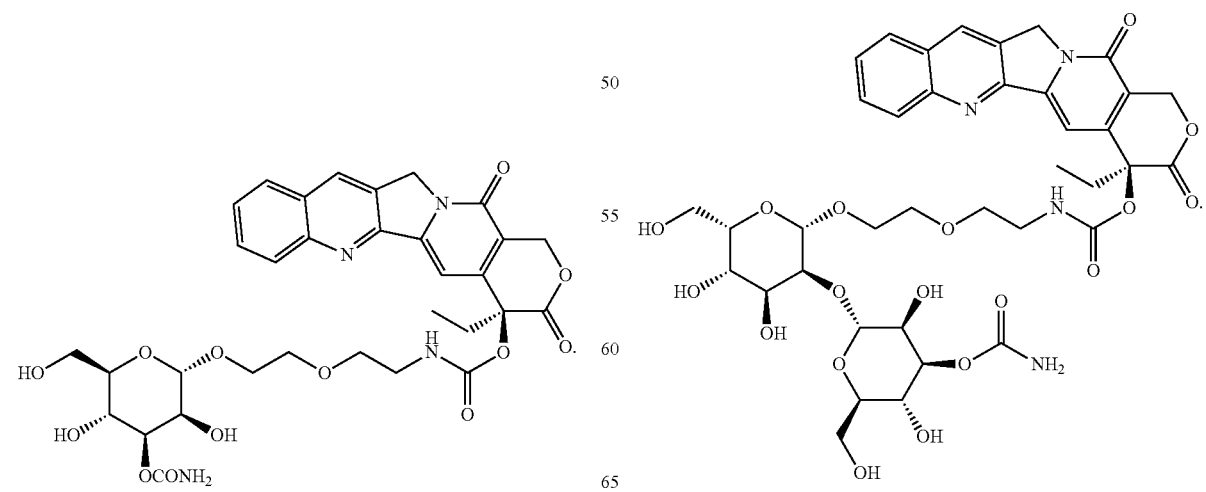

In some embodiments, the conjugate is represented by formula:
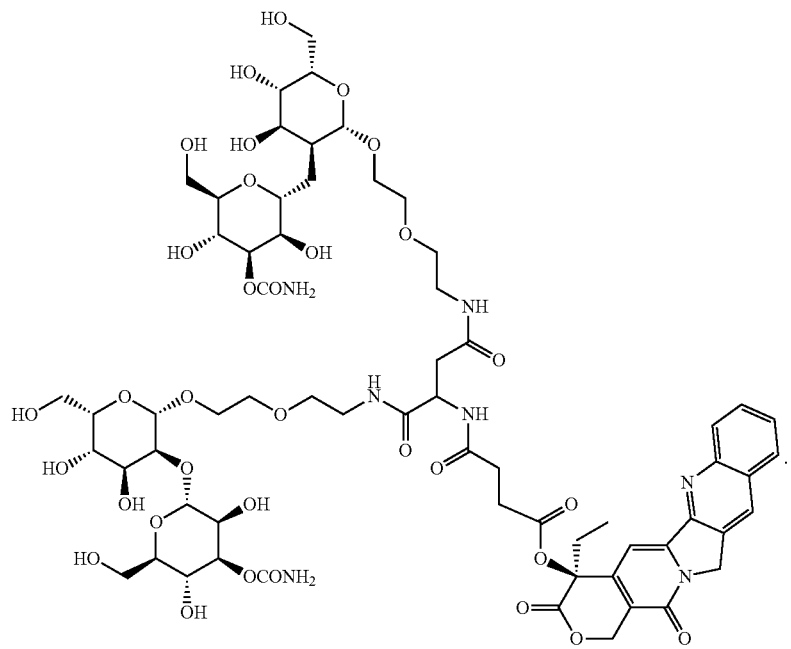
In some embodiments, the conjugate is represented by formula:
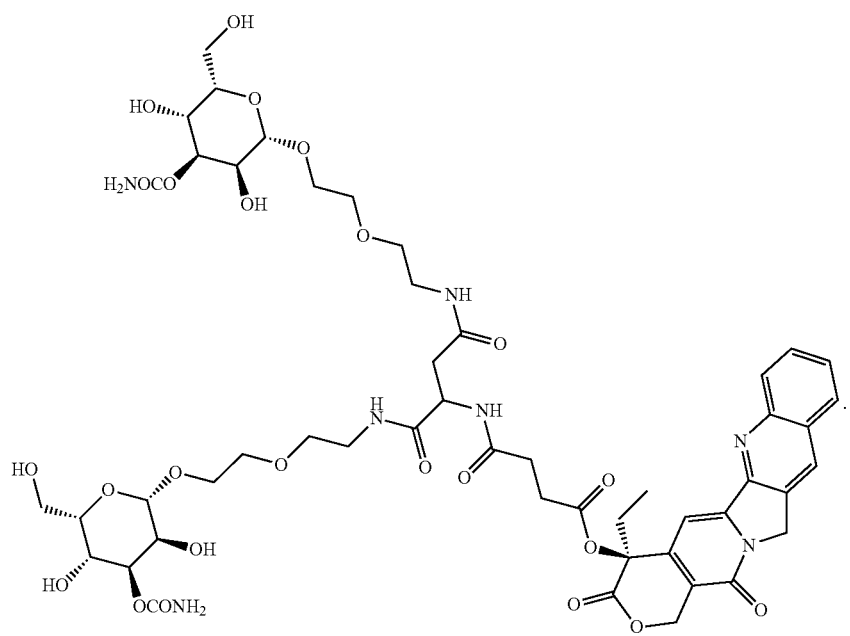

In some embodiments, the conjugate is represented by formula:
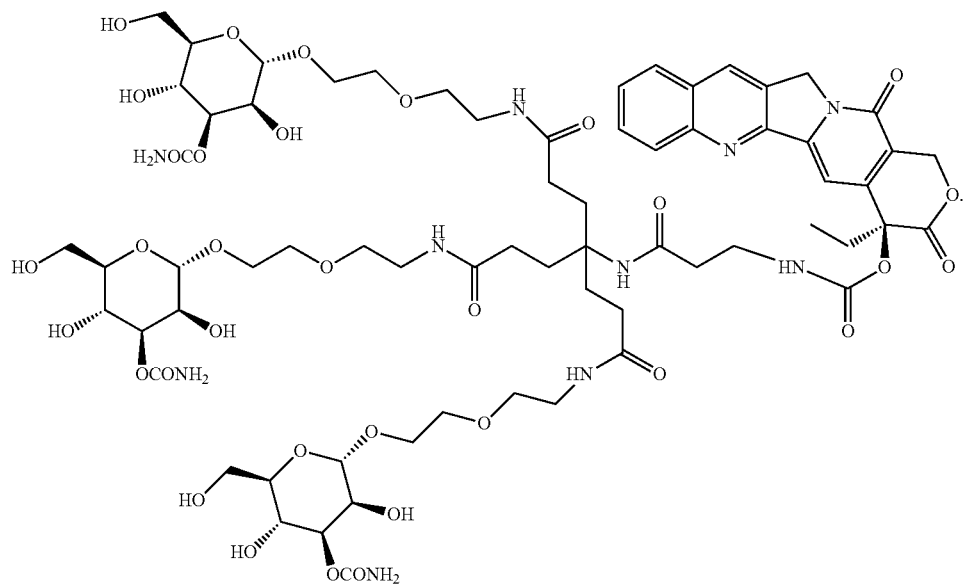
In some embodiments, the conjugate is represented by formula:
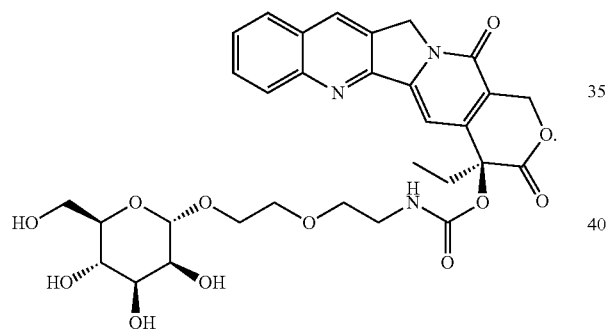
In some embodiments, the conjugate is represented by formula:
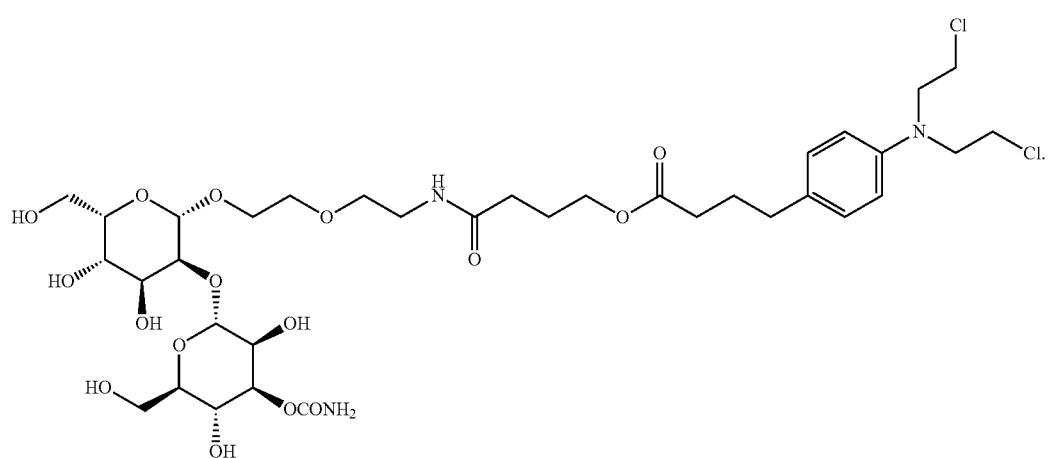

In some embodiments, the conjugate is represented by formula:
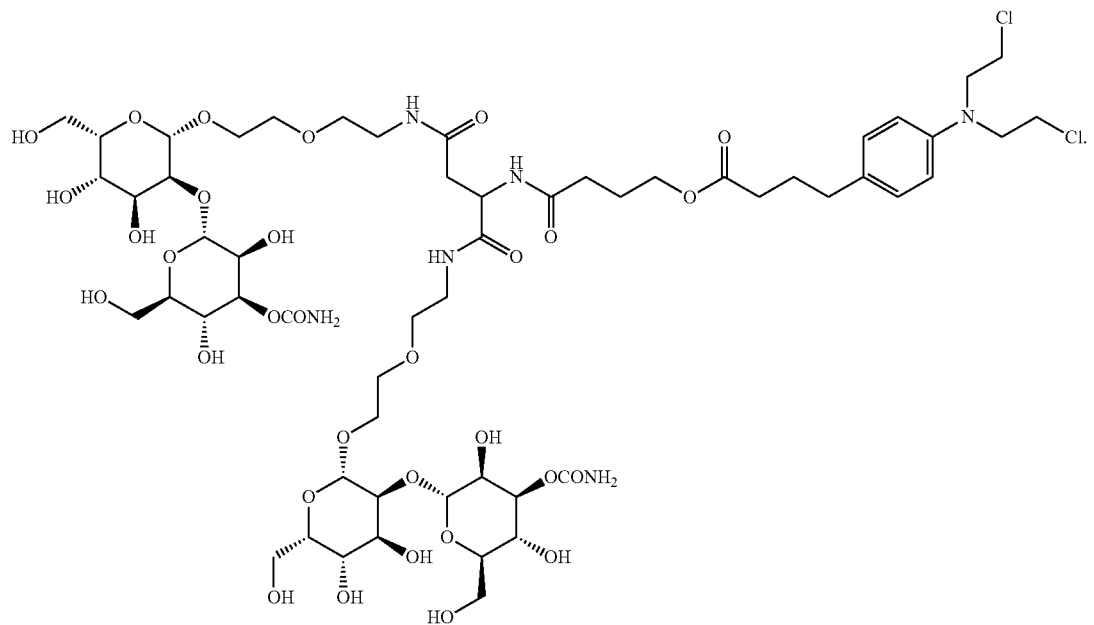
In some embodiments, the conjugate is represented by formula:
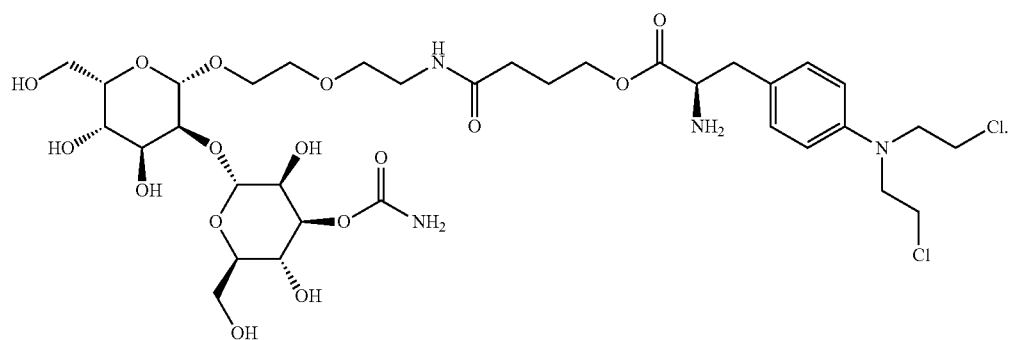 [SMILES: NC(=O)O[C@@H]1[C@H](O)[C@@H](O[C@@H]2[C@@H](OCCOCCNC(=O)CCCOC(=O)[C@H](N)Cc3ccc(N(CCCl)CCCl)cc3)O[C@@H](CO)[C@@H](O)[C@@H]2O)O[C@H](CO)[C@H]1O]

In some embodiments, the conjugate is represented by formula:

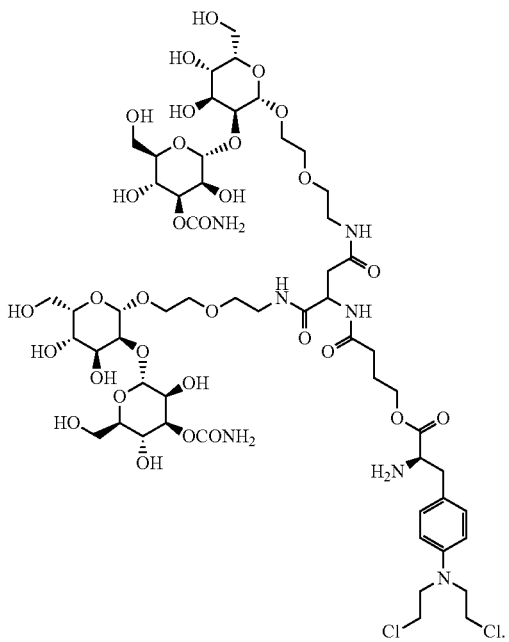

The conjugates of the present disclosure can exist in their free form or, where appropriate, as pharmaceutically acceptable salts thereof.

A "pharmaceutically acceptable salt" means any non-toxic salt of a conjugate of this disclosure that, upon administration to a patient, is capable of providing, either directly or indirectly, a conjugate of this disclosure.

Pharmaceutically acceptable salts of the conjugates of this disclosure include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the disclosure and their pharmaceutically acceptable acid addition salts.

Salts derived from appropriate bases include alkali metal (e.g., sodium and potassium), alkaline earth metal (e.g., magnesium), ammonium and $N^+(C_{1-4}\text{ alkyl})_4$ salts. This disclosure also envisions the quaternization of any basic nitrogen-containing groups of the conjugates disclosed herein. Water or oil-soluble or dispersible products may be obtained by such quaternization.

One of skill in the art would recognize that a variety of conjugates of the present disclosure may be prepared according to methods known in the art, and the synthetic Examples set forth below.

Compositions

The present disclosure provides a pharmaceutical composition comprising a conjugate of formula (I) as described above and a pharmaceutically acceptable carrier.

The term "pharmaceutically acceptable carrier" refers to a non-toxic carrier, adjuvant, or vehicle that does not destroy the pharmacological activity of the compound with which it is formulated. Pharmaceutically acceptable carriers, adjuvants or vehicles that may be used in the present compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The term "pharmaceutically effective amount" refers to an amount required to confer a therapeutic effect on the treated patient. The term "prophylactically effective amount" refers to an amount effective in preventing or substantially lessening a disease or disorder in a patient.

The term "patient", as used herein, means an animal, preferably a mammal, and most preferably, a mouse, rat, other rodent, rabbit, dog, cat, swine, cattle, sheep, horse, or primate, and even more preferably, a human.

The compositions of the present disclosure may be administered orally, parenterally, by inhalation spray, topically, rectally, nasally, buccally, vaginally or via an implanted reservoir. The term "parenteral", as used herein, includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers that are commonly used in the manufacture of pharmaceutically acceptable solid, liquid, or other dosage forms may also be used for the purposes of formulation.

The pharmaceutically acceptable compositions of this disclosure may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this disclosure may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this disclosure may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this disclosure include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this disclosure may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this disclosure are formulated for oral administration.

Dosage levels of between about 0.01 and about 100 mg/kg body weight per day, preferably between 0.5 and about 75 mg/kg body weight per day and most preferably between about 1 and 50 mg/kg body weight per day of the active ingredient compound are useful in a monotherapy for the prevention and treatment of cancer.

Typically, the pharmaceutical compositions of this disclosure will be administered from about 1 to 5 times per day or alternatively, as a continuous infusion. Or, alternatively, the compositions of the present disclosure may be administered in a pulsatile formulation. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

When the compositions of this disclosure comprise a combination of a compound of the present disclosure and one or more additional therapeutic agents, both the compound and the additional agent should be present at dosage levels of between about 10% to 80% of the dosage normally administered in a monotherapy regime.

Upon improvement of a patient's condition, a maintenance dose of a compound, composition or combination of this disclosure may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, and the patient's disposition to the disease and the judgment of the treating physician.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated".

Additional therapeutic agents that may be combined with the conjugates of the present disclosure include, but are not limited to, Gleevec™, adriamycin, dexamethasone, vincristine, cyclophosphamide, fluorouracil, topotecan, taxol, interferons, platinum derivatives, alkylating drugs (mechlorethamine, chlorambucil, Cyclophosphamide. Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, adriamycin, dexamethasone, and cyclophosphamide. For a more comprehensive discussion of updated cancer therapies see, http://www.nci.nih.gov, a list of the FDA approved oncology drugs at http://www.fda.gov/cder/cancer/druglistframe.htm, and The Merck Manual, Seventeenth Ed. 1999, the entire contents of which are hereby incorporated by reference.

The compounds of the present disclosure may also be co-administered with other cytotoxic agents to increase the effect of therapy or prophylaxis. When the compounds of this disclosure are administered in combination therapies with other agents, they may be administered sequentially or concurrently to the patient. Alternatively, pharmaceutical or prophylactic compositions according to this invention comprise a combination of a compound of the present disclosure and another therapeutic or prophylactic agent.

The additional therapeutic agents described above may be administered separately, as part of a multiple dosage regimen, from the sugar-linker-drug conjugate containing composition. Alternatively, these agents may be part of a single dosage form, mixed together with sugar-linker-drug conjugate in a single composition.

Methods of Use

The present disclosure provides a method of using the conjugates of the present disclosure or a pharmaceutically acceptable composition comprising a conjugate.

In some embodiments, the present disclosure provides a method of treating or preventing cancer in a patient. The method comprises administering to a patient in need thereof a conjugate as described above or a pharmaceutical composition as described above.

The term "cancer." as used herein, includes, but is not limited to the following cancers: breast; ovary; cervix; prostate; testis, genitourinary tract; esophagus; larynx, glioblastoma; neuroblastoma; stomach; skin, keratoacanthoma; lung, epidermoid carcinoma, large cell carcinoma, small cell carcinoma, lung adenocarcinoma; bone; colon, adenoma; pancreas, adenocarcinoma; thyroid, follicular carcinoma, undifferentiated carcinoma, papillary carcinoma; seminoma; melanoma; sarcoma; bladder carcinoma; liver carcinoma and biliary passages; kidney carcinoma; myeloid disorders; lymphoid disorders, Hodgkin's, hairy cells; buccal cavity and pharynx (oral), lip, tongue, mouth, pharynx, small intestine; colon-rectum, large intestine, rectum; brain and central nervous system; and leukemia.

In some aspects of this embodiment, the sugar moiety of the conjugate binds to a cancer cell. The drug is released from the sugar moiety at or near the cancer cell by cleavage of the linker, and the drug, when released, is cytotoxic or cytostatic to the cancer cell.

In alternate embodiments, the present disclosure provides a method of reducing the toxic side effects of administering a drug to treat cancer. The method comprises administering to a patient an effective amount of a conjugate as described above or a pharmaceutical composition as described above.

In some aspects of this embodiment, the sugar moiety of the conjugate binds to a cancer cell. The drug is released from the sugar moiety at or near the cancer cell by cleavage of the linker, and the drug, when released, is cytotoxic or cytostatic to the cancer cell.

In an alternate embodiment, the methods of this disclosure that utilize compositions that do not contain an additional therapeutic agent, comprise the additional step of separately administering to said patient an additional therapeutic agent. When these additional therapeutic agents are administered separately, they may be administered to the patient prior to, sequentially with or following administration of the compositions of this disclosure.

In order that this invention be more fully understood, the following examples are set forth. These examples are for the purpose of illustration only and are not to be construed as limiting the scope of the invention in any way.

EXAMPLES

The compounds and methods of the disclosure are illustrated further by the following examples, which are provided for illustrative purposes and not intended to be construed as limiting the disclosure in scope or spirit to the specific compounds and methods described in them.

The chemicals were all ACS reagent grade and were used without further purification. The reactions were carried out under an argon atmosphere unless specified. Flash column chromatography was carried out using silica gel (Silicycle R10030B, 60 particle size, 230-400 mesh), applying a low pressure stream of nitrogen. Analytical thin layer chromatographic separations were carried out on glass plates coated with silica gel (60 particle size F254, SiliCycle TLG-R10011B-323). The TLC chromatograms were developed by immersing the plates in 2.5% potassium permanganate in ethanol or 2% anisaldehyde+5% sulfuric acid+1.5% glacial acetic acid in ethanol, followed by heating, or else visualized by UV irradiation (254 nm). Melting points were recorded on a MelTemp apparatus and are uncorrected. Tetrahydrofuran was distilled from sodium/benzophenone ketyl and dichloromethane from calcium hydride. $^1$H and $^{13}$C NMR spectra were recorded on a Gemini 300 or Varian Inova 400, or on a Varian Inova 500 spectrometer, using $CDCl_3$ as solvent and internal standard, unless otherwise indicated. $^1$H NMR chemical shifts were reported relative to residual $CHCl_3$ at 7.26 ppm, or to residual DMSO-ds at 2.50 ppm; $^{13}$C NMR shifts were reported relative to the central line of $CDCl_3$ at 77.16 ppm, or to $^{13}$C DMSO-$d_6$ at 39.51 ppm. Splitting patterns are designated as s, singlet: br s, broad singlet; d, doublet; dd, doublet of doublets; dt, doublet of triplets; m, multiplet; q, quartet: quin, quintet. Cyanine dyes were obtained from our collaborators at General Electric. High resolution mass spectrometric data was obtained at the Michigan State Mass Spectrometry Facility or at the Arizona State University CLAS High Resolution Mass Spectrometry Facility.

Example 1

In order to permit a study of the efficacy of the BLM-disaccharide as a tumor targeting vehicle for cytotoxic agents, APA (4-amino-4-deoxy-10-N-methylpteroic acid) was conjugated to the BLM-disaccharide (Scheme 1). 2,4-Diamino-6-(hydroxymethyl)pteridine hydrochloride (1) was treated with triphenylphosphine dibromide to generate the alkyl bromide in situ; this was coupled with 4-N-methyl-aminobenzoic acid to obtain APA (2) in 56% yield. Compound 3 was condensed with APA to provide the APA-BLM-disaccharide conjugate 4 in 37% yield. Conjugate 5 was designed to be a tumor selective drug delivery vehicle. Once inside the cell, the cellular esterases should release the cytotoxic drug, in this case APA, from the conjugate. The synthesis started with the esterification of APA 2 with tert-butyl 6-hydroxyhexanoate (7) to obtain compound 8 in 60% yield. The tert-butyl group was removed by the use of $CF_3COOH$ in dichloromethane and the resulting acid was condensed with compound 3 to afford the conjugate 5 in 53% yield.

Scheme 1. Synthesis of APA-BLM-disaccharide conjugates 4 and 5.
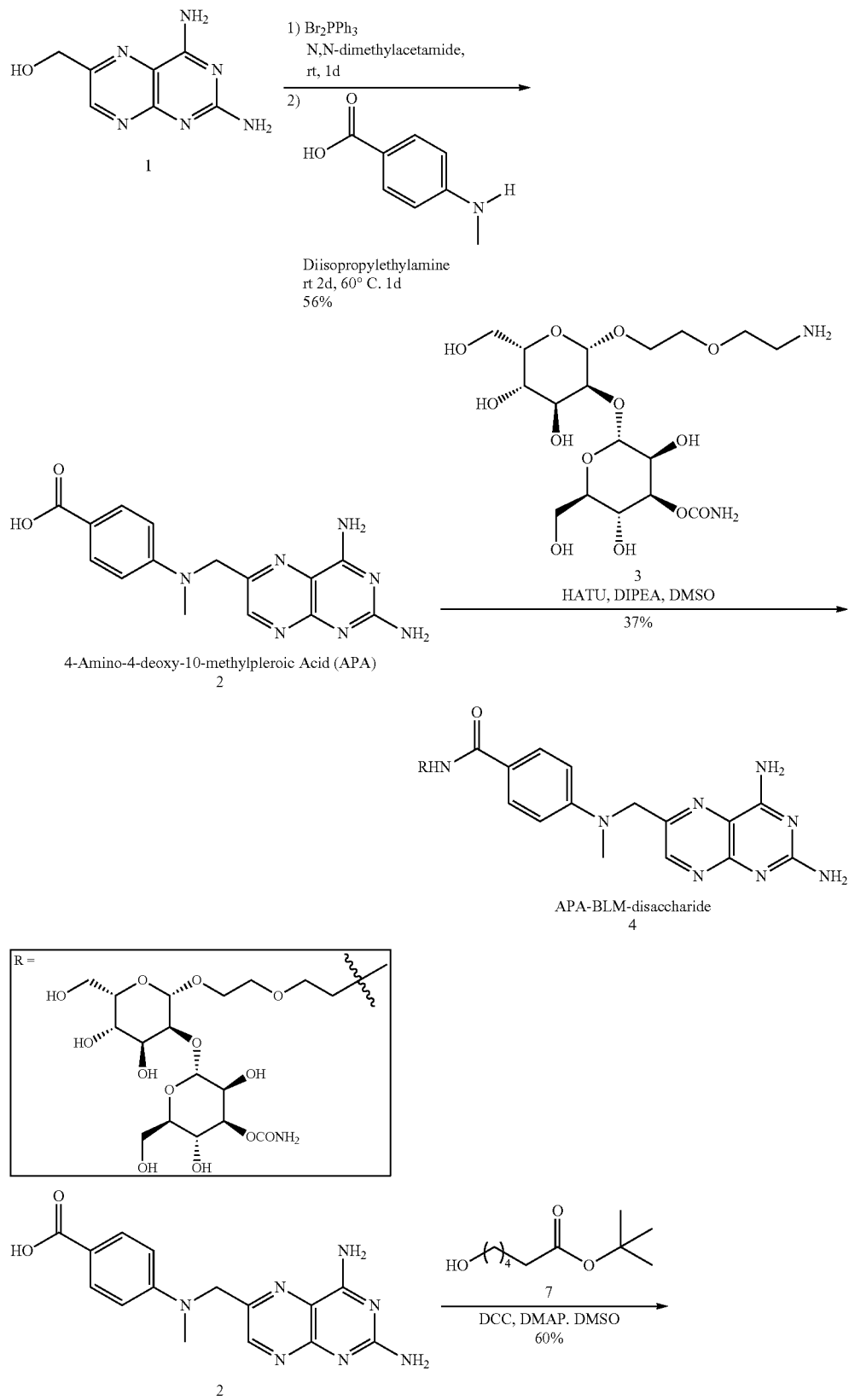

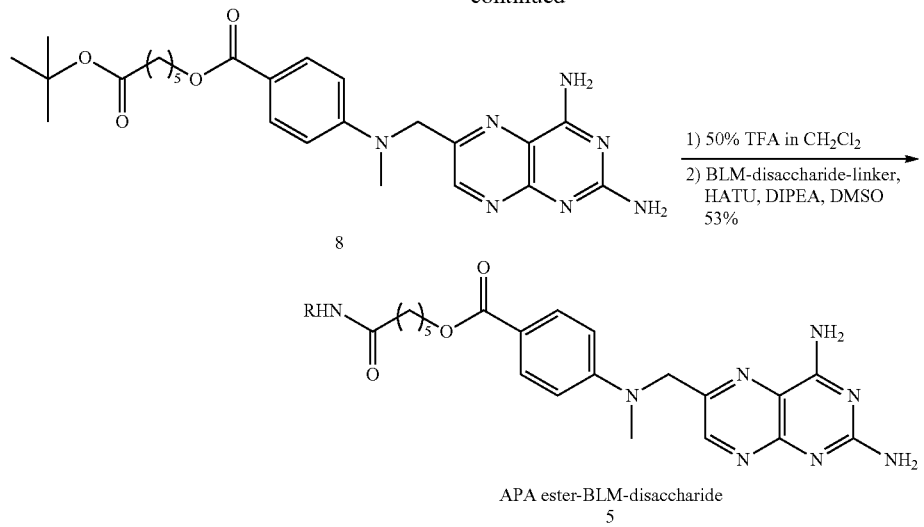

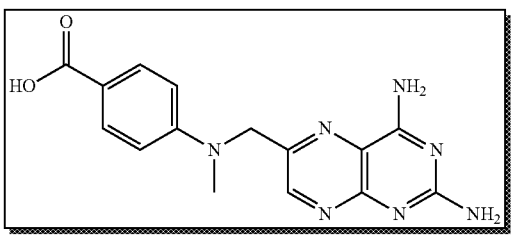

4-Amino-4-deoxy-10-N-methylpteroic Acid (APA, 2)

(Kralovec, J.; Spencer, G.; Blair, A. H.; Mammen, M.; Singh, M.; Ghose, T. *J. Med. Chem.*, 1989, 32, 2426). A mixture of 249 mg (0.59 mmol) dibromotriphenylphosphorane and 45.0 mg (0.20 mmol) 2,4-diamino-6-(hydroxymethyl)pteridine hydrochloride (1) in 1.5 mL of anhydrous dimethylacetamide was stirred at mom temperature for 24 h under an argon atmosphere. To the reaction mixture were added 41 mg (0.27 mmol) of 4-(methylamino)benzoic acid and 0.16 mL (116 mg, 0.90 mmol) of DIPEA and the reaction mixture was stirred at room temperature for 48 h, and then at 60° C. for 24 h. The cooled reaction mixture was poured into 25 mL of 0.33 M aq NaOH and the precipitate was filtered. The filtrate was adjusted to pH 5.5 with 10% acetic acid and the resulting precipitate was collected through filtration, washed with water and dried under diminished pressure at 80° C. overnight to obtain 2 as an orange solid: yield 42 mg (56%); silica gel TLC $R_f$ 0.47 (5:4:1 chloroform-methanol-water); $^1$H NMR (DMSO-$d_6$) δ 3.19 (s, 3H), 4.76 (s, 2H), 6.61 (s, 2H), 6.78 (d, 2H, J=8.9 Hz), 7.72 (d, 2H, J=8.7 Hz) and 8.56 (s, 1H).

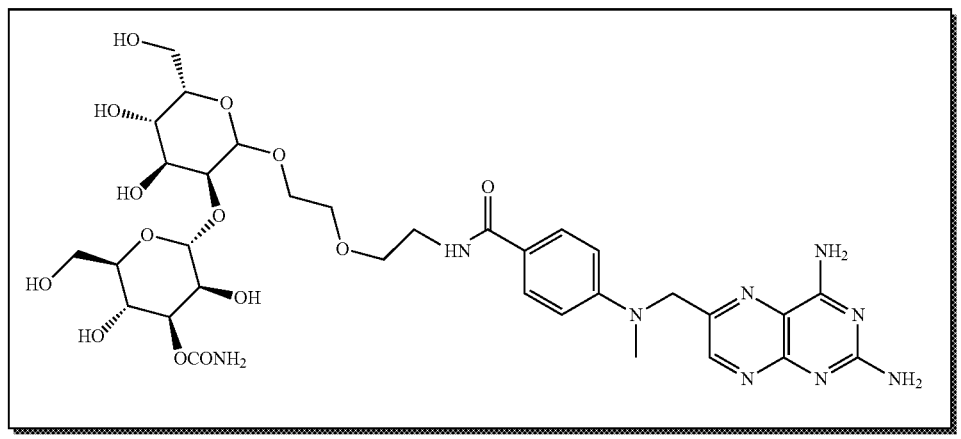

APA-BLM-disaccharide (4)

To a solution containing 3.5 mg (7.4 μmol) of BLM-disaccharide linker 3, 2.5 mg (7.6 μmol) of 6 and 3.0 μL (2.2 mg; 17 μmol) of DIPEA in 0.12 mL of anhydrous DMSO was added 4.3 mg (11 μmol) of HATU. The reaction mixture was stirred at room temperature for 16 h. The reaction mixture was purified on an Econosil $C_{18}$ reversed phase semi-preparative (250×10 mm, 10 μm) HPLC column using 0.1% aq TFA and $CH_3CN$ mobile phases. A linear gradient was employed (99:1 0.1% aq TFA-$CH_3CN$→45:55 0.1% aq TFA-$CH_3CN$) over a period of 30 min at a flow rate of 3 mL/min. Fractions containing the desired product eluted at 26.5 min (monitoring at 292 nm) and were collected, frozen, and lyophilized to give APA-BLM-disaccharide conjugate 4 as a yellow solid: yield 2.2 mg (37%); mass spectrum (ESI), m/z 780.3168 (M+H)$^+$ ($C_{32}H_{46}N_9O_{14}$ requires m/z 780.3159).

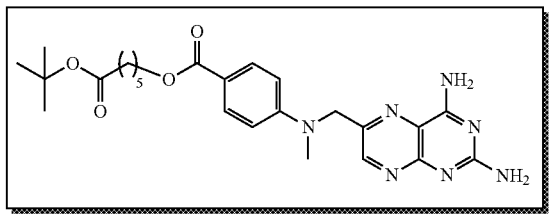

4-Amino-4-deoxy-10-N-methylpteroic Acid 6-(tert-Butoxy)-6-oxohexyl Ester (8)

To a solution of 36 mg (0.2 mmol) of 7, 12 mg (37 μmol) of 6 and 45 mg (0.4 mmol) of DMAP in 1 mL of anhydrous DMSO was added 39 mg (0.2 mmol) of DCC and the reaction mixture was stirred at room temperature for 24 h. The reaction mixture was filtered and the filtrate was purified on a $C_{18}$ reversed phase semi-preparative (250×10 mm, 10 μm) HPLC column using 0.1% aq TFA and $CH_3CN$ mobile phases. A linear gradient was employed (99:1 0.1% aq TFA-$CH_3CN$→1:99 0.1% aq TFA-$CH_3CN$) over a period of 30 min at a flow rate of 3 ml/min. Fractions containing the desired product eluted at 25.8 min (monitoring at 292 nm) and were collected, frozen, and lyophilized to give 8 as a yellow solid: yield 11 mg (60%); $^1$H NMR ($CD_3CN$) δ 1.40 (m, 9H), 1.58 (m, 2H), 1.70 (m, 2H), 2.19 (t, 2H, J=7.3 Hz), 3.24 (s, 3H), 4.19 (t, 2H, J=6.4 Hz), 4.84 (s, 2H), 5.45 (s, 2H), 6.79 (m, 2H), 7.26 (s, 1H), 7.72 (s, 1H), 7.8 (m, 2H) and 8.73 (s, 1H); mass spectrum (ESI), m/z 496.2676 (M+H)$^+$ ($C_{25}H_{34}N_7O_4$ requires m/z 496.2667).

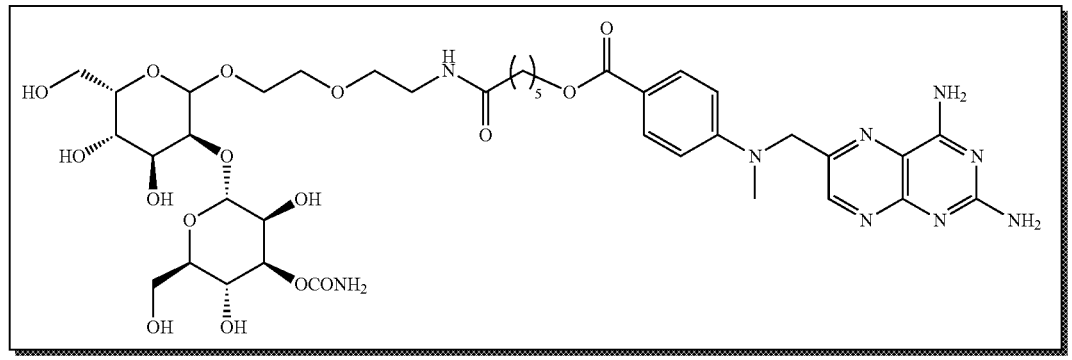

APA Ester-BLM-Disaccharide (5)

A solution containing 2.8 mg (5.6 μmol) of compound 8 in 1:1 TFA-$CH_2Cl_2$ was shaken at room temperature for 1 h and concentrated under diminished pressure. The residue was co-evaporated with five 2-mL portions of toluene and dissolved in 0.1 mL of anhydrous DMSO. To this solution were added 2.9 mg (6.2 μmol) of 3 (Boger, D. L.; Honda, T. *J. Am. Chem. Soc.* 1994, 116, 5647; and Dondoni, A., Marra, A.; Massi, A. *J. Org. Chem.* 1997, 62, 6261) 2.0 μL, (1.5 mg; 12 μmol) of DIPEA and 3.5 mg (9.3 μmol) of HATU. The reaction mixture was stirred at room temperature for 16 h. The reaction was purified on an Econosil $C_{18}$ reversed phase semi-preparative (250×10 mm, 10 μm) HPLC column using 0.1% aq TFA and $CH_3CN$ mobile phases. A linear gradient was employed (99:1 0.1% aq TFA-$CH_3CN$→45:55 0.1% aq TFA-$CH_3CN$) over a period of 30 min at a flow rate of 3 mL/min. Fractions containing the desired product eluted at 20.7 min (monitoring at 292 nm) and were collected, frozen, and lyophilized to give APA-BLM-disaccharide conjugate 5 as a yellow solid: yield 2.2 mg (53%); mass spectrum (ESI), m/z 894.3853 (M+H)$^+$ ($C_{32}H_{46}N_9O_{14}$ requires m/z 894.3840).

Example 2: Synthesis of MTX-di-ester-BLM-disaccharide (15)
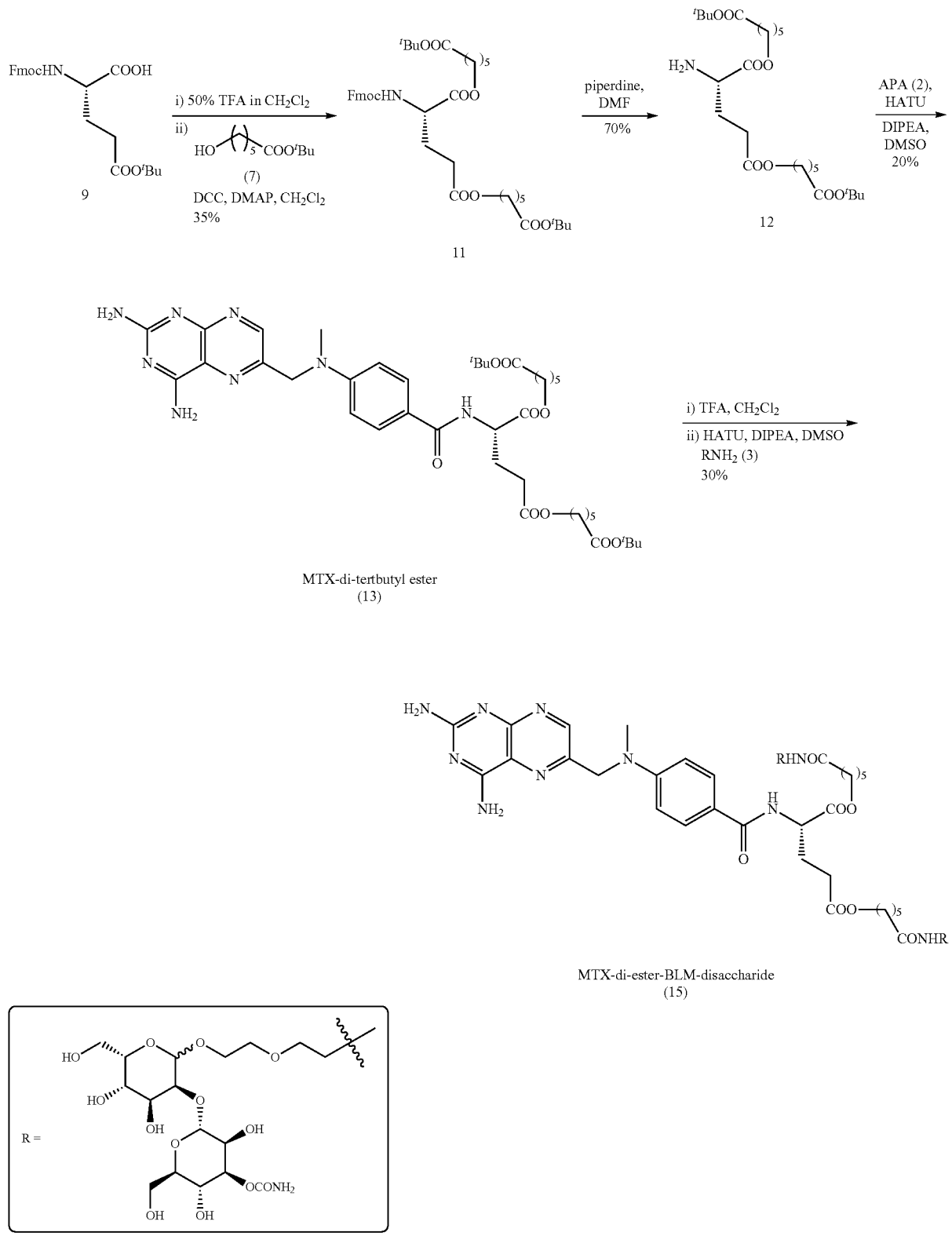

Synthesis of the MTX-sugar conjugate 15 started with the attachment of linker 7 with glutamic acid. Fmoc-Glu(tert-butyl)OH (9) was treated with trifluoroacetic acid to deprotect the tert-butyl ester and the resulting diacid was condensed with compound 7 to afford compound 11. The Fmoc group was removed by the use of piperidine in DMF. Compound 12 was then condensed with APA (2) to provide the MTX derivative 13 equipped with two linkers. Finally the tert-butyl esters were removed by the use of trifluoroacetic acid and the resulting intermediate was coupled with the bleomycin disaccharide linker 3 to afford the MTX conjugate 15 in 30%/o yield.

7.59 (d, 2H, J=3.7 Hz) and 7.76 (d, 2H, J=7.5 Hz); mass spectrum (MALDI), m/z 732.47 (M+Na)$^+$ (C$_{40}$H$_{55}$NO$_{10}$Na requires m/z 732.37).

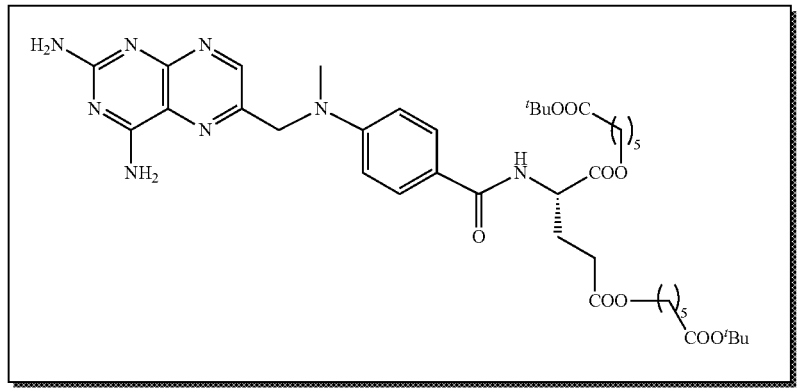

MTX-Di-Tertbutyl Ester (13)

To a solution of 25 mg (35 μmol) of compound 11 in 0.5 mL of anhydrous DMF was added 0.1 mL of piperidine and the solution was stirred at room temperature for 1 h. The reaction mixture was concentrated under diminished pressure. The residue was purified by flash chromatography on a silica gel column (5×3 cm). Elution with 4:1 hexanes-ethyl acetate→100% ethyl acetate gave compound 12 as a colorless oil: yield 12 mg (70%); mass spectrum (MALDI), m/z 510.36 (M+Na)$^+$ (C$_{25}$H$_{45}$NO$_8$Na requires m/z 510.30). To a solution containing 10 mg (20 μmol) of the amine 12, 5 mg (15 μmol) of APA (2) and 25 μL (18 mg, 0.14 mmol) of DIPEA in 0.25 mL of anhydrous DMSO was added 30 mg (79 μmol) of HATU and the reaction mixture was stirred at room temperature for 48 h. The reaction mixture was filtered and the filtrate was purified on a C$_{18}$ reversed phase semi-preparative (250×10 mm, 10 μm) HPLC column using 0.1% aq. TFA and CH$_3$CN mobile phases. A linear gradient was employed (99:1 0.1% aq TFA-CH$_3$CN→1:99 0.1% aq TFA-CH$_3$CN) over a period of 30 min with a flow rate of 3 mL/min. Fractions containing the desired product eluted at 20.1 min (monitoring at 292 nm) and were collected, frozen, and lyophilized to give 13 as an orange solid: yield 2.5 mg (20%); mass spectrum (MALDI), m/z 795.29 (M+H)$^+$ (C$_{40}$H$_{59}$N$_8$O$_9$ requires m/z 795.44), m/z 817.28 (M+Na)$^+$ (C$_{40}$H$_{58}$N$_8$O$_9$Na requires m/z 817.42).

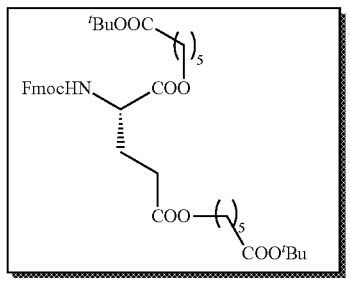

Fmoc-Glu-Di-Tertbutyl Ester (11)

A solution containing 43 mg (0.10 mmol) of compound 9 in 1 mL of 1:1 TFA-CH$_2$Cl$_2$ was shaken at room temperature for 1 h and concentrated under diminished pressure. The residue was co-evaporated with five 2-mL portions of toluene and dissolved in 1.5 mL of anhydrous CH$_2$Cl$_2$. To this solution was added 75 mg (0.40 mmol) of alcohol 10, 61 mg (0.50 mmol) of DMAP and 82 mg (0.40 mmol) of DCC and the reaction mixture was stirred at room temperature for 48 h. The reaction mixture was concentrated under diminished pressure and the residue was suspended in 5 mL of acetonitrile. The suspension was filtered and the filtrate was concentrated under diminished pressure. The residue was purified by flash chromatography on a silica gel column (18×2 cm). Elution with 4:1 hexanes-ethyl acetate gave compound 11 as a colorless oil: yield 25 mg (35%); silica gel TLC R$_f$ 0.76 (1:1 hexanes-ethyl acetate); $^1$H NMR (CDCl$_3$) δ 1.41 (m, 24H), 1.98 (m, 2H), 2.20 (m, 6H), 2.40 (m, 3H), 3.64 (t, 1H, J=6.4 Hz), 4.14 (m, 6H), 4.39 (m, 3H), 5.51 (d, 1H, J=8.1 Hz), 7.31 (t, 2H, J=7.4 Hz), 7.39 (t, 2H, J=7.4 Hz),

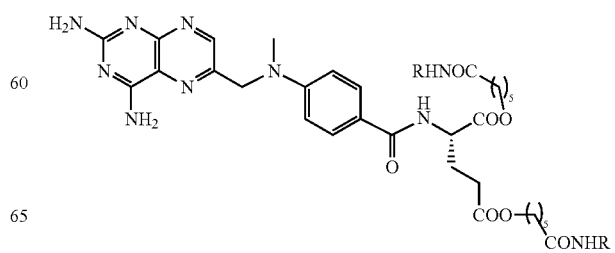

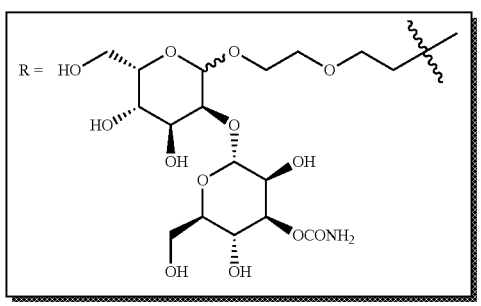

MTX-di-ester-BLM-disaccharide (15)

A solution containing 1 mg (1.2 μmol) of compound 13 in 1:1 TFA-CH$_2$Cl$_2$ was shaken at room temperature for 1 h and concentrated under diminished pressure. The residue was co-evaporated with five 2-mL portions of toluene and dissolved in 0.1 mL of anhydrous DMSO. To this solution was added 2.5 mg (5.2 μmol) of 14, 20 μL (15 mg, 0.11 mmol) of DIPEA and 15 mg (39 μmol) of HATU and the reaction mixture was stirred at room temperature for 24 h. The reaction was purified on an Econosil C$_{18}$ reversed phase semi-preparative (250×10 mm, 10 μm) HPLC column using 0.1% aq. TFA and CH$_3$CN mobile phases. A linear gradient was employed (99:1 0.1% aq. TFA-CH$_3$CN→45:55 0.1% aq. TFA-CH$_3$CN) over a period of 30 min with a flow rate of 3 mL/min. Fractions containing the desired product eluted at 22.1 min (monitoring at 292 nm) and were collected, frozen, and lyophilized to give MTX-di-ester-BLM-disaccharide conjugate 15 as a yellow solid: yield 0.6 mg (30%); mass spectrum (MALDI), m/z 1613.29 (M+H)$^+$ (C$_{66}$H$_{102}$N$_{12}$O$_{33}$Na requires m/z 1613.66).

Example 3: Synthesis of Gulose Acceptor 23

Scheme 3

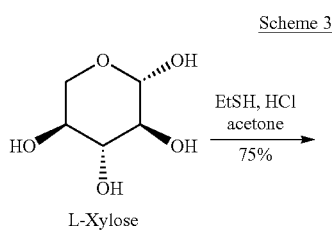

L-Xylose

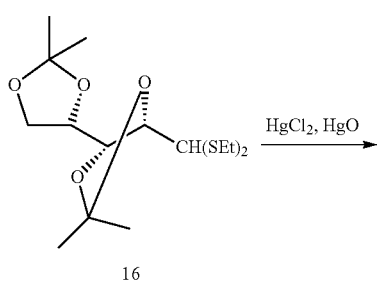

16

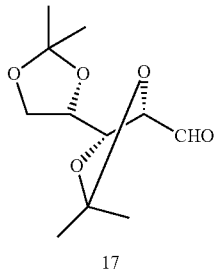

17

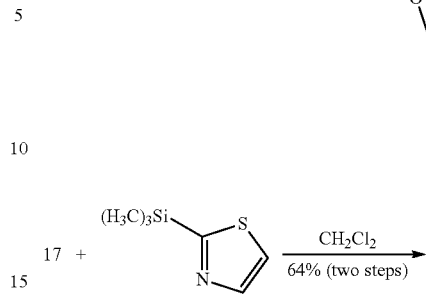

18

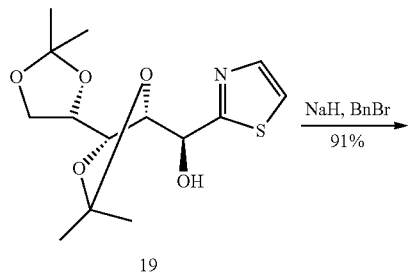

19

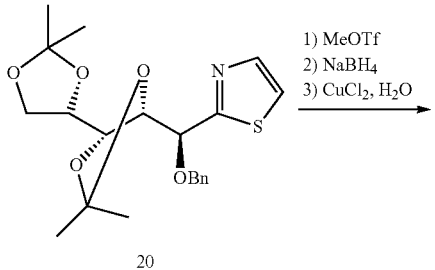

20

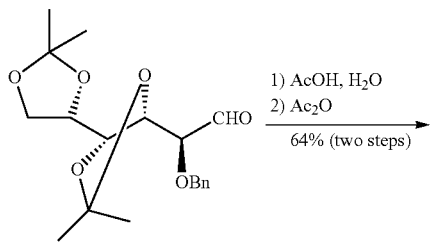

21

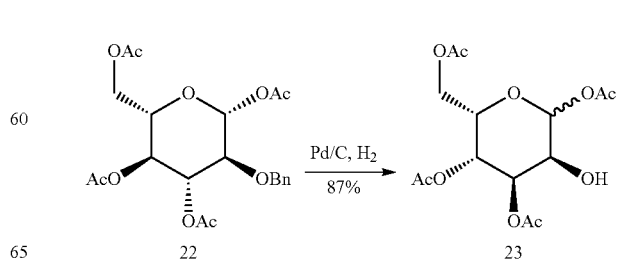

22        23

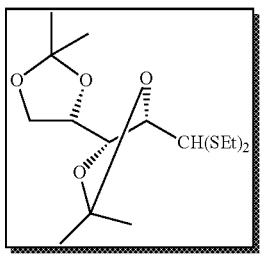

2,3,4,5-Di-O-isoproropylidene-L-xylose Diethyl Dithioacetal (16)

To a suspension of 8.00 g (53.3 mmol) of L-xylose in 3.2 mL of conc HCl was added, with vigorous magnetic stirring, 11.8 mL (10.1 g, 160 mmol) of ethanethiol. Stirring was continued at room temperature until the two layer mixture gave a homogenous solution (usually after 15-20 min) which was then diluted with 160 mL of acetone. After stirring for 5 h, the solution was neutralized with said aq NH$_4$OH solution and co-evaporated with six 20-mL portions of toluene to afford a crude residue. The residue was applied to a silica gel column (28×5 cm). Elution with 1:1 ethyl acetate-hexanes gave 16 as a colorless syrup: yield 13.4 g (75%); $[\alpha]_D$+57.2 (c 1.8, C$_6$H$_6$), lit. $[\alpha]_D$+51.3 (c 1.8, C$_6$H$_6$); silica gel TLC R$_f$ 0.59 (3:1 ethyl acetate-hexanes); $^1$H NMR (CDCl$_3$) δ 1.23-1.28 (m, 6H), 1.36 (s, 3H), 1.41 (s, 6H), 1.45 (s, 3H), 2.68-2.77 (m, 4H), 3.91 (dd, 2H, J=9.8 and 4.5 Hz), 4.02-4.06 (m, 1H), 4.13 (dd, 1H, J=5.3 and 2.1 Hz) and 4.31-4.34 (m, 2H); $^{13}$C NMR (CDCl$_3$) δ 14.26, 14.34, 24.9, 25.3, 25.6, 26.1, 27.1, 27.3, 53.0, 65.9, 75.2, 78.7, 80.1, 109.5 and 110.0.

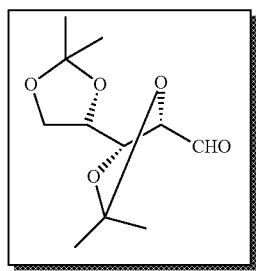

2,3,4,5-Di-O-isopropylidene-aldehydo-L-xylose (17)

To a stirred solution containing 2.60 g (7.70 mmol) of thioacetal 16 in 26 mL of acetone diluted with 2.6 mL of water was added 3.80 g (17.7 mmol) of yellow mercury(II) oxide and 3.80 g (13.9 mmol) of mercuric(II) chloride. The reaction mixture was stirred at 55° C. for 2 h and then allowed to cool to room temperature. The solvent was filtered through a pad of Celite 545® and concentrated under diminished pressure to afford a crude residue. The residue was suspended in three 30-mL portions of dichloromethane and filtered through a pad of Celite 545®. The organic layer was washed with 40 mL of 1 M aq KI, dried (MgSO$_4$) and then concentrated under diminished pressure to afford the crude aldehyde 17. The aldehyde was used for the next reaction immediately.

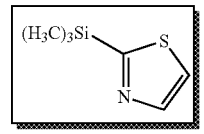

2-(Trimethylsilyl)thiazole (18)

A 500-mL, four-necked, round-bottomed flask, containing a magnetic stirring bar, was equipped with two 100-mL, pressure-equalizing dropping funnels and a low-temperature thermometer. The anh apparatus was filled with argon and kept under a slightly positive pressure during the entire reaction. The flask was charged with 80 mL of freshly distilled Et$_2$O and 42 mL (67 mmol) of a 1.6 M solution of n-BuLi in hexane. One of the two dropping funnels was charged with 5.5 mL (10 g, 61 mmol) of 2-bromothiazole in 20 mL of Et$_2$O and the other with 7.7 mL (6.6 g, 61 mmol) of chlorotrimethylsilane in 20 mL of Et$_2$O. The reaction flask was cooled to −78° C. in an acetone bath. While the solution in the flask was stirred, 2-bromothiazole was added dropwise over a period of 1 h. After 20 min of additional stirring, chlorotrimethylsilane was added dropwise over 30 min and the stirring was continued for a period of 1 h at −78° C. The resulting mixture was then allowed to warm up to room temperature. A said aq NaHCO$_3$ was added and the mixture was transferred into a 1 L separatory funnel. The organic layer was recovered and the aqueous layer was extracted with two 200-mL portions of Et$_2$O. The combined organic layer was dried (Na$_2$SO$_4$), filtered, and concentrated under diminished pressure with the external bath temperature not exceeding 40° C. The residue was distilled from a 100-mL flask at diminished pressure in a Claisen apparatus. The distillation was carried out under diminished pressure at 45° C. after a forerun at 25° C. consisting mainly of bromobutane was collected. The pure product 18 was isolated as a colorless oil: yield 7.3 g (76%); $^1$H NMR (CDCl$_3$) δ 0.39 (s, 12H), 7.50 (1H, d, J=3.0 Hz) and 8.09 (1H, d, J=2.9 Hz); $^{13}$C NMR (CDCl$_3$) δ 1.03, 127.3, 145.6 and 174.2.

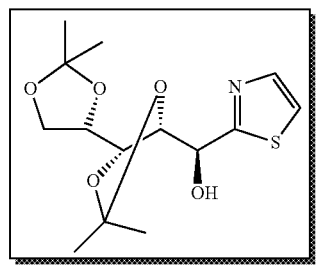

1,2,3,4-bis-O-(1-Methylethethylidene)-5-C-2-thiazolyl-(5S)-D-xylitol (19)

To a stirred solution containing 2.22 g (9.65 mmol) of crude aldehyde 17 in 38 mL of anh dichloromethane cooled to −20° C. was added 2.00 mL (1.97 g, 12.5 mmol) of 2-(trimethylsilyl)thiazole (18) dropwise over a period of 15 min. The solution was stirred at 0° C. for 1 h and then concentrated under diminished pressure to afford a crude residue. The residue was dissolved in 38 mL of anh THF and treated with 3.00 g (9.65 mmol) of n-Bu$_4$NF.3H$_2$O at 20° C. for 30 min and then concentrated under diminished pressure. The residue was diluted by the addition of 250 mL of dichloromethane. The organic layer was washed with three 50-mL portions of water, dried (Na$_2$SO$_4$) and then concentrated under diminished pressure to yield compound 19 as a crude residue. Recrystallization of the residue from cyclohexane afforded alcohol 19 as a colorless crystalline solid: yield 1.94 g (64% over two steps); $[\alpha]_D$+18.2 (c 1.1, CHCl$_3$), lit. $[\alpha]_D$+18.5 (c 1.1, CHCl$_3$); silica gel TLC $R_f$ 0.49 (1:1 ethyl acetate-hexanes); $^1$H NMR (CDCl$_3$) δ 1.28 (s, 3H), 1.36 (s, 6H), 1.40 (s, 3H), 3.67 (t, 1H, J=6.6 Hz), 3.79-3.84 (m, 2H), 4.12 (dd, 1H, J=7.2 and 3.6 Hz), 4.31-4.34 (m, 1H), 4.56 (br s, 1H), 5.10 (d, 1H, J=5.5 Hz), 7.30 (d, 1H, J=3.2 Hz) and 7.71 (d, 1H, J=3.2 Hz); $^{13}$C NMR (CDCl$_3$) δ 25.6, 26.1, 27.07, 27.13, 65.7, 71.7, 75.5, 77.4, 79.8, 109.5, 110.2, 119.7, 142.1 and 170.9.

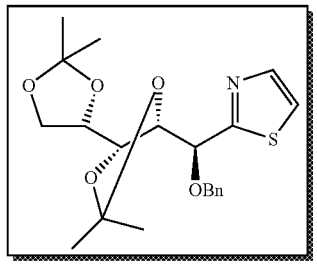

1,2,3,4-bis-O-(1-Methylethylidene)-5-(phenylmethyl)-5-C-2-thiazolyl-(5S)-D-xylitol (20)

To a solution containing 1.94 g (6.15 mmol) of alcohol 19 in anh DMF cooled to 0° C. was added 0.49 g (60% dispersion in oil, 12.3 mmol) of NaH portionwise and the reaction mixture was stirred at 0° C. for 0.5 h. To this solution was then added 1.10 mL (1.58 g, 9.20 mmol) of benzyl bromide and the reaction mixture was stirred at room temperature for 0.5 h. The reaction mixture was quenched by the addition of 1.2 mL of methanol, stirred for 10 min and then diluted with 40 mL of distilled water. The aqueous layer was extracted with three 100-mL portions of ether. The combined organic layer was dried (MgSO$_4$) and concentrated under diminished pressure to afford a crude residue. The residue was applied to a silica gel column (25×4 cm). Elution with 6:1 ethyl acetate-hexanes gave ether 20 as a colorless solid: yield 2.26 g (91%); $[\alpha]_D$–32.2 (c 1.1, CHCl$_3$), lit. $[\alpha]_D$–32.3 (c 1.1, CHCl$_3$); silica gel TLC $R_f$ 0.36 (9:1 toluene-methanol); $^1$H NMR (CDCl$_3$) δ 1.20 (s, 3H), 1.25 (s, 3H), 1.29 (s, 3H), 1.33 (s, 3H), 3.62-3.68 (m, 1H), 3.75-3.80 (m, 1H), 3.89-3.93 (m, 1H), 3.96-3.99 (m, 1H), 4.35 (dd, 1H, J=7.3 and 2.5 Hz), 4.44 (d, 1H, J=12.1 Hz), 4.63 (d, 1H, J=12.1 Hz), 4.80 (d, 1H, J=4.8 Hz), 7.21-7.28 (m, 5H), 7.32 (d, 1H, J=3.2 Hz) and 7.78 (d, 1H, J=3.2 Hz); $^{13}$C NMR (CDCl$_3$) δ 14.0, 25.5, 26.03, 26.05, 26.7, 27.0, 65.5, 72.2, 75.5, 77.7, 78.5, 79.4, 109.4, 110.3, 120.1, 127.9, 128.1, 128.3, 136.8, 142.4 and 168.9.

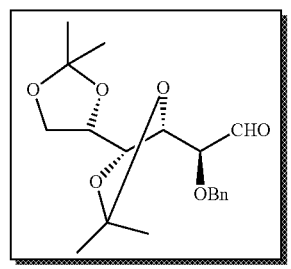

2-O-Benzyl-3,4,5,6-di-O-isopropylidene-aldehydo-L-gulose (21)

A solution containing 0.61 g (1.50 mmol) of O-benzyl ether 20 and 2.80 g of activated 4 Å molecular sieves dissolved in 15 mL of anh acetonitrile was stirred at 20° C. for 10 min and then 0.22 mL (329 mg, 1.95 mmol) of methyl triflate was added dropwise. The suspension was stirred at room temperature for 15 min and then concentrated under diminished pressure to afford the crude N-methylthiazolium salt. To a stirred solution of the crude N-methylthiazolium salt in 15 mL of methanol cooled to 0° C. was added 0.12 g (3.30 mmol) of sodium borohydride. The reaction mixture was stirred at room temperature for 5 min and diluted with 5 mL of acetone. The solvent was filtered through a pad of Celite 545® and concentrated under diminished pressure to afford a crude mixture of thiazolidines. This was dissolved in 14 mL of acetonitrile and 1.4 mL of water and treated under vigorous stirring with 0.96 g (12.0 mmol) of CuO and 0.26 g (1.50 mmol) of CuCl$_2$.2H$_2$O. The reaction mixture was stirred at 20° C. for 15 min, filtered through a pad of Celite 545® and then concentrated under diminished pressure to remove acetonitrile and most of the water (bath temperature not exceeding 40° C.) to afford a crude residue. The brown residue was triturated with four 50-mL portions of ether and the liquid phase was pipetted and filtered through a pad of Florisil® (60-100 mesh) to afford a colorless solution. After a further washing of Florisil® with 50 mL of ethyl acetate, the combined organic layer was concentrated under diminished pressure to yield the crude aldehyde 21 as a brown syrup, which was used immediately for the next reaction.

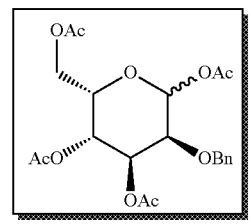

1,3,4,6-Tetra-O-acetyl-2-O-benzyl-L-gulopyranose (22)

A solution containing 470 mg (1.34 mmol) of the crude aldehyde 21 was dissolved in 7.4 mL of glacial acetic acid and 1.9 mL of distilled water and stirred at 100° C. for 40 min. The reaction mixture was then concentrated by co-evaporation three times with toluene to afford the crude 2-O-benzyl-L-gulose as a mixture of β-pyranose, α-pyranose and furanose forms. A solution of the crude residue and 0.16 g (1.34 mmol) of DMAP in 3.4 mL of pyridine and 3.4 mL of acetic anhydride was stirred at 20° C. for 12 h and concentrated under diminished pressure to yield a brown syrup. The crude residue was applied to a silica gel column (38×3 cm). Elution with 3:1 ethyl acetate-hexanes gave 22 as a yellow oil: yield 1.56 g (64% over two steps); silica gel TLC $R_f$ 0.44 (1:1 ethyl acetate-hexanes); $^1$H NMR (CDCl$_3$) δ 2.01 (s, 3H), 2.05 (s, 31H), 2.08 (s, 3H), 2.11 (s, 3H), 3.64 (dd, 1H, J=8.3 and 4.9 Hz), 3.98-4.13 (m, 2H), 4.24-4.32 (m, 1H), 4.49 (d, 1H, J=11.9 Hz), 4.63 (d, 1H, J=11.9 Hz), 4.95 (dd, 1H, J=3.9 and 2.5 Hz), 5.43-5.45 (m, 1H), 5.89 (d, 1H, J=8.3 Hz) and 7.23-7.34 (m, 5H).

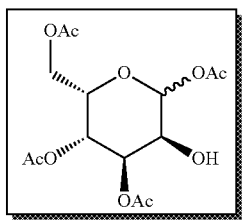

1,3,4,6-Tetra-O-acetyl-L-gulopyranose (23)

To a solution containing 1.47 g (3.35 mmol) of 22 in 23 mL of ethyl acetate was added 0.73 g of 10% Pd/C and the reaction mixture was stirred overnight under 1 atm of H$_2$. The solvent was filtered through a pad of Celite 545® and concentrated under diminished pressure to afford a crude residue. The residue was applied to a silica gel column (15×4 cm). Elution with 1:1 ethyl acetate-hexanes afforded 23 as a 77:20:3 mixture of α-pyranose, β-pyranose and furanose forms as determined by $^1$H NMR; yield 1.02 g (87%); silica gel TLC $R_f$ 0.52 (ethyl acetate); $^1$H NMR (CDCl$_3$) δ 1.91 (s, 3H), 2.00 (s, 3H), 2.03 (s, 6H), 3.22-3.52 (br s, 1H), 3.80 (dd, 1H, J=8.4 and 3.5 Hz), 3.91-3.97 (m, 1H), 3.99-4.04 (m, 1H), 4.14-4.19 (m, 1H), 4.82-4.88 (m, 1H), 5.19 (t, 1H, J=3.6 Hz) and 5.70 (d, 1H, J=8.4 Hz); $^{13}$C NMR (CDCl$_3$) δ 20.4, 20.5, 20.6, 20.8, 61.6, 66.2, 67.5, 69.5, 70.9, 92.1, 169.4, 169.6, 169.7 and 170.5.

Example 4: Synthesis of Mannose Donor 12

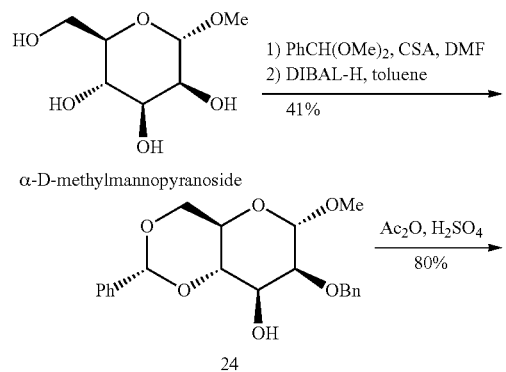

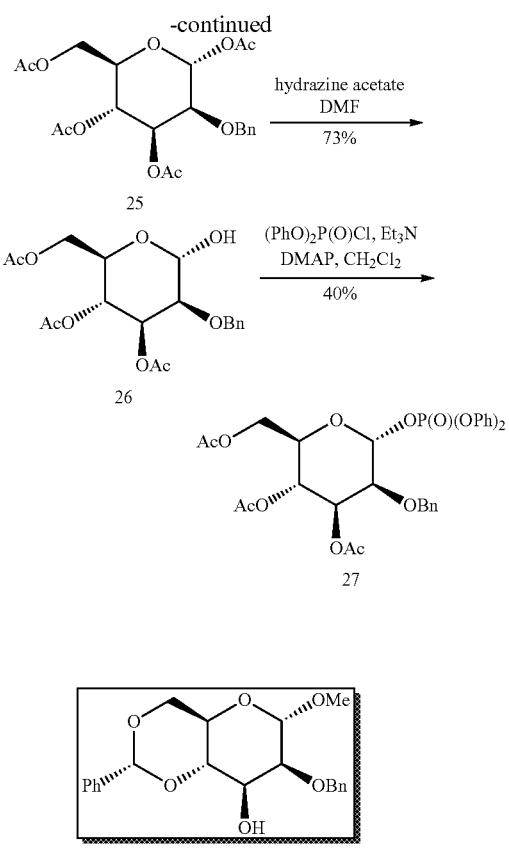

Methyl 4,6-O-Benzylidene-2-O-benzyl-α-D-mannopyranoside (24)

To a solution containing 5.00 g (26.0 mmol) of methyl α-D-mannopyranoside and 60.0 mg (0.26 mmol) of camphorsulfonic acid in 75 mL of DMF was added dropwise 9.7 mL (9.8 g, 65 mmol) of benzaldehyde dimethyl acetal. The resulting solution was heated to 60° C. on a rotary evaporator under a pressure of 250 mbar. After 3 h, analysis by silica gel TLC (1:3 ethyl acetate-hexanes) indicated complete conversion of starting material ($R_f$ 0.0) to two products ($R_f$ 0.50 and 0.80). To the reaction mixture was then added 4.90 mL (4.90 g, 32.4 mmol) of benzaldehyde dimethyl acetal and 30.0 mg (0.13 mmol) of camphorsulfonic acid. The reaction mixture was stirred under diminished pressure. After 2 h, silica gel TLC (1:3 ethyl acetate-hexanes) indicated the formation of a single product ($R_f$ 0.80). The solvent was concentrated under diminished pressure, the residue was co-evaporated with 50 mL of toluene and then dissolved in 100 mL of dichloromethane. The organic layer was washed with 50 mL of satd aq NaHCO$_3$ and brine. The organic phase was then dried (MgSO$_4$), filtered and concentrated under diminished pressure. The resulting crude mixture of endo and exo dibenzylidene derivatives was dissolved in 150 mL of freshly distilled toluene and cooled to −40° C. under an argon atmosphere. Then 65 mL of DIBAL (1 M solution in toluene, 64.9 mmol) was added slowly to the reaction mixture. The reaction mixture was allowed to warm to room temperature slowly. After 2 h, silica gel TLC analysis (1:3 ethyl acetate-hexanes) indicated complete consumption of starting material ($R_f$ 0.80) and formation of two products ($R_f$ 0.40 and $R_f$ 0.30). The reaction mixture was quenched by the dropwise addition of 50 mL of methanol and the mixture was diluted with 250 mL of dichloromethane. The organic layer was washed with 200 mL of 10% solution of Rochelle's salt and brine and then dried (MgSO$_4$). The organic layer was filtered and the filtrate was concentrated under diminished pressure. The resulting residue was purified by flash column chromatography (1:3 ethyl acetate-hexanes) to afford the undesired compound methyl 4,6-O-benzylidene-3-O-benzyl-α-D-mannopyranoside (R$_f$ 0.30) and the desired methyl 4,6-O-benzylidene-2-O-benzyl-α-D-mannopyranoside (24) as a colorless crystalline solid: yield 3.0 g (41%); silica gel TLC R$_f$ 0.40 (1:3 ethyl acetate-hexanes); $^1$H NMR (CDCl$_3$) δ 3.34 (s, 3H), 3.79-3.82 (m, 3H), 3.96 (t, 1H, J=8.0 Hz), 4.10-4.12 (m, 1H), 4.26-4.27 (m, 1H), 4.72-4.75 (m, 3H), 5.53 (s, 1H), 7.33-7.41 (m, 8H) and 7.42-7.55 (m, 2H).

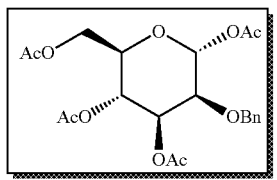

1,3,4,6-Tetra-O-acetyl-2-O-benzyl-α-D-mannopyranoside (25)

To a solution containing 3.57 g (9.59 mmol) of acetal 24 in 70 mL of Ac$_2$O was added a catalytic amount of H$_2$SO$_4$ and the reaction mixture was stirred at 25° C. for 40 min. The reaction mixture was poured into a stirring mixture of 100 mL of ethyl acetate and 80 mL of satd aq NaHCO$_3$. The organic and aqueous layers were separated and the organic layer was washed with 60 mL of brine and dried (MgSO$_4$). The organic layer was filtered and concentrated under diminished pressure to afford a crude residue. The residue was applied to a silica gel column (17×5 cm). Elution with 2:1 ethyl acetate-hexanes afforded 25 as a yellow oil: yield 3.35 g (80%); silica gel TLC R$_f$ 0.66 (1:1 ethyl acetate-hexanes); $^1$H NMR (CDCl$_3$) δ 1.98 (s, 3H), 2.04 (s, 3H), 2.08 (s, 3H), 2.12 (s, 3H), 3.82 (dd, 1H, J=3.2 and 2.2 Hz), 4.01 (ddd, 1H, J=10.0, 4.8 and 2.3 Hz), 4.08-4.15 (m, 1H), 4.23-4.28 (m, 1H), 4.56-4.76 (m, 2H), 5.19 (dd, 1H, J=10.0 and 3.3 Hz), 5.43-5.52 (m, 1H), 6.18 (d, 1H, J=1.9 Hz) and 7.27-7.38 (m, 5H); $^{13}$C NMR (CDCl$_3$) δ 20.8, 20.90, 20.93, 21.1, 62.4, 66.0, 70.7, 71.1, 73.0, 74.0, 91.3, 128.1, 128.2, 128.6, 137.3, 168.8, 169.6, 170.4 and 170.9.

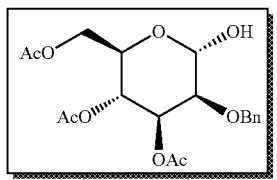

3,4,6-Tri-O-acetyl-2-O-benzyl-α-D-mannopyranoside (26)

To a solution containing 1.13 g (2.58 mmol) of compound 25 in 21 mL of anh DMF was added 286 mg (3.10 mmol) of hydrazine acetate. The reaction mixture was stirred at room temperature for 1.5 h and quenched by the addition of 100 mL of ethyl acetate. The organic layer was washed with three 50-mL portions of brine and dried (MgSO$_4$). The solvent was concentrated under diminished pressure to afford a crude residue. The residue was applied to a silica gel column (20×3 cm). Elution with 1:2 ethyl acetate-hexanes afforded pyranoside 26 as a colorless oil: yield 793 mg (73%); silica gel TLC R$_f$ 0.23 (1:1 ethyl acetate-hexanes); $^1$H NMR (CDCl$_3$) δ 1.97 (s, 3H), 2.00 (s, 3H), 2.02 (s, 3H), 3.81-3.87 (m, 1H), 4.05-4.17 (m, 2H), 4.20 (dt, 1H, J=9.3 and 4.7 Hz), 4.56-4.63 (m, 3H), 5.21-5.33 (m, 2H), 5.40 (t, 1H, J=9.9 Hz) and 7.21-7.36 (m, 5H); $^{13}$C NMR (CDCl$_3$) δ 20.57, 20.58, 20.7, 62.7, 66.6, 68.2, 70.9, 72.8, 75.6, 92.2, 127.70, 127.72, 128.2, 137.6, 169.8, 170.2 and 171.1; mass spectrum (APCI), m/z 397.1498 (M+H)$^+$ (C$_{19}$H$_{25}$O$_9$ requires 397.1498).

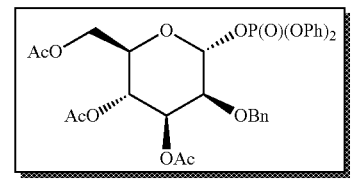

3,4,6-Tri-O-acetyl-2-O-benzyl-α-D-mannopyranosyl Diphenyl Phosphate (27)

To a stirred solution containing 793 mg (2.00 mmol) of 26 in 120 mL of anh dichloromethane was added 305 mg (2.50 mmol) of 4-dimethylaminopyridine (DMAP), 3.00 mL (2.17 g, 21.6 mmol) of Et$_3$N and 4.00 mL (5.20 g, 19.2 mmol) of diphenyl chlorophosphate. The reaction mixture was stirred at 0° C. for 2 h and poured into a stirring mixture of 300 mL of ethyl acetate and 150 mL of satd aq NaHCO$_3$. The aqueous and organic layers were separated and the organic layer was washed with three 50-mL portions of water and brine and then dried (MgSO$_4$). The solvent was concentrated under diminished pressure to afford a crude residue. The residue was applied to a silica gel column (20×3 cm). Elution with 1:2 ethyl acetate-hexanes afforded 27 as a colorless oil: yield 508 mg (40%); silica gel TLC R$_f$ 0.44 (1:1 ethyl acetate-hexanes); $^1$H NMR (CDCl$_3$) δ 2.17 (s, 3H), 2.20 (s, 3H), 2.23 (s, 3H), 4.10-4.25 (m, 3H), 4.42 (dd, 1H, J=12.2 and 3.9 Hz), 4.76-4.88 (m, 2H), 5.49 (d, H, J=8.0 Hz), 5.73 (t, 1H, J=10.1 Hz), 6.21 (d, 1H, J=5.7 Hz) and 7.33-7.62 (m, 15H); $^{13}$C NMR (CDCl$_3$) δ 20.39, 20.46, 20.53, 61.7, 65.3, 69.8, 70.8, 73.1, 74.4, 96.6, 119.9, 120.05, 120.09, 120.14, 124.59, 125.63, 127.8, 127.9, 128.3, 129.3, 129.8, 136.8, 149.9, 150.1, 150.8, 169.3, 169.8 and 170.53; mass spectrum (APCI), m/z 629.1788 (M+H)$^+$ (C$_{31}$H$_{34}$O$_{12}$P requires 629.1788).

Example 5: Synthesis of Mannose Donor 32

Scheme 5

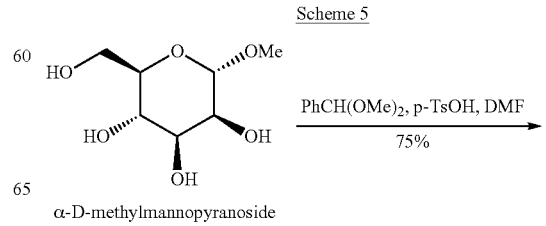

α-D-methylmannopyranoside

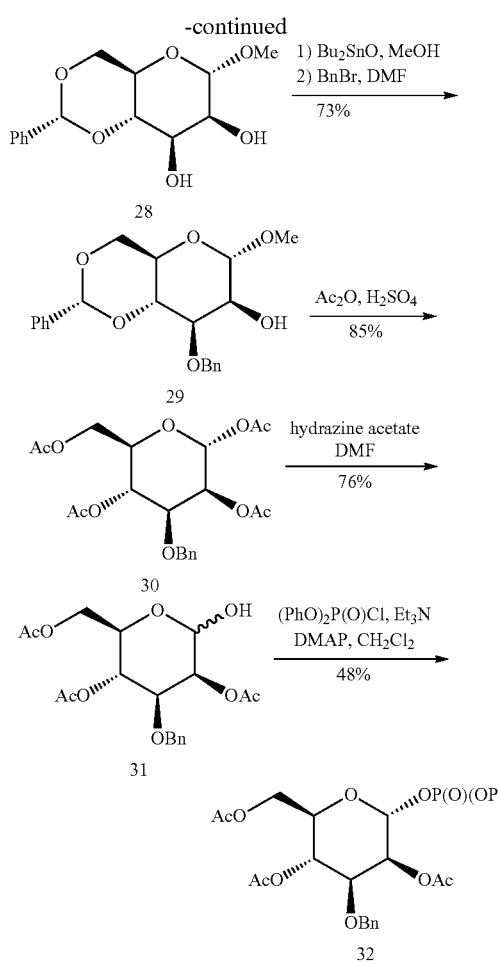

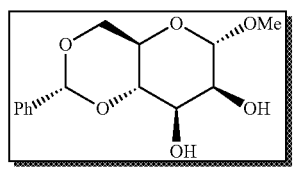

Methyl-4,6-O-benzylidene-α-D-mannopyranoside (28)

To a solution containing 7.00 g (36.0 mmol) of α-D-mannopyranoside in 85 mL of DMF was added 5.60 mL (5.68 g, 37.3 mmol) of benzaldehyde dimethyl acetal and a catalytic amount of p-TsOH. The reaction mixture was stirred at 60° C. under diminished pressure for 1 h, allowed to cool to room temperature and then poured into a stirring mixture of 120 mL of ethyl acetate and 100 mL satd aq NaHCO₃. The organic layer was washed with three 50-mL portions of brine and dried (MgSO₄). The solvent was concentrated under diminished pressure to afford a crude residue. The residue was applied to a silica gel column (30×5 cm). Elution with 4:1 ethyl acetate-hexanes afforded acetal 28 as a colorless solid: yield 7.13 g (70%); silica gel TLC $R_f$ 0.31 (1:1 ethyl acetate-hexanes); ¹H NMR (CDCl₃) δ 3.38 (s, 3H), 3.78 (m, 2H), 3.87 (m, 1H), 3.98 (m, 2H), 4.25 (m, 1H), 4.72 (d, 1H), 5.55 (s, 1H), 7.36 (m, 3H) and 7.47 (m, 2H); ¹³C NMR (CDCl₃) δ 55.2, 63.3, 68.8, 69.0, 71.1, 79.0, 101.6, 102.4, 126.5, 128.6, 129.5 and 137.4.

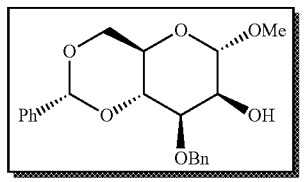

Methyl 4,6-O-Benzylidene-3-O-benzyl-α-D-mannopyranoside (29)

To a solution containing 2.00 g (7.10 mmol) of acetal 28 in 60 mL of methanol was added 1.94 g (7.79 mmol) of Bu₂SnO. The solution was heated to reflux for 1.5 h affording a clear solution. The solvent was concentrated under diminished pressure and the resulting solid was dried under vacuum overnight. The white residue was dissolved in 60 mL of DMF and treated with 1.69 mL (2.43 g, 14.2 mmol) of benzyl bromide and then warmed to 100° C. for 30 min. The cooled reaction mixture was poured into a stirred mixture of 90 mL of ethyl acetate and 60 mL of said aq NaHCO₃. The organic layer was separated and washed with 60 mL of brine and dried (MgSO₄). The solvent was concentrated under diminished pressure to afford a crude residue. The residue was applied to a silica gel column (30×5 cm). Elution with 3:7 ethyl acetate-hexanes afforded acetal 29 as a colorless oil: yield 1.93 g (73%); silica gel TLC $R_f$ 0.30 (3:7 ethyl acetate-hexanes); ¹H NMR (CDCl₃) δ 3.38 (s, 3H), 3.77 (m, 3H), 4.05 (m, 2H), 4.27 (m, 1H), 4.70 (m, 2H), 4.84 (m, 1H), 5.62 (s, 1H) and 7.28-7.52 (m, 10H); ¹³C NMR (CDCl₃) δ 55.2, 60.7, 63.5, 65.4, 69.1, 70.1, 73.2, 75.8, 79.0, 101.3, 101.8, 126.3, 127.2, 127.8, 128.11, 128.16, 128.5, 128.7, 129.2, 137.8 and 138.2.

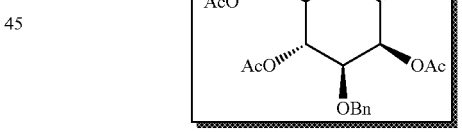

1,2,4,6-Tetra-O-acetyl-3-O-benzyl-α-D-mannopyranoside (30)

To a solution containing 1.93 g (4.40 mmol) of acetal 29 in 30 mL of Ac₂O was added a catalytic amount of H₂SO₄ and the solution was stirred at room temperature for 40 min. The reaction mixture was quenched by the addition of 120 mL of ethyl acetate and 80 mL of satd aq NaHCO₃. The organic and aqueous layers were separated and the organic layer was washed with brine and dried (MgSO₄). The solvent was concentrated under diminished pressure to afford a crude residue. The residue was applied to a silica gel column (30×5 cm). Elution with 2:1 ethyl acetate-hexanes afforded pyranoside 30 as a yellow oil: yield 1.94 g (85%); silica gel TLC $R_f$ 0.34 (3:7 ethyl acetate-hexanes); ¹H NMR (CDCl₃) δ 2.02 (s, 3H), 2.07 (s, 3H), 2.11 (s, 3H), 2.15 (s, 3H), 3.83 (dd, 1H, J=9.7 and 3.4 Hz), 3.90 (m, 1H), 4.04 (m, 1H), 4.19 (m, 1H), 4.41 (m, 1H), 4.64 (m, 1H), 5.24 (m, 1H), 5.34 (dd, 1H, J=3.4 and 2.1 Hz), 6.09 (d, 1H, J=2.0 Hz) and 7.24-7.37 (m, 5H); $^{13}$C NMR (CDCl$_3$) δ 14.4, 20.98, 21.08, 21.13, 62.6, 67.0, 67.2, 71.0, 71.7, 74.3, 91.2, 128.0, 128.2, 128.6, 137.6, 168.3, 169.8, 170.2 and 171.0.

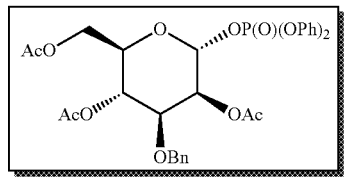

2,4,6-Tri-O-acetyl-3-O-benzyl-α-D-mannopyranosyl Diphenyl Phosphate (32)

To a solution containing 1.40 g (3.19 mmol) of acetate 30 in 25 mL of DMF was added 353 mg (3.83 mmol) of hydrazine acetate. The solution was stirred at room temperature for 1.5 h and quenched by the addition of 100 mL of ethyl acetate. The organic phase was washed with three 50-mL portions of brine and dried (MgSO$_4$). The solvent was concentrated under diminished pressure to afford a crude residue. The residue was applied to a silica gel column (20×4 cm). Elution with 1:2 ethyl acetate-hexanes afforded monosaccharide 31 as a colorless oil. This material was used for the next reaction immediately: yield 968 mg (76%); $^1$H NMR (CDCl$_3$) δ 1.95 (s, 3H), 2.02 (s, 3H), 2.10 (s, 3H), 3.90 (dd, 1H, J=9.7 and 3.3 Hz), 4.00-4.11 (m, 2H), 4.16 (ddd, 1H, J=12.3, 7.7 and 4.6 Hz), 4.33 (s, 1H), 4.38 (dd, 1H, J=12.3 and 4.3 Hz), 4.60 (d, 1H, J=12.2 Hz), 5.13-5.23 (m, 2H), 5.28-5.33 (m, 1H) and 7.18-7.31 (m, 5H); $^{13}$C NMR (CDCl$_3$) δ 14.2, 20.78, 20.85, 21.0, 60.6, 62.9, 67.5, 68.5, 68.8, 71.4, 74.0, 92.3, 127.78, 127.83, 128.4, 137.7, 169.9, 170.6 and 171.1.

To a stirred solution containing 968 mg (2.44 mmol) of pyranoside 31 in 144 mL of anh dichloromethane was added 372 mg (3.05 mmol) of DMAP, 3.67 mL (2.66 g, 26.3 mmol) of Et$_3$N and 4.83 mL (6.26 g, 23.4 mmol) of diphenyl chlorophosphate. The reaction mixture was stirred at 0° C. for 2 h and poured into a mixture of 300 mL of ethyl acetate and 150 mL of said aq NaHCO$_3$. The organic layer was washed with three 50-mL portions of water and brine and then dried (MgSO$_4$). The solvent was concentrated under diminished pressure to afford a crude residue. The residue was applied to a silica gel column (20×4 cm). Elution with 1:2 ethyl acetate-hexanes afforded 32 as a colorless oil: yield 737 mg (48%); silica gel TLC R$_f$ 0.38 (1:1 ethyl acetate-hexanes); $^1$H NMR (CDCl$_3$) δ 1.93 (s, 3H), 1.97 (s, 3H), 2.10 (s, 3H), 3.84 (dd, 1H, J=9.7 and 3.3 Hz), 3.89-4.03 (m, 2H), 4.10-4.20 (m, 1H), 4.33 (d, 1H, J=12.1 Hz), 4.57 (d, 1H, J=12.1 Hz), 5.27 (t, 1H, J=10.0 Hz), 5.38 (dd, 1H, J=8.6 and 6.2 Hz), 5.91 (dd, 1H, J=6.4 and 1.6 Hz) and 7.16-7.38 (m, 15H); $^{13}$C NMR (CDCl$_3$) δ 20.5, 20.62, 20.67, 61.8, 66.2, 67.2, 67.3, 70.9, 71.5, 73.4, 77.4, 96.5, 119.90, 119.95, 125.67, 125.71, 127.9, 128.3, 129.85, 137.2, 150.08, 150.15, 169.3, 169.6 and 170.4; mass spectrum (APCI), m/z 629.1770 (M+H)$^+$ (C$_{31}$H$_{34}$O$_{12}$P requires 629.1788).

Example 6: Synthesis of Mannose Donor 35

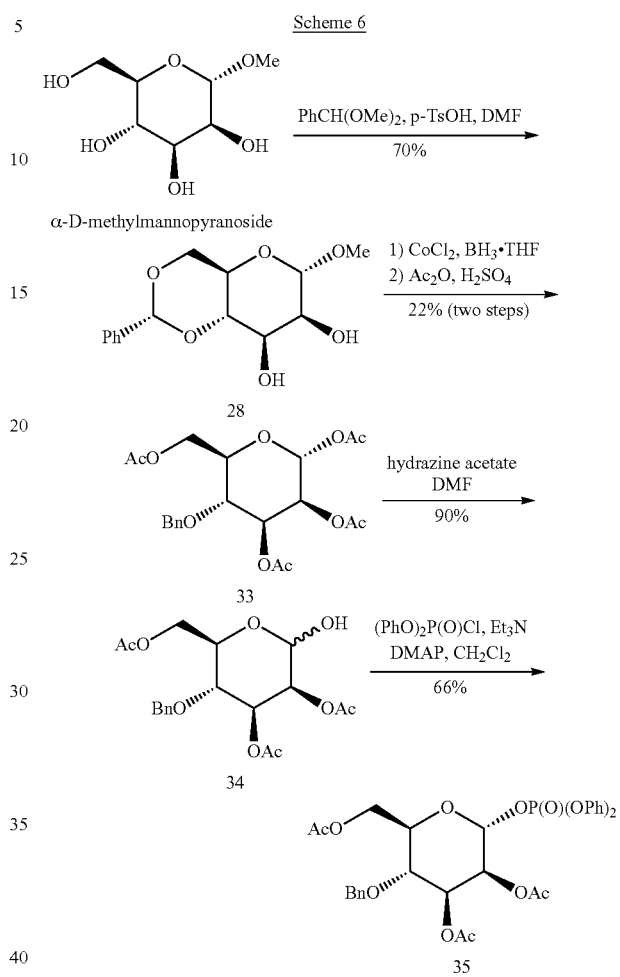

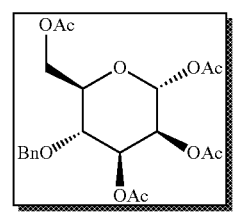

1,2,3,6-Tetra-O-acetyl-4-O-benzyl-α-D-mannopyranoside (33)

To a stirred solution containing 5.43 g (19.2 mmol) of acetal 28 in 50 mL of anh THF was added 58.0 mL (57.6 mmol) of a 1 M solution of BH$_3$ in THF and 7.48 g (57.6 mmol) of anh CoCl$_2$ at room temperature. The reaction mixture was stirred for 15 min at room temperature and quenched by the addition of 100 mL of ethyl acetate. The organic phase was filtered and the filtrate was treated with 20 mL of a 20% aq solution of NaBH$_4$. The solution was again filtered and washed successively with sat aq NaHCO$_3$ and water, and then dried (MgSO$_4$). The solution was concentrated under diminished pressure to afford a crude residue. To a solution containing 3.44 g (12.1 mmol) of the crude residue in 85 mL of Ac$_2$O was added a catalytic amount of H$_2$SO$_4$. The solution was stirred at room temperature for 12 h. The reaction mixture was quenched by the addition of 120 mL of ethyl acetate and 80 mL of satd aq NaHCO$_3$. The organic and aqueous layers were separated and the organic layer was washed with brine and dried (MgSO$_4$). The solution was concentrated under diminished pressure to afford a crude residue. The residue was applied to a silica gel column (30×5 cm). Elution with 2:1 ethyl acetate-hexanes afforded pyranoside 33 as a yellow oil: yield 1.17 g (22% over two steps); silica gel TLC R$_f$ 0.26 (2:1 ethyl acetate-hexanes); $^1$H NMR (CDCl$_3$) δ 2.00 (s, 3H), 2.08 (s, 3H), 2.13 (s, 3H), 2.15 (s, 3H), 3.87 (t, 1H, J=9.7), 3.99 (dt, 1H, J=9.9 and 3.4 Hz), 4.32 (d, 2H, J=3.5 Hz), 4.59 (d, 1H, J=11.2 Hz), 4.70 (d, 1H, J=10.8 Hz), 5.26 (dd, 1H, J=3.3 and 2.1 Hz), 5.37 (dd, 1H, J=9.5 and 3.4 Hz), 6.04 (t, 1H, J=6.1 Hz), and 7.24-7.38 (m, 5H); $^{13}$C NMR (CDCl$_3$) δ 20.92, 20.97, 20.99, 21.04, 62.9, 68.9, 71.6, 71.8, 72.6, 75.2, 90.8, 127.9, 128.3, 128.7, 137.5, 168.4, 169.8, 169.9 and 170.8.

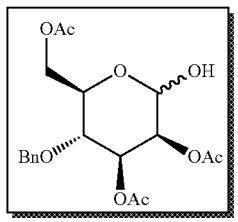

2,3,6-Tri-O-acetyl-4-O-benzyl-α,β-D-mannopyranose (34)

To a stirred solution containing 1.09 g (2.49 mmol) of acetate 33 in 20 mL of anh DMF was added 274 mg (2.98 mmol) of hydrazine acetate. The reaction mixture was stirred at room temperature for 1.5 h and quenched by the addition of 100 mL of ethyl acetate. The organic layer was washed with three 50-mL portions of brine and dried (MgSO$_4$). The solvent was concentrated under diminished pressure to afford a crude residue. The residue was applied to a silica gel column (20×3 cm). Elution with 1:2 ethyl acetate-hexanes afforded pyranoside 34 as a colorless oil: yield 884 mg (90%); silica gel TLC R$_f$ 0.36 (1:1 ethyl acetate-hexanes); $^1$H NMR (CDCl$_3$) δ 1.92 (s, 3H), 2.01 (s, 3H), 2.08 (s, 3H), 3.77 (t, 1H, J=10.0 Hz), 4.11 (ddd, 1H, J=9.7, 4.1 and 2.1 Hz), 4.17-4.34 (m, 2H), 4.69-4.48 (m, 3H), 5.09 (s, 1H), 5.17-5.23 (m, 1H), 5.33-5.38 (m, 1H) and 7.18-7.32 (m, 5H); $^{13}$C NMR (CDCl$_3$) δ 20.69, 20.73, 63.1, 69.2, 70.5, 71.5, 72.8, 74.6, 77.4, 91.8, 127.6, 127.8, 128.3, 137.5, 170.0, 170.2 and 171.0; HRMS (APCI), m/z 397.1483 (M+H)$^+$ (C$_{19}$H$_{25}$O$_9$ requires m/z 397.1498).

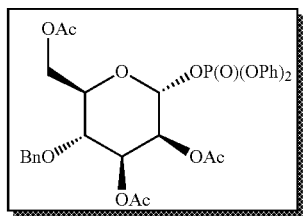

2,3,6-Tri-O-acetyl-4-O-benzyl-α-D-mannopyranosyl Diphenyl Phosphate (35)

To a stirred solution containing 812 mg (2.05 mmol) of 34 in 80 mL of anh dichloromethane was added 313 mg (2.56 mmol) of DMAP and 3.10 mL (2.25 g, 22.1 mmol) of Et$_3$N, 4.10 mL (5.33 g, 19.7 mmol) of diphenyl chlorophosphate. The reaction mixture was stirred at 0° C. for 2 h and then poured into a mixture of 300 mL of ethyl acetate and 150 mL of said aq NaHCO$_3$. The aqueous and organic layers were separated and the organic layer was washed with three 50-mL portions of distilled water and brine and then dried (MgSO$_4$). The solvent was concentrated under diminished pressure to afford a crude residue. The residue was applied to a silica gel column (20×4 cm). Elution with 1:2 ethyl acetate-hexanes afforded 35 as a colorless oil: yield 857 mg (66%); silica gel TLC R$_f$ 0.29 (1:1 ethyl acetate-hexanes); $^1$H NMR (CDCl$_3$) δ 1.93 (s, 3H), 1.96 (s, 3H), 2.09 (s, 3H), 3.80 (t, 1H, J=9.6 Hz), 3.91-4.12 (m, 2H), 4.18 (dd, 1H, J=12.2 and 4.2 Hz), 4.50-4.68 (m, 2H), 5.27-5.38 (m, 2H), 5.80 (d, 1H, J=6.1 Hz) and 7.11-7.38 (nm, 15H); $^{13}$C NMR (CDCl$_3$) δ 20.74, 20.9, 62.4, 69.1, 70.9, 71.8, 72.1, 75.0, 77.4, 96.3, 120.1, 120.4, 125.7, 125.9, 127.9, 128.2, 128.6, 129.9, 130.0, 137.3, 150.1, 150.3, 169.5, 169.6 and 170.5; HRMS (APCI), m/z 629.1794 (M+H)$^+$ (C$_{31}$H$_{34}$O$_{12}$P requires m/z 629.1788).

Example 7: Synthesis of Mannose Donor 40

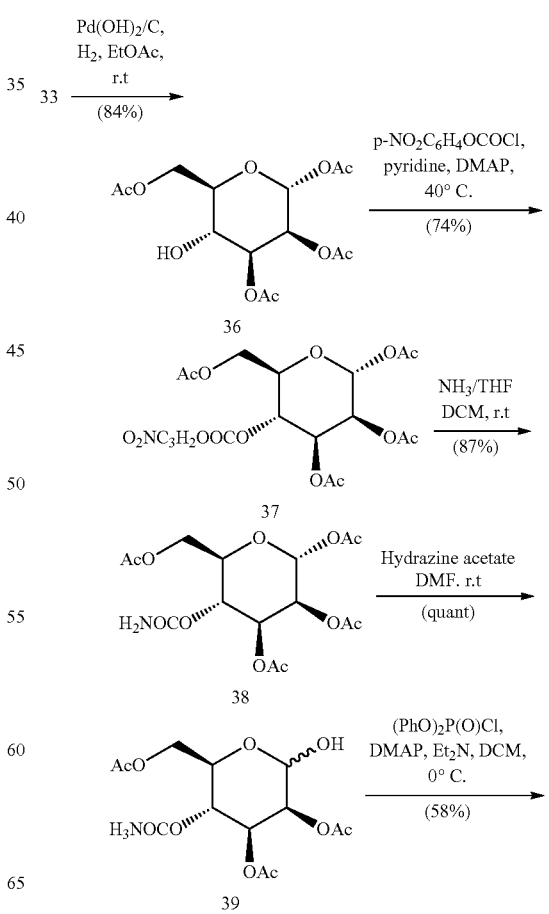

Scheme 7

-continued

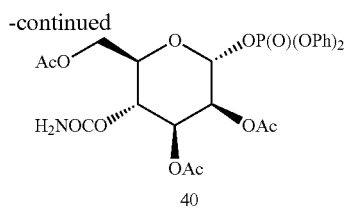

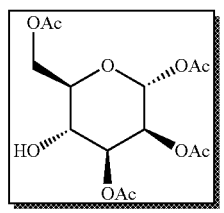

1,2,3,6-Tetra-O-acetyl-α-D-mannopyranoside (36)

To a solution of 1.63 g (3.72 mmol) of 33 in 33 mL of ethyl acetate was added a 308 mg of Pd(OH)$_2$/C and the reaction was placed under 1 atm of H$_2$ overnight. The catalyst was removed by filtration through a pad of Celite 545® and concentrated under diminished pressure. The residue was purified by flash chromatography on a silica gel column (5×20 cm). Elution with 2:1 hexanes-ethyl acetate afforded 36 as a colorless oil: yield 1.09 g (84%); silica gel TLC R$_f$ 0.25 (1:1 ethyl acetate-hexanes). $^1$H NMR (CDCl$_3$) δ 2.06 (s, 3H), 2.12 (s, 6H), 2.14 (s, 3H), 2.94 (br s, 1H), 3.83-3.92 (m, 2H), 4.24-4.27 (m, 1H), 4.50-4.54 (m, 1H), 5.18-5.23 (m, 2H), 6.04 (d, 1H, J=1.6 Hz).

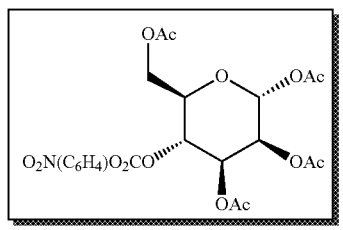

1,2,3,6-Tetra-O-acetyl-4-O-(p-nitrophenyl)carbamoyl-α-D-mannopyranoside (37)

To a solution of 1.74 g (5.00 mmol) of 36 in 17.8 mL of pyridine was added 2.44 g (20.0 mmol) of DMAP and 4.03 g (20.0 mmol) of p-nitrophenyl chloroformate. The reaction was stirred at 40° C. for 2.5 h at which time it was poured into a two phase mixture of 50 mL ethyl acetate and 19 mL of water. The organic layer was washed with three 25-mL portions of 1N HCl, 25 mL of satd aq. NaHCO$_3$ and 25 mL of brine. The solution was dried (MgSO$_4$) and concentrated under diminished pressure to afford a crude residue. The residue was purified by flash chromatography on a silica gel column (5×28 cm). Elution with 1:2 ethyl acetate-hexanes afforded 37 as a white foam: yield 1.91 g (74%); silica gel TLC R$_f$ 0.21 (2:1 ethyl acetate-hexanes). $^1$H NMR (CDCl$_3$) δ 2.05 (s, 3H), 2.11 (s, 3H), 2.18 (s, 3H), 2.19 (s, 3H), 4.15-4.20 (m, 2H), 4.53-4.58 (m, 1H), 5.23 (t, 1H, J=9.9 Hz), 5.32-5.33 (m, 1H), 5.45 (dd, 1H, J=10.1, 3.5 Hz), 6.12 (d, 1H, J=1.9 Hz), 7.38 (d, 2H, J=9.2 Hz), 8.29 (d, 2H, J=8.8 Hz); $^{13}$C NMR (CDCl$_3$) δ 20.66, 20.69, 20.8, 61.6, 68.3, 68.6, 70.1 70.9, 90.4, 121.6, 125.4, 145.7, 151.7, 155.1, 167.9, 169.5, 169.8, 170.6.

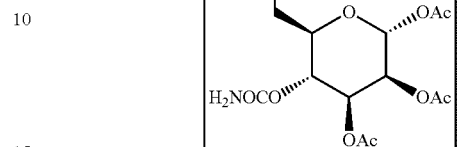

1,2,3,6-Tetra-O-acetyl-4-O-(carbamoyloxy)-α-D-mannopyranoside (38)

To a solution of 2.02 g (3.93 mmol) of 37 in 107 mL of dichloromethane was added a solution of 37 mL of anh THF satd with NH$_3$ at 0° C. The reaction mixture was allowed to warm to room temperature and stirred at room temperature overnight. The solution was concentrated under diminished pressure and the residue was purified by flash chromatography on a silica gel column (3×15 cm). Elution with 1:1 ethyl acetate-hexanes afforded 38 as a white foam: yield 1.22 g (87%); silica gel TLC R$_f$ 0.12 (1:1 hexanes-ethyl acetate). $^1$H NMR (CDCl$_3$) δ 2.03 (s, 3H), 2.09 (s, 3H), 2.16 (s, 3H), 2.17 (s, 3H), 4.00-4.05 (m, 1H), 4.15-4.19 (m, 1H), 4.26-4.31 (m, 1H), 4.73 (br s, 2H), 5.19 (t, 1H, J=10.1 Hz), 5.24-5.25 (m, 1H), 5.34-5.37 (m, 1H), 6.07 (d, H, J=1.9 Hz); $^{13}$C NMR (CDCl$_3$) δ 20.68, 20.72, 20.76, 20.85, 62.3, 66.7, 68.4, 68.6, 70.7, 90.6, 154.9, 168.0, 169.8, 170.1, 170.7; mass spectrum (APCI), m/z 392.1203 (M+H)$^+$ (C$_{15}$H$_{22}$NO$_{11}$ requires m/z 392.1193).

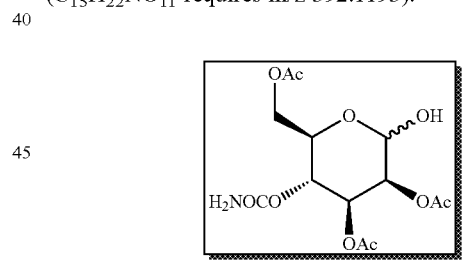

2,3,6-Tri-O-acetyl-4-O-(carbamoyloxy)-α-D-mannopyranoside (39)

To a solution containing 553 mg (1.41 mmol) of 38 in 9.20 mL of anh DMF was added 182 mg (1.98 mmol) of hydrazine acetate. The solution was stirred at 25° C. for 2 h and then treated with 120 mL of ethyl acetate. The organic solution was washed with 120 mL of water, 120 mL of said aq. NaHCO$_3$, 120 mL of brine, and then dried (MgSO$_4$). The solvent was concentrated under diminished pressure to afford 39 as a white foam: yield 501 mg (quant.); silica gel TLC R$_f$ 0.28 (1:3 hexanes-ethyl acetate). $^1$H NMR (CDCl$_3$) δ 2.00 (s, 3H), 2.08 (s, 3H), 2.14 (s, 3H), 4.17-4.24 (m, 3H), 4.58-4.64 (br s, 1H), 5.10 (t, 1H, J=9.6 Hz), 5.07-5.15 (br s, 2H), 5.20-5.22 (m, 2H), 5.37-5.41 (m, 1H).

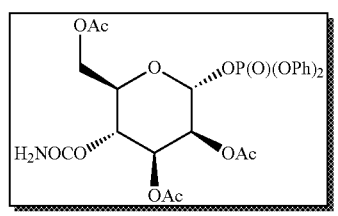

2,3,6-Tri-O-acetyl-4-O-(carbamoyloxy)-α-D-mannopyranosyl Diphenyl Phosphate (40)

To a solution of 496 mg (1.42 mmol) of 39 in 29 mL of dichloromethane at 0° C. was added 217 mg (1.78 mmol) of DMAP, 2.1 mL (15.0 mmol) of Et$_3$N, and 2.8 mL (13.6 mmol) of diphenyl phosphoryl chloride under an argon atmosphere. The reaction mixture was stirred for 1.5 h and the solution was poured into a two phase mixture of 43 mL of ethyl acetate and 20 mL of said aq NaHCO$_3$. The organic layer was washed with two 20-mL portions of brine, dried (MgSO$_4$) and concentrated under diminished pressure to afford a crude residue. The residue was purified by flash chromatography on a silica gel column (3×20 cm). Elution with 2:3 hexanes-ethyl acetate afforded 40 as a colorless oil: yield 460 mg (56%); silica gel TLC $R_f$ 0.33 (1:3 hexanes-ethyl acetate). $^1$H NMR (CDCl$_3$) δ 2.06 (s, 3H), 2.12 (s, 3H), 2.24 (s, 3H), 4.15-4.19 (m, 1H), 4.28-4.32 (m, 1H), 4.37-4.41 (m, 1H), 4.80 (s, 1H), 4.82-4.90 (br s, 2H), 5.21-5.30 (m, 1H), 5.41-5.50 (m, 1H), 5.95-5.97 (m, 1H), 7.24-7.36 (m, 6H), 7.44-7.48 (m, 4H); $^{13}$C NMR (400 MHz, CDCl$_3$) δ 20.56, 20.62, 20.7, 61.9, 66.3, 68.0, 68.7, 68.8, 70.8, 96.0, 120.01, 120.05, 120.16, 120.21, 125.7, 125.85, 125.86, 129.93, 129.99, 169.6, 169.9, 170.6; mass spectrum (APCI), m/z 582.1387 (M+H)$^+$ (C$_{25}$H$_{29}$NO$_{13}$P requires m/z 582.1377).

Example 8: Synthesis of Altrose Donor 32

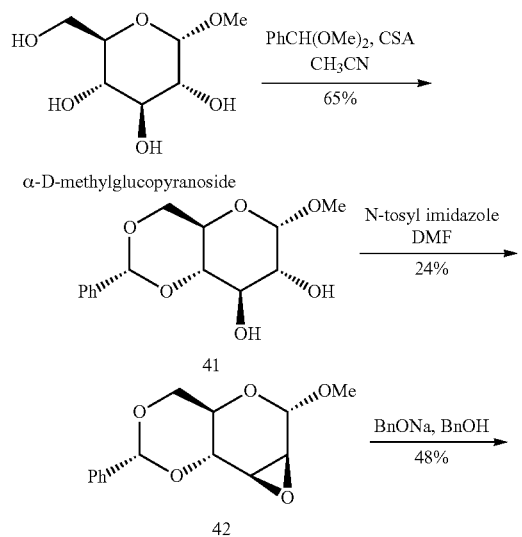

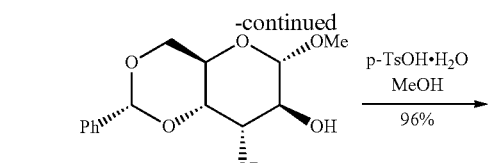

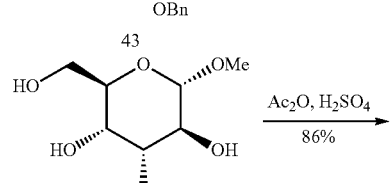

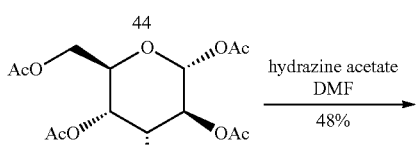

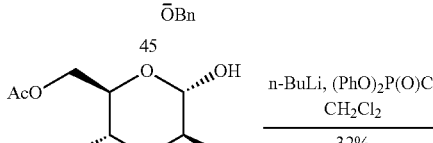

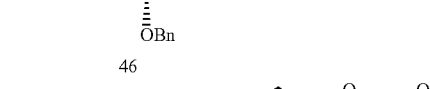

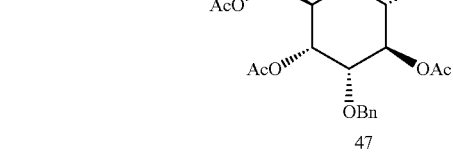

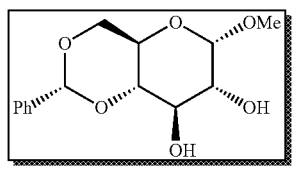

Methyl-4,6-O-benzylidene-α-D-glucopyranoside (41)

To a solution containing 10.0 g (51.5 mmol) of α-D-methyl glucopyranoside in 200 mL of acetonitrile was added 14.0 mL (14.2 g, 92.7 mmol) of benzaldehyde dimethyl acetal and 600 mg (2.57 mmol) of camphorsulfonic acid. The reaction mixture was heated to reflux for 20 min and then allowed to cool to room temperature and neutralized by the addition of 400 μL of triethylamine. The reaction mixture was diluted with 800 mL of ethyl acetate. The organic layer was washed with three 250-mL portions of water and dried (MgSO$_4$). The organic layer was concentrated under diminished pressure to afford a crude residue. The residue was crystallized from 1:7 dichloromethane-hexanes to afford acetal 41 as a colorless solid: yield 9.48 g (65%); silica gel TLC $R_f$ 0.17 (2:1 ethyl acetate-hexanes); $^1$H NMR (CDCl$_3$) δ 3.45-3.47 (m, 4H), 3.63 (dd, 1H, J=9.1 and 3.9 Hz), 3.71-3.85 (m, 2H), 3.93 (t, 1H, J=9.2 Hz), 4.29 (dd, 1H, J=9.7 and 4.3 Hz), 4.80 (d, 1H, J=3.9 Hz), 5.53 (s, 1H) and 7.33-7.53 (m, 5H); $^{13}$C NMR (CDCl$_3$) δ 55.7, 62.5, 69.1, 72.0, 73.0, 81.0, 99.9, 102.1, 126.4, 128.4, 129.4 and 137.2.

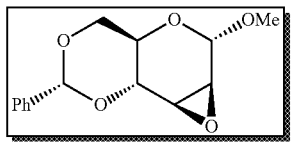

Methyl 2,3-Anhydro-4,6-O-benzyl-α-D-mannopyranoside (42)

To a solution containing 2.44 g (60% in oil dispersion, 60.9 mmol) of NaH in 290 mL of anh DMF at 0° C. was added 8.20 g (29.0 mmol) of acetal 41 under an argon atmosphere. The reaction mixture was stirred at room temperature for 0.5 h. To the above stirred solution at 0° C. was then added 7.10 g (31.9 mmol) of N-tosylimidazole. The suspension was stirred at room temperature for 1 h. The reaction mixture was poured with stirring into 2.5 L of ice-cold water and the resulting solid was filtered and washed with water to afford a crude residue. The residue so obtained was triturated with methanol to obtain the epoxide 42 as a colorless solid: yield 1.83 g (24%); silica gel TLC $R_f$ 0.68 (1:1 ethyl acetate-hexanes); $^1$H NMR (CDCl$_3$) δ 3.17 (d, 1H, J=3.6 Hz), 3.45-3.49 (m, 4H), 3.64-3.79 (m, 3H), 4.21-4.32 (m, 1H), 4.91 (s, 1H), 5.57 (s, 1H), 7.35-7.53 (m, 5H); $^{13}$C NMR (CDCl$_3$) δ 50.7, 54.0, 55.9, 61.8, 69.6, 75.0, 97.0, 102.6, 126.3, 128.5, 129.4 and 137.2.

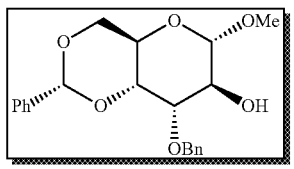

Methyl 4,6-O-Benzylidene-3-O-benzyl-α-D-altropyranoside (43)

A solution containing 214 mg (9.32 mmol) of sodium metal in 2.9 mL of anh benzyl alcohol was heated (~100° C.) until all of the sodium metal had dissolved. The cooled solution was treated with 1.07 g (4.05 mmol) of anhydromannopyranoside 42. The reaction mixture was then heated to reflux for 15 min, cooled and diluted by the addition of 20 mL of ether. The solvent was concentrated under diminished pressure to afford a crude residue. The residue was applied to a silica gel column (20×5 cm). Elution with 1:4 ethyl acetate-hexanes afforded acetal 43 as a colorless solid: yield 723 mg (48%); silica gel TLC $R_f$ 0.55 (1:1 ethyl acetate-hexanes); $^1$H NMR (CDCl$_3$) δ 2.30 (s, 1H), 3.42 (s, 3H), 3.77 (t, 1H, J=10.3 Hz), 3.84 (t, 1H, J=2.8 Hz), 3.93 (d, 1H, J=2.8 Hz), 3.98 (dt, 1H, J=9.3 and 4.6 Hz), 4.28-4.45 (m, 2H), 4.55 (d, 1H, J=6.0 Hz), 4.70-4.90 (m, 2H), 5.56 (s, 1H) and 7.23-7.53 (m, 10H); $^{13}$C NMR (CDCl$_3$) δ 55.8, 58.7, 69.4, 70.2, 72.9, 74.9, 77.2, 102.0, 102.4, 126.3, 127.5, 127.7, 128.30, 128.36, 129.1, 137.7 and 138.7.

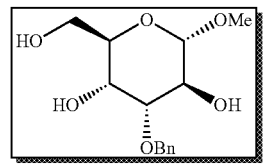

Methyl-3-O-benzyl-α-D-altropyranoside (44)

To a solution containing 1.67 g (4.48 mmol) of acetal 43 in 4.2 mL of methanol was added 43.0 mg (0.22 mmol) of p-toluenesulfonic acid monohydrate at 0° C. The reaction mixture was allowed to warm to room temperature and stirred for 4 h. The reaction mixture was quenched by the addition of 1.90 mL (1.38 g, 13.4 mmol) of triethylamine and concentrated under diminished pressure to afford a crude residue. The residue was applied to a silica gel column (10×3 cm). Elution with 5:1 ethyl acetate-hexanes afforded methyl pyranoside 44 as a colorless oil: yield 1.22 g (96%); silica gel TLC $R_f$ 0.17 (ethyl acetate); $^1$H NMR (CDCl$_3$) δ 3.01 (d, 1H, J=9.3 Hz), 3.33 (s, 3H), 3.53 (d, 1H, J=15.3 Hz), 3.70-3.77 (m, 2H), 3.80 (dt, 2H, J=8.8 and 4.3 Hz), 3.96 (s, 2H), 4.40-4.78 (m, 4H) and 7.21-7.35 (m, 5H); $^{13}$C NMR (CDCl$_3$) δ 55.5, 61.9, 63.4, 67.3, 69.2, 72.0, 77.4, 101.5, 127.9, 128.0, 128.5 and 138.0.

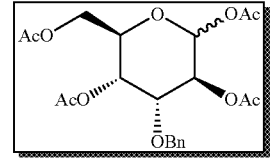

1,2,4,6-Tetra-O-acetyl-3-O-benzyl-β-D-altropyranoside (45)

To a solution containing 532 mg (1.87 mmol) of methyl pyranoside 44 in 13 mL of Ac$_2$O was added a catalytic amount of H$_2$SO$_4$. The solution was stirred overnight at room temperature. The reaction mixture was then poured into a stirred mixture of 120 mL of ethyl acetate and 80 mL of satd aq NaHCO$_3$. The organic and aqueous layers were separated and the organic layer was washed with brine and dried (MgSO$_4$). The solvent was concentrated under diminished pressure to afford a crude residue. The residue was applied to a silica gel column (30×3 cm). Elution with 1:2 ethyl acetate-hexanes afforded the product 45 as a 3:2 mixture of α and β anomers as determined by $^1$H NMR; yield 705 mg (86%); silica gel TLC $R_f$ 0.55 (1:1 ethyl acetate-hexanes); α anomer $^1$H NMR (CDCl$_3$) δ 2.01 (s, 3H), 2.06-2.09 (m, 6H), 2.14 (s, 3H), 3.96 (t, 1H, J=3.2 Hz), 4.11-4.16 (m, 1H), 4.24-4.37 (m, 2H), 4.55-4.75 (m, 2H), 5.03-5.09 (m, 1H), 5.29 (s, 1H), 5.99 (d, 1H, J=11.3 Hz) and 7.27-7.38 (m, 5H), $^{13}$C NMR (CDCl$_3$) δ 20.91, 20.92, 21.04, 21.05, 62.6, 66.3, 66.6, 68.0, 72.46, 72.49, 91.4, 127.8, 128.1, 128.5, 137.5, 169.0, 169.7, 169.8 and 170.9; HRMS (APCI), m/z 379.1387 (M-CH$_3$COO)$^+$ (C$_{19}$H$_{23}$O$_8$ requires m/z 379.1393).

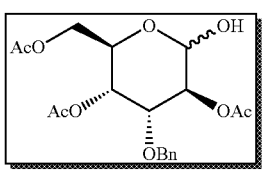

2,4,6-Tri-O-acetyl-3-O-benzyl-α,β-D-altropyrano-side (46)

To a solution containing 1.93 g (4.40 mmol) of monosaccharide 45 in 35 mL of anh DMF was added 486 mg (5.28 mmol) of hydrazine acetate. The reaction mixture was stirred at room temperature for 1.5 h and quenched by the addition of 100 mL of ethyl acetate. The organic layer was then washed with three 50-mL portions of brine and dried (MgSO$_4$). The solvent was concentrated under diminished pressure to afford a crude residue. The residue was applied to a silica gel column (20×4 cm). Elution with 1:2 ethyl acetate-hexanes afforded 46 as a colorless oil. The product was isolated as a mixture of anomers as analyzed by $^1$H NMR: yield 837 mg (48%); silica gel TLC R$_f$ 0.31 (1:1 ethyl acetate-hexanes); $^1$H NMR (CDCl$_3$) δ 1.95 (s, 3H), 1.96 (s, 3H), 2.05 (s, 3H), 2.07 (s, 3H), 2.11 (s, 3H), 2.15 (s, 3H), 3.73-3.95 (br s, 1H), 3.98-4.05 (m, 1H), 4.09 (d, 1H, J=8.6 Hz), 4.12-4.27 (m, 4H), 4.32 (dt, 1H, J=14.2 and 7.1 Hz), 4.36-4.46 (m, 1H), 4.54-4.75 (m, 4H), 4.89-4.94 (m, 2H), 4.96-5.08 (m, 4H), 5.24 (t, 1H, J=12.1 Hz) and 7.41-7.27 (m, 10H); $^{13}$C NMR (CDCl$_3$) δ 20.80, 20.82, 20.86, 20.98, 21.02, 62.9, 63.2, 64.1, 66.2, 66.9, 68.3, 70.0, 70.3, 72.9, 73.3, 73.8, 74.2, 91.6, 92.8, 128.1, 128.2, 128.4, 128.5, 128.7, 128.8, 136.2, 137.3, 169.73, 169.78, 169.83, 170.4, 170.95 and 170.96; HRMS (APCI), m/z 379.1394 (M-OH)$^+$ (C$_{19}$H$_{23}$O$_8$ requires m/z 379.1393).

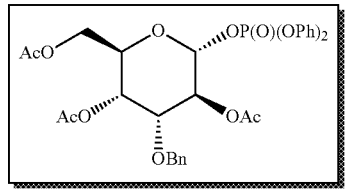

2,4,6-Tri-O-acetyl-3-O-benzyl-α-D-altropyranosyl Diphenyl Phosphate (47)

To a stirred solution containing 637 mg (1.61 mmol) of pyranoside 36 in 2.7 mL of anh dichloromethane was added 1.21 mL (1.6 M, 1.93 mmol) of n-BuLi solution at −78° C. The reaction mixture was stirred at this temperature for 10 min and 400 μL (520 mg, 1.93 mmol) of diphenyl chlorophosphate was added dropwise. The reaction mixture was stirred at −78° C. for an additional 10 min and then poured into a mixture of 20 mL of ethyl acetate and 10 mL of satd aq NaHCO$_3$. The organic and aqueous layers were separated and the organic layer was washed with three 10-mL portions of water and brine and then dried (MgSO$_4$). The solvent was concentrated under diminished pressure to afford a crude residue. The residue was applied to a silica gel column (20×3 cm). Elution with 1:2 ethyl acetate-hexanes afforded phosphate ester 47 as a colorless oil: yield 324 mg (32%); 121 mg of unreacted starting material was also recovered; silica gel TLC R$_f$ 0.40 (1:1 ethyl acetate-hexanes); $^1$H NMR (CDCl$_3$) δ 1.97 (s, 3H), 1.98 (s, 3H), 2.00 (d, 3H, J=2.1 Hz), 3.99 (dd, 1H, J=6.3 and 3.1 Hz), 4.05-4.28 (m, 3H), 4.50-4.62 (m, 2H), 5.13 (dd, 1H, J=7.0 and 3.2 Hz), 5.19 (dd, 1H, J=6.4 and 2.2 Hz), 5.96 (dd, 1H, J=7.1 and 2.2 Hz) and 7.12-7.36 (m, 15H); $^{13}$C NMR (CDCl$_3$) δ 20.74, 20.76, 20.9, 62.8, 66.9, 68.20, 68.28, 71.6, 72.94, 72.97, 95.5, 120.30, 120.35, 125.7, 128.0, 128.2, 128.5, 129.8, 129.9, 137.1, 150.2, 150.4, 169.9 and 170.6; HRMS (APCI), m/z 569.1598 (M-CH$_3$COO)$^+$ (C$_{29}$H$_{30}$O$_{10}$P requires m/z 569.1576).

Example 9: Synthesis of C2 Modified Mannose Disaccharide-Linkers 57 and 58c

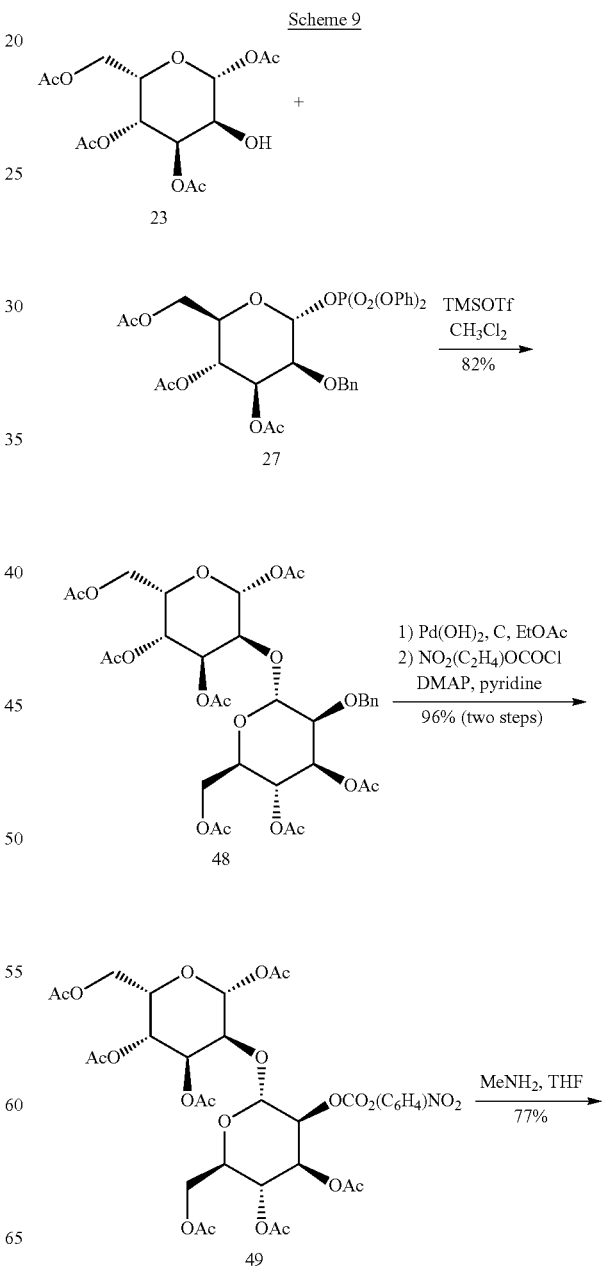

Scheme 9

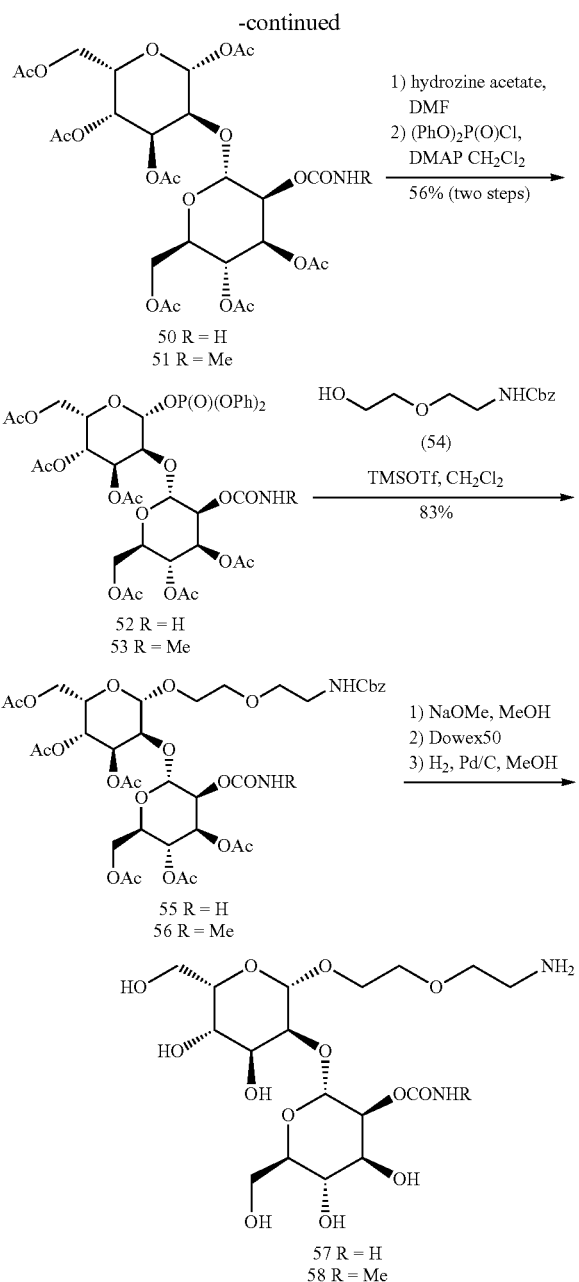

1,3,4,6-Tetra-4-acetyl-2-O-(3,4,6-tri-O-acetyl-2-O-benzyl-α-D-mannopyranosyl)-β-L-gulopyranose (48)

To a stirred solution containing 234 mg (0.67 mmol) of glycosyl acceptor 23 and 508 mg (1.17 mmol) of glycosyl donor 27 in 4.8 mL of anh dichloromethane at 0° C., was added 244 μL (300 mg, 1.35 mmol) of TMSOTf. The reaction mixture was stirred at 0° C. for 10 min at which time it was poured into a two phase mixture of 30 mL of ethyl acetate and 30 mL of said aq NaHCO$_3$. The organic and aqueous layers were separated and the organic layer was washed with two 20-mL portions of brine and dried (MgSO$_4$). The solvent was concentrated under diminished pressure to afford a crude residue. The residue was applied to a silica gel column (30×3 cm). Elution with 2:1 ethyl acetate-hexanes afforded compound 48 as a colorless oil: yield 302 mg (62%); silica gel TLC R$_f$ 0.2 (1:1 ethyl acetate-hexanes); $^1$H NMR (CDCl$_3$) δ 1.84 (s, 3H), 1.94 (s, 3H), 1.99 (s, 3H), 2.04 (s, 3H), 2.08 (s, 3H), 2.09 (m, 6H), 3.51-3.61 (m, 1H), 3.87-4.23 (m, 5H), 4.31 (t, 1H, J=6.3 Hz), 4.44-4.47 (m, 1H), 4.56-4.69 (m, 1H), 4.80-4.97 (m, 2H), 5.02-5.07 (m, 2H), 5.27-5.47 (m, 2H), 5.78 (d, 1H, J=8.5 Hz) and 7.16-7.36 (m, 5H); $^{13}$C NMR (CDCl$_3$) δ 20.61, 20.63, 20.66, 20.67, 20.69, 20.72, 61.3, 62.2, 65.3, 65.7, 66.0, 67.7, 68.8, 69.2, 70.4, 71.3, 72.2, 73.9, 90.6, 94.2, 127.7, 128.1, 128.2, 137.6, 168.7, 169.36, 169.37, 169.4, 170.0, 170.3 and 170.6; mass spectrum (APCI), m/z 727.2453 (M+H)$^+$ (C$_{33}$H$_{43}$O$_{41}$ requires 727.2450).

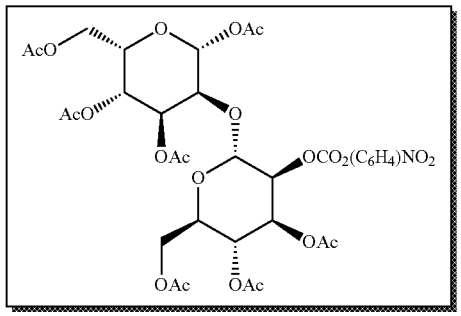

1,3,4,6-Tetra-O-acetyl-2-O-(3,4,6-tri-O-acetyl-2-O-((p-nitrophenyl)carbamoyl)-α-D-mannopyranosyl)-β-L-gulopyranose (49)

To a solution containing 200 mg (0.27 mmol) of disaccharide 48 in 38 mL of ethyl acetate was added a catalytic amount of Pd(OH)$_2$/C and the reaction mixture was stirred overnight under 1 atm of H$_2$. The solvent was filtered through a pad of Celite 545® and the filtrate was concentrated under diminished pressure to afford a crude residue. The residue was used for the next reaction; silica gel TLC R$_f$ 0.08 (1:1 ethyl acetate-hexanes).

To a solution containing 198 mg (0.31 mmol) of the crude residue in 1.2 mL of anh pyridine was added 151 mg (1.24 mmol) of DMAP and 276 mg (1.24 mmol) of p-nitrophenyl chloroformate. The reaction mixture was stirred at 40° C. overnight at which time it was poured into a mixture of 30 mL ethyl acetate and 10 mL of H$_2$O. The organic and aqueous layers were separated and the organic layer was washed with three 10-mL portions of 1 N HCl and 10 mL of satd aq NaHCO$_3$ and then brine. The solution was dried

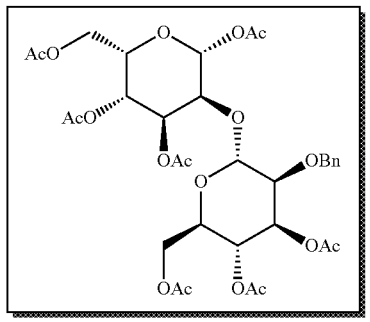

(MgSO$_4$) and filtered and the filtrate was concentrated under diminished pressure to afford a crude residue. The residue was applied to a silica gel column (25×3 cm). Elution with 1:1 ethyl acetate-hexanes afforded 49 as a colorless foam: yield 211 mg (96% over two steps); silica gel TLC R$_f$ 0.30 (1:1 ethyl acetate-hexanes); $^1$H NMR (CDCl$_3$) δ 1.98 (m, 3H), 2.03 (s, 6H), 2.10 (s, 3H), 2.12 (s, 3H), 2.14 (s, 3H), 2.17 (s, 3H), 3.96-4.18 (m, 2H), 4.19-4.29 (m, 2H), 4.35 (t, 1H, J=6.5 Hz), 4.96-5.03 (m, 2H), 5.06-5.23 (m, 3H), 5.27-5.40 (m, 2H), 5.44 (t, 1H, J=3.0 Hz), 5.88 (d, 1H, J=8.4 Hz), 7.39 (d, 2H, J=8.0 Hz) and 8.26 (d, 2H, J 9.1 Hz); $^{13}$C NMR (CDCl$_3$) δ 20.70, 20.72, 20.75, 20.76, 20.9, 61.3, 62.0, 65.5, 65.7, 67.8, 68.8, 69.4, 70.1, 71.4, 73.5, 90.6, 94.5, 121.7, 125.4, 145.6, 149.8, 151.6, 155.3, 168.7, 169.3, 169.5, 169.7, 169.7, 170.5 and 170.6; HRMS (APCI), m/z 802.2053 (M+H)$^+$ (C$_{33}$H$_{40}$NO$_{22}$ requires nm/z 802.2042).

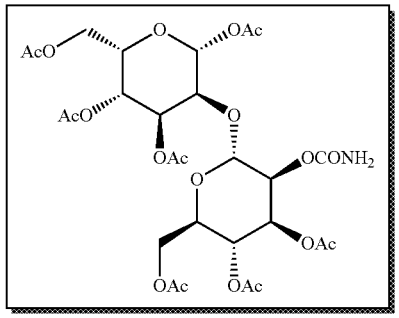

1,3,4,6-Tetra-O-acetyl-2-O-(3,4,6-tri-O-acetyl-2-O-(carbamoyl)-α-D-mannopyranosyl)-β-L-gulopyranose (50)

To a solution containing 94 mg (0.12 mmol) of 49 in 5.0 mL of dichloromethane was added 2.2 mL of THE saturated with NH$_3$. The reaction mixture was stirred at room temperature for 3 h. The solvent was concentrated under diminished pressure to afford a crude residue. The residue was purified by flash chromatography on a silica gel column (2.5×15 cm). Elution with 3:1 ethyl acetate-hexanes afforded 50 as a white foam: yield 73 mg (92%); silica gel TLC R$_f$ 0.13 (3:1 ethyl acetate-hexanes). $^1$H NMR (CDCl$_3$) δ 1.98 (s, 3H), 2.02 (s, 3H), 2.04 (s, 3H); 2.11 (s, 3H), 2.13 (s, 3H), 2.14 (s, 3H), 2.18 (s, 3H), 3.98 (dd, 1H, J=8.4, 3.3 Hz), 4.06-4.11 (m, 2H), 4.14-4.15 (m, 1H), 4.17-4.19 (m, 1H), 4.22-4.27 (m, 1H), 4.33-4.37 (m, 1H), 4.85 (br s, 2H), 4.95-4.97 (m, 1H), 5.00-5.02 (m, 2H), 5.08-5.14 (m, 1H), 5.22-5.27 (m, 1H), 5.44 (t, 1H, J=3.6 Hz), 5.89 (d, 1H, J=8.4 Hz); $^{13}$C NMR (CDCl$_3$) δ 20.62, 20.65, 20.68, 20.71, 20.82, 61.35, 62.11, 65.59, 65.74, 67.59, 68.88, 69.10, 69.43, 69.79, 71.30, 90.67, 95.29, 154.88, 168.68, 169.21, 169.64, 169.87, 170.43, 170.53; mass spectrum (APCI), m/z 680.2026 (M+H)$^+$ (C$_{27}$H$_{38}$O$_{19}$ requires m/z 680.2038).

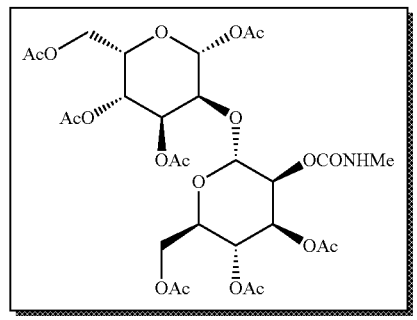

1,3,4,6-Tetra-O-acetyl-2-O-(3,4,6-tri-O-acetyl-2-O-(methylcarbamoyl)-α-D-mannopyranosyl)-β-L-gulopyranose (51)

To a solution containing 201 mg (0.25 mmol) of nitrophenyl ester 49 in 6 mL of anh THF was added dropwise at 0° C. 125 μL (2 M solution in THF, 0.25 mmol) of CH$_3$NH$_2$. The reaction mixture was stirred at room temperature for 15 h at which time silica gel TLC analysis indicated that the reaction was complete. The solvent was concentrated under diminished pressure to afford a crude residue. The residue was applied to a silica gel column (25×3 cm). Elution with 1:1 ethyl acetate-hexanes afforded disaccharide 51 as a colorless oil: yield 134 mg (77%); silica gel TLC R$_f$ 0.14 (1:1 ethyl acetate-hexanes); $^1$H NMR (CDCl$_3$) δ 1.94 (s, 3H), 1.98-2.15 (m, 18H), 2.75 (d, 3H, J=3.7 Hz), 3.93-4.13 (m, 4H), 4.18-4.22 (m, 2H), 4.30-4.33 (m, 1H), 4.87-5.10 (m, 4H), 5.17-5.21 (m, 2H) and 5.33 (m, 2H); $^{13}$C NMR (CDCl$_3$) δ 20.62, 20.63, 20.68, 20.72, 20.75, 20.77, 20.85, 27.6, 61.4, 62.0, 65.9, 67.6, 68.0, 70.5, 71.4, 90.7, 93.2, 155.38, 155.40, 155.49, 169.24, 169.27, 169.30, 170.50, 170.51, 170.6 and 170.9; HRMS (APCI), m/z 694.2169 (M+H)$^+$ (C$_{28}$H$_{40}$NO$_{19}$ requires m/z 694.2195).

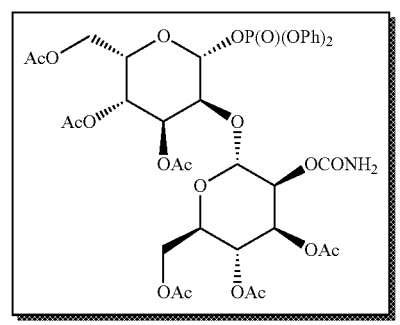

3,4,6-Tri-1-acetyl-2-O-(3,4,6-tri-O-acetyl-2-O-(carbamoyl)-α-D-mannopyranosyl)-β-L-gulopyranosyl Diphenyl Phosphate (52)

To a solution containing 66 mg (0.10 mmol) of disaccharide 50 in 1.0 mL of anh DMF was added 13.0 mg (0.14 mmol) of hydrazine acetate. The reaction mixture was stirred at room temperature for 3 h and quenched by the addition of 14 mL of ethyl acetate. The organic solution was washed with 12 mL of water, 12 mL of satd aq. NaHCO$_3$, 12 mL of brine and then dried (MgSO$_4$). The solvent was concentrated under diminished pressure to afford the crude product as a light yellow oil: yield 56 mg (90%); silica gel TLC $R_f$ 0.23 (1:4 hexanes-ethyl acetate). MALDI, m/z 660.18 for (M+Na)⁺. The residue was used for next reaction.

To a stirred solution containing 56.0 mg (0.09 mmol) of the crude residue in 3.30 mL of anh dichloromethane was added 13.0 mg (0.11 mmol) of DMAP, 133 µL (96 mg, 0.95 mmol) of Et₃N and 176 µL (229 mg, 0.85 mmol) of diphenyl chlorophosphate. The reaction mixture was stirred at 0° C. for 2 h and poured into a mixture of 5 mL of ethyl acetate and 5 mL of satd aq NaHCO₃. The organic layer was washed with three 10-mL portions of water and brine and then dried (MgSO₄). The solvent was concentrated under diminished pressure to afford a crude residue. The residue was applied to a silica gel column (20×2 cm). Elution with 2:1 ethyl acetate-hexanes afforded phosphate ester 52 as a colorless oil: yield 36 mg (47% over two steps); silica gel TLC $R_f$ 0.18 (2:1 ethyl acetate-hexanes); ¹H NMR (CDCl₃) δ 1.77 (s, 3H), 2.03 (s, 3H), 2.05 (s, 3H), 2.13 (s, 3H), 2.21 (s, 3H), 2.27 (s, 3H), 4.03-4.10 (m, 2H), 4.14-4.21 (m, 2H), 4.24-4.28 (m, 1H), 4.36-4.42 (m, 2H), 4.87 (br s, 2H), 5.05-5.10 (m, 3H), 5.24-5.27 (m, 1H), 5.29-5.35 (m, 1H), 5.51-5.53 (m, 1H), 5.75-5.79 (m, 1H), 7.22-7.28 (m, 2H), 7.32-7.43 (m, 8H). ¹³C NMR (CDCl₃) δ 20.3, 20.63, 20.64, 20.68, 20.71, 61.2, 61.8, 65.3, 65.6, 67.4, 69.0, 69.1, 69.5, 71.1, 71.2, 71.6, 95.6, 96.17, 96.22, 120.19, 120.24, 125.57, 125.71, 125.70, 129.6, 129.9, 150.05, 150.10, 154.9, 169.2, 169.6, 169.7, 170.4, 170.6; mass spectrum (APCI), m/z 870.2224 (M+H)⁺ ($C_{37}H_{45}NO_{21}P$ requires m/z 870.2222).

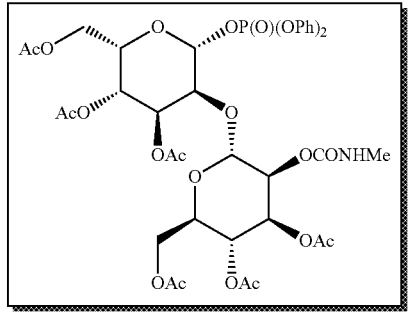

3,4,6-Tri-O-acetyl-2-O-(3,4,6-tri-O-acetyl-2-O-(methylcarbamoyl)-α-D-mannopyranosyl)-β-L-gulopyranosyl Diphenyl Phosphate (53)

To a solution containing 108 mg (0.16 mmol) of disaccharide 51 in 1.2 mL of anh DMF was added 17.0 mg (0.19 mmol) of hydrazine acetate. The reaction mixture was stirred at room temperature for 1.5 h and quenched by the addition of 20 mL of ethyl acetate. The organic solution was washed with three 10-mL portions of brine and dried (MgSO₄). The solvent was concentrated under diminished pressure to afford a crude residue. The residue was used for the next reaction.

To a stirred solution containing 90.0 mg (0.14 mmol) of the crude residue in 8.2 mL of anh dichloromethane was added 21.0 mg (0.17 mmol) of DMAP, 210 µL (152 mg, 1.49 mmol) of Et₃N and 270 µL (351 mg, 1.32 mmol) of diphenyl chlorophosphate. The reaction mixture was stirred at 0° C. for 2 h and poured into a mixture of 40 mL of ethyl acetate and 20 mL of satd aq NaHCO₃. The organic layer was washed with three 10-mL portions of water and brine and then dried (MgSO₄). The solvent was concentrated under diminished pressure to afford a crude residue. The residue was applied to a silica gel column (25×3 cm). Elution with 2:1 ethyl acetate-hexanes afforded phosphate ester 53 as a colorless oil: yield 82 mg (56% over two steps); silica gel TLC $R_f$ 0.18 (2:1 ethyl acetate-hexanes); ¹H NMR (CDCl₃) δ 1.67 (s, 3H), 1.94 (d, 6H, J=7.4 Hz), 2.01 (s, 3H), 2.11 (s, 3H), 2.16 (s, 3H), 2.76 (s, 3H), 3.89-4.39 (m, 7H), 4.75-5.05 (m, 4H), 5.10-5.30 (m, 2H), 5.44 (s, 1H), 5.68 (s, 1H) and 7.11-7.39 (m, 10H); ¹³C NMR (CDCl₃) δ 20.4, 20.70, 20.76, 20.8, 20.9, 27.7, 61.2, 62.0, 65.5, 65.8, 67.5, 69.1, 69.3, 69.4, 71.4, 71.5, 71.7, 95.9, 96.34, 120.31, 120.33, 125.6, 125.72, 125.78, 125.83, 129.7, 130.0, 155.4, 169.3, 169.7, 169.8, 170.4, 170.67 and 170.68; HRMS (APCI), m/z 884.2371 (M+H)⁺ ($C_{38}H_{47}NO_{19}$ requires m/z 884.2378).

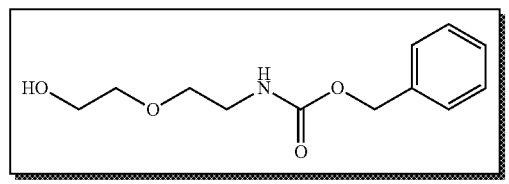

Benzyl 2-(2-Hydroxyethoxy)ethylcarbamate (54)

To a solution containing 1.01 g (9.61 mmol) of 2-(2-aminoethoxy)ethanol in 100 mL of THF at room temperature was added 1.34 mL (9.61 mmol) of Et₃N and 1.49 mL (1.78 g, 10.6 mmol) of CBzCl. The reaction mixture was stirred for 1 h and was then diluted with 250 mL of ethyl acetate. The organic layer was washed with two 250-mL portions of H₂O, two 250-mL portions of brine, and was then dried (MgSO₄) and concentrated under diminished pressure. The residue was purified by flash chromatography on a silica gel column (30×4 cm). Elution with 9:1 ethyl acetate-hexanes afforded alcohol 54 as a colorless oil: yield 2.21 g (96%); silica gel TLC $R_f$ 0.30 (9:1 ethyl acetate-hexanes); ¹H NMR (CDCl₃) 3.30 (m, 2H), 3.45 (m, 4H), 3.52 (s, 1H), 3.62 (m, 2H), 5.03 (s, 2H), 5.86 (m, 1H) and 7.27 (m, 5H); ¹³C NMR (CDCl₃) 40.5, 61.1, 66.3, 69.7, 72.0, 127.72, 127.75, 128.1, 136.3 and 156.5.

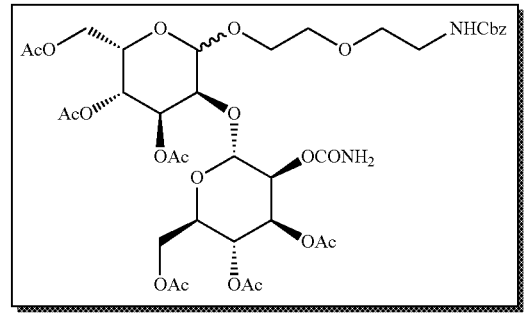

3,4,6-Tri-O-acetyl-2-O-(3,4,6-tri-O-acetyl-2-O-(carbamoyl)-α-D-mannopyranosyl)-α,β-L-gulopyranosyl Benzyl 2-(2-Ethoxy)ethylcarbamate (55)

To a stirred solution containing 31.0 mg (0.04 mmol) of phosphate ester 52 in 3.9 mL, of anh dichloromethane was added a solution of 9.40 mg (0.04 mmnl) of CBz linker 54 in 4.5 mL of anh dichloromethane at 0° C. To the cooled reaction mixture was then added 41.0 μL (51.0 mg, 0.23 mmol) of TMSOTf and the reaction mixture was stirred at 0° C. for 15 min at which time it was poured into a mixture of 20 mL of ethyl acetate and 20 mL of said aq NaHCO$_3$. The aqueous and organic layers were separated and the organic layer was washed with three 10-mL portions of water and brine, and then dried (MgSO$_4$). The solvent was concentrated under diminished pressure to afford a crude residue. The residue was applied to a silica gel column (12×2 cm). Elution with 3:1 ethyl acetate-hexanes afforded disaccharide-linker conjugate 55 as a colorless oil: yield 12 mg (39%); silica gel TLC R$_f$ 0.12 (3:1 ethyl acetate-hexanes); $^1$H NMR (CDCl$_3$) δ 1.99 (s, 3H), 2.02 (s, 2H), 2.04 (s, 3H), 2.07 (s, 3H), 2.09 (s, 3H), 2.12 (s, 3H), 3.37-3.42 (m, 2H), 3.55-3.65 (m, 3H), 3.67-3.69 (m, 2H), 3.83-3.88 (m, 1H), 3.97 (t, 1H, J=3.9 Hz), 4.03-4.09 (m, 2H), 4.10-4.15 (m, 1H), 4.28 (dd, 1H, J=11.9, 5.2 Hz), 4.46 (t, 1H, J=6.6 Hz), 4.77-4.90 (br s, 2H), 4.93 (d, J=3.9 Hz, 1H), 5.03-5.06 (m, 3H), 5.09 (s, 2H), 5.23-5.29 (m, 3H), 5.46-5.48 (m, 1H), 7.28-7.37 (m, 5H); $^{13}$C NMR (CDCl$_3$) δ 20.62, 20.65, 20.72, 20.76, 40.9, 62.1, 62.5, 63.8, 65.8, 66.1, 66.6, 67.6, 68.6, 68.7, 69.0, 70.07, 70.16, 70.3, 71.0, 77.2, 97.0, 97.6, 128.10, 128.18, 128.5, 136.5, 155.0, 169.3, 169.72, 169.73, 170.0, 170.56, 170.59; mass spectrum (APCI), m/z 859.2987 (M+H)$^+$ (C$_{37}$H$_{51}$N$_2$O$_{21}$ requires m/z 859.2984).

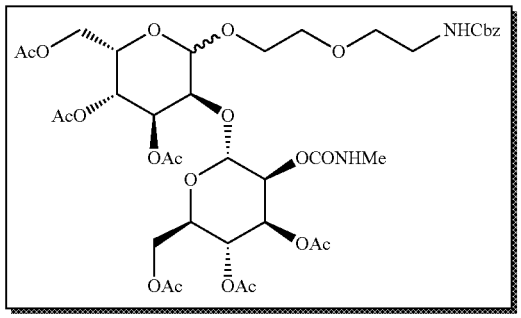

3,4,6-Tri-1-acetyl-2-O-(3,4,6-tri-O-acetyl-2-O-(methylcarbamoyl)-α-D-mannopyranosyl)-α,β-L-gulopyranosyl Benzyl 2-(2-Ethoxy)ethylcarbamate (56)

To a stirred solution containing 90.0 mg (0.10 mmol) of phosphate ester 53 in 1.1 mL of anh dichloromethane was added a solution of 22.0 mg (0.09 mmol) of CBz linker 54 in 1.1 mL of anh dichloromethane at 0° C. To the cooled reaction mixture was then added 33.0 μL (41.0 mg, 0.18 mmol) of TMSOTf and the reaction mixture was stirred at 0° C. for 15 min at which time it was poured into a mixture of 20 mL of ethyl acetate and 20 mL of satd aq NaHCO$_3$. The aqueous and organic layers were separated and the organic layer was washed with three 10-mL portions of water and brine, then dried (MgSO$_4$). The solvent was concentrated under diminished pressure to afford a crude residue. The residue was applied to a silica gel column (25×3 cm). Elution with 12:12:1 ethyl acetate-hexanes-methanol afforded disaccharide-linker conjugate 56 as a colorless oil: yield 56 mg (63%); silica gel TLC R$_f$ 0.20 (12:12:1 ethyl acetate-hexanes-methanol); $^1$H NMR (CDCl$_3$) δ 1.96 (s, 3H), 2.00 (s, 3H), 2.01 (s, 3H), 2.05-2.08 (m, 6H), 2.10 (s, 3H), 2.78 (d, 3H, J=4.6 Hz), 3.38 (d, 2H, J=4.4 Hz), 3.51-3.70 (m, 4H), 3.78-3.87 (m, 1H), 3.95 (d, 1H, J=3.5 Hz), 4.00-4.15 (m, 4H), 4.20-4.30 (m, 2H), 4.45 (t, 1H, J=6.1 Hz), 4.89-5.12 (m, 6H), 5.20-5.30 (m, 3H), 5.42-5.49 (m, 1H), 5.46 (s, 1H) and 7.27-7.38 (m, 5H); $^{13}$C NMR (CDCl$_3$) δ20.71, 20.73, 20.77, 20.80, 20.84, 20.88, 27.7, 62.3, 62.7, 63.9, 66.0, 66.3, 66.7, 68.7, 68.9, 69.2, 70.1, 70.2, 70.4, 97.2, 97.9, 128.21, 128.23, 128.28, 128.59, 128.61, 136.7, 155.5, 169.4, 169.80, 169.84, 170.0, 170.66 and 170.69; HRMS (APCI), m/z 873.3166 (M+H)$^+$ (C$_{38}$H$_{53}$N$_2$O$_{21}$ requires m/z 873.3141).

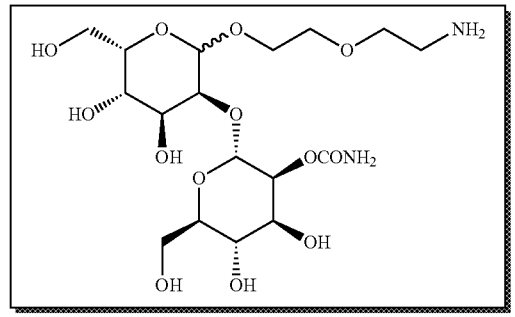

(2-O-carbamoyl-α-D-mannopyranosyl)-α,β-L-gulopyranosyl 2-(2-aminoethoxy)ethanol (57)

To a solution of 2.20 mg (2.60 μmol) of compound 55 in 1 mL of anh methanol was added a freshly prepared solution of 0.4 M sodium methoxide in methanol. The reaction mixture was allowed to stir at room temperature for 3 h, and the complete consumption of starting material was confirmed by MALDI-TOF mass spectral analysis. The reaction mixture was then quenched by the addition of 500 mg of Dowex 50x resin, shaken for 15 min and filtered. To the solution of the crude product in methanol was added Pd/C and H$_2$ gas was bubbled through for 1 h. The complete consumption of starting material was confirmed by MALDI-TOF mass spectral analysis. The reaction mixture was filtered through Celite 545® and then concentrated under diminished pressure to afford 57, which was used for the next reaction. HRMS (APCI), m/z 473.1986 (M+H)$^+$ (C$_{17}$H$_{33}$N$_2$O$_{13}$ requires m/z 473.1983).

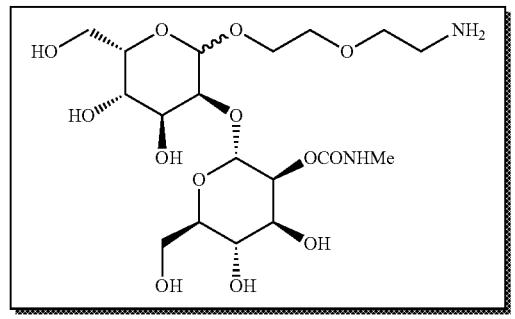

(2-O-(methylcarbamoyl-)α-D-mannopyranosyl)-α,β-L-gulopyranosyl 2-(2-aminoethoxy)ethanol (58)

To a solution of 4.40 mg (5.00 μmol) of compound 56 in 2 mL of anh methanol was added a freshly prepared solution of 0.4 M sodium methoxide in methanol. The reaction mixture was allowed to stir at room temperature for 3 h, and the complete consumption of starting material was confirmed by MALDI-TOF mass spectral analysis. The reaction mixture was then quenched by the addition of 500 mg of Dowex 50× resin, shaken for 15 min and filtered. To the solution of the crude product in methanol was then added Pd/C and H₂ gas was bubbled through for 1 h. The complete consumption of starting material was confirmed by MALDI-TOF mass spectral analysis. The reaction mixture was filtered through Celite 545® and concentrated under diminished pressure to afford 58, which was used for the next reaction; HRMS (APCI), m/z 487.2140 (M+H)⁺ ($C_{18}H_{35}N_2O_{13}$ requires m/z 487.2139).

Example 10: Synthesis of C3 Modified Mannose Disaccharide-Linker 64

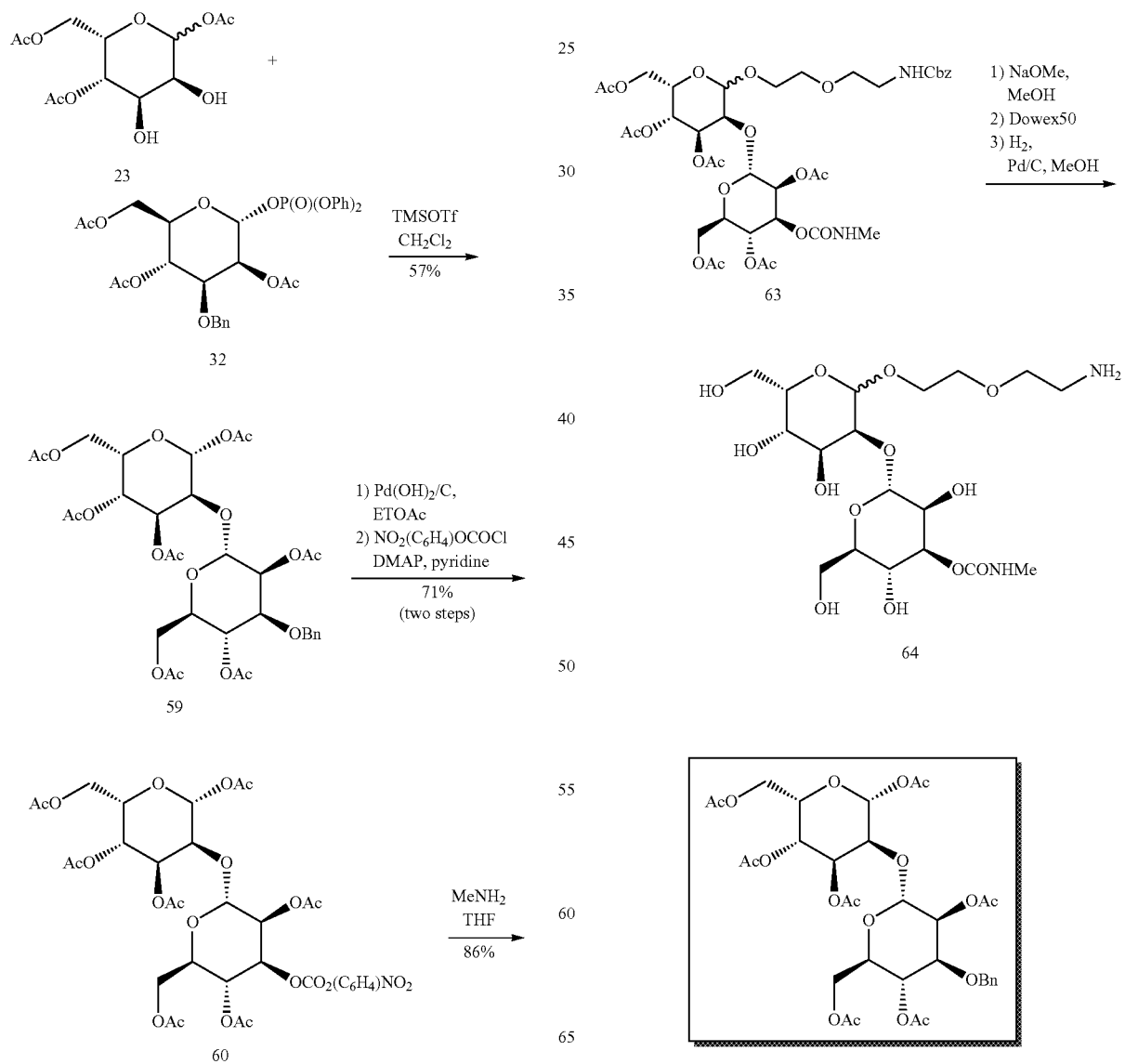

1,3,4,6-Tetra-O-acetyl-2-O-(2,4,6-tri-O-acetyl-3-O-benzyl-α-D-mannopyranosyl)-β-L-gulopyranose (59)

To a stirred solution containing 340 mg (098 mmol) of gulose acceptor 23 and 737 mg (1.17 mmol) of mannose donor 32 in 7.0 mL of anh dichloromethane cooled to 0° C. was added 352 μL (526 mg, 1.95 mmol) of TMSOTf at 0° C. The reaction mixture was stirred for 10 min at which time it was poured into a mixture of 30 mL of ethyl acetate and 30 mL of said aq NaHCO$_3$. The organic and aqueous layers were separated and the organic layer was washed with two 20-mL portions of brine and dried (MgSO$_4$). The solvent was concentrated under diminished pressure to afford a crude residue. The residue was applied to a silica gel column (30×3 cm). Elution with 2:1 ethyl acetate-hexanes afforded disaccharide 59 as a colorless oil: yield 407 mg (57%); silica gel TLC R$_f$ 0.31 (1:1 ethyl acetate-hexanes); $^1$H NMR (CDCl$_3$) δ 1.92 (s, 3H), 2.00-2.01 (m, 6H, J=2.8 Hz), 2.04 (s, 3H, J=5.3 Hz), 2.08 (d, 6H, J=1.9 Hz), 2.12 (s, 3H), 3.61 (ddd, 0.1, J=12.7, 9.6 and 3.3 Hz, 3.84-3.95 (m, 2H), 3.96-4.20 (m, 4H), 4.26-4.37 (m, 2H), 4.59 (t, 1H, J=10.4 Hz), 4.90-5.18 (m, 4H), 5.39 (dd, 1H, J=11.1 and 3.3 Hz), 5.86 (d, 1H, J=8.3 Hz) and 7.24 (m, 5H); $^{13}$C NMR (CDCl$_3$) δ 20.56, 20.59, 20.61, 20.64, 20.65, 20.75, 20.78, 61.4, 62.3, 65.5, 66.9, 67.2, 67.5, 69.4, 71.3, 73.8, 90.5, 95.1, 127.6, 127.7, 127.9, 128.3, 137.4, 168.7, 168.8, 168.9, 169.1, 169.4, 169.6, 170.3 and 170.4; mass spectrum (APCI), m/z 727.2444 (M+H)$^+$ (C$_{33}$H$_{43}$O$_{18}$ requires 727.2450).

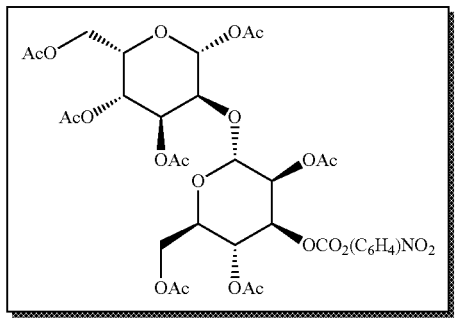

1,3,4,6-Tetra-O-acetyl-2-O-(2,4,6-tri-O-acetyl-3-O-((p-nitrophenyl)carbamoyl)-α-D-mannopyranosyl)-β-L-gulopyranose (60)

To a solution containing 470 mg (0.56 mmol) of disaccharide 59 in 40 mL of ethyl acetate was added a catalytic amount of Pd(OH)$_2$/C and the reaction mixture was stirred overnight under 1 atm of H$_2$. The solvent was filtered through a pad of Celite 545® and the filtrate was concentrated under diminished pressure to afford a crude residue. The residue was used for the next reaction; silica gel TLC R$_f$ 0.16 (1:2 ethyl acetate-hexanes); mass spectrum (APCI), m/z 637.1993 (M+H)$^+$ (C$_{26}$H$_{37}$O$_{18}$ requires 637.1980).

To a solution containing 338 mg (0.53 mmol) of the crude residue in 2 mL of pyridine was added 259 mg (2.12 mmol) of DMAP and 471 mg (2.12 mmol) of p-nitrophenyl chloroformate. The reaction mixture was stirred at 40° C. overnight at which time it was poured into a mixture of 30 mL of ethyl acetate and 10 mL of distilled water. The organic and aqueous layers were separated and the organic layer was washed with three 10-mL portions of 1 N HCl and 10 mL of satd aq NaHCO$_3$. The organic layer was then washed with brine and dried (MgSO$_4$). The solvent was concentrated under diminished pressure to afford a crude residue. The residue applied to a silica gel column (25×3 cm). Elution with 1:1 ethyl acetate-hexanes afforded the ester 60 as a colorless foam: yield 320 mg (71% over two steps); silica gel TLC R$_f$ 0.24 (1:1 ethyl acetate-hexanes); $^1$H NMR (CDCl$_3$) δ 1.99 (s, 3H), 2.05 (s, 3H), 2.06-2.14 (m, 15H), 3.95 (dd, 1H, J=8.4 and 3.0 Hz), 3.99-4.16 (m, 4H), 4.16-4.27 (m, 2H), 4.30 (dd, 1H, J=15.0 and 8.7 Hz), 5.21-5.35 (m, 2H), 5.39 (dd, 1H, J=14.8 and 11.5 Hz), 4.91-5.08 (m, 2H), 5.84 (d, 1H, J=8.4 Hz), 7.33 (d, 2H, J=9.0 Hz) and 8.21 (d, 2H, J=9.0 Hz); $^{13}$C NMR (CDCl$_3$) δ 20.57, 20.63, 20.64, 20.70, 20.71, 20.8, 61.3, 61.9, 65.3, 65.5, 67.6, 67.7, 69.2, 69.8, 71.3, 74.3, 90.5, 94.9, 122.0, 125.3, 145.6, 151.4, 155.2, 168.6, 169.2, 169.37, 169.41, 169.7, 170.36 and 170.43; mass spectrum (APCI), m/z 742.1841 (M-AcOH)$^+$ (C$_{31}$H$_{36}$NO$_{20}$ requires 742.1831).

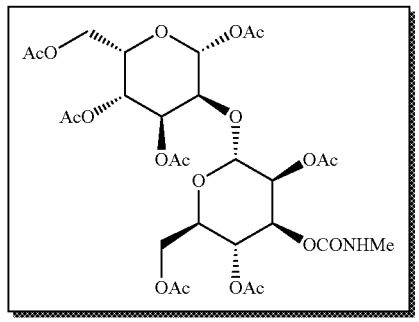

1,3,4,6-Tetra-O-acetyl-2-O-(2,4,6-tri-O-acetyl-3-O-(methylcarbamoyl)-α-D-mannopyranosyl)-β-L-gulopyranose (61)

To a solution containing 320 mg (0.40 mmol) of disaccharide 60 in 12 mL of THF was added 200 μL (0.4 mmol) of 2 M methylamine in THF at 0° C. The reaction mixture was stirred at room temperature for 15 h at which time silica gel TLC analysis indicated that the reaction was complete. The solvent was concentrated under diminished pressure to afford a crude residue. The residue was applied to a silica gel column (25×3 cm). Elution with 1:1 ethyl acetate-hexanes afforded disaccharide 61 as a colorless oil: yield 239 mg (86%); silica gel TLC R$_f$ 0.17 (1:1 ethyl acetate-hexanes); $^1$H NMR (CDCl$_3$) δ 1.98 (d, 6H, J=7.5 Hz), 2.03-2.11 (m, 12H), 2.13 (d, 3H, J=8.8 Hz), 2.69 (d, 3H, J=4.2 Hz), 3.88-4.22 (m, 6H), 4.31 (t, 1H, J=6.0 Hz), 4.67 (d, 1H, J=4.1 Hz), 4.89-5.01 (m, 2H), 5.00-5.10 (m, 2H), 5.12-5.20 (m, 1H), 5.38 (s, 1H) and 5.82 (d, 1H, J=8.3 Hz); $^{13}$C NMR (CDCl$_3$) δ 20.66, 20.69, 20.71, 20.79, 27.6, 61.4, 62.1, 65.4, 66.0, 67.7, 69.17, 69.27, 69.33, 69.38, 71.31, 77.36, 90.6, 94.8, 155.4, 168.6, 169.2, 169.4, 169.8, 170.42 and 170.49; mass spectrum (APCI), m/z 694.2206 (M+H)$^+$ (C$_{28}$H$_{40}$NO$_{19}$ requires 694.2195).

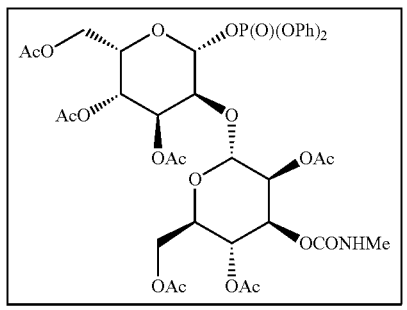

3,4,6-Tri-O-acetyl-2-O-(2,4,6-tri-O-acetyl-3-O-(methylcarbamoyl)-α-D-mannopyranosyl)-β-L-gulopyranosyl Diphenyl Phosphate (62)

To a solution containing 65.0 mg (0.09 mmol) of disaccharide 61 in 0.8 mL of anh DMF was added 11.0 mg (0.11 mmol) of hydrazine acetate. The reaction mixture was stirred at room temperature for 1.5 h and quenched by the addition of 20 mL of ethyl acetate. The organic layer was washed with three 10-mL portions of brine and dried (MgSO$_4$). The solvent was concentrated under diminished pressure to afford a crude residue which was used for next reaction; mass spectrum (APCI), m/z 652.2086 (M+H)$^+$ ($C_{26}H_{38}NO_{18}$ requires 652.2089).

To a stirred solution containing 43.0 mg (0.07 mmol) of the crude residue in 4.0 mL of anh dichloromethane was added 10.0 mg (0.08 mmol) of DMAP and 100 μL (72.0 mg, 0.71 mmol) of Et$_3$N and 131 μL (170 mg, 0.06 mmol) of diphenyl chlorophosphate. The reaction mixture was stirred at 0° C. for 2 h and then poured into a mixture of 40 mL of ethyl acetate and 20 mL of satd aq NaHCO$_3$. The organic and aqueous layers were separated and the organic layer was washed with three 10-mL portions of water and brine and then dried (MgSO$_4$). The solvent was concentrated under diminished pressure to afford a crude residue. The residue was applied to a silica gel column (25 k 3 cm). Elution with 2:1 ethyl acetate-hexanes afforded phosphate ester 62 as a colorless oil: yield 44 mg (76% over two steps); silica gel TLC R$_f$ 0.25 (3:1 ethyl acetate-hexanes); $^1$H NMR (CDCl$_3$) δ 1.70 (s, 3H), 1.98 (s, 3H), 2.06 (s, 3H), 2.12 (d, 6H, J=11.4 Hz), 2.21 (s, 3H), 2.75 (d, 3H, J=4.5 Hz), 3.93-4.22 (m, 5H), 4.25-4.40 (m, 2H), 4.56 (d, 1H, J=4.6 Hz), 4.93-5.05 (m, 2H), 5.12-5.24 (m, 2H), 5.29 (s, 1H), 5.44 (s, 1H), 5.65-5.73 (m, 1H) and 7.13-7.40 (m, 10H); $^{13}$C NMR (CDCl$_3$) δ 20.5, 20.9, 27.7, 36.7, 61.3, 62.0, 65.7, 67.5, 69.2, 69.4, 69.7, 71.2, 71.3, 71.7, 95.6, 96.29, 96.34, 120.36, 120.41, 125.7, 125.8, 129.7, 130.0, 150.2, 150.3, 150.4, 150.5, 155.3, 169.36, 169.42, 169.49, 169.9, 170.5 and 170.7; mass spectrum (APCI), m/z 884.2369 (M+H)$^+$ ($C_{38}H_{47}O_{21}PN$ requires 884.2378).

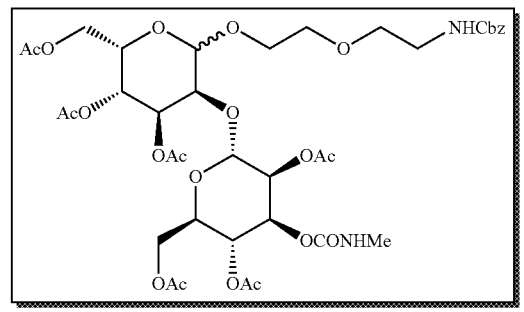

3,4,6-Tri-O-acetyl-2-O-(2,4,6-tri-O-acetyl-3-O-(methylcarbamoyl)-α-D-mannopyranosyl)-α,β-L-gulopyranosyl Benzyl 2-(2-Ethoxy)ethylcarbamate (63)

To a stirred solution containing 44 mg (50 μmol) of the phosphate ester 62 in 0.6 mL of anh dichloromethane was added a solution of 1 mg (40 lμmol) of the CBz-protected linker 54 in 0.6 mL of anh dichloromethane at 0° C. To the cooled reaction mixture was added 16 μL (20 mg, 90 μmol) of TMSOTf and the reaction mixture was stirred at 0° C. for 15 min. The reaction mixture was poured into a mixture of 10 mL ethyl acetate and 10 mL satd aq NaHCO$_3$. The organic and aqueous layers were separated and the organic layer was washed with three 10-mL portions of water and brine and then dried (MgSO$_4$). The organic layer was concentrated under diminished pressure to afford a crude residue. The residue was applied to a silica gel column (25×3 cm). Elution with 12:12:1 ethyl acetate-hexanes-methanol afforded linker conjugate 63 as a colorless oil. The product was isolated as a (5:3) mixture of anomers: yield 32 mg (73%); silica gel TLC R$_f$ 0.11 (12:12:1 ethyl acetate-hexanes-methanol); $^1$H NMR (CDCl$_3$) (major anomer) δ 2.03 (s, 3H), 2.05 (s, 3H), 2.06-2.15 (m, 12H), 2.71 (d, 3H, J=4.8 Hz), 3.40 (s, 1H), 3.51-3.74 (m, 614H), 3.79-3.89 (m, 1H), 3.92-4.01 (m, 1H), 3.99-4.21 (m, 4H), 4.21-4.41 (m, 2H), 4.55-4.63 (m, 2H), 4.89-5.04 (m, 2H), 5.09 (d, 2H, J=5.6 Hz), 5.12-5.30 (m, 3H), 5.32-5.41 (m, 1H), 5.65-5.73 (m, 1H) and 7.27-7.39 (m, 5H); $^{13}$C NMR (CDCl$_3$) δ 20.78, 20.83, 20.87, 20.91, 20.93, 20.98, 21.0, 27.67, 27.69, 40.9, 41.1, 53.6, 61.8, 61.9, 62.3, 62.7, 63.9, 65.6, 65.7, 66.1, 66.4, 66.7, 67.9, 68.0, 68.6, 68.8, 69.0, 69.3, 69.5, 69.72, 69.76, 70.0, 70.1, 70.3, 70.4, 70.52, 70.55, 70.7, 72.3, 97.1, 97.2, 120.38, 120.43, 128.2, 128.3, 128.60, 128.65, 129.8, 130.0, 136.8, 155.7, 156.7, 169.33, 169.37, 169.39, 169.47, 169.54, 169.6, 170.0, 170.5, 170.6, 170.7, 170.8 and 170.9; mass spectrum (APCI), m/z 873.3150 (M+H)$^+$ ($C_{38}H_{53}N_2O_{21}$ requires 873.3141).

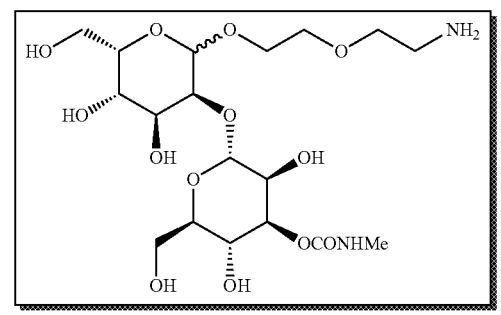

(3-O-(methylcarbamoyl)-α-D-mannopyranosyl)-α,β-L-gulopyranosyl 2-(2-aminoethoxy)ethanol (64)

To a solution of 5.80 mg (6.60 μmol) of compound 63 in 2 mL of anh methanol was added a freshly prepared solution of 0.4 M sodium methoxide in methanol. The reaction mixture was allowed to stir at room temperature for 3 h, and the complete consumption of starting material was confirmed by MALDI-TOF mass spectral analysis. The reaction mixture was then quenched by the addition of 500 mg of Dowex 50× resin, shaken for 15 min and filtered. To the solution of the crude product in methanol was added Pd/C and H$_2$ gas was bubbled through for 1 h. The complete consumption of starting material was confirmed by MALDI-TOF mass spectral analysis. The reaction mixture was filtered through Celite 545® and then concentrated under diminished pressure to afford 64, which was used for the next reaction. HRMS (APCI), m/z 487.2133 (M+H)$^+$ (C$_{18}$H$_{35}$N$_2$O$_{13}$ requires m/z 487.2139).

Example 11: Synthesis of C4 Modified Mannose Disaccharide-Linker 73 and 74

Scheme 11

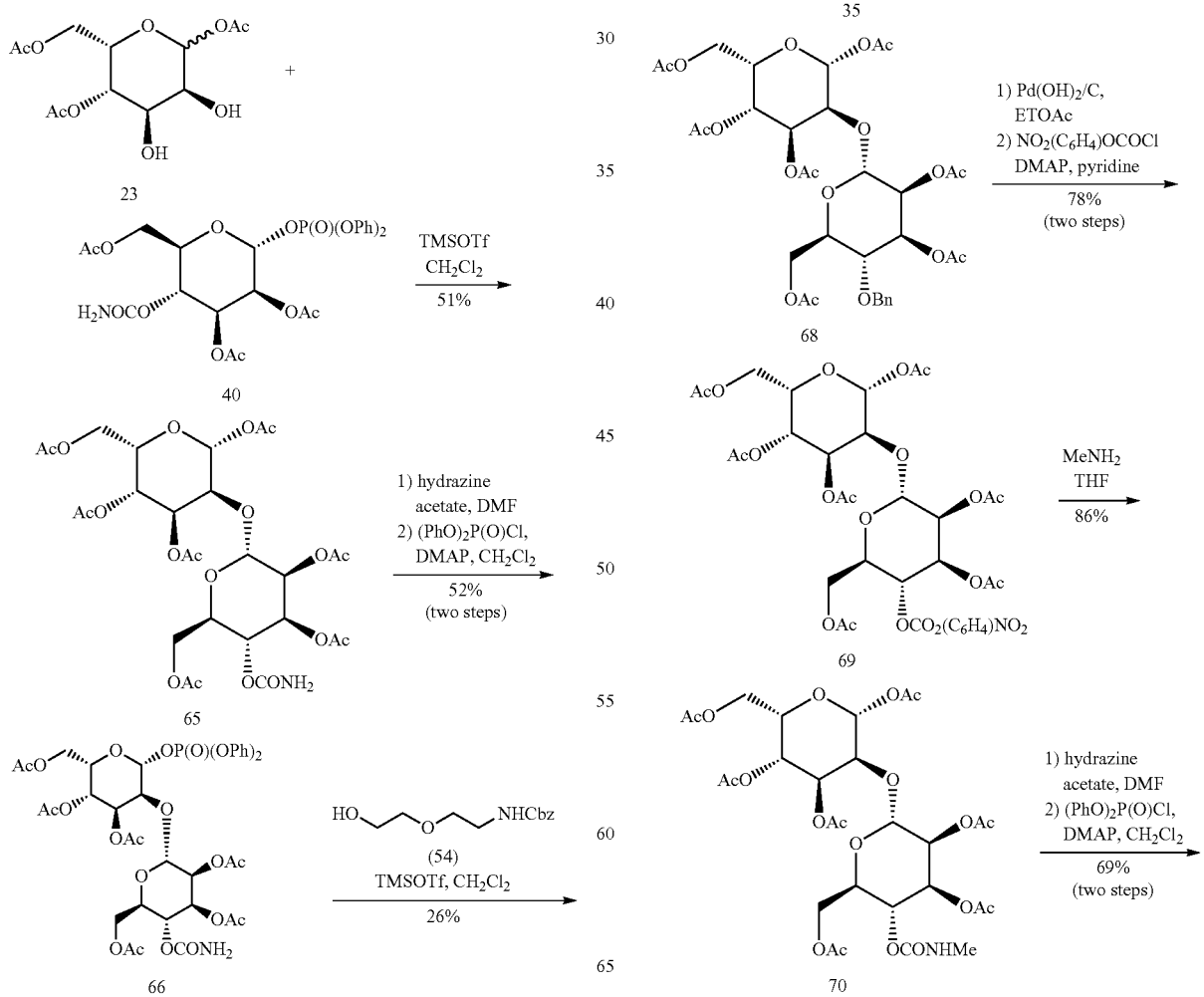

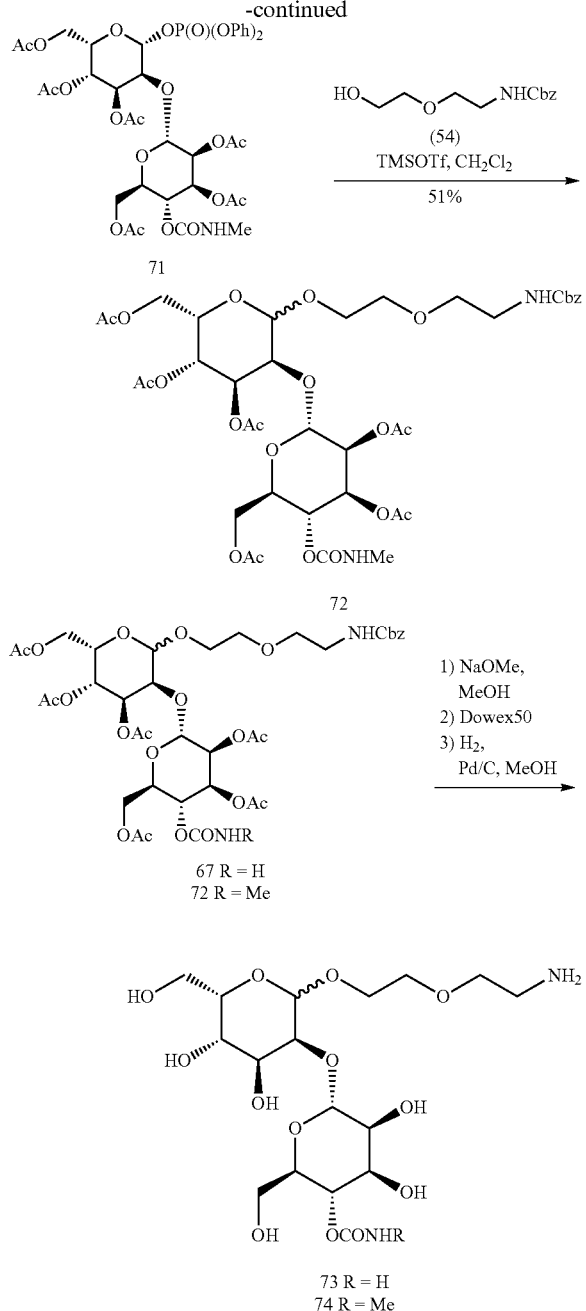

1,3,4,6-Tetra-O-acetyl-2-O-(2,3,6-tri-O-acetyl-4-O-(carbamoyl)-α-D-mannopyranosyl)-β-L-gulopyranose (65)

To activated molecular sieves, a solution of 460 mg (0.79 mmol) of 23 in 5.10 mL of dichloromethane and 191 mg (0.33 mmol) of 40 in 4.80 mL of dichloromethane were added. The solution was cooled to 0° C., and was then treated with 220 µL (1.22 mmol) of TMSOTf. The reaction mixture was stirred for 20 min at which time it was poured into a two phase solution of 70 mL of ethyl acetate and 43 mL of said aq. NaHCO₃. The organic layer was washed with two 50-mL portions of brine, dried (MgSO₄) and concentrated under diminished pressure to afford a crude residue. The residue was purified by flash chromatography on a silica gel column (25×3 cm). Elution with 3:1 ethyl acetate-hexanes afforded 65 as a colorless oil: yield 275 mg (51%); silica gel TLC $R_f$ 0.26 (3:1 ethyl acetate-hexanes). $^1$H NMR (CDCl₃) β 1.99 (s, 3H), 2.05 (s, 3H), 2.12 (s, 3H), 2.13 (s, 6H), 2.14 (s, 3H), 2.18 (s, 3H), 3.97-4.00 (m, 1H), 4.03-4.16 (m, 2H), 4.26-4.28 (m, 1H), 4.33-4.37 (m, 1H), 4.73 (br s, 2H), 4.94-4.97 (m, 1H), 4.99-5.01 (m, 1H), 5.06-5.09 (m, 2H), 5.13-5.15 (m, 2H), 5.14-5.15 (m, 1H), 5.43 (t, 1H, J=3.6 Hz), 5.88 (d, 1H, J=8.3 Hz), $^{13}$C NMR (CDCl₃) 20.56, 20.63, 20.68, 20.69, 20.7, 20.8, 20.9, 61.3, 62.2, 65.5, 65.89, 66.9, 67.0, 67.57, 67.60, 68.66, 68.71, 69.4, 69.8, 71.3, 90.6, 95.1, 155.0, 155.2, 168.7, 169.24, 169.26, 169.5, 170.0, 170.4, 170.6; mass spectrum (FAB), m/z 680.2045 (M+H)⁺ (C₂₇H₃₈NO₁₉ requires m/z 680.2038).

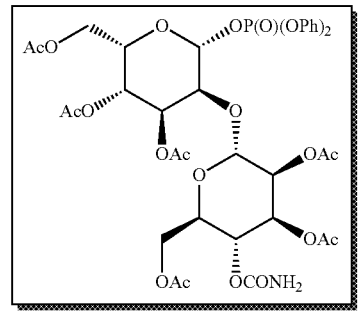

3,4,6-Tri-O-acetyl-2-O-(2,6-tri-O-acetyl-4-O-(carbamoyl)-α-D-mannopyranosyl)-β-L-gulopyranosyl Diphenyl Phosphate (66)

To a solution containing 62.0 mg (0.09 mmol) of disaccharide 65 in 1.0 mL of anh DMF was added 12.0 mg (0.13 mmol) of hydrazine acetate. The reaction mixture was stirred at room temperature for 2.5 h and quenched by the addition of 15 mL of ethyl acetate. The organic solution was washed with 10 mL of water, satd aq NaHCO₃, brine and dried (MgSO₄). The solvent was concentrated under diminished pressure to afford the product as a yellow oil: yield 51 mg (88%); silica gel TLC $R_f$ 0.1 (1:3 hexanes-ethyl acetate). $^1$H NMR (400) MHz, CDCl₃) δ 2.00 (s, 3H), 2.07 (s, 3H), 2.12 (s, 3H), 2.13 (s, 3H), 2.14 (s, 3H), 2.17 (s, 3H), 3.74-3.77 (m, 1H), 4.11-4.19 (m, 2H), 4.23-4.26 (m, 2H), 4.33-4.38 (m, 1H), 4.53-4.56 (br s, 2H), 4.94-4.95 (m, 1H), 4.97-5.01 (m, 2H), 5.09-5.15 (m, 3H), 5.26-5.30 (m, 1H), 5.39 (t, 1H, J=3.6 Hz). MALDI, m/z 660.18 for (M+Na)⁺. The crude residue was used for the next reaction.

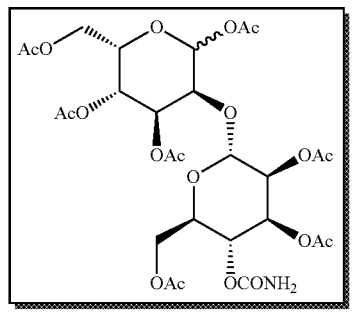

To a stirred solution containing 51.0 mg (0.10 mmol) of the crude residue in 3.00 mL of anh dichloromethane was added 15.0 mg (0.12 mmol) of DMAP, 147 µL (106 mg, 1.04 mmol) of Et$_3$N and 194 µL (252 mg, 0.94 mmol) of diphenyl chlorophosphate. The reaction mixture was stirred at 0° C. for 2 h and then poured into a mixture of 40 mL of ethyl acetate and 20 mL of satd aq NaHCO$_3$. The aqueous and organic layers were separated and the organic layer was washed with three 10-mL portions of water and brine and then dried (MgSO$_4$). The solvent was concentrated under diminished pressure to afford a crude residue. The residue was applied to a silica gel column (20×2 cm). Elution with 2:1 ethyl acetate-hexanes afforded the phosphate ester 66 as a colorless oil: yield 41 mg (52% over two steps); silica gel TLC R$_f$ 0.23 (3:1 ethyl acetate-hexanes); $^1$H NMR (CDCl$_3$) δ 1.95 (s, 3H), 1.97 (s, 3H), 2.07 (s, 3H), 2.11 (s, 3H), 2.13 (s, 3H), 2.20 (s, 3H), 3.95-4.06 (m, 2H), 4.08-4.15 (m, 1H), 4.17-4.21 (m, 2H), 4.25-4.35 (m, 2H), 4.94-5.00 (m, 2H), 5.05-5.13 (m, 3H), 5.20-5.23 (m, 1H), 5.40-5.45 (br s, 2H), 5.70 (t, 1H, J=8.0 Hz), 7.15-7.21 (m, 4H), 7.28-7.38 (m, 6H); $^{13}$C NMR (CDCl$_3$) δ 20.62, 20.68, 20.76, 61.13, 61.98, 65.42, 66.41, 67.39, 68.60, 68.92, 69.21, 71.58, 95.06, 96.19, 120.18, 120.23, 120.44, 120.49, 125.59, 125.66, 129.66, 129.93, 154.86, 169.28, 169.48, 169.80, 170.40, 170.63; mass spectrum (APCI), m/z 870.2230 (M+H)$^+$ (C$_{37}$H$_{45}$NO$_{21}$P requires m/z 870.2222).

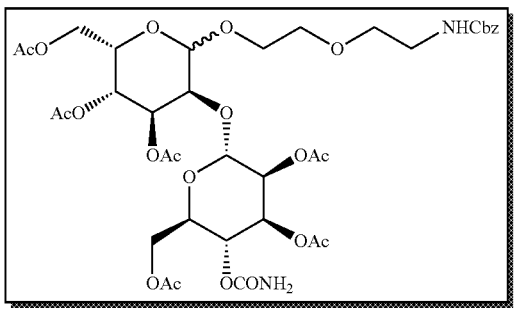

3,4,6-Tri-O-acetyl-2-O-(2,3,6-tri-O-acetyl-4-O-(carbamoyl)-α-D-mannopyranosyl)-α,β-L-gulopyranosyl Benzyl 2-(2-Ethoxy)ethylcarbamate (67)

To a stirred solution containing 27.0 mg (0.03 mmol) of phosphate ester 66 in 3.9 mL of anh dichloromethane was added a solution of 8.20 mg (0.03 mmol) of CBz-protected linker 54 in 3.9 mL of anh dichloromethane at 0° C. To the cooled reaction mixture was then added 8.20 µL (10.1 mg, 0.04 mmol) of TMSOTf. The reaction mixture was stirred at 0° C. for 15 min and then poured into a mixture of 20 mL of ethyl acetate and 4 mL of satd aq NaHCO$_3$. The aqueous and organic layers were separated and the organic layer was washed with three 10-mL portions of water and brine and then dried (MgSO$_4$). The solvent was concentrated under diminished pressure to afford a crude residue. The residue was applied to a silica gel column (12×2 cm). Elution with 3:1 ethyl acetate-hexanes afforded 67 as a colorless oil. The product isolated as a mixture of anomers: yield 7 mg (26%); silica gel TLC R$_f$ 0.11 (4:1 ethyl acetate-hexanes); $^1$H NMR (CDCl$_3$) δ 1.99 (s, 3H), 2.04 (s, 3H), 2.09 (s, 3H), 2.10 (s, 3H), 2.12 (s, 3H), 2.13 (s, 3H), 3.33-3.45 (br s, 2H), 3.5-3.65 (m, 2H), 3.67-3.73 (m, 2H), 3.82-3.88 (m, 1H), 3.96 (t, 1H, J=4.0 Hz), 4.03-4.11 (m, 3H), 4.12-4.19 (m, 2H), 4.30 (dd, 1H, J=12.0, 5.7 Hz), 4.42 (t, 1H, J=6.5 Hz), 4.93-4.98 (m, 3H), 5.00-5.03 (m, 1H), 5.07 (s, 2H), 5.12-5.17 (m, 2H), 5.24-5.30 (m, 3H), 7.30-7.36 (m, 5H); $^{13}$C NMR (CDCl$_3$) 20.81, 20.89, 20.90, 20.93, 21.0, 29.8, 41.2, 62.3, 62.9, 63.8, 65.7, 67.0, 67.1, 68.1, 68.69, 68.72, 69.6, 70.1, 71.1, 77.5, 97.2, 97.6, 128.32, 128.38, 128.7, 136.5, 155.5, 156.9, 169.5, 169.8, 169.9, 170.2, 170.7, 170.8; mass spectrum (APCI), m/z 859.2975 (M+H)$^+$ (C$_{37}$H$_{51}$N$_2$O$_{21}$ requires m/z 859.2984).

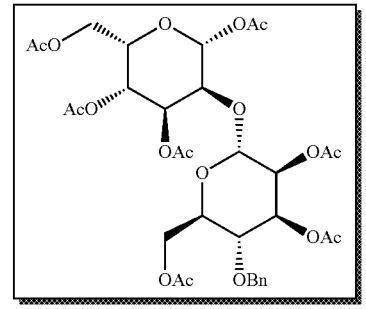

1,4,6-Tetra-O-acetyl-2-O-(2,3,6-tri-O-acetyl-4-O-benzyl-α-D-mannopyranosyl)-β-L-gulopyranose (68)

To a stirred solution containing 217 mg (0.62 mmol) of gulose acceptor 23 and 471 mg (0.75 mmol) of mannose donor 35 in 4.50 mL of anh dichloromethane cooled to 0° C. was added 230 µL (283 mg, 1.25 mmol) of TMSOTf. The reaction mixture was stirred at 0° C. for 10 min and then poured into a mixture of 30 mL of ethyl acetate and 30 mL of satd aq NaHCO$_3$. The aqueous and organic layers were separated and the organic layer was washed with two 20-mL portions of brine and dried (MgSO$_4$). The solvent was concentrated under diminished pressure to afford a crude residue. The residue was applied to a silica gel column (30×3 cm). Elution with 2:1 ethyl acetate-hexanes afforded 68 as a colorless oil: yield 330 mg (73%); silica gel TLC R$_f$ 0.25 (1:1 ethyl acetate-hexanes); $^1$H NMR (CDCl$_3$) δ 1.92 (s, 3H), 2.02 (s, 3H), 2.07 (t, 6H, J=3.2 Hz), 2.08-2.11 (m, 6H), 2.15 (d, 3H, J=3.7 Hz), 3.70-3.83 (m, 1H), 3.92-4.18 (m, 4H), 4.23-4.40 (m, 2H), 4.50-4.71 (m, 2H), 4.89 (dd, 1H, J=7.2 and 1.7 Hz), 4.96-4.99 (m, 1H), 5.01-5.10 (m, 2H), 5.10-5.16 (m, 1H), 5.35-5.45 (m, 1H), 5.85 (d, 1H, J=8.4 Hz) and 7.18-7.34 (m, 5H); $^{13}$C NMR (CDCl$_3$) δ 20.68, 20.71, 20.73, 20.79, 20.84, 20.88, 20.9, 61.4, 65.6, 67.7, 69.1, 69.5, 70.3, 71.3, 71.7, 72.4, 74.8, 90.7, 95.0, 127.6, 127.89, 127.99, 128.46, 128.49, 137.6, 168.8, 169.32, 169.36, 169.4, 169.7, 170.5 and 170.6; HRMS (APCI), m/z 727.2439 (M+H)$^+$ (C$_{33}$H$_{43}$O$_{18}$ requires m/z 727.2450).

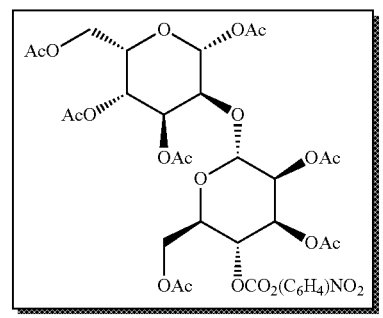

1,3,4,6-Tetra-O-acetyl-2-O-(2,3,6-tri-O-aectyl-4-O-((p-nitrophenyl)carbamoyl)-α-D-mannopyranosyl)-β-L-gulopyranose (69)

To a solution containing 140 mg (0.19 mmol) of disaccharide 68 in 13 mL of ethyl acetate was added a catalytic amount of Pd(OH)$_2$/C and the reaction mixture was stirred overnight under 1 atm of H$_2$. The solvent was filtered through a pad of Celite 545® and the filtrate was concentrated under diminished pressure to afford a crude residue. The residue was used for the next reaction; silica gel TLC R$_f$ 0.08 (1:1 ethyl acetate-hexanes).

To a solution containing 120 mg (0.19 mmol) of the crude residue in 2.0 mL of anh pyridine was added 92.0 mg (0.76 mmol) of DMAP and 168 mg (0.76 mmol) of p-nitrophenyl chloroformate. The reaction mixture was stirred at 40° C. overnight and then poured into a mixture of 30 mL of ethyl acetate and 10 mL of H$_2$O. The aqueous and organic layers were separated and the organic layer was washed with three 10-mL portions of 1 N HCl and 10 mL of satd aq NaHCO$_3$ and brine. The organic solution was dried (MgSO$_4$) and concentrated under diminished pressure to afford a crude residue. The residue was applied to a silica gel column (25×3 cm). Elution with 1:1 ethyl acetate-hexanes afforded ester 69 as a colorless foam: yield 121 mg (78% over two steps); silica gel TLC R$_f$ 0.30 (1:1 ethyl acetate-hexanes); $^1$H NMR (CDCl$_3$) δ 1.98 (s, 3H), 2.03 (s, 3H), 2.11 (d, 6H, J=5.0 Hz), 2.14 (s, 3H), 2.19 (d, 3H, J=5.4 Hz), 3.99 (dd, H, J=8.4 and 3.3 Hz), 4.02-4.25 (m, 4H), 4.27 (d, 1H, J=2.4 Hz), 4.35 (t, 1H, J=6.0 Hz), 4.46-4.55 (m, 2H), 4.93-5.01 (m, 2H), 5.11-5.18 (m, 2H), 5.24 (dd, 1H, J 10.1 and 3.3 Hz), 5.32 (dd, 1H, J=7.7 and 4.3 Hz), 5.43 (t, 1H, J=3.5 Hz), 5.89 (d, 1H, J=8.5 Hz), 7.29-7.39 (m, 2H) and 8.25 (t, 2H, J=6.0 Hz); $^{13}$C NMR (CDCl$_3$) δ 20.69, 20.71, 21.0, 61.3, 61.7, 65.6, 67.7, 68.6, 68.8, 70.0, 71.3, 71.4, 90.6, 95.1, 121.7, 125.4, 145.7, 151.8, 155.2, 168.7, 169.29, 169.33, 169.38, 169.58, 169.65, 169.7, 169.8, 170.44, 170.46 and 170.58; HRMS (APCI), m/z 802.2035 (M+H)$^+$ (C$_{33}$H$_{40}$NO$_{22}$ requires m/z 802.2042).

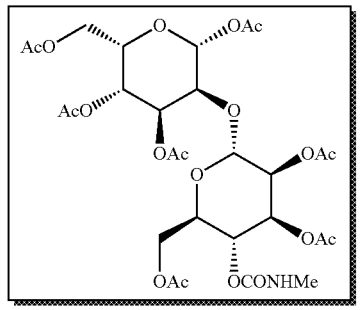

1,3,4,6-Tetra-O-acetyl-2-O-(2,3,6-tri-O-acetyl-4-O-(methylcarbamoyl)-α-D-mannopyranosyl)-β-L-gulopyranose (70)

To a solution containing 121 mg (0.15 mmol) of 69 in 3.2 mL of anh THF was added 76.0 µL (0.15 mmol) of a 2 M solution of CH$_3$NH$_2$ in THF at 0° C. The reaction mixture was stirred at room temperature for 15 h at which time silica gel TlC analysis indicated that the reaction was complete. The solvent was concentrated under diminished pressure to afford a crude residue. The residue was applied to a silica gel column (25×3 cm). Elution with 1:1 ethyl acetate-hexanes afforded disaccharide 70 as a colorless oil: yield 90 mg (86%); silica gel TLC R$_f$ 0.14 (1:1 ethyl acetate-hexanes); $^1$H NMR (CDCl$_3$) δ 1.96 (t, 3H, J=3.4 Hz), 2.04 (d, 3H, J=6.4 Hz), 2.11 (dd, 12H, J=5.4 and 2.8 Hz), 2.17 (d, 3H, J=2.5 Hz), 2.76 (d, 3H, J=4.8 Hz), 3.97 (dd, 1H, J=8.4 and 3.2 Hz), 4.00-4.39 (m, 3H), 4.48-4.80 (m, 1H), 4.93 (d, 1H, J=7.2 Hz), 4.99 (dd, 1H, J=7.0 and 4.4 Hz), 5.04-5.10 (m, 2H), 5.08-5.17 (m, 2H), 5.29 (dd, 1H, J=13.2 and 9.8 Hz), 5.42 (t, 1H, J=3.5 Hz), 5.87 (d, 1H, J=8.4 Hz) and 6.28 (d, 1H, J=4.2 Hz); $^{13}$C NMR (CDCl$_3$) δ 20.68, 20.75, 20.76, 20.80, 20.82, 20.84, 27.8, 61.5, 61.8, 62.5, 62.7, 65.6, 66.0, 66.3, 66.8, 67.8, 68.9, 69.75, 69.79, 71.4, 90.7, 169.3, 169.59, 169.61, 169.65, 170.53, 170.55 and 170.7; HRMS (APCI), m/z 694.2199 (M+H)$^+$ (C$_{28}$H$_{40}$NO$_{19}$ requires m/z 694.2195).

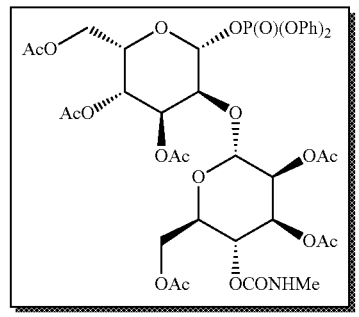

3,4,6-Tri-O-acetyl-2-O-(2,3,6-tri-O-acetyl-4-O-(methylcarbamoyl)-α-D-mannopyranosyl)-β-L-gulopyranosyl Diphenyl Phosphate (71)

To a solution containing 44.0 mg (0.06 mmol) of disaccharide 70 in 0.50 mL of anh DMF was added 7.00 mg (0.08 mmol) of hydrazine acetate. The reaction mixture was stirred at room temperature for 1.5 h and quenched by the addition of 20 mL of ethyl acetate. The organic solution was washed with three 10-mL portions of brine and dried (MgSO$_4$). The solvent was concentrated under diminished pressure to afford a crude residue. The crude residue was used for the next reaction.

To a stirred solution containing 43.0 mg (0.07 mmol) of the crude residue in 4.00 mL of anh dichloromethane was added 10.0 mg (0.08 mmol) of DMAP, 100 µL (72.0 mg, 0.71 mmol) of Et$_3$N and 130 µL (160 mg, 0.63 mmol) of diphenyl chlorophosphate. The reaction mixture was stirred at 0° C. for 2 h and then poured into a mixture of 40 mL of ethyl acetate and 20 mL of satd aq NaHCO$_3$. The aqueous and organic layers were separated and the organic layer was washed with three 10-mL portions of water and brine and then dried (MgSO$_4$). The solvent was concentrated under diminished pressure to afford a crude residue. The residue was applied to a silica gel column (25×3 cm). Elution with 2:1 ethyl acetate-hexanes afforded the phosphate ester 71 as a colorless oil: yield 38 mg (69% over two steps); silica gel TLC R$_f$ 0.48 (2:1 ethyl acetate-hexanes); $^1$H NMR (CDCl$_3$) δ 1.95 (s, 3H), 2.00 (s, 3H), 2.09 (s, 3H), 2.12 (s, 3H), 2.15 (s, 31), 2.21 (s, 3H), 2.57 (d, 3H, J=4.0 Hz), 3.70 (s, 1H), 4.03 (s, 2H), 4.15 (d, 2H, J=9.6 Hz), 4.24 (d, 2H, J=12.2 Hz), 4.32-4.38 (m, 2H), 4.99 (d, 2H, J=12.6 Hz), 5.05-5.25 (m, 2H), 5.30 (s, 1H), 5.45 (s, 1H), 5.71 (d, 1H, J=7.4 Hz) and 7.19-7.41 (m, 10H); $^{13}$C NMR (CDCl$_3$) δ 20.77, 20.83, 20.89, 20.93, 27.6, 61.3, 62.3, 65.6, 66.3, 67.5, 68.8, 69.2, 69.5, 70.7, 70.8, 71.7, 95.1, 96.4, 120.4, 125.7, 129.8, 130.0, 150.4, 155.4, 169.37, 169.39, 169.6, 169.9, 170.5 and 170.73, 170.76; HRMS (APCI), m/z 884.2381 (M+H)+ ($C_{38}H_{47}NO_{21}P$ requires m/z 884.2378).

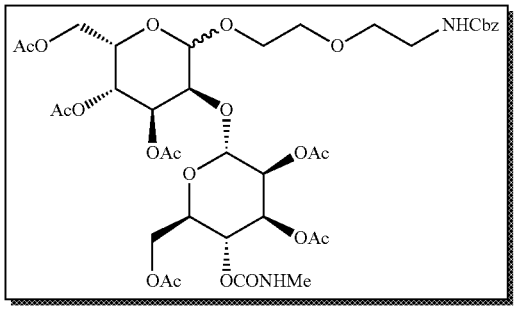

3,4,6-Tri-O-acetyl-2-O-(2,3,6-tri-O-acetyl-4-O-(methylcarbamoyl)α-D-mannopyranosyl)-α,β-L-gulopyranosyl Benzyl 2-(2-Ethoxy)ethylcarbamate (72)

To a stirred solution containing 38.0 mg (0.04 mmol) of phosphate ester 71 in 0.5 mL of anh dichloromethane was added a solution of 10.0 mg (0.04 mmol) of CBz-protected linker 54 in 0.5 mL of anh dichloromethane at 0° C. To the cooled reaction mixture was then added 14.0 µL (17.0 mg, 0.08 mmol) of TMSOTf. The reaction mixture was stirred at 0° C. for 15 min and then poured into a mixture of 20 mL of ethyl acetate and 20 mL of satd aq $NaHCO_3$. The aqueous and organic layers were separated and the organic layer was washed with three 10-mL portions of water and brine and then dried ($MgSO_4$). The solvent was concentrated under diminished pressure to afford a crude residue. The residue was applied to a silica gel column (25×3 cm). Elution with 12:12:1 ethyl acetate-hexanes-methanol afforded 72 as a colorless oil. The product isolated as a mixture of anomers: yield 19 mg (51%); silica gel TLC $R_f$ 0.14 (12:12:1 ethyl acetate-hexanes-methanol); $^1H$ NMR ($CDCl_3$) δ 1.92-2.14 (m, 18H), 2.71 (t, 3H, J=4.1 Hz), 3.40 (d, 3H, J=4.9 Hz), 3.52-3.77 (m, 8H), 3.85 (dd, H, J=8.4 and 3.2 Hz), 3.95 (t, 1H, J=3.9 Hz), 4.27 (dd, 21-H, J=13.4 and 7.3 Hz), 4.40 (t, 1H, J=6.4 Hz), 4.88-5.04 (m, 3H), 5.05-5.22 (m, 6H), 5.25 (dd, 1H, J=7.3 and 3.6 Hz) and 7.28-7.40 (m, 5H); $^{13}C$ NMR ($CDCl_3$) δ 20.78, 20.83 20.85, 20.87, 20.92, 20.95, 27.7, 61.9, 62.3, 63.1, 63.8, 65.7, 66.8, 66.9, 68.1, 68.7, 68.8, 69.6, 69.8, 70.2, 71.0, 72.3, 97.2, 97.5, 128.27, 128.33, 128.65, 128.67, 169.5, 169.7, 169.8, 169.9, 170.57, 170.63 and 170.7; HRMS (APCI), m/n 873.3142 (M+H)+ ($C_{38}H_{53}N_2O_{21}$ requires m/z 873.3141).

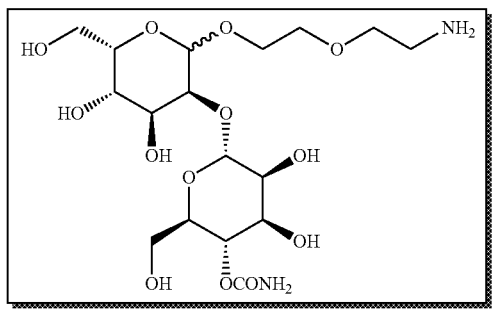

(4-O-carbamoyl-α-D-mannopyranosyl)-α,β-L-gulopyranosyl 2-(2-aminoethoxy)ethanol (73)

To a solution containing 2.20 mg (2.56 µmol) of compound 67 in 1 mL of anh methanol was added a freshly prepared solution of 0.4 M sodium methoxide in methanol. The reaction mixture was allowed to stir at room temperature for 3 h, and the complete consumption of starting material was confirmed by MALDI-TOF mass spectral analysis. The reaction mixture was then quenched by the addition of 500 mg of Dowex 50x resin, shaken for 15 min and filtered. To the solution of the crude product in methanol was then added Pd/C and Hz gas was bubbled through for 1 h. The complete consumption of starting material was confirmed by MALDI-TOF mass spectral analysis. The reaction mixture was filtered through Celite 545® and then concentrated under diminished pressure to afford 73, which was used for the next reaction; HRMS (APCI), m/z 473.1972 (M+H)+ ($C_{17}H_{33}N_2O_{13}$ requires m/z 473.1983).

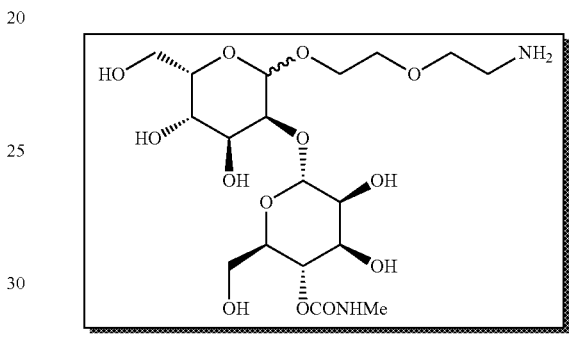

(4-O-(methylcarbamoyl)-α-D-mannopyranosyl)-α,β-L-gulopyranosyl 2-(2-aminoethoxy)ethanol (74)

To a solution containing 2.70 mg (3.10 µmol) of 72 in 2 mL of anh methanol was added a freshly prepared solution of 0.4 M sodium methoxide in methanol. The reaction mixture was allowed to stir at room temperature for 3 h, and the complete consumption of starting material was confirmed by MALDI-TOF mass spectral analysis. The reaction mixture was then quenched by the addition of 500 mg of Dowex 50x resin, shaken for 15 min and filtered. To the solution of the crude product in methanol was added Pd/C and $H_2$ gas was bubbled through for 1 h. The complete consumption of starting material was confirmed by MALDI-TOF mass spectral analysis. The reaction mixture was filtered through Celite 545® and concentrated under diminished pressure to afford 74, which was used for the next reaction; HRMS (APCI), m/z 487.2153 (M+H)+ ($C_{18}H_{35}N_2O_{13}$ requires m/z 487.2139).

Example 12: Synthesis of C3 Modified Altrose Disaccharide-Linker 83 and 84

Scheme 12

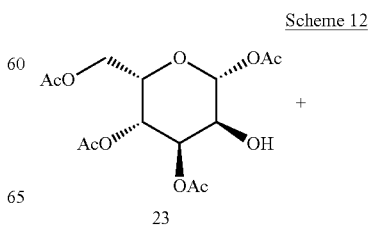

23

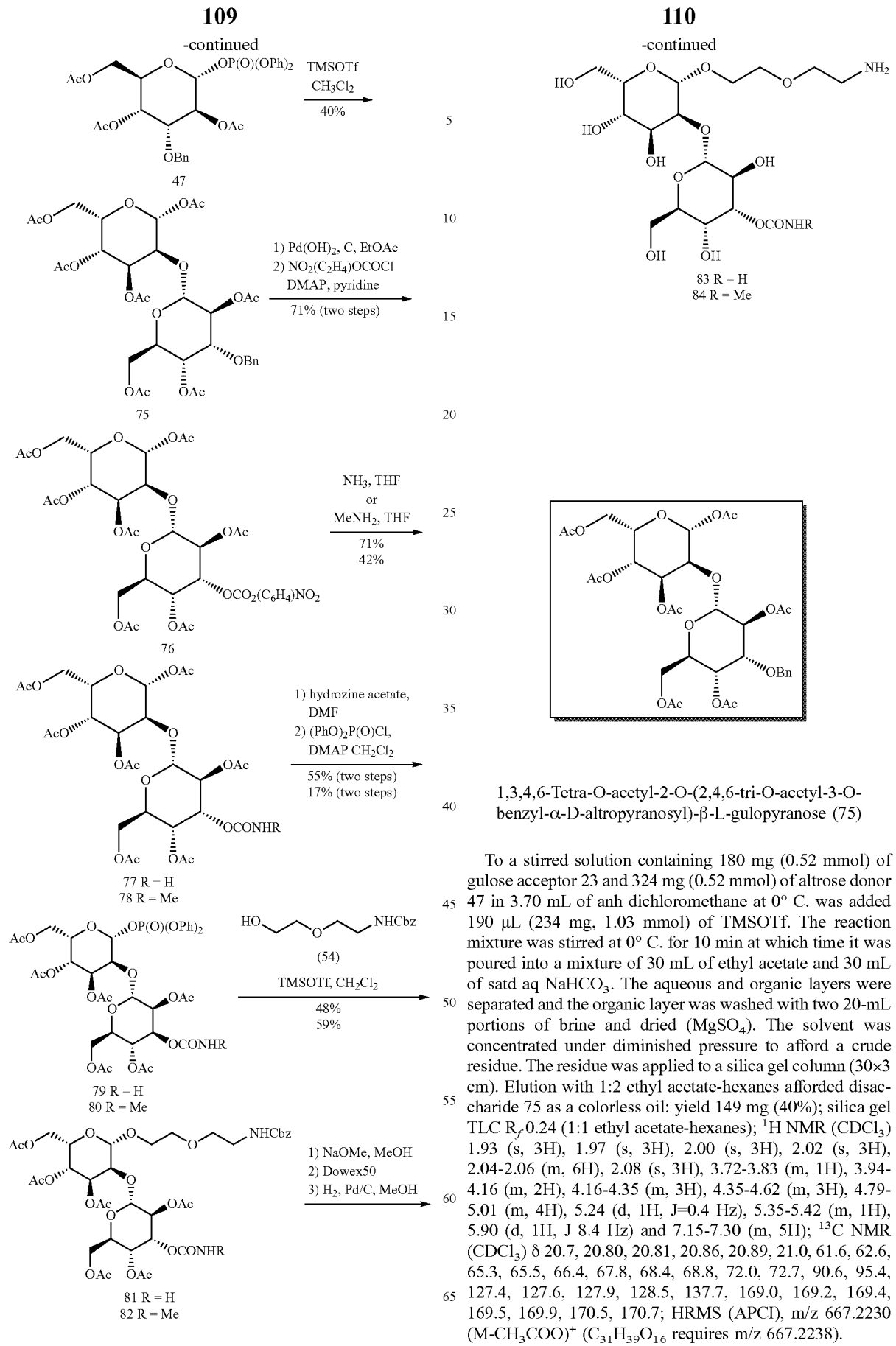

1,3,4,6-Tetra-O-acetyl-2-O-(2,4,6-tri-O-acetyl-3-O-benzyl-α-D-altropyranosyl)-β-L-gulopyranose (75)

To a stirred solution containing 180 mg (0.52 mmol) of gulose acceptor 23 and 324 mg (0.52 mmol) of altrose donor 47 in 3.70 mL of anh dichloromethane at 0° C. was added 190 μL (234 mg, 1.03 mmol) of TMSOTf. The reaction mixture was stirred at 0° C. for 10 min at which time it was poured into a mixture of 30 mL of ethyl acetate and 30 mL of satd aq $NaHCO_3$. The aqueous and organic layers were separated and the organic layer was washed with two 20-mL portions of brine and dried ($MgSO_4$). The solvent was concentrated under diminished pressure to afford a crude residue. The residue was applied to a silica gel column (30×3 cm). Elution with 1:2 ethyl acetate-hexanes afforded disaccharide 75 as a colorless oil: yield 149 mg (40%); silica gel TLC $R_f$ 0.24 (1:1 ethyl acetate-hexanes); $^1$H NMR ($CDCl_3$) 1.93 (s, 3H), 1.97 (s, 3H), 2.00 (s, 3H), 2.02 (s, 3H), 2.04-2.06 (m, 6H), 2.08 (s, 3H), 3.72-3.83 (m, 1H), 3.94-4.16 (m, 2H), 4.16-4.35 (m, 3H), 4.35-4.62 (m, 3H), 4.79-5.01 (m, 4H), 5.24 (d, 1H, J=0.4 Hz), 5.35-5.42 (m, 1H), 5.90 (d, 1H, J 8.4 Hz) and 7.15-7.30 (m, 5H); $^{13}$C NMR ($CDCl_3$) δ 20.7, 20.80, 20.81, 20.86, 20.89, 21.0, 61.6, 62.6, 65.3, 65.5, 66.4, 67.8, 68.4, 68.8, 72.0, 72.7, 90.6, 95.4, 127.4, 127.6, 127.9, 128.5, 137.7, 169.0, 169.2, 169.4, 169.5, 169.9, 170.5, 170.7; HRMS (APCI), m/z 667.2230 (M-$CH_3COO$)$^+$ ($C_{31}H_{39}O_{16}$ requires m/z 667.2238).

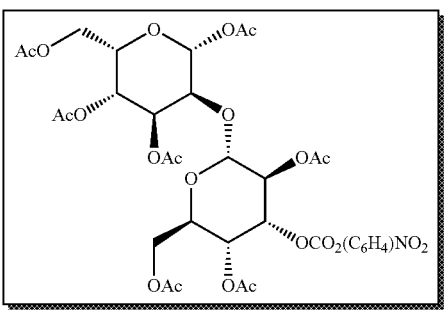

1,3,4,6-Tetra-O-acetyl-2-O-(2,4,6-tri-O-acetyl-3-O-((p-nitrophenyl)carbamoyl)-α-D-altropyranosyl)-β-L-gulopyranose (76)

To a solution containing 190) mg (0.26 mmol) of disaccharide 75 in 18 mL of ethyl acetate was added a catalytic amount of Pd(OH)$_2$/C and the reaction mixture was stirred overnight under 1 atm of H$_2$. The solvent was filtered through a pad of Celite 545® and the filtrate was concentrated under diminished pressure to afford a crude residue. The crude product was used for the next reaction; silica gel TLC R$_f$ 0.12 (1:1 ethyl acetate-hexanes).

To a solution containing 198 mg (0.31 mmol) of the crude residue in 1.1 mL of anh pyridine was added 151 mg (1.24 mmol) of DMAP and 280 mg (1.24 mmol) of p-nitrophenyl chloroformate. The reaction mixture was stirred at 40° C. overnight and then poured into a mixture of 30 mL ethyl acetate and 10 mL of H$_2$O. The aqueous and organic layers were separated and the organic layer was washed with three 10-mL portions of 1 N HCl and 10 mL of satd aq NaHCO$_3$ and brine. The solvent was dried (MgSO$_4$) and then concentrated under diminished pressure to afford a crude residue. The residue was applied to a silica gel column (25×3 cm). Elution with 1:1 ethyl acetate-hexanes afforded ester 76 as a colorless foam: yield 177 mg (71% over two steps); silica gel TLC R$_f$ 0.28 (1:1 ethyl acetate-hexanes); $^1$H NMR (CDCl$_3$) δ 2.02 (s, 3H), 2.04 (s, 3H), 2.09 (s, 3H), 2.10 (s, 3H), 2.12 (s, 3H), 2.13 (s, 3H), 2.14 (s, 3H), 3.99-4.17 (m, 3H), 4.23-4.38 (m, 2H), 4.41-4.50 (m, 1H), 4.89-5.02 (m, 2H), 5.02-5.13 (m, 2H), 5.20 (dt, 1H, J=10.4 and 5.2 Hz), 5.25-5.34 (m, 1H), 5.43 (t, 1H, J=3.5 Hz), 5.94 (d, 1H, J=8.4 Hz), 7.42 (t, 2H, J=7.1 Hz) and 8.22-8.30 (m, 2H); $^{13}$C NMR (CDCl$_3$) δ 20.66, 20.71, 20.72, 20.76, 20.9, 61.5, 62.2, 64.7, 65.1, 65.4, 67.6, 68.1, 68.6, 71.3, 72.1, 90.5, 94.5, 121.4, 125.4, 136.0, 145.6, 149.8, 151.6, 155.2, 168.8, 168.9, 169.1, 169.3, 169.5, 170.4 and 170.6; HRMS (APCI), m/z 742.1851 (M-CH$_3$COO)$^+$ (C$_{31}$H$_{36}$NO$_{20}$ requires m/z 742.1831).

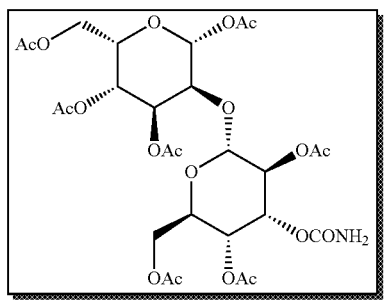

1,3,4,6-Tetra-O-acetyl-2-O-(2,4,6-tri-O-acetyl-3-O-carbamoyl-α-D-altropyranosyl)-β-L-gulopyranoside (77)

To a solution containing 73.0 mg (0.09 mmol) of ester 76 in 2 mL of anh THF was added a solution of 0.7 mL of anh THF saturated with NH$_3$ at 0° C. The reaction mixture was allowed to warm to room temperature and then stirred for 2.5 h at which time silica gel TLC analysis indicated that the reaction was complete. The solvent was concentrated under diminished pressure to afford a crude residue. The residue was applied to a silica gel column (20×3 cm). Elution with 3:1 ethyl acetate-hexanes afforded disaccharide 77 as a colorless oil: yield 44 mg (71%); silica gel TLC R$_f$ 0.38 (ethyl acetate); $^1$H NMR (CDCl$_3$) δ 2.00 (s, 3H), 2.05 (s, 3H), 2.11 (s, 6H), 2.13 (s, 3H), 2.16 (s, 3H), 2.17 (s, 3H), 3.98 (dd, 1H, J=8.1 and 3.3 Hz), 4.02-4.38 (m, 7H), 4.75 (d, 1H, J=3.3 Hz), 4.82-4.96 (m, 2H), 4.99-5.12 (m, 2H), 5.13 (dd, 1H, J=7.8 and 4.4 Hz), 5.44 (t, 1H, J=3.7 Hz) and 6.11 (d, 1H, J=8.1 Hz); $^{13}$C NMR (CDCl$_3$) δ 20.72, 20.75, 20.79, 20.82, 20.83, 20.87, 21.2, 61.8, 62.4, 64.6, 64.9, 65.5, 66.8, 67.6, 69.0, 69.5, 71.7, 91.0, 94.4, 155.6, 168.9, 169.3, 169.4, 169.6, 170.2, 170.5 and 170.7; HRMS (APCI), m/z 680.2039 (M+H)$^+$ (C$_{27}$H$_{38}$NO$_{19}$ requires m/z 680.2038).

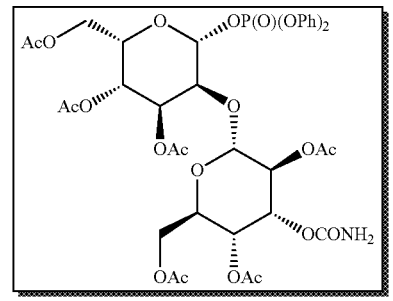

3,4,6-Tri-O-acetyl-2-O-(2,4,6-Tri-O-acetyl-3-O-carbamoyl-α-D-altropyranosyl)-β-L-gulopyranosyl Diphenyl Phosphate (79)

To a solution containing 44.0 mg (60.0 µmol) of disaccharide 77 in 0.50 mL of anh DMF was added 7.00 mg (80.0 µmol) of hydrazine acetate. The reaction mixture was stirred at room temperature for 1.5 h and then quenched by the addition of 20 mL of ethyl acetate. The organic layer was washed with three 10-mL portions of brine and dried (MgSO$_4$). The solvent was concentrated under diminished pressure to afford a crude residue. The residue was used for the next reaction.

To a stirred solution containing 41.0 mg (60.0 µmol) of the crude residue in 4.00 mL of anh dichloromethane was added 10.0 mg (80.0 µmol) of DMAP, 100 µL (72.0 mg, 0.68 mmol) of Et$_3$N and 125 µL (162 mg, 0.61 mmol) of diphenyl chlorophosphate at 0° C. The reaction mixture was stirred at 0° C. for 2 h and then poured into a mixture of 40 mL of ethyl acetate and 20 mL of satd aq NaHCO$_3$. The aqueous and organic layers were separated and the organic layer was washed with three 10-mL portions of distilled water and brine and then dried (MgSO$_4$). The solvent was concentrated under diminished pressure to afford a crude residue. The residue was applied to a silica gel column (25×2 cm). Elution with 2:1 ethyl acetate-hexanes afforded phosphate ester 79 as a colorless oil: yield 31 mg (55% over two steps);

silica gel TLC $R_f$ 0.30 (2:1 ethyl acetate-hexanes); $^1$H NMR (CDCl$_3$) δ 1.83 (s, 3H), 1.98 (s, 3H), 2.04 (s, 3H), 2.12 (d, 3H, J=2.8 Hz), 2.15 (d, 6H, J=3.9 Hz), 3.98-4.09 (m, 2H), 4.09-4.25 (m, 4H), 4.26-4.36 (m, 2H), 4.66 (d, 1H, J=9.8 Hz), 4.83 (d, 1H, J=2.1 Hz), 4.91 (d, 1H, J=6.4 Hz), 5.03 (t, 1H, J=5.7 Hz), 5.09-5.19 (m, 2H), 5.45 (d, 1H, J=3.2 Hz), 5.74 (t, 1H, J=8.0 Hz) and 7.09-7.41 (m, 10H); $^{13}$C NMR (CDCl$_3$) δ 20.62, 20.66, 20.77, 20.83, 20.88, 61.6, 62.2, 64.5, 64.7, 65.1, 67.1, 67.3, 68.9, 71.7, 94.1, 120.28, 120.32, 120.37, 125.98, 125.99, 126.23, 126.24, 129.93, 129.94, 130.1, 155.9, 168.8, 169.0, 169.3, 169.5, 170.4, and 170.8; HRMS (APCI), m/z 870.2230 (M+H)$^+$ (C$_{37}$H$_{45}$NO$_{21}$P requires m/z 870.2222).

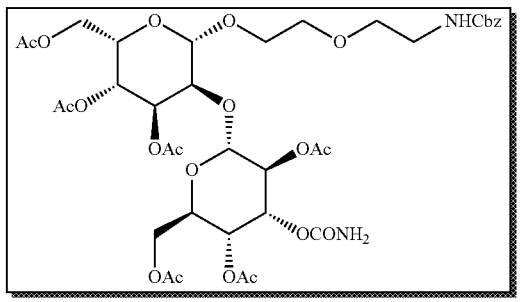

3,4,6-Tri-O-acetyl-2-O-(2,4,6-Tri-O-acetyl-3-O-carbamoyl-α-D-altropyranosyl)-β-L-gulopyranosyl Benzyl 2-(2-Ethoxy)ethylcarbamate (81)

To a stirred solution containing 31 mg (40 μmol) of phosphate ester 79 in 0.45 mL of anh dichloromethane was added a solution of 8.0 mg (30 μmol) of CBz-protected linker 54 in 0.45 mL of anh dichloromethane at 0° C. To the reaction mixture was added 12 μL (15 mg, 80 μmol) of TMSOTf and the reaction mixture was stirred at 0° C. for 15 min. The reaction mixture was poured into a mixture of 10 mL of ethyl acetate and 10 mL satd aq NaHCO$_3$. The aqueous and organic layers were separated and the organic layer was washed with three 10-mL portions of water and brine and then dried (MgSO$_4$). The solvent was concentrated under diminished pressure to afford a crude residue. The residue was applied to a silica gel column (25×2 cm). Elution with 12:12:1 ethyl acetate-hexanes-methanol afforded 81 as a colorless oil: yield 15 mg (48%); silica gel TLC $R_f$ 0.17 (11:11:1 ethyl acetate-hexanes-methanol); $^1$H NMR (CDCl$_3$) δ $^1$H NMR (CDCl$_3$) δ 1.95-2.07 (m, 6H), 2.07-2.15 (m, 12H), 3.41 (t, 2H, J=9.5 Hz), 3.59 (d, 2H, J=5.0 Hz), 3.61-3.71 (m, 3H), 3.87 (dt, 1H, J=12.8 and 6.5 Hz), 3.94-4.04 (m, 1H), 4.04-4.20 (m, 3H), 4.21-4.26 (m, 1H), 4.36-4.48 (m, 1H), 4.49-4.60 (m, 1H), 4.75 (d, H, J=7.5 Hz), 4.84-5.05 (m, 4H), 5.05-5.20 (m, 4H), 5.21-5.29 (m, 1H), 5.32-5.49 (m, 2H) and 7.27-7.38 (m, 51H); $^{13}$C NMR (CDCl$_3$) δ 20.75, 20.77, 20.82, 20.85, 20.88, 20.92, 40.9, 62.1, 62.3, 62.6, 65.1, 65.2, 66.9, 67.8, 68.1, 68.5, 68.6, 69.2, 70.37, 70.45, 99.5, 128.3, 128.4, 128.5, 128.7, 136.6, 155.7, 169.0, 169.4, 169.61, 169.65, 170.6, 170.82 and 170.89; HRMS (APCI), m/z 859.2973 (M+H)$^+$ (C$_{37}$H$_{51}$N$_2$O$_{21}$ requires m/z 859.2984).

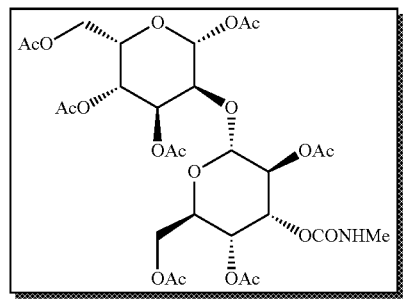

1,3,4,6-Tetra-O-acetyl-2-O-(2,4,6-tri-O-acetyl-3-O-(methylcarbamoyl)-α-D-altropyranosyl)-β-L-gulopyranose (78)

To a solution containing 86.0 mg (0.11 mmol) of ester 76 in 2.4 mL of anh THF was added 54.0 μL (0.11 mmol) of a 2 M solution of CH$_3$NH$_2$ in THF at 0° C. The reaction mixture was stirred at room temperature for 15 h at which time analysis by silica gel TLC indicated that the reaction was complete. The solvent was concentrated under diminished pressure to afford a crude residue. The residue was applied to a silica gel column (35×2 cm). Elution with 2:1 ethyl acetate-hexanes afforded disaccharide 78 as a colorless oil: yield 31 mg (42%); silica gel TLC $R_f$ 0.13 (3:1 ethyl acetate-hexanes); $^1$H NMR (CDCl$_3$) δ 2.01 (s, 3H), 2.05 (s, 3H), 2.11 (s, 6H), 2.13 (s, 3H), 2.15 (s, 3H), 2.16 (s, 3H), 2.79 (d, 3H, J=4.7 Hz), 3.98 (dd, 1H, J=8.0 and 3.3 Hz), 4.04-4.30 (m, 4H), 4.33 (dt, 1H. J=12.1 and 6.1 Hz), 4.71-4.77 (m, 1H), 4.84-4.95 (m, 1H), 5.06 (dd, 2H, J=10.1 and 6.6 Hz), 5.11-5.19 (m, 1H), 5.21-5.41 (m, 2H), 5.43 (dd, 1H, J=10.0 and 6.3 Hz) and 6.10 (d, 1H, J=8.0 Hz); $^{13}$C NMR (CDCl$_3$) δ 20.77, 20.81, 20.82, 20.85, 20.88, 20.9, 21.3, 27.8, 61.8, 62.5, 64.8, 65.0, 65.5, 66.4, 66.7, 67.6, 69.2, 71.6, 91.1, 94.7, 155.9, 169.0, 169.3, 169.4, 169.6, 170.1, 170.5 and 170.8; HRMS (APCI), m/z 694.2204 (M+H)$^+$ (C$_{28}$H$_{40}$NO$_{19}$ requires m/z 694.2195).

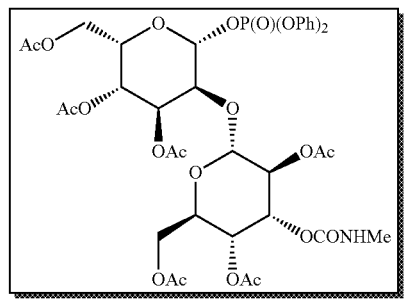

3,4,6-Tri-O-acetyl-2-O-(2,4,6-tri-O-acetyl-3-O-(methylcarbamoyl)-α-D-altropyranosyl)-β-L-gulopyranosyl Diphenyl Phosphate (80)

To a solution containing 31.0 mg (40.0 μmol) of disaccharide 78 in 0.5 mL of anh DMF was added 5.00 mg (50.0 μmol) of hydrazine acetate. The reaction mixture was stirred at room temperature for 1.5 h and then quenched by the addition of 20 mL of ethyl acetate. The organic solution was washed with three 10-mL portions of brine and dried (MgSO$_4$). The solvent was concentrated under diminished pressure to afford a crude residue. The residue was used for the next reaction.

To a stirred solution containing 22.0 mg (30.0 μmol) of the residue in 2 mL of anh dichloromethane was added 6.00 mg (40.0 μmol) of DMAP, 52.0 μL (38.0 mg, 370 μmol) of Et$_3$N and 70.0 μL (91.0 mg, 330 μmol) of diphenyl chlorophosphate at 0° C. The reaction mixture was stirred at 0° C. for 2 h and then poured into a mixture of 40 mL of ethyl acetate and 20 mL of satd aq NaHCO$_3$. The aqueous and organic layers were separated and the organic layer was washed with three 10-mL portions of distilled water and brine and then dried (MgSO$_4$). The solvent was concentrated under diminished pressure to afford a crude residue. The residue was applied to a silica gel column (25×2 cm). Elution with 2:1 ethyl acetate-hexanes afforded phosphate ester 80 as a colorless oil: yield 7.0 mg (17% over two steps); silica gel TLC R$_f$ 0.28 (3:1 ethyl acetate-hexanes); $^1$H NMR (CDCl$_3$) δ 1.85 (s, 3H), 1.98 (s, 3H), 2.04 (s, 3H), 2.12 (s, 3H), 2.15 (d, 6H, J=2.5 Hz), 2.63 (d, 3H, J=4.7 Hz), 3.98-4.08 (m, 2H), 4.09-426 (m, 3H), 4.30 (t, 1H, J=6.1 Hz), 4.63 (d, 1H, J=10.5 Hz), 4.80 (d, 1H, J=3.0 Hz), 4.89 (s, 1H), 5.00-5.06 (m, 1H), 5.13 (dd, 1H, J=10.5 and 3.1 Hz), 5.18 (d, H, J=3.0 Hz), 5.45 (d, 1H, J=2.9 Hz), 5.73 (t, 1H, J=8.0 Hz), 6.46 (d, 1H, J=4.8 Hz) and 7.12-7.40 (m, 10H); $^{13}$C NMR (CDCl$_3$) δ 20.67, 20.72, 20.77, 20.8, 20.9, 27.4, 61.6, 62.3, 64.67, 64.72, 65.1, 66.7, 67.2, 69.1, 71.7, 94.2, 96.52, 96.56, 120.1, 120.2, 120.32, 120.37, 126.0, 126.1, 129.9, 130.1, 156.1, 168.8, 169.0, 169.4, 169.5, 170.5 and 170.8; HRMS (APCI), m/z 884.2403 (M+H)$^+$ (C$_{38}$H$_{47}$NO$_{21}$P requires m/z 884.2378).

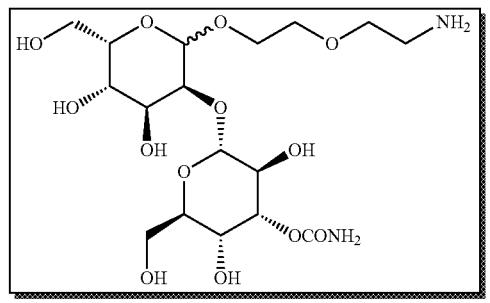

3,4,6-Tri-O-acetyl-2-O-(2,4,6-tri-O-acetyl-3-O-(methylcarbamoyl)-α-D-altropyranosyl)-α,β-L-gulopyranosyl Benzyl 2-(2-Ethoxy)ethylcarbamate (82)

To a stirred solution containing 17 mg (19 μmol) of phosphate ester 80 in 0.25 mL of anh dichloromethane was added a solution of 5.0 mg (17 mol) of CBz-protected linker 54 in 0.25 mL of anh dichloromethane at 0° C. To the reaction mixture was added 7.0 μL (8.6 mg, 34 μmol) of TMSOTf. The reaction mixture was stirred at 0° C. for 15 min and then poured into a mixture of 10 mL ethyl acetate and 10 mL satd aq NaHCO$_3$. The aqueous and organic layers were separated and the organic layer was washed with three 10-mL portions of distilled water and brine and then dried (MgSO$_4$). The solvent was concentrated under diminished pressure to afford a crude residue. The residue was applied to a silica gel column (25×2 cm). Elution with 12:12:1 ethyl acetate-hexanes-methanol afforded 82 as a colorless oil: yield 10 mg (59%); silica gel TLC R$_f$ 0.14 (11:11:1 ethyl acetate-hexanes-methanol); $^1$H NMR (CDCl$_3$) δ 1.97 (d, 3H, J=8.6 Hz), 2.04 (d, 3H, J=4.2 Hz), 2.07-2.15 (m, 12H), 2.75 (d, 3H, J=4.7 Hz), 3.34-3.44 (m, 2H), 3.51-3.70 (m, 8H), 3.72 (dd, 1H, J=10.3 and 5.6 Hz), 3.82-3.93 (m, 1H), 3.95-4.25 (m, 3H), 4.26-4.56 (m, 1H), 4.63 (d, 1H, J=7.2 Hz), 4.86-5.02 (m, 1H), 4.96-5.28 (m, 6H), 5.33-5.51 (m, 1H), 5.83 (d, 1H, J=4.7 Hz) and 7.27-7.39 (m, 5H); $^{13}$C NMR (CDCl$_3$) δ 20.79, 20.84, 20.86, 20.89, 20.93, 21.0, 29.8, 41.0, 61.9, 62.2, 62.3, 62.7, 62.9, 65.26, 65.33, 66.9, 67.1, 70.2, 70.4, 70.5, 72.3, 128.3, 128.4, 128.66, 128.67, 136.6, 169.61, 169.65, 169.68, 170.6, 170.7, 170.8 and 170.9; HRMS (APCI), m/z 873.3150 (M+H)$^+$ (C$_{38}$H$_{53}$N$_2$O$_{21}$ requires m/z 873.3141).

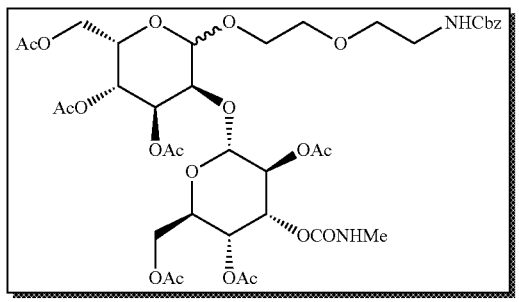

(3-O-carbamoyl-α-D-altropyranosyl)-α,β-L-gulopyranosyl 2-(2-aminoethoxy)ethanol (83)

To a solution containing 2.40 mg (2.80 μmol) of compound 81 in 2 mL of anh methanol was added a freshly prepared solution of 0.4 M sodium methoxide in methanol. The reaction mixture was allowed to stir at room temperature for 3 h, and the complete consumption of starting material was confirmed by MALDI-TOF mass spectral analysis. The reaction mixture was then quenched by the addition of 500 mg of Dowex 50× resin, shaken for 15 min and filtered. To the solution of the crude product in methanol was then added Pd/C and H$_2$ gas was bubbled through for 1 h. The complete consumption of starting material was confirmed by MALDI-TOF mass spectral analysis. The reaction was filtered through Celite 545® and then concentrated under diminished pressure to afford 83, which was used for the next reaction. HRMS (APCI), m/z 473.1978 (M+H)$^+$ (C$_{17}$H$_{33}$N$_2$O$_{13}$ requires m/z 473.1983).

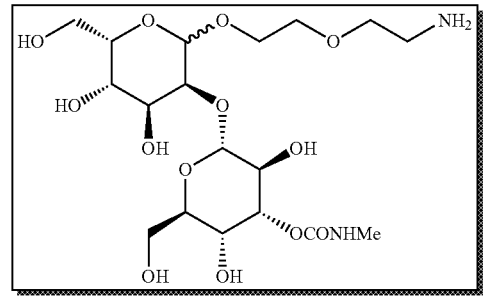

(4-O-(methylcarbamoyl)-α-D-altropyranosyl)-α,β-L-gulopyranosyl 2-(2-aminoethoxy)ethanol (84)

To a solution containing 1.00 mg (1.10 μmol) of compound 82 in 2 mL of anh methanol was added a freshly prepared solution of 0.4 M sodium methoxide in methanol. The reaction mixture was allowed to stir at room temperature for 3 h, and the complete consumption of starting material was confirmed by MALDI-TOF mass spectral analysis. The reaction mixture was then quenched by the addition of 300 mg of Dowex 50x resin, shaken for 15 min and filtered. To the solution of the crude product in methanol was added Pd/C and $H_2$ gas was bubbled through for 1 h. The complete consumption of starting material was confirmed by MALDI-TOF mass spectral analysis. The reaction mixture was filtered through Celite 545® and then concentrated under diminished pressure to afford 84, which was used for the next reaction. HRMS (APCI), m/z 487.2143 $(M+H)^+$ ($C_{18}H_{35}N_2O_{13}$ requires m/z 487.2139).

Example 13: Synthesis of Bleomycin Disaccharide Linker 3

Scheme 13

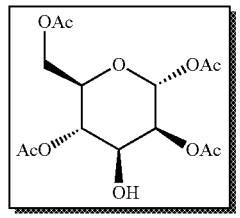

1,2,4,6-Tetra-O-acetyl-α-D-mannopyranose (85)

To a solution containing 0.88 g (2.00 mmol) of compound 30 in 24 mL of ethyl acetate was added a catalytic amount of $Pd(OH)_2/C$ and the reaction was maintained under 1 atm of $H_2(g)$ overnight. The catalyst was removed by filtration through a pad of Celite and the filtrate was concentrated under diminished pressure. The residue was purified by flash chromatography on a silica gel column (20×3 cm). Elution with 75% ethyl acetate in hexanes afforded compound 85 as a colorless oil: yield 550 mg (79%); silica gel TLC $R_f$ 0.11 (1:1 ethyl acetate-hexanes); $^1$H NMR ($CDCl_3$) δ 2.04 (s, 3H), 2.09 (s, 3H), 2.13 (s, 3H), 2.15 (s, 3H), 2.97 (s, 1H), 3.95 (m, 1H), 4.04 (m, 1H), 4.09 (m, 1H), 4.19 (dd, 1H, J=12.3 and 4.8 Hz), 5.07 (m, 1H), 5.13 (m, 1H) and 5.99 (m, 1H); $^{13}$C NMR ($CDCl_3$) δ 20.7, 20.8, 62.3, 68.0, 68.6, 70.3, 70.9, 90.4, 168.2, 170.3, 170.8 and 170.9.

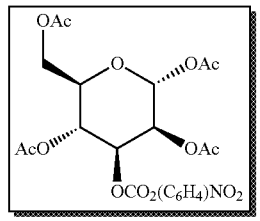

1,2,4,6-Tetra-O-acetyl-3-O-((p-nitrophenyl)carbamoyl)-α-D-mannopyranose (86)

To a solution containing 0.55 g (1.60 mmol) of 85 in 5.6 mL of pyridine were added 0.77 g (6.30 mmol) of DMAP and 1.30 g (6.30 mmol) of p-nitrophenyl chloroformate. The reaction mixture was stirred at 40° C. for 2 h at which time it was poured into a two-phase solution of 40 mL of ethyl acetate and 10 mL of $H_2O$. The organic layer was washed successively with three 10-mL portions of 1 N HCl, 10 mL of satd aq $NaHCO_3$ and 10 mL of brine. The solution was dried ($Na_2SO_4$) and concentrated under diminished pressure. The residue was purified by flash chromatography on a silica gel column (20×3 cm). Elution with 50% ethyl acetate in hexanes afforded compound 86 as a yellow oil: yield 0.66 g (81%); silica gel TLC $R_f$ 0.58 (1:1 ethyl acetate-hexanes); $^1$H NMR ($CDCl_3$) δ 2.07 (s, 3H), 2.09 (s, 3H), 2.14 (s, 3H), 2.17 (s, 3H), 4.08 (m, 2H), 4.25 (m, 1H), 5.15 (dd, 1H), 5.41 (m, 2H), 6.11 (s, 1H), 7.34 (d, 2H) and 8.23 (d, 2H); $^{13}$C NMR ($CDCl_3$) δ 20.6, 20.9, 61.8, 64.9, 67.4, 70.5, 74.1, 90.5, 121.8, 125.2, 145.5, 151.6, 155.1, 167.8, 169.3, 169.9 and 170.5.

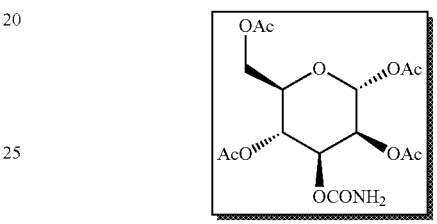

1,2,4,6-Tetra-O-acetyl-3-O-carbamoyl-α-D-mannopyranose (87)

To a solution of 0.51 g (1.31 mmol) of carbonate 86 in 27 mL of anh $CH_2Cl_2$ was added 15 mL of THF that had been saturated with $NH_3$ (g). The solution was stirred at room temperature for 1.5 h (at which time silica gel TLC analysis indicated that the reaction was complete). The solution was concentrated under diminished pressure. The residue was purified by flash chromatography on a silica gel column (14×3 cm). Elution with 3:1→1:2 hexanes-ethyl acetate afforded compound 87 as a colorless oil: yield 355 mg (91%); silica gel TLC $R_f$ 0.10 (1:1 hexanes-ethyl acetate). $^1$H NMR ($CDCl_3$) δ 2.02 (s, 3H), 2.04 (s, 3H), 2.11 (s, 3H), 2.12 (s, 3H), 4.04 (m, 2H), 4.22 (dd, 1H, J=12.6 and 5.0 Hz), 5.03 (br s, 2H), 5.24 (m, 3H) and 6.03 (d, 1H, J=1.7 Hz); $^{13}$C NMR ($CDCl_3$) δ 20.6, 20.6, 20.7, 61.9, 65.4, 68.6, 69.4, 70.4, 90.3, 155.2, 168.0, 169.6, 169.6 and 170.5.

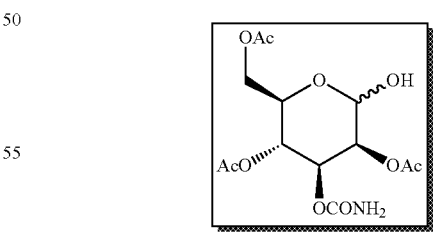

2,4,6-Tri-O-carbamoyl-α,β-D-mannopyranose (88)

To a solution of 365 mg (0.93 mmol) of compound 87 in 10.5 mL of dry DMF was added 120 mg (1.31 mmol) of acetate salt of hydrazine. The reaction mixture was stirred at room temperature for 1 h (at which time silica gel TLC analysis indicated that 87 had been consumed) and diluted with 80 mL of ethyl acetate. The solution was washed with three 25-mL portions of brine and concentrated under diminished pressure. The residue was purified by flash chromatography on a silica gel column (15×3 cm). Elution with 1:1 hexanes-ethyl acetate afforded compound 88 as a colorless oil: yield 285 mg (87%); silica gel TLC R$_f$ 0.24 (1:1 hexanes-ethyl acetate). $^1$H NMR (CDCl$_3$) δ 2.06 (s, 3H), 2.09 (s, 3H), 2.15 (s, 3H), 4.15 (m, 1H), 4.23 (m, 2H), 4.83 (s, 2H) and 5.25 (m, 4H).

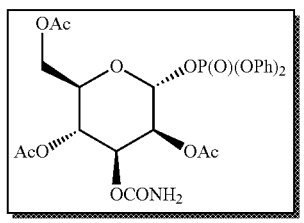

2,4,6-Tri-O-acetyl-3-O-carbamoyl-α-D-mannopyranosyl Diphenyl Phosphate (89)

To a solution of 160 mg (0.46 mmol) of intermediate 88, 64.0 mg (0.57 mmol) of DMAP and 640 μL (468 mg; 4.63 mmol) of Et$_3$N in 12.0 mL of CH$_2$Cl$_2$ at 0° C. was added dropwise 0.95 mL (1.23 g; 4.6 mmol) of diphenyl chlorophosphate. The solution was stirred at 0° C. for 1.5 h and was poured into a two-phase solution of EtOAc (100 mL) and saturated aq NaHCO$_3$ (40 mL). The organic layer was washed with two 30-mL portions of brine, dried over Na$_2$SO$_4$, filtered and concentrated under diminished pressure. The residue was purified by flash chromatography on a silica gel column (15×3 cm). Elution with 2:1→1:2 hexanes-ethyl acetate afforded the phosphate ester 89 as a colorless oil: yield 201 mg (75%); silica gel TLC R$_f$ 0.41 (2:3 hexanes-ethyl acetate). $^1$H NMR (CDCl$_3$) δ 1.95 (s, 3H), 2.03 (s, 3H), 2.12 (s, 3H), 3.91 (d, 1H, J=12.4 and 2.2 Hz), 4.08 (m, 1H), 4.17 (dd, 1H, J=12.4 and 4.7 Hz), 4.66 (br s, 2H), 5.30 (m, 3H), 5.87 (dd, 1H, J=6.5 and 1.6 Hz) and 7.28 (m, 10H); $^{13}$C NMR (CDCl$_3$) δ 20.6, 20.7, 20.7, 61.7, 65.3, 69.0, 69.1, 69.2, 70.7, 96.0, 96.1, 120.1, 120.1, 120.2, 120.3, 125.8, 125.9, 130.0, 129.0, 150.0, 150.1, 150.2, 150.3, 155.2, 169.5, 169.8 and 170.6.

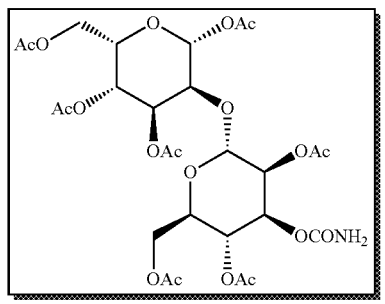

1,3,4,6-Tetra-O-acetyl-2-O-(2,4,6-tri-O-acetyl-3-O-carbamoyl-α-D-mannopyranosyl)-α-L-gulopyranoside (90)

To a round bottom flask containing 200 mg (0.34 mmol) of 89 was added a solution of 95.0 mg (0.27 mmol) of 23 in 3.80 mL of anhydrous CH$_2$Cl$_2$. The solution was cooled to 0° C. and to it was added 98.0 μL (120 mg; 0.55 mmol) of TMSOTf dropwise. The reaction mixture was stirred at 0° C. for 17 min at which time it was poured into a two-phase solution of EtOAc (60 mL) and saturated aq NaHCO$_3$ (25 mL). The organic layer was washed with two 20-mL portions of brine, dried (Na$_2$SO$_4$), filtered and concentrated under diminished pressure. The residue was purified by flash chromatography on a silica gel column (25×2 cm). Elution with 3:2→1:3 hexanes-ethyl acetate afforded the disaccharide 90 as a colorless oil: yield 115 mg (62%); silica gel TLC R$_f$ 0.38 (1:4 hexanes-ethyl acetate); $^1$H NMR (CDCl$_3$) δ 2.05 (s, 3H), 2.06 (s, 3H), 2.07 (s, 3H), 2.14 (s, 6H), 2.16 (s, 3H), 2.20 (s, 3H), 3.98 (dd, 1H, J=8.4 and 3.3 Hz), 4.19 (m, 2H), 4.38 (m, 1H), 4.85 (s, 2H), 5.13 (m, 7H), 5.45 (m, 1H) and 5.88 (d, 1H, J=8.4 Hz); $^{13}$C NMR (CDCl$_3$) δ 14.4, 20.9, 21.0, 21.0, 21.2, 21.3, 60.6, 61.6, 62.3, 65.7, 66.1, 67.9, 69.3, 69.4, 69.9, 71.5, 90.8, 95.2, 155.4, 168.9, 169.5, 169.6, 170.0, 170.7 and 170.8.

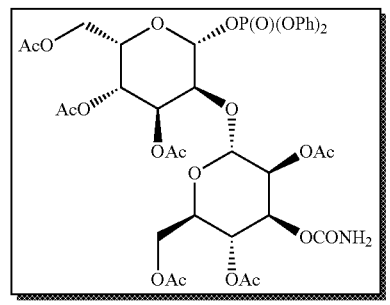

3,4,6-Tri-4-acetyl-2-O-(2,4,6-tri-O-acetyl-3-O-carbamoyl-α-D-mannopyranosyl)-α-L-gulopyranosyl Diphenyl Phosphate (91)

To a solution containing 112 mg (0.165 mmol) of 90 in 0.80 mL of anhydrous DMF was added 21 mg (0.23 mmol) of the acetate salt of hydrazine. The reaction mixture was stirred at room temperature for 1 h and quenched by the addition of 60 mL of ethyl acetate. The organic layer was washed with three 10-mL portions of brine and dried (Na$_2$SO$_4$). The solvent was filtered and then concentrated under diminished pressure to afford the deacetylated intermediate as a crude residue which was used for next reaction without further purification.

To a solution of 115 mg of the crude residue, 26.0 mg (0.21 mmol) of DMAP and 242 μL (177 mg, 1.75 mmol) of Et$_3$N in 16.5 mL of anhydrous CH$_2$Cl$_2$ at 0° C. was added 0.33 mL (428 mg, 1.59 mmol) of diphenyl chlorophosphate dropwise. The solution was stirred at 0° C. for 1.5 h and was then poured into a two-phase solution of EtOAc (80 mL) and saturated aq NaHCO$_3$ soln (30 mL). The organic layer was washed with three 25-mL portions of H$_2$O, two 25-mL portions of brine, then dried over Na$_2$SO$_4$, filtered, and concentrated under diminished pressure. The residue was purified by flash chromatography on a silica gel column (22×2 cm). Elution with 1:1→1:3 hexanes-ethyl acetate afforded compound 91 a colorless oil: yield 121 mg (84%); $^1$H NMR (CDCl$_3$) δ 1.70 (s, 3H), 1.97 (s, 3H), 2.05 (s, 3H), 2.11 (s, 3H), 2.13 (s, 3H), 2.19 (s, 3H), 4.13 (m, 5H), 4.31 (m, 2H), 4.76 (s, 2H), 4.96 (m, 1H), 4.98 (m, 1H), 5.18 (m, 3H), 5.43 (m, 1H), 5.69 (m, 1H) and 7.25 (m, 10H); $^{13}$C NMR (CDCl$_3$) δ 20.2, 20.6, 20.7, 61.1, 61.7, 65.3, 65.4, 67.3, 69.0, 69.8, 71.5, 95.3, 96.1, 120.1, 120.2, 125.5, 129.6, 129.8, 129.9, 155.0, 169.2, 169.3, 169.7, 170.3 and 170.5.

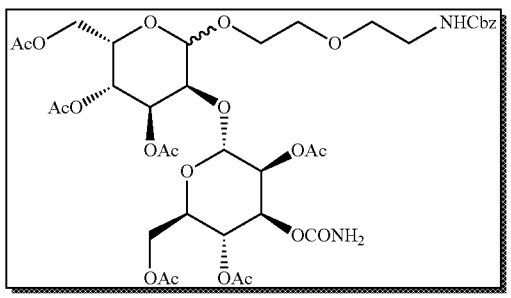

3,4,6-Tri-O-acetyl-2-O-(2,4,6-tri-O-acetyl-3-O-carbamoyl-α-D-mannopyranosyl)-α-L-gulopyranosyl benzyl 2-(2-ethoxy)ethylcarbamate (92)

To a solution of 78 mg (91 μmol) of 91 and 19 mg (79 μmol) of 54 in 2.4 mL of anhydrous $CH_2Cl_2$ was added 28 μL (34 mg, 0.16 mmol) of TMSOTf at 0° C. The reaction mixture was stirred at 0° C. for 17 min, at which time it was poured into a two-phase solution of EtOAc (50 mL) and saturated aq $NaHCO_3$ (20 mL). The organic layer was washed with two 20-mL portions of brine, dried ($Na_2SO_4$), filtered and concentrated under diminished pressure. The residue was purified by flash chromatography on a silica gel column (25×2 cm). Elution with 15:32:1→11:36:1 hexanes-ethyl acetate-methanol afforded compound 92 as a colorless oil: yield 62 mg (80%); silica gel TLC $R_f$ 0.30 (1:4 hexanes-ethyl acetate); $^1$H NMR ($CDCl_3$) δ 2.03 (s, 6H), 2.07 (s, 3H), 2.09 (s, 3H), 2.11 (s, 3H), 2.12 (s, 3H), 3.54 (m, 8H), 3.83 (m, 1H), 3.96 (m, 1H), 4.05 (m, 4H), 4.25 (m, 1H), 4.46 (m, 1H), 4.69 (s, 1H), 4.91 (m, 1H), 5.12 (m, 8H), 5.61 (m, 1H) and 7.34 (m, 5H); $^{13}$C NMR ($CDCl_3$) δ 20.6, 20.7, 20.8, 29.6, 40.9, 62.1, 62.5, 63.7, 65.5, 66.1, 66.6, 67.6, 68.5, 69.1, 69.6, 69.7, 70.0, 70.3, 70.6, 97.0, 97.1, 128.1, 128.2, 128.4, 136.5, 156.5, 169.3, 169.5, 169.8 and 170.5.

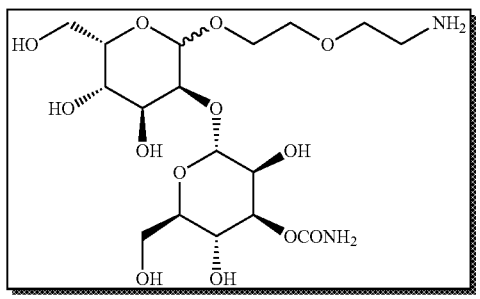

(3-O-carbamoyl-α-D-mannopyranosyl)-α,β-L-gulopyranosyl 2-(2-aminoethoxy)ethanol (3)

To a solution containing 15.00 mg (8.06 μmol) of compound 92 in 5 mL of anh methanol was added a freshly prepared solution of 0.4 M sodium methoxide in methanol. The reaction mixture was allowed to stir at room temperature for 3 h, and the complete consumption of starting material was confirmed by MALDI-TOF mass spectral analysis. The reaction mixture was then quenched by the addition of 300 mg of Dowex 50× resin, shaken for 15 min and filtered. To the solution of the crude product in methanol was added Pd/C and $H_2$ gas was bubbled through for 1 h. The complete consumption of starting material was confirmed by MALDI-TOF mass spectral analysis. The reaction mixture was filtered through Celite 545® and then concentrated under diminished pressure to afford 3, which was used for the next reaction. Mass spectrum (MALDI), m/z 473.35 $(M+H)^+$, 495.32 $(M+Na)^+$ ($C_{18}H_{35}N_2O_{13}$ requires m/z 472.19).

Example 14: Synthesis of Bleomycin Disaccharide-Trimer Linker 102

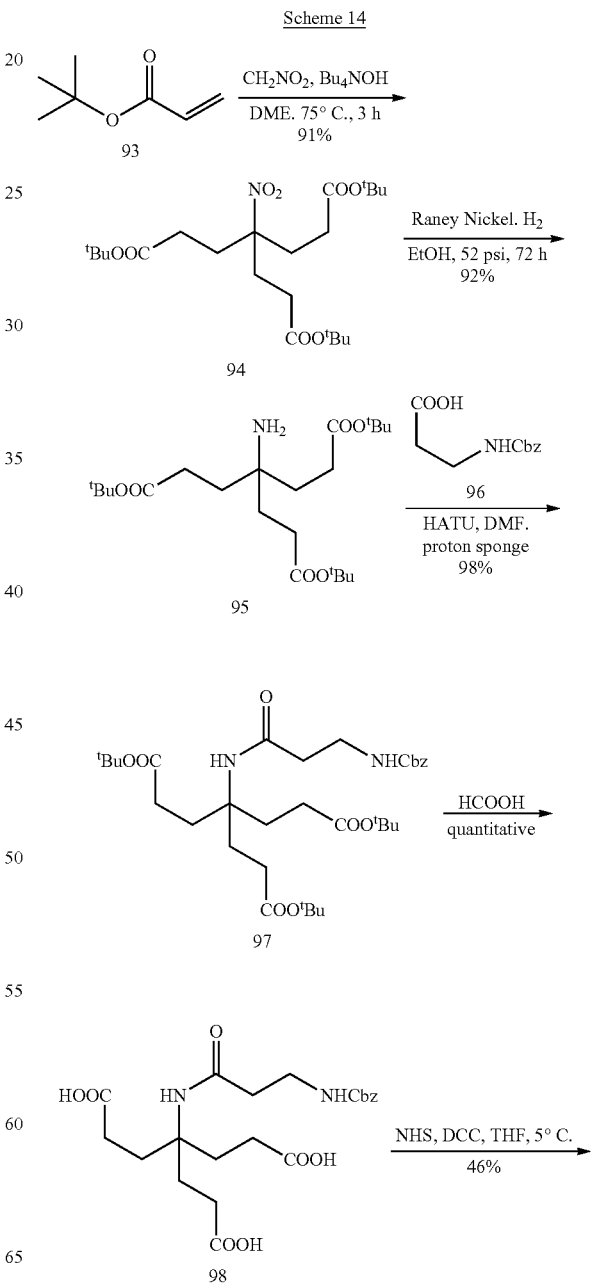

-continued

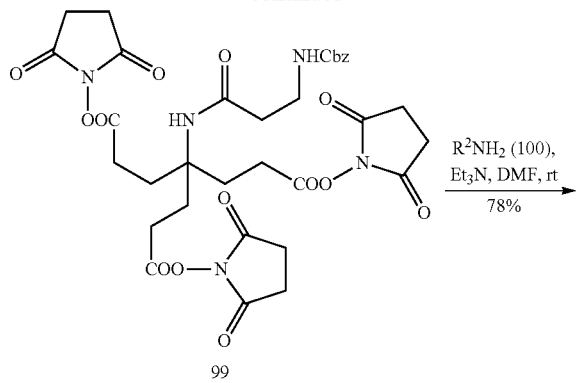

99

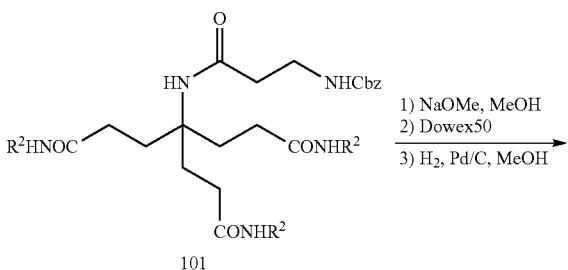

101

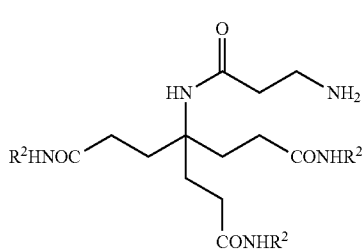

102

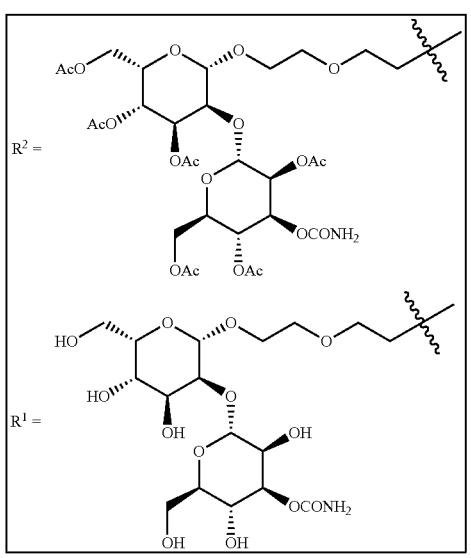

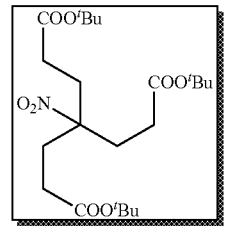

4-(2-tert-Butoxycarbonyl-ethyl)-4-nitro-heptanedioic Acid Di-tert-butyl Ester (94)

To a solution of 2.14 mL (2.43 g; 39.8 mmol) of nitromethane in 10 mL of dimethoxyethane at 65° C. was added 0.4 mL of 40% aq tetrabutylammonium hydroxide soln and the reaction mixture was heated to 75° C. To the reaction mixture was added dropwise 18.2 mL (125 mmol) of tert-butyl acrylate (93). To this mixture was added 0.8 mL of 40% aq tetrabutylammonium hydroxide soln in portions over a period of 1 h. The reaction mixture was stirred at 75° C. for 2 h. The reaction mixture was concentrated under diminished pressure and the residue was diluted in 100 mL of diethyl ether. The ether layer was washed with two 30-mL portions of 10% aq citric acid soln, two 30-mL portions of sat aq $NaHCO_3$ soln, 20 mL of brine, then dried over anhydrous $Na_2SO_4$, filtered and concentrated under diminished pressure. The residue was recrystallized from absolute ethanol to afford compound 94 as colorless needles: yield 16.1 g (91%); mp 92-94° C., $^1$H NMR ($CDCl_3$) δ 1.43 (s, 27H) and 2.19 (m, 12H); $^{13}$C NMR ($CDCl_3$) δ 28.2, 29.9, 30.5, 81.3, 92.3 and 171.2.

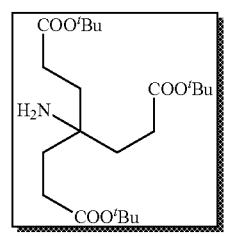

4-Amino-4-(2-tert-butoxycarbonylethyl)heptanedioic Acid Di-tert-butyl Ester (95)

A mixture of 1.02 g (2.29 mmol) of compound 94, ~6 mL of Tl-Raney Ni (suspension in ethanol) and 18 mL of absolute ethanol was shaken in a Parr shaker at room temperature and 52 psi $H_2$ for 72 h. The reaction mixture was filtered through a pad of Celite and the filtrate was concentrated under diminished pressure to afford the amine 95 as a waxy solid which was used directly in the next step: yield 0.88 g (92%); silica gel TLC $R_f$ 0.14 (1:3 hexanes-ethyl acetate); $^1$H NMR (CDCl$_3$) δ 1.42 (s, 27H), 1.58 (t, 6H, J=8.4 Hz) and 2.22 (1, 6H, J=8.4 Hz); $^{13}$C NMR (CDCl$_3$) δ 28.0, 29.9, 34.4, 52.3, 80.3 and 173.0.

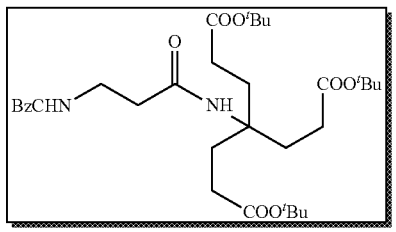

4-(3-Bezyloxycarbonylaminopropionylamino)-4-(2-tert-butoxycarbonyl-ethyl)-heptanedioic Acid Di-tert-butyl Ester (97)

To a solution of 0.84 g (2.02 mmol) of compound 95 and 0.43 g (1.91 mmol) of CBz-f-alanine (96) in 15 mL of dry DMF were added 0.74 g (1.95 mmol) of HATU and 0.82 g (3.82 mmol) of proton sponge. The resulting yellow mixture was stirred at room temperature for 16 h. The reaction mixture was concentrated under diminished pressure and the residue was dissolved in 80 mL of ethyl acetate. The ethyl acetate layer was washed with two 40-mL portions of 2 M aq HCl, two 30-mL portions of –20, and 20 mL of brine, then dried over anhydrous Na$_2$SO$_4$, filtered and concentrated under diminished pressure. The residue was purified by flash chromatography on a silica gel column (12×3 cm). Elution with 1:1 hexanes-ethyl acetate gave compound 97 as a colorless solid: yield 1.17 g (98%); silica gel TLC $R_f$ 0.40 (1:1 hexanes-ethyl acetate); $^1$H NMR (CDCl$_3$) δ 1.42 (s, 27H), 1.94 (t, 6H, J=8.0 Hz), 2.19 (t, 6H, J=8.4 Hz), 2.34 (m, 2H), 3.44 (m, 2H), 5.09 (s, 2H), 5.57 (brs, 1H), 5.99 (brs, 1H) and 7.32 (m, 5H); $^{13}$C NMR (CDCl$_3$) δ 28.1, 29.8, 30.0, 36.8, 37.3, 57.8, 66.6, 80.8, 128.0, 128.5, 136.7, 156.6, 170.9 and 172.9; mass spectrum (ESI), m/z 621.3753 (M+H)$^+$ (C$_{33}$H$_{53}$N$_2$O$_9$ requires m/z 621.3746).

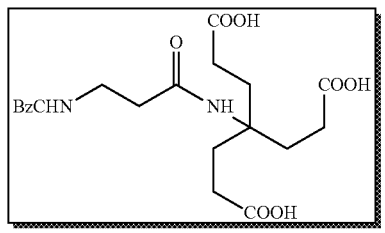

4-(3-Benzyloxycarbonylaminopropionylamino)-4-(2-carboxyethyl)-heptanedioic Acid (98)

A solution of 1.21 g (1.93 mmol) of 97 in 25 mL of formic acid was stirred at room temperature for 12 h. The reaction mixture was concentrated under diminished pressure. The residue was co-evaporated with six 10-mL portions of toluene to afford the tri-acid 98 as colorless oil: yield 0.91 g (100%); $^1$H NMR (CD$_3$OD) δ 2.01 (m, 6H), 2.26 (m, 6H), 2.40 (m, 2H), 3.36 (m, 2H), 5.07 (s, 2H) and 7.31 (m, 5H); $^{13}$C NMR (DMSO-d$_6$) δ 28.1, 29.0, 36.2, 37.3, 56.4, 65.2, 127.71, 127.75, 137.2, 156.0, 170.0 and 174.5; mass spectrum (ESI), m/z 453.1886 (M+H)$^+$ (C$_{21}$H$_{29}$N$_2$O$_9$ requires m/z 453.1868).

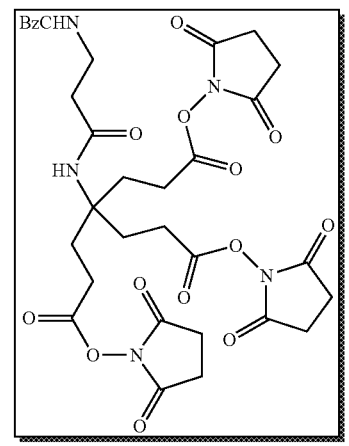

4-(3-Benzyloxycarbonylaminopropionylamino)-4-[2-(2,5-dioxo-pyrrolidin-1-yloxycarbonyl)ethyl]heptanedioic Acid Bis-(N-hydroxysuccinimide) Ester (99)

To a solution of 0.48 g (1.06 mmol) of compound 98 and 0.44 g (3.82 mmol) of N-hydroxysuccinimide in 9.00 mL of dry THF at 0° C. was added dropwise a solution of 0.83 g (4.03 mmol) of DCC in 2.00 mL of dry THF. The reaction mixture was stirred at 5° C. for 16 h. The reaction mixture was concentrated under diminished pressure and the residue was suspended in 10 mL of acetonitrile. The suspension was filtered and the filtrate was concentrated under diminished pressure. The residue was the purified by crystallization from absolute ethanol to afford 99 as colorless crystals: yield 366 mg (46%); $^1$H NMR (CD$_3$CN) δ 2.08 (m, 6H), 2.31 (m, 2H), 2.58 (m, 6H), 2.74 (s, 12H), 3.28 (m, 2H), 5.02 (s, 2H), 5.73 (brs, 1H), 6.10 (brs, 1H) and 7.32 (m, 5H); $^{13}$C NMR (CD$_3$CN) δ 25.9, 26.3, 29.5, 37.0, 37.9, 58.0, 66.7, 128.6, 128.7, 129.3, 138.3, 157.2, 169.8, 171.0 and 172.1, mass spectrum (ESI), m/z 744.2342 (M+H)$^+$ (C$_{33}$H$_{38}$N$_5$O$_{15}$ requires m/z 744.2359).

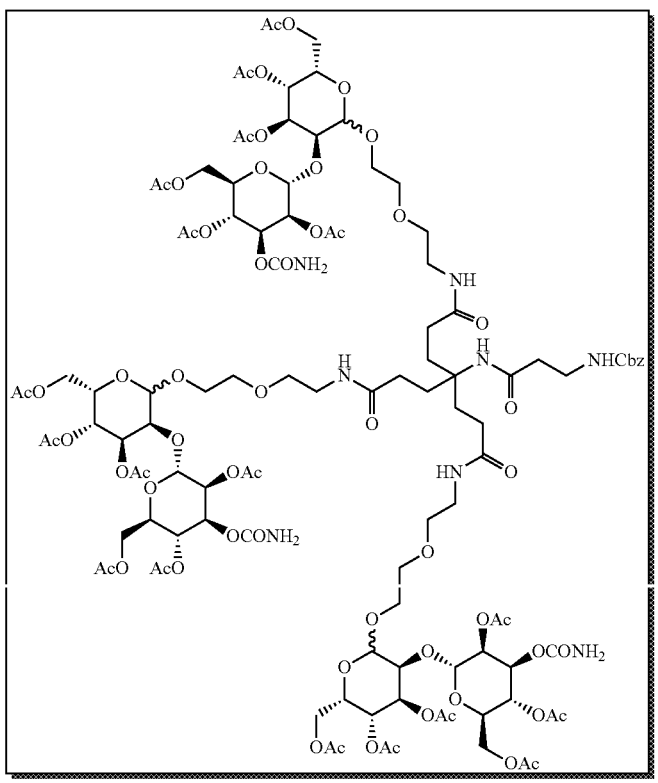

TrimerBLM-disaccharide (101)

H$_2$ gas was bubbled through a mixture containing 18 mg (21 µmol) of 92 and a catalytic amount of Pd/C in 5.0 mL of dry THF for 45 min. The reaction mixture was filtered through a pad of Celite and the filtrate was concentrated under diminished pressure to obtain crude 100 as a colorless oil, which was used immediately in the next step: crude yield 14 mg; mass spectrum (MALDI) m/z 725.28 (M+H)$^+$ (theoretical m/z 725.26).

To a solution containing 14 mg (19 µmol) of 100 and 20 µL (15 mg, 0.14 mmol) of triethylamine in 1.5 mL of dry DMF was added 1.6 mg (2.2 µmol) of 99 and the mixture was stirred at room temperature for 20 h. The reaction mixture was concentrated under diminished pressure. The residue was purified by flash chromatography on a silica gel column (14×1 cm). Elution with 32:15:1→11:10:1 chloroform-acetone-methanol afforded trimerBLM-disaccharide 101 as a colorless oil: yield 4.5 mg (81%); silica gel TLC R$_f$ 0.60 (4:4:1 chloroform-acetone-methanol); mass spectrum (MALDI), m/z 2595.11 (M+Na)$^+$ (theoretical m/z 2594.90); mass spectrum (ESI), m/z 1297.4575 (M+H+Na)$^{2+}$ (C$_{108}$H$_{155}$N$_8$O$_{63}$Na requires m/z 1297.4529).

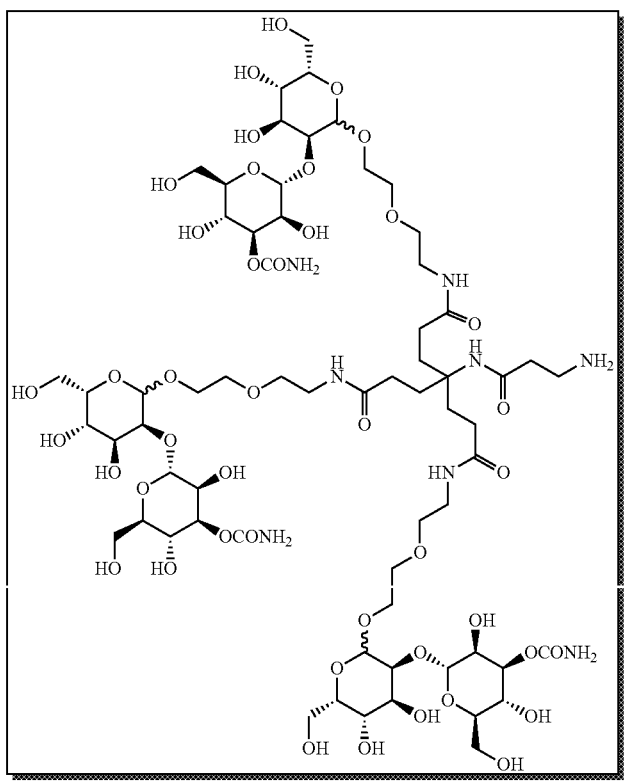

TrimerBLM-Disaccharide Linker (102)

To a solution of 5.0 mg (1.94 μmol) of 101 in 2 mL of dry MeOH was added 0.3 mL of a 25% w/w solution of NaOMe in MeOH. The reaction mixture was shaken at room temperature for 2 h. One hundred mg of Dowex 50W resin was added and the mixture was shaken at room temperature for 30 min. The mixture was filtered, diluted to 5 mL with methanol and a catalytic amount of Pd/C was added. $H_2$ gas was bubbled through the mixture for 30 min and the mixture was filtered. The filtrate was concentrated to obtain compound 102 as colorless solid: crude yield 2.6 mg (80%).

Example 15S: Synthesis of Monosaccharide-Linker 104

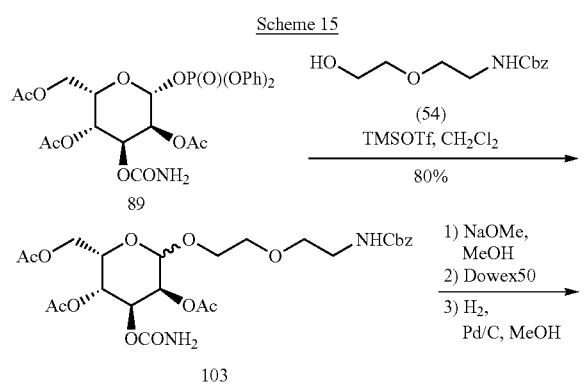

Scheme 15

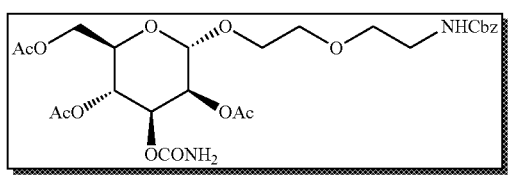

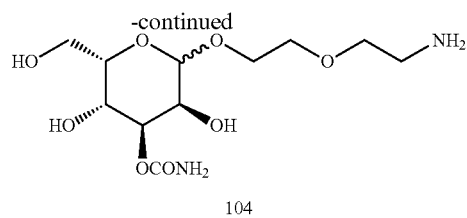

2,4,6-tri-O-acetyl-3-O-(carbamoyl)-α-D-mannopyranosyl Benzyl 2-(Ethoxy)ethylcarbamate (103)

To a solution of 121 mg (0.21 mmol) of 89 and 45 mg (0.19 mmol) of 54 in 3.5 mL of anhydrous $CH_2Cl_2$ was added 68 μL (83 mg, 0.38 mmol) of TMSOTf at 0° C. The reaction mixture was stirred at 0° C. for 20 min, at which time it was poured into a two-phase solution of EtOAc (70 mL) and saturated aq $NaHCO_3$ (28 mL). The organic layer was washed with two 28-mL portions of brine, dried (Na$_2$SO$_4$), filtered and concentrated under diminished pressure. The residue was purified by flash chromatography on a silica gel column (25×2.5 cm). Elution with 1:1→1:2→1:3 hexanes-ethyl acetate afforded compound 103 as a colorless oil: yield 95 mg (80%); silica gel TLC R$_f$ 0.26 (1:3 hexanes-ethyl acetate); $^1$H NMR (CDCl$_3$) δ 2.02 (s, 31H), 2.08 (s, 3H), 2.12 (s, 3H), 3.39 (m, 2H), 3.54 (m, 2H), 3.64 (m, 3H), 3.79 (m, 1H), 4.08 (m, 2H), 4.26 (m, 1H), 4.71 (br s, 2H), 4.91 (s, 1H), 5.10 (s, 2H), 5.25 (m, 3H), 5.37 (br s, 1H) and 7.35 (m, 5H); $^{13}$C NMR (CDCl$_3$) δ 20.8, 20.9, 21.0, 41.1, 62.7, 66.5, 66.8, 67.3, 68.5, 70.0, 70.1, 70.3, 70.4, 77.4, 97.6, 128.1, 128.2, 128.6, 136.8, 155.3, 170.1, 170.2, 170.8.

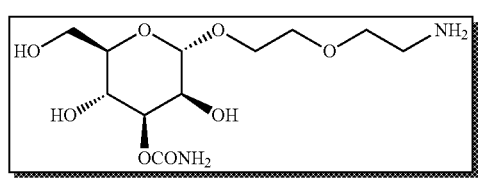

3-O-(carbamoyl)-α-D-mannopyranosyl 2-(2-aminoethoxy)ethanol 104

To a solution of 4.60 mg (8.06 mol) of compound 103 in 2 mL of anh methanol was added a freshly prepared solution of 0.4 M sodium methoxide in methanol. The reaction mixture was allowed to stir at room temperature for 3 h, and the complete consumption of starting material was confirmed by MALDI-TOF mass spectral analysis. The reaction mixture was then quenched by the addition of 500 mg of Dowex 50× resin, shaken for 15 min and filtered; mass spectrum (MALDI), m/z 467.27 (M+Na)$^+$ (theoretical m/z 444.17). To the solution of the crude product in methanol was added Pd/C and H$_2$ gas was bubbled through for 1 h. The complete consumption of starting material was confirmed by MALDI-TOF mass spectral analysis. The reaction mixture was filtered through Celite 545' and then concentrated under diminished pressure to afford 104, which was used for the next reaction; mass spectrum (MALDI), m/z 311.12 (M+H)$^+$ (theoretical m/z 310.14).

Example 16: Synthesis of Monosaccharide-Trimer Linker 107

Scheme 16

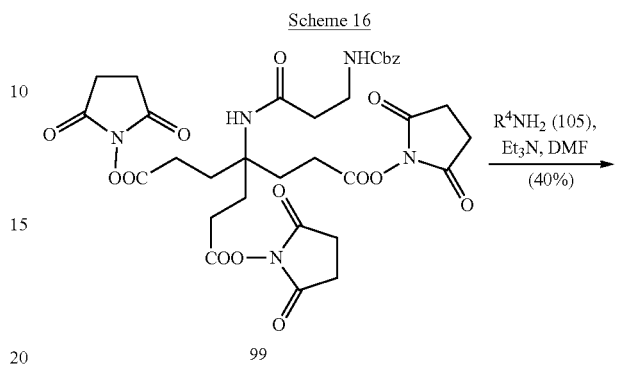

99

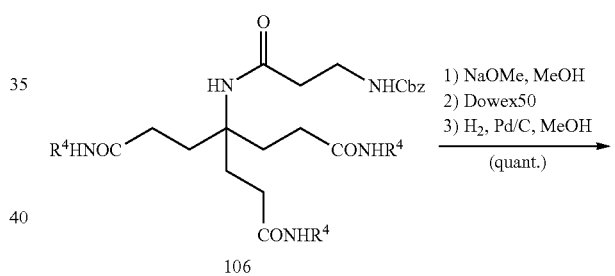

106

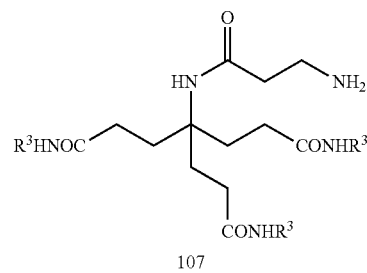

107

-continued

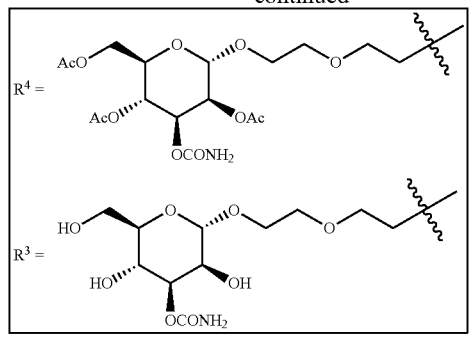

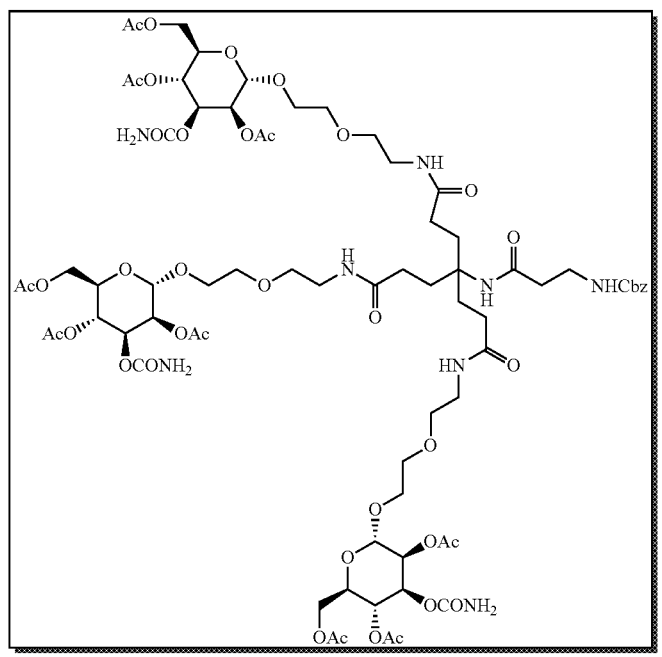

Trimer BLM-Monosaccharide (106)

H₂ gas was bubbled through a mixture containing 36 mg (21 μmol) of 103 and a catalytic amount of Pd/C in 6 mL of dry THF for 45 min. The reaction mixture was filtered through a pad of Celite and the filtrate was concentrated under diminished pressure to obtain crude 105 as a colorless oil, which was used immediately in the next step: crude yield 27 mg (99%); silica gel TLC $R_f$ 0.29 (1:3 hexanes-ethyl acetate); mass spectrum (MALDI), m/z 459.26 (M+Na)⁺; mass spectrum (APCI), m/z 437.1768 (M+H)⁺ ($C_{17}H_{29}N_2O_{11}$ requires m/z 437.1772).

To a solution containing 27 mg (61.8 μmol) of 105 in 0.53 mL of dry DMF, 13 μL (0.09 mmol) of triethylamine was added 15.2 mg (204 μmol) of 99 were added and stirred at room temperature for 24 h. The reaction mixture was concentrated under diminished pressure. The residue was purified by flash chromatography on a silica gel column (1.5×15 cm). Elution with 16:12:1→411:12:1 chloroform-acetone-methanol afforded trimer BLM monosaccharide 106 as a colorless oil: yield 15 mg (43%); silica gel TLC $R_f$ 0.56 (4:4:1 chloroform-acetone-methanol); mass spectrum (MALDI), m/z 1730.76 (M+Na)⁺; mass spectrum (TOF), m/z 854.3351 (M+2H)²⁺ ($C_{72}H_{108}N_8O_{39}$ requires m/z 854.3357).

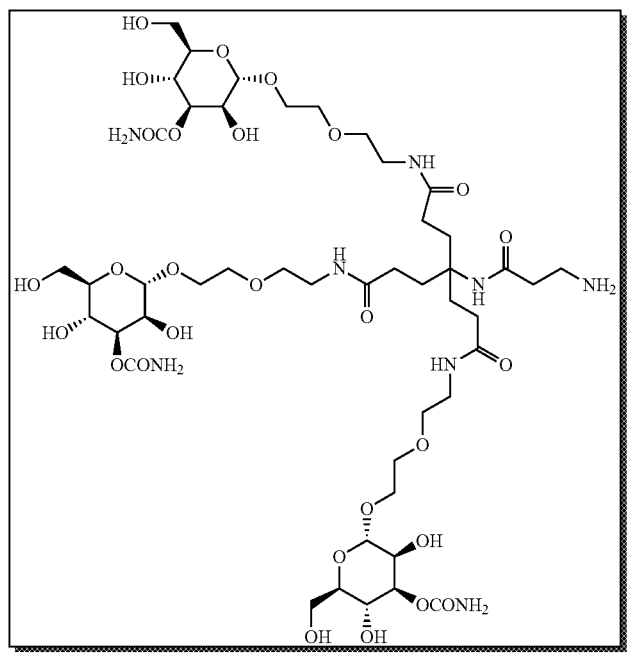

Trimer BLM Monosaccharide-Linker (107)

To a solution of 4.2 mg (2.46 μmol) of 106 in 2 mL of anh methanol was added 0.2 mL of 25% w/w freshly prepared solution of sodium methoxide in methanol. The reaction mixture was allowed to stir at room temperature for 2.5 h, and the complete consumption of starting material was confirmed by MALDI-TOF mass spectral analysis. The reaction mixture was then quenched by the addition of 500 mg of Dowex 50× resin, shaken for 15 min and filtered; mass spectrum (MALDI), m/z 1351.40 (M+Na)$^+$ (theoretical m/z 1328.56). To the solution of the crude product in methanol was added Pd/C and H$_2$ gas was bubbled through for 45 min. The complete consumption of starting material was confirmed by MALDI-TOF mass spectral analysis. The reaction mixture was filtered through Celite 545® and then concentrated under diminished pressure to afford 2.9 mg of 107 (quant.), which was used for the next reaction; mass spectrum (MALDI), m/z 1217.62 (M+Na)$^+$; mass spectrum (TOF), m/1 1229.4961 (M+Cl)$^-$ (C$_{46}$H$_{82}$N$_8$O$_{28}$Cl requires m/z 1229.4927).

Example 17: Synthesis of Decarbamoyl Monosaccharide Linker 112

Scheme 17

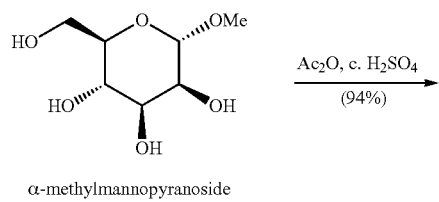

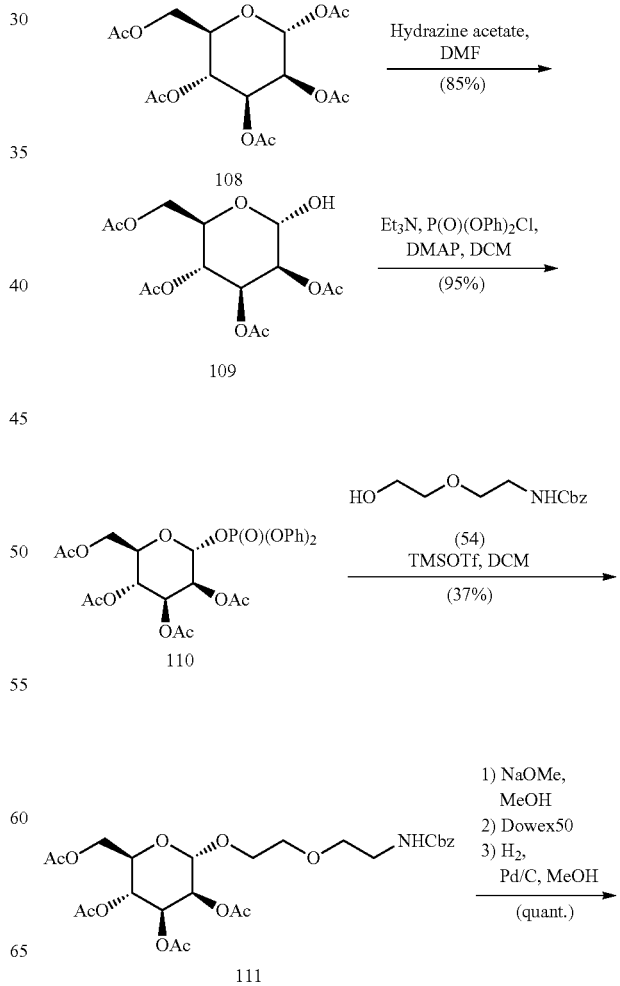

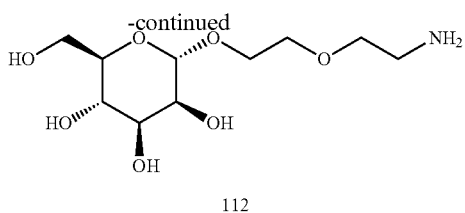

112

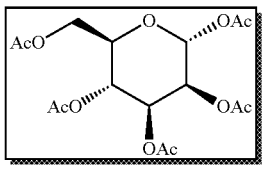

Penta-O-acetyl-α-D-mannopyranose (108)

To a solution containing 1.00 g (5.15 mmol) of O-methyl-α-D-mannopyranose in 18.9 mL of Ac$_2$O, was added a catalytic amount of H$_2$SO$_4$, and the solution was stirred at room temperature for 12 h. The reaction mixture was poured into a stirred mixture of 150 mL of ethyl acetate and 80 mL of said aq NaHCO$_3$. The organic phase was separated and washed with 40 mL of satd aq NaHCO$_1$, 30 mL of brine, then dried (Na$_2$SO$_4$) and concentrated under diminished pressure. The residue was purified by flash chromatography on a silica gel column (5×18 cm). Elution with 5:1→3:1 hexanes-ethyl acetate afforded 108 as a colorless oil: yield 1.97 g (98%); silica gel TLC R$_f$ 0.60 (1:2 hexanes-ethyl acetate); $^1$H NMR (CDCl$_3$) δ1.86 (s, 31H), 1.91 (s, 3H), 1.95 (m, 3H), 2.04 (m, 6H), 3.94 (m, 2H), 4.13 (m, 1H), 5.12 (s, 1H), 5.20 (m, 2H) and 5.94 (s, 1H); $^{13}$C NMR (CDCl$_3$) δ 20.40, 20.43, 20.47, 20.53, 20.6, 61.9, 65.3, 68.1, 68.6, 70.4, 76.8, 77.2, 77.5, 167.8, 169.3, 169.5, 169.7 and 170.3.

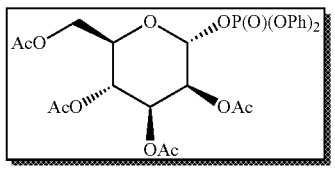

2,3,4,6-Tetra-O-acetyl-α-D-mannopyranosyl Diphenyl Phosphate (110)

To a solution of 525 mg (1.34 mmol) 108 in 8.1 mL of dry DMF, was added 170 mg (1.88 mmol) of hydrazine acetate. The reaction was stirred at room temperature for 2 h until analysis by silica gel TLC indicated it was complete. The reaction mixture was diluted with 50 mL of ethyl acetate and washed with three 20-mL portions of brine. The aq layer was re-extracted with three 30-mL portions of ethyl acetate. The combined organic layer was dried (Na$_2$SO$_4$) and concentrated under diminished pressure and dried to afford compound 109 as a colorless oil: yield 397 mg (85%); silica gel TLC R$_f$ 0.39 (3:1 hexanes-ethyl acetate).

To a solution of 397 mg (1.14 mmol) of 109 in 16.5 mL of dry CH$_2$Cl$_2$, 180 mg (1.47 mmol) of DMAP and 1.6 mL (11.4 mmol) of Et$_3$N. The reaction mixture was stirred for 10 min, followed by the addition of 2.3 mL (10.9 mmol) of diphenyl chlorophosphate dropwise at 0° C. The solution was stirred at 0° C. for 1.5 h and was poured into a two-phase solution of EtOAc (200 mL) and saturated aq NaHCO$_3$ soln (80 mL). The organic layer was washed with two 50-mL portions of brine, dried over Na$_2$SO$_4$, filtered, and concentrated under diminished pressure. The residue was purified by flash chromatography on a silica gel column (18×5 cm). Elution with 3:1→2:1 hexanes-ethyl acetate afforded compound 110 as a colorless oil: yield 424 mg (54% over two steps); silica gel TLC R$_f$ 0.54 (3:1 hexanes-ethyl acetate); $^1$H NMR (CDCl$_3$) δ 2.04 (s, 3H), 2.06 (s, 3H), 2.10 (s, 3H), 2.22 (s, 3H), 3.98 (dd, 1H, J=12.4 and 2.0 Hz), 4.14 (m, 1H), 4.25 (dd, 1H, J=12.4 and 4.8 Hz), 5.40 (m, 3H), 5.92 (dd, 1H, J=6.8 and 1.6 Hz), 7.28-7.33 (m, 6H) and 7.40-7.45 (m, 4H); $^{13}$C NMR (CDCl$_3$) δ 20.70, 20.72, 20.78, 20.84, 61.8, 65.2, 68.3, 68.7, 68.8, 70.9, 96.17, 96.22, 120.18, 120.22, 120.3, 120.4, 125.90, 125.91, 126.0, 130.1, 130.2, 169.6, 169.9 and 170.7.

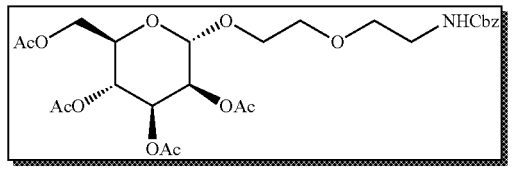

2,3,4,6-Tetr-O-acetyl-α-D-mannopyranosyl benzyl 2-(2-ethoxy)ethylcarbamate (111)

To a solution of 300 mg (0.52 mmol) of phosphate ester 110 and 111 mg (0.46 mmol) of the alcohol 54 in 5.5 mL of anhydrous CH$_2$Cl$_2$, was added 168 µL (207 mg, 0.93 mmol) of TMSOTf at 0° C. The reaction was stirred at 0° C. for 18 min and was then poured into a two-phase solution of EtOAc (100 mL) and saturated aq NaHCO$_3$ (40 mL). The organic layer was washed with two 40-mL portions of brine, dried (Na$_2$SO$_4$), filtered and concentrated under diminished pressure. The residue was purified by flash chromatography on a silica gel column (2.5×25 cm). Elution with 2:1→1:2 hexanes-ethyl acetate afforded compound 111 as a colorless oil: yield 110 mg (37%); silica gel TLC R$_f$ 0.35 (1:3 hexanes-ethyl acetate); $^1$H NMR (CDCl$_3$) δ 1.61 (s, 1H), 1.96 (s, 3H), 1.98 (s, 3H), 2.06 (s, 3H), 2.11 (s, 3H), 3.38 (m, 2H), 3.53 (m, 2H), 3.63 (m, 3H), 3.77 (m, 1H), 4.05 (m, 1H), 4.09 (m, 1H), 4.24 (dd, 1H, J=12.4 and 5.2 Hz), 4.87 (d, 1H, J=1.2 Hz), 5.08 (s, 2H), 5.22 (m, 1H), 5.26 (m, 1H), 5.31 (br s, 11H), 5.34 (m, 511H), 7.26-7.34 (m, 5H); $^{13}$C NMR (CDCl$_3$) δ 20.80, 20.82, 20.9, 21.0, 39.4, 41.1, 62.7, 66.4, 66.8, 67.2, 68.6, 69.1, 69.8, 70.1, 70.4, 97.7, 128.2, 128.6, 136.8, 169.9, 170.0, 170.3, 170.8 and 170.9; mass spectrum (MALDI), m/z 592.34 (M+Na)$^+$; mass spectrum (APCI), m/z 570.2182 (M+H)$^+$ (C$_{26}$H$_{36}$NO$_{13}$ requires m/z 570.2187).

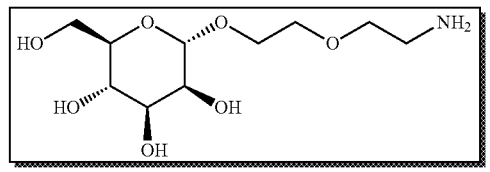

139
Decarbamoyl BLM Monosaccharide-Dye Conjugate
112

To a solution of 8.9 mg (15.6 μmol) of compound 111 in 2 mL of anh methanol was added, 0.2 mL of 25% w/w freshly prepared solution of sodium methoxide in methanol. The reaction mixture was allowed to stir at room temperature for 2.5 h, and the complete consumption of starting material was confirmed by MALDI-TOF mass spectral analysis. The reaction mixture was then quenched by the addition of 500 mg of Dowex 50× resin, shaken for 15 min and filtered; mass spectrum (MALDI), m/z 424.24 (M+Na)$^+$; Mass spectrum (APCI), m/z 402.1759 (M+H)$^+$ ($C_{18}H_{28}NO_9$ requires m/z 402.1764). To the solution of the crude product in 5 mL methanol was added Pd/C and $H_2$ gas was bubbled through for 45 min. The complete consumption of starting material was confirmed by MALDI-TOF mass spectral analysis. The reaction mixture was filtered through Celite 545 and then concentrated under diminished pressure to afford 112, which was used for the next reaction, mass spectrum (MALDI), m/z 268.25 (M+H)$^+$, 290.25 (M+Na)$^+$; mass spectrum (APCI), m/z 268.1391 (M+H)$^+$ ($C_{10}H_{22}NO_7$ requires m/z 268.1396).

Example 18: Synthesis of Camptothecin (CPT)-Saccharide Conjugates 115, 116, 117 and 118

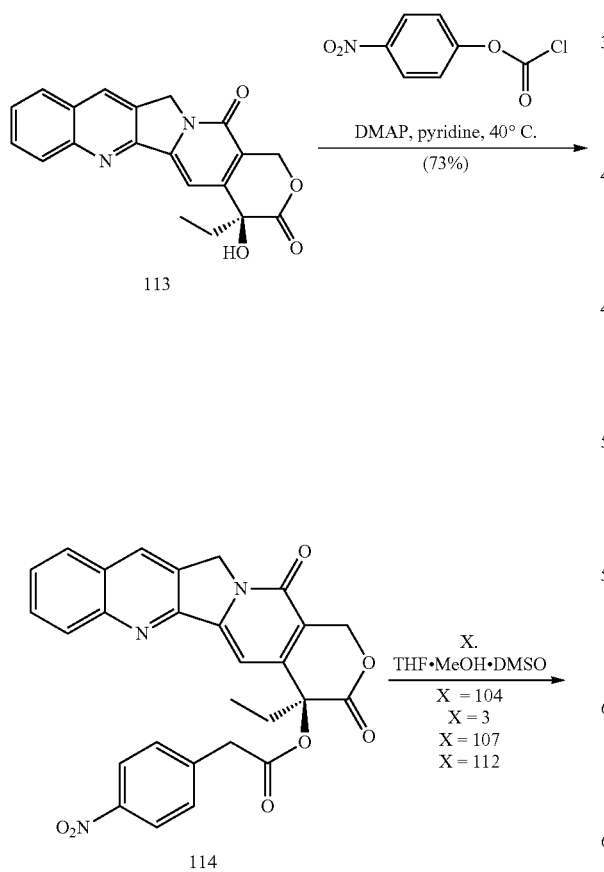

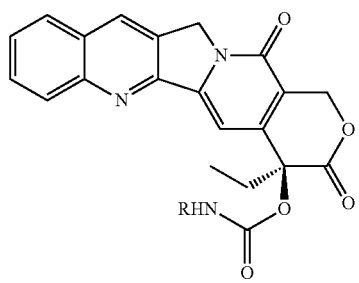

115 R = R$_1$ (22%)
116 R = R$_2$, (30%)
117 R = R$_3$, (20%)
118 R = R$_4$, (29%)

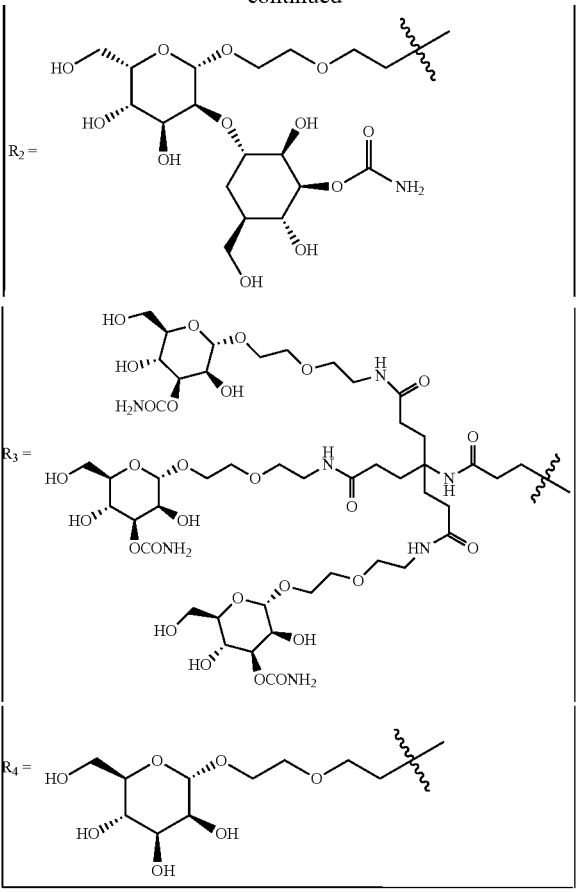

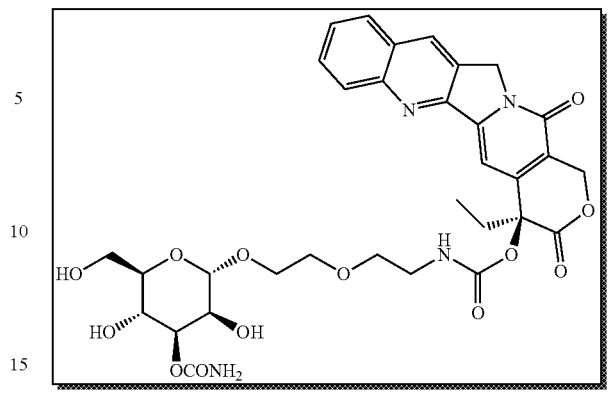

CPT-Carbamate-Monosaccharide (115)

To 6 mg (19.47 μmol) 104 in 1.75 mL of THF-MeOH-DMSO (2:4:1), was added 5 mg (9.74 μmol) of 114 and stirred overnight. The reaction mixture was purified on an Econosil $C_{18}$ reversed phase semi-preparative (250×10 mm, 10 μm) HPLC column using aq 0.1% TFA and $CH_3CN$ mobile phases. A linear gradient was employed (99:1 0.1% aq TFA-$CH_3CN$→60:40 0.1% aq TFA-$CH_3CN$) over a period of 18 min at a flow rate of 4.5 mL/min. The fractions containing the desired product eluted at 15.9 min (monitoring at 364 nm) and were collected, frozen and lyophilized to give 115 as a light yellow solid: yield 1.5 mg (22%); mass spectrum (MALDI), m/z 685.72 $(M+Na)^+$.

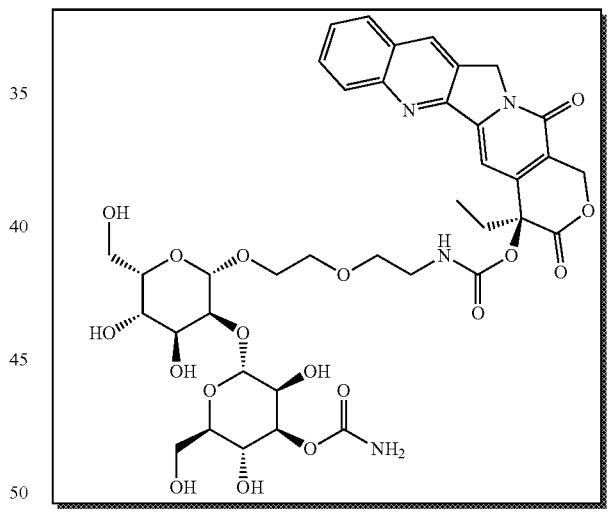

CPT-Carbamate-Disaccharide (116)

CPT-Carbamate (114)

To a solution of 40 mg (0.11 mmol) of 113 in 0.42 mL of pyridine was added 56 mg (0.46 mmol) of DMAP and 92 mg (0.46 mmol) of p-nitrophenyl chloroformate and was stirred at 40° C. overnight.

The solution was cooled and poured into a two-phase solution of 210 mL EtOAc and 3 mL of $H_2O$. The organic layer was washed with three 5 mL portions of 1N HCl, 5 mL of saturated aq. $NaHCO_3$ and 3 mL of brine. The solution was dried over $MgSO_4$, filtered, and concentrated under diminished pressure. The residue was purified by flash chromatography on a silica gel column (2.5×20 cm). Elution with 15:1→8:1 chloroform-methanol afforded 114 as a light yellow solid: yield 43 mg (73%); silica gel TLC $R_f$ 10.30 (7:1 hexanes-ethyl acetate). $^1H$ NMR (500 MHz, $CDCl_3$) δ 1.07 (m, 3H), 2.25 (m, 1H), 2.37 (m, 1H), 5.31 (m, 2H), 5.42 (d, 1H, J=16.5 Hz), 5.72 (d, 1H, J=17.0 Hz), 7.40 (m, 2H), 7.70 (m, 1H), 7.86 (m, 1H), 7.96 (d, 1H, J=7.5 Hz), 8.23 (m, 3H), 8.42 (s, 1H).

To 6.6 mg (13.97 mol) 3 in 1.8 mL of THF-MeOH (2:1), was added 3.6 mg (7.01 μmol) of 114 and stirred overnight. The reaction mixture was purified on an Econosil $C_{18}$ reversed phase semi-preparative (250×10 mm, 10 μm) HPLC column using aq 0.1% TFA and $CH_3CN$ mobile phases. A linear gradient was employed (99:1 0.1% aq TFA-$CH_3CN$→60:40 0.1% aq TFA-$CH_3CN$) over a period of 18 min at a flow rate of 4.5 mL/min. The fractions containing the desired product eluted at 13.8 min (monitoring at 364 nm) and were collected, frozen and lyophilized to give 116 as a white solid: yield 1.8 mg (30%); mass spectrum (MALDI), m/z 869.43 $(M+Na)^+$; mass spectrum (ESI), m/z 869.2706 $(M+Na)^+$ ($C_{38}H_{46}N_4O_{18}Na$ requires m/z 869.2705).

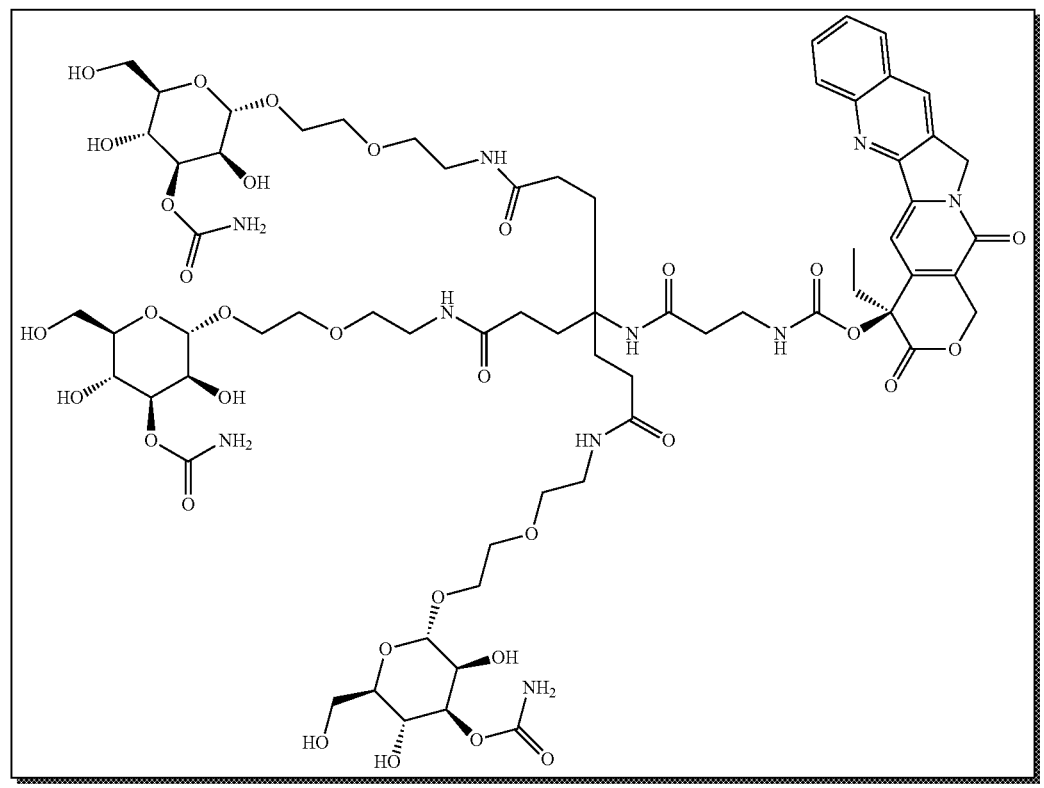

CPT-Carbamate-Trimer-Monosaccharide (117)

To 9.3 mg (7.78 μmol) 107 in 1.5 mL of THF-MeOH-DMSO (2:4:1), was added 2 mg (3.90 μmol) of 114 and stirred overnight. The reaction mixture was purified on an Econosil $C_{18}$ reversed phase semi-preparative (250×10 mm, 10 μm) HPLC column using aq 0.1% TFA and $CH_3CN$ mobile phases. A linear gradient was employed (99:1 0.1% aq TFA-$CH_3CN$→60:40 0.1% aq TFA-$CH_3CN$) over a period of 18 min at a flow rate of 4.5 mL/min. The fractions containing the desired product eluted at 16.5 min (monitoring at 364 nm) and were collected, frozen and lyophilized to give 117 as a light yellow solid: yield 1.2 mg (20%); mass spectrum (MALDI), m/z 1591.89 (M+Na)$^+$, 1607.88 (M+K)$^+$.

CPT-Carbamate-Decarbamoylmonosaccharide (118)

To 5.2 mg (19.47 μmol) 112 in 1.5 mL of THF-MeOH (2:1), was added 5 mg (9.74 μmol) of 114 and stirred overnight. The reaction mixture was purified on an Econosil $C_{14}$ reversed phase semi-preparative (250×10 mm, 10 μm) HPLC column using aq 0.1% TFA and $CH_3CN$ mobile phases. A linear gradient was employed (99:1 0.1% aq TFA-$CH_3CN$→60:40 0.1% aq TFA-$CH_3CN$) over a period of 18 min at a flow rate of 4.5 mL/min. The fractions containing the desired product eluted at 15.2 min (monitoring at 364 nm) and were collected, frozen and lyophilized to give 118 as a white solid: yield 1.8 mg (29%); mass spectrum (APCI), m/z 642.2280 (M+H)$^+$ ($C_{31}H_{36}N_3O_{12}$ requires m/z 642.2299).

Example 19: Synthesis of Camptothecin (CPT)-Saccharide Ester Conjugates 122 and 123

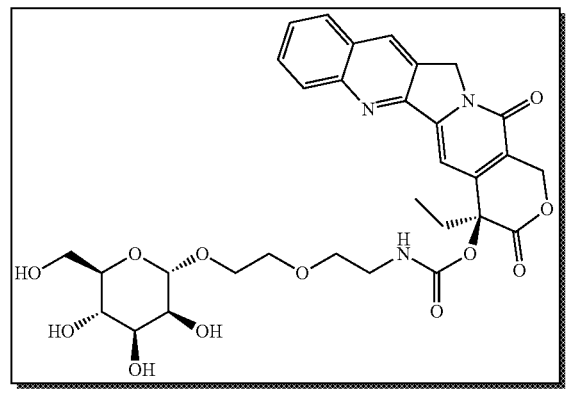

113

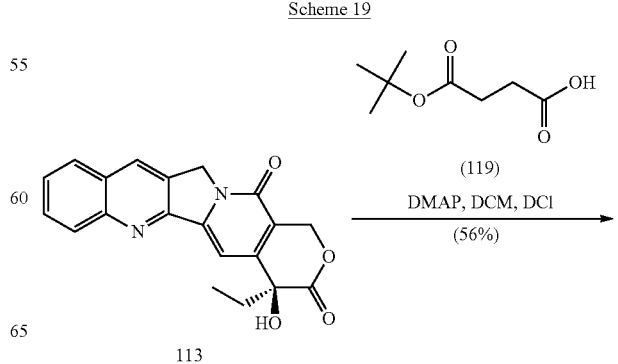

Scheme 19

(119)

DMAP, DCM, DCI (56%)

-continued

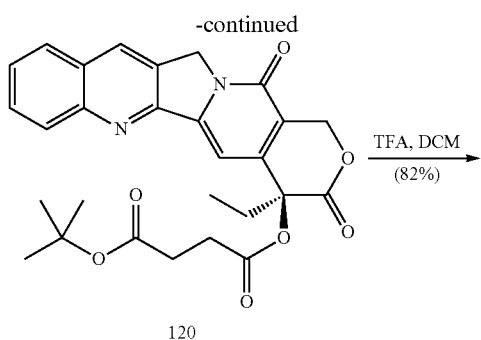

120

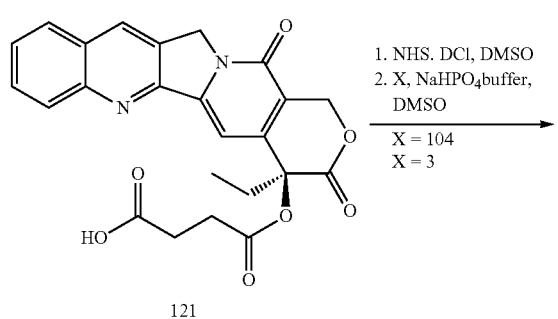

121

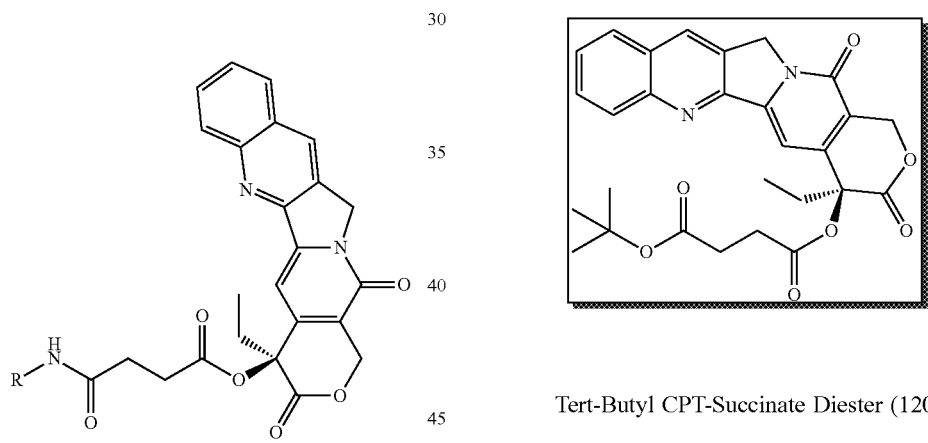

122 R = R₁ (17% over two steps)
123 R = R₂ (12% over two steps)

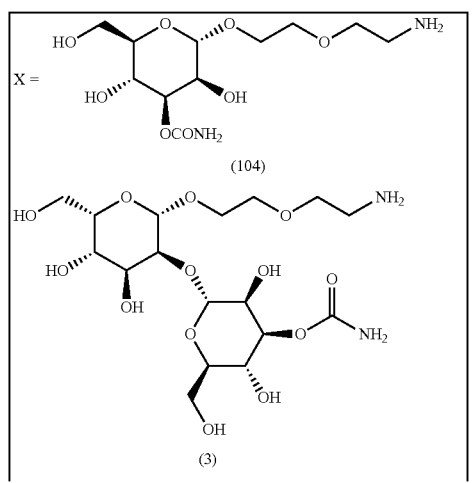

-continued

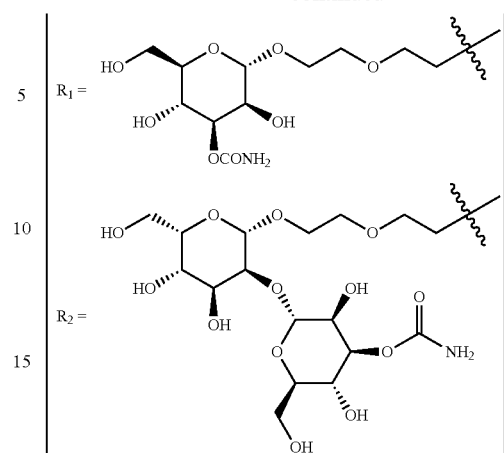

Tert-Butyl CPT-Succinate Diester (120)

To a solution of 198 mg (3.13 mmol) of 117 in 12 mL of dry $CH_2Cl_2$ was added 93 rag (0.76 mmol) of DMAP, 0.18 mL (145 mg, 0.1.15 mmol) of diisopropylcarbodiimide and 200 mg (0.57 mmol) of 113. The solution was stirred at room temperature overnight, diluted with 10 mL $CH_2Cl_2$ and washed with 3 mL of 0.1 N HCl solution, then dried over $MgSO_4$, filtered, and concentrated under diminished pressure. The residue was crystallized from methanol, filtered, washed with cold MeOH and dried to afford 120 as a yellow solid: yield 170 mg (56%); silica gel TLC $R_f$ 0.30 (12:1 chloroform-MeOH); $^1$H NMR (400 MHz, $CDCl_3$) δ 0.99 (t, 3H, J=7.2 Hz), 1.36 (s, 9H), 2.15 (m, 1H), 2.26 (m, 1H), 2.56 (m, 2H), 2.78 (m, 2H), 5.26 (d, 2H, J=3.2 Hz), 5.38 (d, 1H, J=17.2 Hz), 5.68 (d, 1H, J=17.2 Hz), 7.31 (s, 1H), 7.66 (m, 1H), 7.82 (m, 1H), 7.92 (d, 1H, J=8.4 Hz), 8.22 (d, 1H, J=8.4 Hz) and 8.37 (s, 1H); $^{13}$C NMR ($CDCl_3$) δ 7.75, 28.08, 29.27, 30.18, 31.90, 50.02, 67.15, 76.29, 81.06, 96.60, 120.19, 128.09, 128.26, 128.30, 128.57, 129.86, 130.68, 131.18, 146.19, 146.29, 149.03, 152.56, 157.52, 167.57, 171.16 and 171.64.

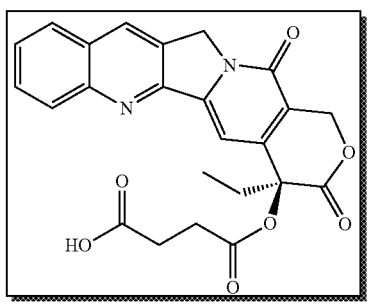

CPT-Succinate Acid (121)

To 134 mg (0.27 mmol) 120 in 1.5 mL of CH$_2$Cl$_2$, was added 0.6 µL of TFA and the reaction mixture was stirred for 5 h. The reaction mixture was concentrated under diminished pressure and crystallized from methanol, then filtered, washed with MeOH and ether, and dried to afford 121 as a pale yellow solid: yield 98 mg (82%) silica gel TLC R$_f$ 0.29 (12:1 chloroform-MeOH). $^1$H NMR (400 MHz, DMSO-d$_6$) δ 1.05 (m, 3H), 2.29 (m, 2H), 2.61 (m, 2H), 2.90 (m, 2H), 5.41 (d, 2H, J=1.2 Hz), 5.62 (s, 2H), 7.26 (s, 1H), 7.84 (t, 1H, J=7.2 Hz), 8.00 (m, 1H), 8.25 (d, 1H, J=8.0 Hz), 8.30 (d, 1H, J=8.4 Hz) and 8.80 (s, 11H); $^{13}$C NMR (DMSO-d$_6$) δ 7.52, 28.37, 28.56, 30.39, 50.17, 66.29, 75.87, 95.11, 118.90, 127.68, 127.95, 128.50, 128.99, 129.75, 130.37, 131.52, 145.25, 145.90, 145.88, 152.37, 156.52, 167.16, 171.26 and 172.97.

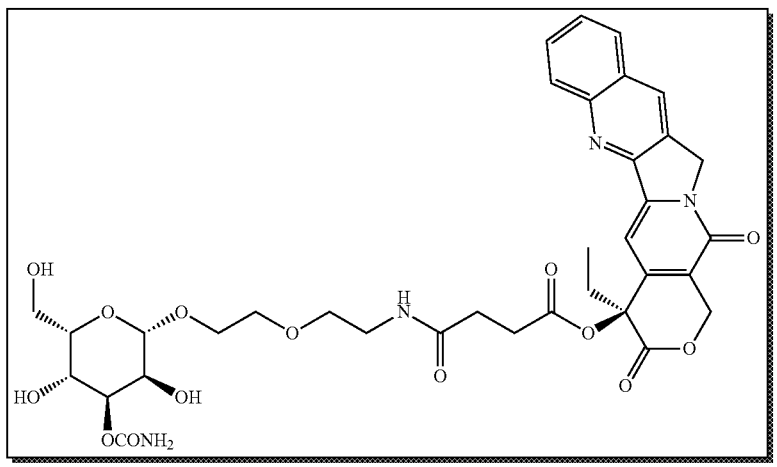

CPT-Carbamate-Monosaccharide (122)

To 5.0 mg (11 µmol) 121 in 0.15 mL of DMSO was added 1.5 mg (13 µmol) of N-hydroxysuccinimide and 1.7 mL (1.4 mg, 11 µmol) of diisopropylcarbodiimide and the reaction mixture was stirred at room temperature. After 24 h, 3.5 µg (11 µmol) of 104 in 0.5 mL of 1:1 0.2 M sodium phosphate buffer and DMSO was added, and the reaction mixture was stirred overnight. The reaction mixture was purified on an Econosil C$_{18}$ reversed phase semi-preparative HPLC column (250×10 mm, 10 µm) using aq 0.1% TFA and CH$_3$CN mobile phases. A linear gradient was employed (99:1 0.1% aq TFA-CH$_3$CN→60:40 0.1% aq TFA-CH$_3$CN) over a period of 18 min at a flow rate of 4.5 mL/min. The fractions containing the desired product eluted at 18.8 min (monitoring at 364 nm) and were collected, frozen and lyophilized to give 122 as a light yellow solid: yield 1.4 mg (17% over two steps); mass spectrum (MALDI), m/z 778.68 (M+K)$^+$.

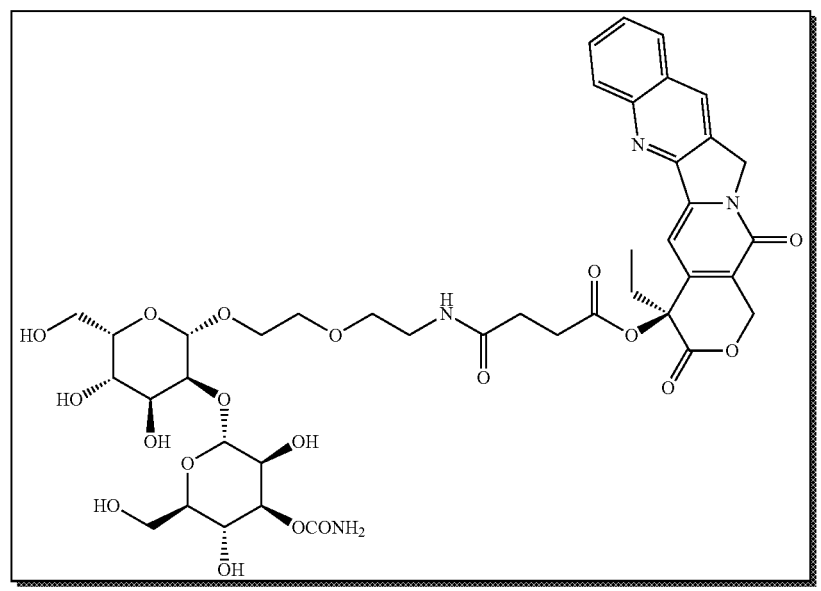

CPT-Carbamate-Disaccharide (123)

To 2.0 mg (4.5 mol) 121 in 0.15 mL of DMSO was added 1.0 mg (8.9 μmol) N-hydroxysuccinimide and 1.4 μL (1.1 mg, 8.9 μmol) of diisopropylcarbodiimide and the reaction mixture was stirred at room temperature. After 24 h, 3.2 mg (6.77 μmol) of 3 in 0.4 mL of 1:1 0.2 M sodium phosphate buffer, pH 8.0, and DMSO was added, and then the reaction mixture was stirred overnight. The reaction mixture was purified on an Econosil $C_{18}$ reversed phase semi-preparative HPLC column (250×10 mm, 10 μm) using aq 0.1% TFA and $CH_3CN$ mobile phases. A linear gradient was employed (99:1 0.1% aq TFA-$CH_3CN$→60:40 0.1% aq TFA-$CH_3CN$) over a period of 18 min at a flow rate of 4.5 mL/min. The fractions containing the desired product eluted at 17.9 min (monitoring at 364 nm) and were collected, frozen and lyophilized to give 123 as a light yellow solid: yield 0.5 mg (12% over two steps).

Example 20: In Vitro Cell Growth Inhibition Tests

A methotrexate resistant cell line. DU 145(MTX) was developed from parental DU 145 cells by exposure to increasing concentrations (starting at 0.1 μM) of methotrexate over a period of 6 months. DU 145(MTX) was at least 250-fold less sensitive to methotrexate than parental cells. After five passages in drug-free medium, the resistant cells retained their drug resistance, suggesting the stability of the cell line.

Cell Culture.

The human prostate cancer cell lines DU-145 (ATCC) was cultured in MEM media with glutamine and supplemented with 10% fetal bovine serum, penicillin (100 U/mL) and streptomycin (100 U/mL) in air enriched with 5% $CO_2$ at 37° C.

In Vitro Cell Growth Inhibition Tests.

Cell viability was determined using the MTT assay. Briefly, cells were seeded in 96-well plates at a density of 3000 cells per well in 0.1 mL MEM media supplemented with 10% fetal bovine serum, and test compounds were concomitantly added in a concentration range of 0.001-1000 μM. Dilutions were made using the culture medium from 1 mM stock solutions of the drugs in anhydrous DMSO. Controls were treated with an equivalent amount of solvent, diluted as above, to assess the absence of toxicity due to the solvent. After 72 h of incubation, 15 μL of 5 mg $mL^{-1}$ MTT dye (3-[4,5-dimethylthiazol-2-yl]-2,5-diphenyltetrazolium bromide, sigma) was added for 4 h at 37° C. Media was removed and the monolayer suspended in 0.15 mL of DMSO, after which the absorbance at 570 nm was measured using a microplate reader. The control value corresponding to untreated cells was defined as 100% and the viability of treated samples was expressed as a percentage of the control.

TABLE 1

Cytotoxicity of MTX-Disaccharide Conjugates Toward MTX Resistant DU-145 Cells

| Compound | DU-145-MTX (% cell survival) |
|---|---|
| Methotrexate (MTX) | |
| 100 nM | 82 |
| 1 μM | 84 |
| 10 μM | 83 |
| Compound 5 | |
| 100 nM | 84 |
| 1 μM | 69 |
| 10 μM | 41 |
| Compound 15 | |
| 100 nM | 83 |
| 1 μM | 60 |
| 10 μM | 56 |

While particular materials, formulations, operational sequences, process parameters, and end products have been set forth to describe and exemplify this invention, they are not intended to be limiting. Rather, it should be noted by those ordinarily skilled in the art that the written disclosures are exemplary only and that various other alternatives, adaptations, and modifications may be made within the scope of the present invention. Accordingly, the present

What is claimed is:

1. A sugar-linker-drug conjugate of formula (I)

[A—B]$_m$—L—D  (I)

or a pharmaceutically acceptable salt thereof,
wherein A is:

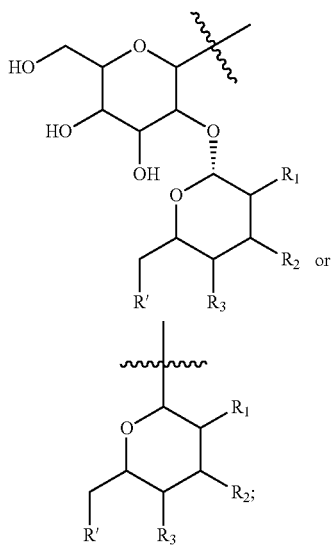

$R_1$ is selected from the group consisting of H, OH, SH, $NH_2$, $OR_4$, $OC(O)R_4$, $OC(O)NHR_4$, $OC(O)NR_4R_5$, $OC(S)NHR_4$, $OC(S)NR_4R_5$, $SC(O)NHR_4$, $SC(O)NR_4R_5$, $NHC(O)NHR_4$, $NHC(O)NR_4R_5$, $NHC(S)NHR_4$, $NHC(S)NR_4R_5$, $NHC(N)NHR_4$, $NHC(N)NR_4R_5$, $OCH_2C(O)NHR_4$, $OCH_2C(O)NR_4R_5$, $OCH_2C(S)NHR_4$, $OCH_2C(S)NR_4R_5$, $SCH_2C(O)NHR_4$, $SCH_2C(O)NR_4R_5$, $NHCH_2C(O)NHR_4$, $NHCH_2C(O)NR_4R_5$, $NHCH_2C(S)NHR_4$ and $NHCH_2C(S)NR_4R_5$;

each $R_4$ is selected from the group consisting of H, $C_1$-$C_6$ alkyl, $C_2$-$C_6$ alkenyl and $C_2$-$C_6$ alkynyl;

each $R_5$ is selected from the group consisting of $C_1$-$C_6$ alkyl, $C_2$-$C_6$ alkenyl and $C_2$-$C_6$ alkynyl;

$R_2$ is selected from the group consisting of H, OH, SH, $NH_2$, $OR_4$, $OC(O)R_4$, $OC(O)NHR_4$, $OC(O)NR_4R_5$, $OC(S)NHR_4$, $OC(S)NR_4R_5$, $SC(O)NHR_4$, $SC(O)NR_4R_5$, $NHC(O)NHR_4$, $NHC(O)NR_4R_5$, $NHC(S)NHR_4$, $NHC(S)NR_4R_5$, $NHC(N)NHR_4$, $NHC(N)NR_4R_5$, $OCH_2C(O)NHR_4$, $OCH_2C(O)NR_4R_5$, $OCH_2C(S)NHR_4$, $OCH_2C(S)NR_4R_5$, $SCH_2C(O)NHR_4$, $SCH_2C(O)NR_4R_5$, $NHCH_2C(O)NHR_4$, $NHCH_2C(O)NR_4R_5$, $NHCH_2C(S)NHR_4$ and $NHCH_2C(S)NR_4R_5$;

$R_3$ is selected from the group consisting of H, OH, SH, $NH_2$, $OR_4$, $OC(O)R_4$, $OC(O)NHR_4$, $OC(O)NR_4R_5$, $OC(S)NHR_4$, $OC(S)NR_4R_5$, $SC(O)NHR_4$, $SC(O)NR_4R_5$, $NHC(O)NHR_4$, $NHC(O)NR_4R_5$, $NHC(S)NHR_4$, $NHC(S)NR_4R_5$, $NHC(N)NHR_4$, $NHC(N)NR_4R_5$, $OCH_2C(O)NHR_4$, $OCH_2C(O)NR_4R_5$, $OCH_2C(S)NHR_4$, $OCH_2C(S)NR_4R_5$, $SCH_2C(O)NHR_4$, $SCH_2C(O)NR_4R_5$, $NHCH_2C(O)NHR_4$, $NHCH_2C(O)NR_4R_5$, $NHCH_2C(S)NHR_4$ and $NHCH_2C(S)NR_4R_5$;

R' is selected from the group consisting of H, OH and $NHR_4$;

B is X-($L^1$-Y)$_m$-$L^2$-Z,
wherein X is $CH_2$ or O;
$L^1$ is $C_2$-$C_6$ alkyl;
Y is O, S, or $NR^y$, wherein $R^y$ is hydrogen or $C_1$-$C_6$ alkyl;
m is an integer selected from 1 to 10;
$L^2$ is $C_1$-$C_{20}$ alkyl, $C_2$-$C_{20}$ alkenyl, $C_2$-$C_{20}$ alkynyl, aryl, heteroaryl, heterocyclyl, $C_3$-$C_5$ cycloalkyl; and
Z is absent, O, $NR^x$, S, C(O), S(O), S(O)$_2$, OC(O), N($R^x$)C(O), N($R^x$)S(O), N($R^x$)S(O)$_2$, C(O)O, C(O)N($R^x$), S(O)N($R^x$), S(O)$_2$N($R^x$), OC(O)O, OC(O)N($R^x$), N($R^x$)C(O)O, N($R^x$)C(O)N($R^x$), or N($R^x$)S(O)$_2$N($R^x$), wherein
each $R^x$ is independently hydrogen or $C_1$-$C_6$ alkyl;
n is an integer selected from 1 to 3;
L is (E-$L^3$-F-$L^4$)$_p$-G,
wherein each E is bond, O, $NR^x$, S, C(O), S(O), S(O)$_2$, OC(O), N($R^x$)C(O), N($R^x$)S(O), N($R^x$)S(O)$_2$, C(O)O, C(O)N($R^x$), S(O)N($R^x$), S(O)$_2$N($R^x$), OC(O)O, OC(O)N($R^x$), N($R^x$)C(O)O, N($R^x$)C(O)N($R^x$), or N($R^x$)S(O)$_2$N($R^x$);
each $L^3$ is $C_2$-$C_6$ alkyl;
each F is bond, O, $NR^x$, S, C(O), S(O), S(O)$_2$, OC(O), N($R^x$)C(O), N($R^x$)S(O), N($R^x$)S(O)$_2$, C(O)O, C(O)N($R^x$), S(O)N($R^x$), S(O)$_2$N($R^x$), OC(O)O, OC(O)N($R^x$), N($R^x$)C(O)O, N($R^x$)C(O)N($R^x$), or N($R^x$)S(O)$_2$N($R^x$);
each $L^4$ is $C_0$-$C_6$ alkyl;
p is 1 or 2; and
G is a bond, O, $NR^x$, S, C(O), S(O), S(O)$_2$, OC(O), N($R^x$)C(O), N($R^x$)S(O), N($R^x$)S(O)$_2$, C(O)O, C(O)N($R^x$), S(O)N($R^x$), S(O)$_2$N($R^x$), OC(O)O, OC(O)N($R^x$), N($R^x$)C(O)O, N($R^x$)C(O)N($R^x$), or N($R^x$)S(O)$_2$N($R^x$); and
D is a Drug Unit selected from the group consisting of mitomycin-C, mitomycin-A, daunorubicin, doxorubicin, N-(5,5-diacetoxypentyl)doxorubicin, aminopterin, actinomycin, bleomycin, 9-amino camptothecin, N8-acetyl spermidine, 1-(2 chloroethyl)-1,2-dimethanesulfonyl hydrazide, tallysomycin, methotrexate, amsacrin, cis-platin, mercaptopurine, etoposide, camptothecin, taxol, esperamicin, 1,8-dihydroxy-bicyclo[7.3.1]trideca-4,9-diene-2,6-diyne-13-one, anguidine, doxorubicin, morpholino-doxorubicin, N-(5,5-diacetoxypentyl)doxorubicin, vincristine, vinblastine, bleomycin, teniposide, podophyllotoxin, esperamicin, 6-mercaptopurine, methotrexate, camptothecin (ring-opened form of the lactone), butyric acid, retinoic acid, nitrogen mustard drugs, chlorambucil, melphalan, cinnamaldehyde, inosine dialdehyde, diglycoaldehyde, anthracycline and epothilone.

2. The conjugate according to claim 1, wherein A is

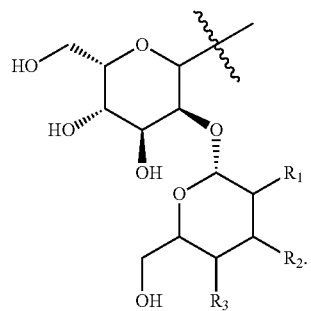

3. The conjugate according to claim 1, wherein A is selected from the group consisting of:

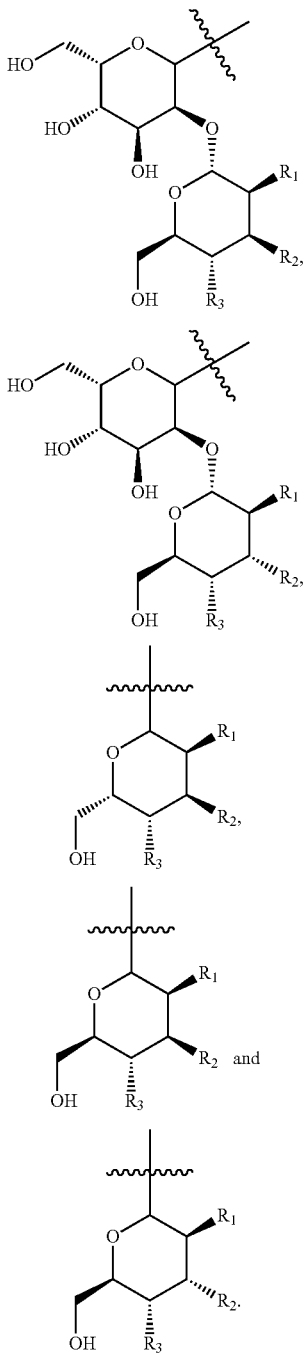

4. The conjugate according to claim 1, wherein $R_1$ is selected from the group consisting of H, OH, $OR_4$, $OC(O)R_4$, $NHC(N)NHR_4$, $NHC(N)NR_4R_5$, $OC(O)R_4$, $OCONHR_4$, and $OCONR_4R_5$.

5. The conjugate according to claim 1, wherein $R_2$ is selected from the group consisting of H, OH, $OR_4$, $OC(O)R_4$, $NHC(N)NHR_4$, $NHC(N)NR_4R_5$, $OC(O)R_4$, $OCONHR_4$, $OCONR_4R_5$, $OCSNHR_4$, $NHCONHR_4$, $OCH_2CONHR_4$, and $OCH_2CONR_4R_5$.

6. The conjugate according to claim 1, wherein $R_3$ is selected from the group consisting of H, OH, $OR_4$, $OC(O)R_4$, $NHC(N)NHR_4$, $NHC(N)NR_4R_5$, $OC(O)R_4$, and $OCONHR_4$.

7. The conjugate according to claim 1, wherein R' is H or OH.

8. The conjugate according to claim 1, wherein each $R_4$ is selected from the group consisting of H, methyl and ethyl.

9. The conjugate according to claim 1, wherein each $R_5$ is selected from the group consisting of methyl, ethyl, and isobutyl.

10. The conjugate according to claim 1, wherein A is selected from the group consisting of:

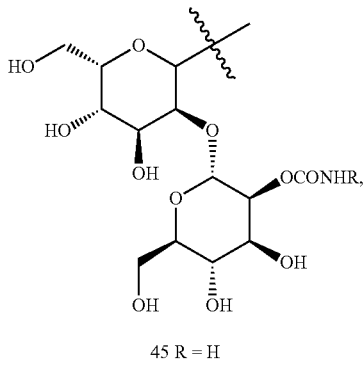

45 R = H
46 R = CH₃

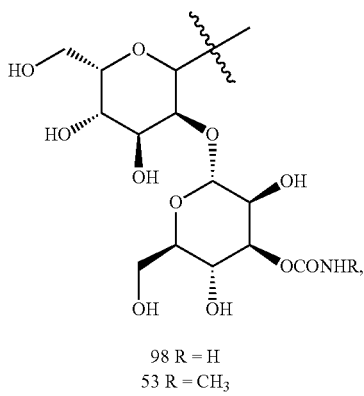

98 R = H
53 R = CH₃

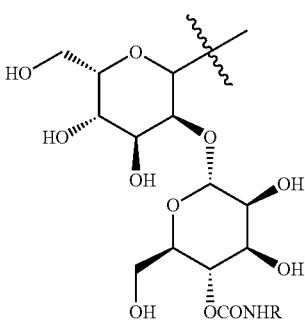

64 R = H
65 R = CH₃

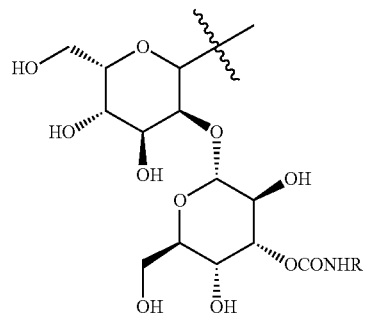
76 R = H
77 R = CH₃
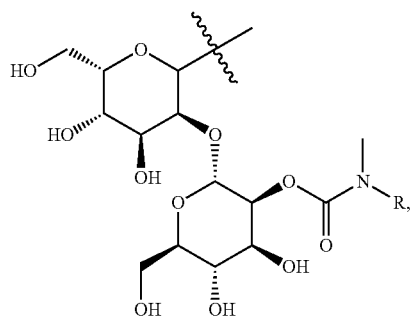
99 R = CH₃
100 R = C₂H₅
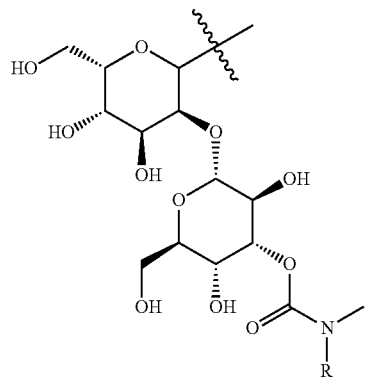
101 R = CH₃
102 R = C₂H₅
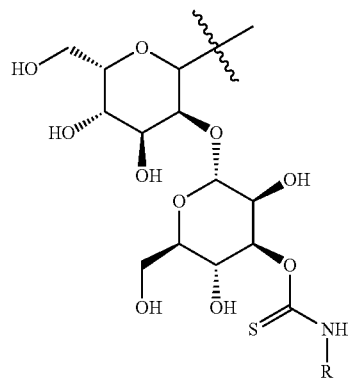
103 R = H
104 R = CH₃
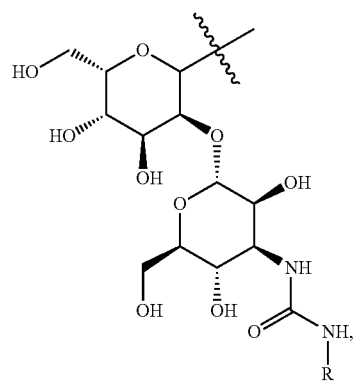
107 R = H
108 R = CH₃
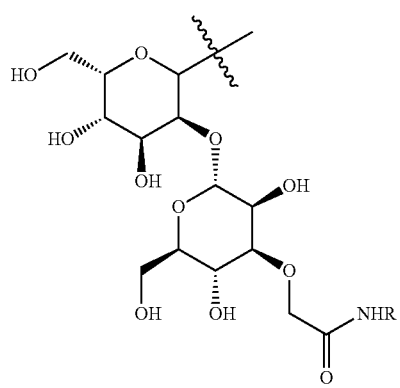
109 R = H
110 R = CH₃
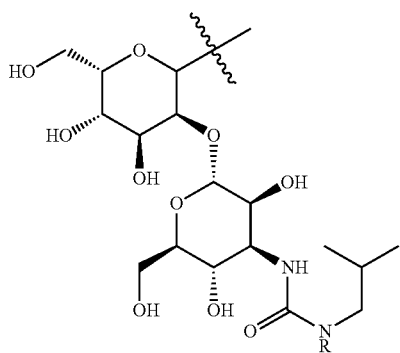
111 R = H
112 R = CH₃

157

-continued

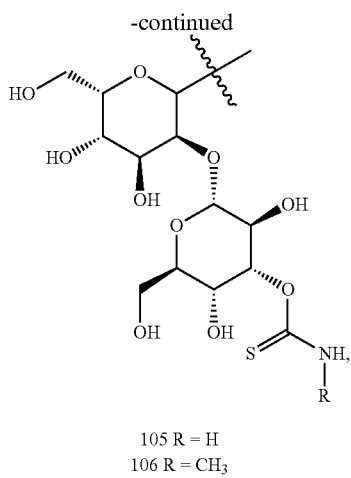

105 R = H
106 R = CH₃

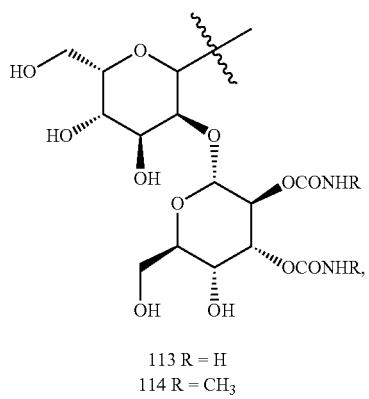

113 R = H
114 R = CH₃

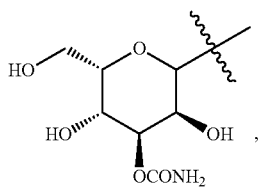

158

-continued

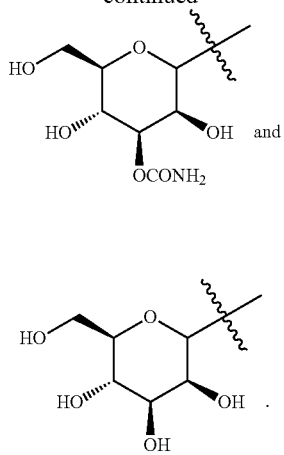

11. The conjugate according to claim 1, wherein E is $NR^x$ or C(O);

$L^3$ is $C_4$-$C_6$ alkyl;

$L^4$ is $C_0$-$C_2$ alkyl;

p is 1 or 2;

F is a bond, $NR^x$, $N(R^x)C(O)$, OC(O), C(O)O or $C(O)N(R^x)$; and

G is O, S, C(O) or $NR^x$.

12. The conjugate according to claim 1, wherein D is a drug selected from the group consisting of a cytotoxic drug, a cytostatic drug, antiproliferative drug, antitumor agent, an inhibitor of a cellular metabolic event and is an enzyme or protein inhibitor.

13. A pharmaceutical composition comprising a conjugate of formula (I) according to claim 1, and a pharmaceutically acceptable carrier.

14. A method of treating cancer in a patient comprising administering to a patient in need thereof a conjugate according to claim 1, or a pharmaceutical composition according to claim 13.

15. A method of reducing the toxic side effects of administering a drug to treat cancer, comprising administering to a patient an effective amount of a conjugate according to claim 1, or a pharmaceutical composition according to claim 13.

16. A conjugate represented by formula:

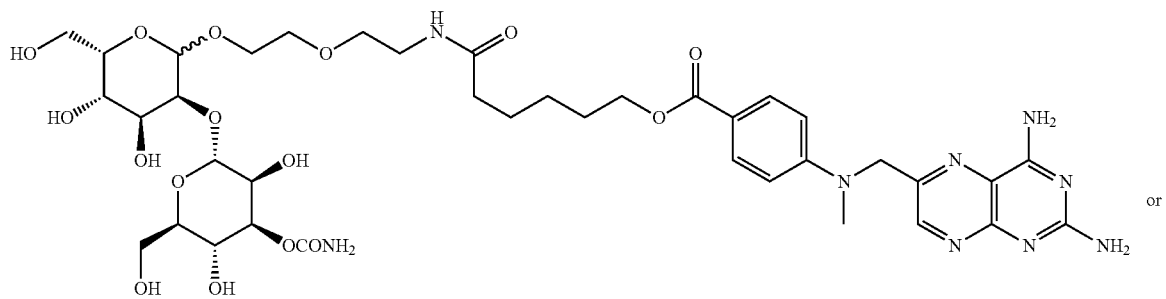

or

-continued
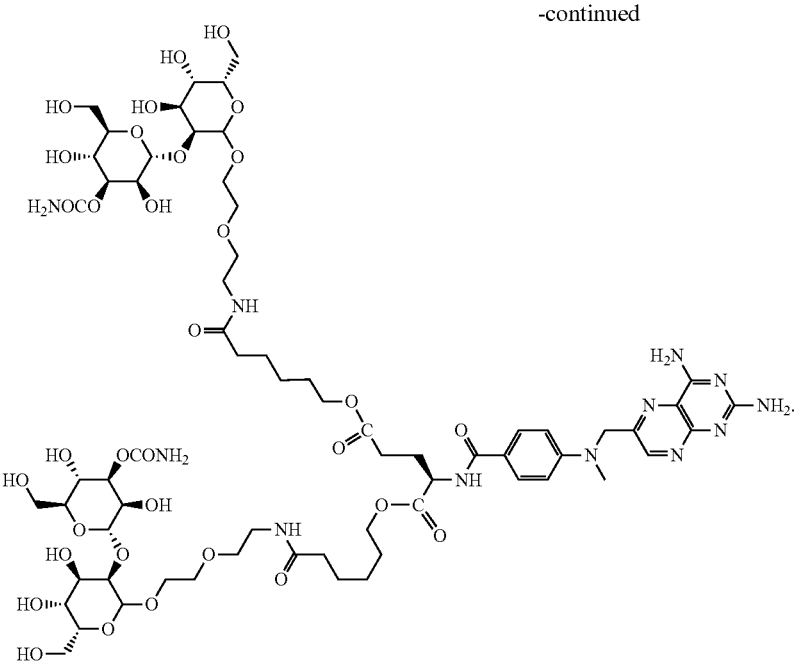
17. A conjugate represented by formula:
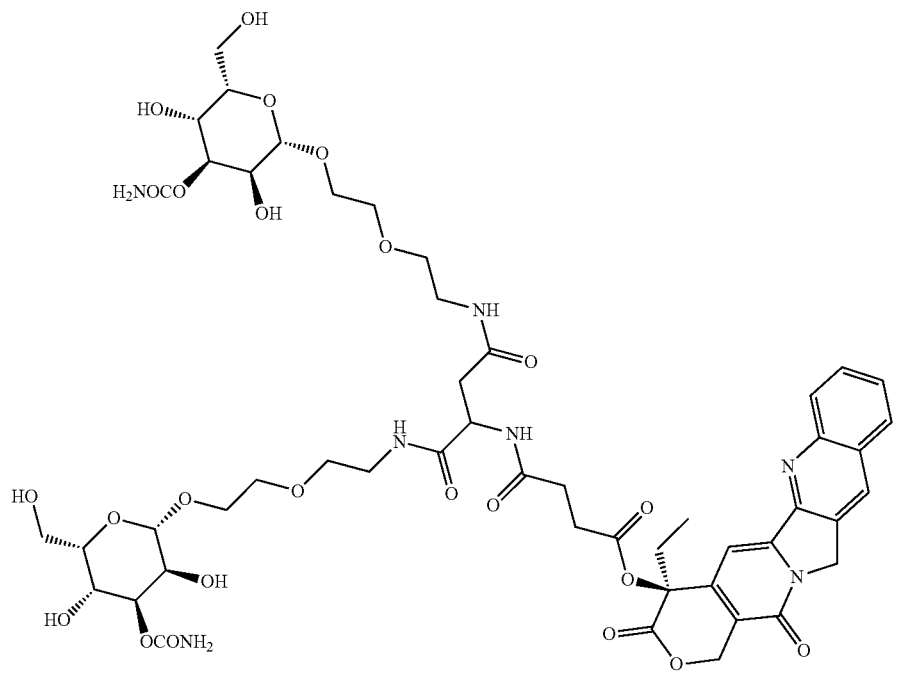
or a pharmaceutically acceptable salt thereof.
* * * * *